(12) United States Patent
Ladner et al.

(10) Patent No.: US 6,989,369 B2
(45) Date of Patent: Jan. 24, 2006

(54) KUNITZ DOMAIN PEPTIDES

(75) Inventors: Robert Charles Ladner, Ijamsville, MD (US); Arthur C. Ley, Newton, MA (US)

(73) Assignee: Dyax Corp., Cambridge, MA (US)

( * ) Notice: Subject to any disclaimer, the term of this patent is extended or adjusted under 35 U.S.C. 154(b) by 95 days.

(21) Appl. No.: 10/361,997

(22) Filed: Feb. 7, 2003

(65) Prior Publication Data

US 2004/0171794 A1 Sep. 2, 2004

(51) Int. Cl.
*A61K 38/00* (2006.01)
*A61K 38/16* (2006.01)

(52) U.S. Cl. .......................................... 514/12; 530/324

(58) Field of Classification Search ................... 514/12; 530/324

See application file for complete search history.

(56) References Cited

U.S. PATENT DOCUMENTS

| | | |
|---|---|---|
| 4,595,674 A | 6/1986 | Tschesche et al. |
| 4,657,893 A | 4/1987 | Krantz et al. |
| 4,845,242 A | 7/1989 | Powers et al. |
| 4,980,287 A | 12/1990 | Kokubo et al. |
| 5,118,668 A | 6/1992 | Auerswald et al. |
| 5,166,133 A | 11/1992 | Houston et al. |
| 5,223,409 A | 6/1993 | Ladner et al. |
| 5,278,144 A | 1/1994 | Wolf |
| 5,278,285 A | 1/1994 | Ebbers et al. |
| 5,373,090 A | 12/1994 | Norris et al. |
| 5,407,915 A | 4/1995 | Fritz et al. |
| 5,409,895 A | 4/1995 | Morishita et al. |
| 5,576,294 A | 11/1996 | Norris et al. |
| 5,583,107 A | 12/1996 | Wolf et al. |
| 5,589,359 A | 12/1996 | Innis et al. |
| 5,663,143 A | 9/1997 | Ley et al. |
| 5,719,041 A | 2/1998 | Lazarus et al. |
| 5,736,364 A | 4/1998 | Kelley et al. |
| 5,770,568 A | 6/1998 | Auerswald et al. |
| 5,780,265 A | 7/1998 | Denis et al. |
| 5,786,328 A | 7/1998 | Denis et al. |
| 5,795,865 A | 8/1998 | Markland et al. |
| 5,795,954 A | 8/1998 | Lazarus et al. |
| 5,843,895 A | 12/1998 | Lazarus et al. |
| 5,994,125 A | 11/1999 | Markland et al. |
| 6,004,579 A | 12/1999 | Bathurst et al. |
| 6,010,880 A | 1/2000 | Markland et al. |
| 6,057,287 A | 5/2000 | Markland et al. |
| 6,071,723 A | 6/2000 | Markland et al. |
| 6,087,473 A | 7/2000 | Conklin et al. |
| 6,103,499 A | 8/2000 | Markland et al. |
| 6,333,402 B1 | 12/2001 | Markland et al. |
| 6,423,498 B1 | 7/2002 | Markland et al. |
| 2003/0175919 A1 | 9/2003 | Ley et al. |
| 2003/0223977 A1 | 12/2003 | Ley et al. |
| 2004/0038893 A1 * | 2/2004 | Ladner et al. ................. 514/12 |
| 2004/0053206 A1 | 3/2004 | Cicardi et al. |

FOREIGN PATENT DOCUMENTS

| | | |
|---|---|---|
| EP | 0 195 212 A2 | 9/1986 |
| EP | 0 486 001 A1 | 5/1992 |
| EP | 0 643 075 A1 | 3/1995 |
| WO | WO 90/02809 | 3/1990 |
| WO | WO 92/15605 | 9/1992 |
| WO | WO 93/14120 | 7/1993 |
| WO | WO 93/14121 | 7/1993 |
| WO | WO 93/14122 | 7/1993 |
| WO | WO 03/66824 | 8/2003 |

OTHER PUBLICATIONS

Albrecht, G.J., et al., "Elastase Inhibition by the Inter–α Trypsin Inhibitor and Derived Inhibitors of Man and Cattle," *Hoppe–Seyler's Z. Physiol. Chem.*, 364:1703–1708 (1983).

Albrecht, G.J., et al., "Kunitz–Type Proteinase Inhibitors Derived by Limited Proteolysis of the Inter–α–Trypsin Inhibitor, IX," *Hoppe–Seyler's Z. Physiol. Chem.*, 364: 1697–1702 (1983).

Angelastro, M.R., et al., "α–Diketone and α–Keto Ester Derivatives of N–Protected Amino Acids and Peptides as Novel Inhibitors of Cysteine and Serine Proteinases," *J. Med. Chem.*, 33:11–13 (1990).

An–Zhi, W., et al., The Refined 2.3 Å Crystal Structure of Human Leukocyte Elastase in a Complex With a Valine Chloromethyl Ketone Inhibitor, *FEBS Lett.*, 234(2):367–373 (1988).

Baek, D.–J., et al., "Alternate Substrate Inhibitors of an α–Chymotrypsin: Enantioselective Interaction of Aryl–Substituted Enol Lactones," *Biochemistry*, 29:4305–4311 (1990).

Beckmann, J., et al., "Preparation of Chemically 'Mutated' Aprotinin Homologues by Semisynthesis–$P_1$ Substitutions Change Inhibitory Specificity," *Eur. J. Biochem.*, 176: 675–682 (1988).

Blow, D.M., et al., "A Model for the Association of Bovine Pancreatic Trypsin Inhibitor With Chymotrypsin and Trypsin," *J. Mol. Biol.*, 69: 137–144 (1972).

Brinkmann, T., and Tschesche, H., "Design of an Aprotinin Variant With Inhibitory Activity Against Chymotrypsin and Cathepsin G by Recombinant DNA Technology," *Biol. Chem. Hoppe–Seyler*, 371: 43–52 (1990).

Broze, Jr., G.J., et al., "Regulation of Coagulation by a Multivalent Kunitz–Type Inhibitor," *Biochemistry*, 29(33):7539–7546 (1990).

(Continued)

*Primary Examiner*—Robert A. Wax
*Assistant Examiner*—Suzanne M. Mayer
(74) *Attorney, Agent, or Firm*—Fish & Richardson P.C.

(57) ABSTRACT

The invention relates to a Kunitz domain peptide, designated DPI-14 herein, for inhibiting human neutrophil elastase. The invention also relates to a method of using a DPI-14 for treating cystic fibrosis or cystic fibrosis-related disease or disorder.

27 Claims, 6 Drawing Sheets

OTHER PUBLICATIONS

Cantor, J.O., and Turino, G.M., "Elastin and Elastases in Lung Disease," Ch. 16 in *Elastin and Elastases,* II:159–168 (1989).

Carey, F.A., and Sundberg, R.J., Eds. "Multistep Syntheses," Ch. 13 in *Advanced Organic Chemistry; Part B: Reactions & Synthesis,* 3$^{rd}$ Ed.:678–686 (1990).

Chazin, W.J., et al., "Comparative Studies of Conformation and Internal Mobility in Native and Circular Basic Pancreatic Trypsin Inhibitor by $^1$H Nuclear Magnetic Resonance in Solution," *Eur. J. Biochem., 152*:429–437 (1985).

Chen, L., et al., "Identification of a Factor in Fetal Bovine Serum That Stabilizes the Cumulus Extracellular Matrix,"*J. Biol. Chem.,* 267(17): 12380–12386 (1992).

Diarra–Mehrpour, M., et al., "Structural Analysis of the Human Inter–α–Trypsin Inhibitor Light–Chain Gene," *Eur. J. Biochem., 191*:131–139 (1990).

Dixon, J. S., "Computer–Aided Drug Design: Getting the Best Results," *Trends Biotechnol., 10:*357–363 (1992).

Dufton, M.J., "Proteinase Inhibitors and Dendrotoxins," *Eur. J. Biochem., 153*: 647–654 (1985).

Engchild, J.J., et al., "Chondroitin 4–Sulfate Covalently Cross–links the Chains of the Human Blood Protein Pre–α–inhibitor," *J. Biol. Chem.,* 266(2): 747–751 (1991).

Enghild, J.J., et al., "Presence of the Protein–Glycosaminoglycan–Protein Covalent Cross–link in the Inter–α–inhibitor–related Proteinase Inhibitor Heavy Chain 2/bikunin," *J. Biol. Chem.,* 268(12):8711–8716 (1993).

Engleberg, N.C., et al., "DNA Sequence of mip, a *Legionella pneumophila* Gene Associated with Macrophage Infectivity," *Infect. Immun.,* 57(4):1263–1270 (1989).

Escribano, J., et al., "Location and Characterization of the Three Carbohydrate Prosthetic Groups of Human Protein HC," *FEBS Lett., 266(1–2)*:167–170 (1990).

Escribano, J., et al., "The Protein HC Chromophore Is Linked to the Cystein Residue at Position 34 of the Polypeptide Chain by a Reduction–resistant Bond and Causes the Charge Heterogeneity of Protein HC," *J. Biol. Chem., 266(24)*:15758–15763 (1991).

Filler, R., "Oxidations and Dehydrogenations with N–Bromosuccinimide and Related N–Haloimides," *Chem. Rev., 63*:21–43 (1963).

Ganu, V.S., et al., "Improved Synthetic Inactivators of Plasmin," *Thromb. Res., 45*:1–6 (1987).

Gebhard, W., et al., "Structure of Inter–α–Inhibitor (Inter–α–Trypsin Inhibitor) and Pre–α–Inhibitor: Current State and Proposition of a New Terminology," *Biol. Chem. Hoppe–Seyler, 371*:13–22 (1990).

Gebhard, W., and Hochstrasser, K., "Inter–α–trypsin inhibitor and its close relatives," Ch. 11 in *Proteinase Inhibitors,* Barrett and Salvesen (Eds.):389–401 (1986).

Goodman and Gilman, Eds. *The Pharmacological Basis of Therapeutics,* 8$^{th}$ Ed. pp 396, 407, 446–449, 473–475, 1117–1125 (Pergamon Press, New York, 1990).

Girard, T.J., et al., "Functional Significance of the Kunitz–type Inhibitory Domains of Lipoprotein–Associated Coagulation Inhibitor," *Nature,* 338:518–520 (1989).

Goldenberg, D.P., and Creighton, T.E., "Circular and Circularly Permuted Forms of Bovine Pancreatic Trypsin Inhibitor," *J. Mol. Biol.* 165: 407–13 (1983).

Goldstein, W., and Doring, G., "Lysosomal Enzymes from Polymorphonuclear Leukocytes and Proteinase Inhibitors in Patients with Cystic Fibrosis," *Am. Rev. Respir. Dis.,* 134:49–56 (1986).

Govardhan, C.P., and Abeles, R.H., "Structures–Activity Studies of Fluoroketone Inhibitors of α–Lytic Protease and Human Leukocyte Elastase," *Arch. Biochem. Biophys., 280*(1):137–143 (1990).

Heidtmann, H., and Travis, J., "Human α$_1$–Proteinase Inhibitor," Ch. 14 in *Proteinase Inhibitors,* Barrett and Salvesen (Eds.):441–456 (1986).

Xu, Y., et al., "The Crystal Structure of Bikunin from the Inter–α–Inhibitor Complex: A Serine Protease Inhibitor with Two Kunitz Domains," *J. Mol. Biol.,* 276:955–966 (1998).

Hochstrasser, K., et al., "Kunitz–Type Proteinase Inhibitors Derived by Limited Proteolysis of the Inter–α–Trypsin Inhibitor, V: Attachments of Carbohydrates in the Human Urinary Trypsin Inhibitor Isolated by Affinity Chromatography," *Hoppe–Seyler's Z. Physiol. Chem., 362*:1357–1362 (1981).

Hochstrasser, K., et al., "Kunitz–Type Proteinase Inhibitors Derived by Limited Proteolysis of the Inter–α–Trypsin Inhibitor, VII: Determination of the Amino–Acid Sequence of the Trypsin–Released Inhibitor from Bovine Inter–α–Trypsin Inhibitor," *Hoppe–Seyler's Z. Physiol. Chem., 364*:1679–1687 (1983).

Hochstrasser, K., et al., "Kunitz–Type Proteinase Inhibitors Derived by Limited Proteolysis of the Inter–α–Trypsin Inhibitor, VIII: Characterization of the Bovine Inhibitor as Double–Headed Trypsin–Elastase Inhibitor," *Hoppe–Seyler's Z. Physiol. Chem., 364*:1689–1696 (1983).

Hochstrasser, K., et al., "Kunitz–Type Proteinase Inhibitors Derived by Limited Proteolysis of the Inter–α–Trypsin Inhibitor, X: The Amino–Acid Sequences of the Trypsin–Released Inhibitors from Horse and Pig Inter–α–Trypsin Inhibitors,"*Biol. Chem. Hoppe–Seyler,* 366:473–478 (1985).

Huber, R., et al., "The Structure of the Complex Formed by Bovine Trypsin and Bovine Pancreatic Trypsin Inhibitor: III. Structure of the Anhydro–Trypsin–Inhibitor Complex," *Biophys. Struct. Mechanism, 1*(3):189–201 (1975).

Hynes, T.R., et al., "X–ray Crystal Structure of the Protease Inhibitor Domain of Alzheimer's Amyloid β–Protein Precursor," *Biochemistry,* 29:10018–10022 (1990).

Imperiali, B., and Abeles, R.H., "Extended Binding Inhibitors of Chymotrypsin that Interact with Leaving Group Subsites $S_1$—$S_3$," *Biochemistry,* 26:4474–77 (1987).

Imperiali, B., and Abeles, R.H., "Inhibition of Serine Proteases by Peptidyl Fluoromethyl Ketones," *Biochemistry,* 25:3760–67 (1986).

Kaumeyer, J.F., et al., "The mRNA for a Proteinase Inhibitor Related to the HI–30 Domain of Inter–α–Trypsin Inhibitor Also Encodes α–1–Microglobulin (Protein HC)," *Nucl. Acids Res.,* 14(20):7839–7850 (1986).

Laskowski, Jr., M., and Kato, I., "Protein Inhibitors of Proteinases," *Ann. Rev. Biochem., 49*:593–626 (1980).

Lindquist, A., and Åkerström, B.,, "Bovine α$_1$–Microglobulin/Bikunin. Isolation and Characterization of Liver cDNA and Urinary α$_1$–Microglobulin,"*Biochim. Biophys. Acta, 1306*:98–106 (1996).

López, C., et al., "Human Protein HC Displays Variability in its Carboxyl–Terminal Amino Acid Sequence," *FEBS Lett., 144*(2):349–353 (1982).

March, J., Advanced Organic Chemistry; Reactions, Mechanisms, and Structure, 3$^{rd}$ Ed. 1057–1060 (John Wiley & Sons, New York, 1990).

Markland, B.L., et al., "Selection for Protease Inhibitors Using the Bacteriophage–Display Technology," Keystone Symposium on Structural and Molecular Biology of Protease Function and Inhibition, Santa Fe, New Mexico, USA, Mar. 5–12, 1994, *J. Cell. Biochem. Supp. O* 18D: 157, Abstract S 331 (1994).

Marquart, M., et al., "The Geometry of the Reactive Site and of the Peptide Groups in Trypsin, Trypsinogen, and its Complexes with Inhibitors," *Acta Cryst., B39*:480–490 (1983).

Matteson, D.S., et al., "Synthesis and Properties of Pinanediol α–Amido Boronic Esters," *Organometallics, 3*:1284–1288 (1984).

McElvaney, N.G., et al., "Aerosol α1–Antitrypsin Treatment for Cystic Fibrosis," *Lancet, 337*:392–394 (1991).

Mehdi, S., et al., "The Inhibition of Human Neutrophil Elastase and Cathepsin G by Peptidyl 1,2–Dicarbonyl Derivatives," *Biochem. Biophys. Res. Commun., 166*(2):595–600 (1990).

Morelle, W., et al., "Chondroitin Sulphate Covalently Cross–links the Three Polypeptide Chains of Inter–α–Trypsin Inhibitor," *Eur. J. Biochem., 221*:881–888 (1994).

Morii, M., and Travis, J., "The Reactive Site of Human Inter–α–Trypsin Inhibitor is in the Amino–Terminal Half of the Protein," *Biol. Chem. Hoppe–Seyler, 366*:19–21 (1985).

Nakao, A., et al., "SC–39026, A Specific Human Neutrophil Elastase Inhibitor," *Biochem. Biophys. Res. Commun., 147*(2): 666–674 (1987).

Ødum, L., "Inter–α–Trypsin Inhibitor: A Plasma Proteinase Inhibitor with a Unique Chemical Structure," *Int. J. Biochem., 22*(9):925–930 (1990).

Oleksyszyn, J. and Powers, J.C., "Irreversible Inhibition of Serine Proteases by Peptide Derivatives of (α–Aminoalkyl) phosphonate Diphenyl Esters," *Biochemistry, 30*:485–493 (1991).

Otin, C.L., et al., "The Complete Amino Acid Sequence of Human Complex–Forming Glycoprotein Heterogeneous in Charge (Protein HC) from One Individual," *Arch. Biochem. Biophys., 228*(2): 544–554 (1984).

Pabo, C.O., and Suchanek, E.G., "Computer–Aided Model–Building Strategies for Protein Design," *Biochemistry, 25*:5987–5991 (1986).

Peet, N.P., et al., "Synthesis of Peptidyl Fluoromethyl Ketones and Peptidyl α–Keto Esters as Inhibitors of Porcine Pancreatic Elastase, Human Neutrophil Elastase, and Rat and Human Neutrophil Cathepsin G," *J. Med. Chem., 33*:394–407 (1990).

Peters, K., and Fittkau, S., "Affinitätschromatographie von Proteasen mit Peptidmethylketonen als Liganden," *Biomed. Biochim. Acta, 49*:173–178 (1990).

Reed, P.E., and Katzenellenbogen, J.A., "Proline–Valine Pseudo Peptide Enol Lactones: Effective and Selective Inhibitors of Chymotrypsin and Human Leukocyte Elastase," *J. Biol. Chem., 266*:13–21 (1991).

Reisinger, P., et al., "Human Inter–α–Trypsin Inhibitor: Localization of the Kunitz–Type Domains in the N–terminal Part of the Molecule and Their Release by a Trypsin–Like Proteinase," *Biol. Chem. Hoppe–Seyler, 366*:479–483 (1985).

Roberts, B.L., et al., "Protease Inhibitor Display M13 Phage: Selection of High–affinity Neutrophil Elastase Inhibitors," *Gene, 121*9–15 (1992).

Roberts, B.L., et al., "Directed Evolution of a Protein: Selection of Potent Neutrophil Elastase Inhibitor Displayed on M13 Fusion Phage," *Proc. Natl. Acad. Sci USA., 89*:2429–2433 (1992).

Salier, J.-P., "Inter–α–Trypsin Inhibitor: Emergence of a Family Within the Kunitz–type Protease Inhibitor Superfamily," *Trends Biochem. Sci., 15*:435–439 (1990).

Scheeter, I., and Berger, A., "On the Size of the Active Site in Proteases. I. Papain" *Biochem. Biophys. Res. Commun., 27*(2):157–162 (1967).

Schwartz, H., et al., "Stability Studies on Derivatives of the Bovine Pancreatic Trypsin Inhibitor," *Biochemistry., 26*:3544–51 (1987).

Selloum, L., et al., "The Effect of the Glycosaminoglycan Chain Removal on Some Properties of the Human Urinary Trypsin Inhibitor," *Biol. Chem. Hoppe–Seyler, 368*:47–55 (1987).

Sinha, S., et al., "Conversion of the Alzheimer's β–Amyloid Precursor Protein (APP) Kunitz Domain into a Potent Human Neutrophil Elastase Inhibitor," *J. Biol. Chem., 266*(31):21011–21013 (1991).

Snider, G.L., et al., "Putative Role of Neutrophil Elastase in the Pathogenesis of Emphysema," *Ann. NY Acad. Sci., 624*:45–59 (1991).

Sommerhoff, C.P., et al., "Inhibition of Human Neutrophil Elastase by ICI 200,355," *Eur. J. Pharmacol., 193*:153–158 (1991).

Spatola, A.F., "Peptide Backbone Modifications: A Structure–Activity Analysis of Peptides Containing Amide Bond Surrogates, Conformational Constraints, and Relations," Ch. 5 in *Chemistry and Biochemistry of Amino Acids, Peptides and Proteins, A Survey of Recent Developments* (Weinstein ed.):267–357 (Marcel Dekker, Inc., New York, 1983).

States, D.J., et al., "Conformations of Intermediates in the Folding of the Pancreatic Trypsin Inhibitor," *J. Mol. Biol., 195*:731–739 (1987).

Stone, R., "Biology Approaches the Teraflop Era," *Science, 256*:440–442 (1992).

Swaim, M.W., and Pizzo, S.V., "Modification of the Tandem Reactive Centers of Human Inter–α–Trypsin Inhibitor With Butanedione and cis–Dichlorodiammineplatinum (II)," *Biochem. J., 254*:171–178 (1988).

Takagi, T., et al., "Complete Amino Acid Sequence of Human $\alpha_1$–Microglobulin," *Biochem. Biophys. Res. Commun., 98*(4):997–1001 (1981).

Traboni, C., and Cortese, R., "Sequence of a Full Length cDNA Coding for Human Protein HC ($\alpha_1$ Microglobulin)," *Nucl. Acids Res., 14*(15):6340 (1986).

Travis, J., and Fritz, H., "Potential Problems in Designing Elastase Inhibitors for Therapy," *Am. Rev. Respir. Dis., 143*:1412–1415 (1991).

Tschesche, H., et al., "Semisynthetic Engineering of Proteinase Inhibitor Homologues," *Biochim. Biophys. Acta, 913*:97–101 (1987).

Tsuda, Y., et al., "Synthesis of Peptide Chloromethyl Ketones and Examination of Their Inhibitory Effects on Human Spleen Fibrinolytic Proteinase (SFP) and Human Leukocyte Elastase (LE)," *Chem. Pharm. Bull., 35*(9):3576–3584 (1987).

Vetr, H., and Gebhard, W., "Structure of the Human $\alpha_1$–Microglobulin–Bikunin Gene," *Biol. Chem. Hoppe–Seyler, 371*1185–1196 (1990).

Wagner, G., et al., "Reinvestigation of the Aromatic Side–chains in the Basic Pancreatic Trypsin Inhibitor by Heteronuclear Two–dimensional Nuclear Magnetic Resonance," *J. Mol. Biol., 196*:227–31 (1987).

Weiss, S.J., "Tissue Destruction by Neutrophils," *N. Engl. J. Med. 320*(6):365–376 (1989).

Wlodawer, A., et al., "Structure of Bovine Pancreatic Trypsin Inhibitor. Results of Joint Neutron and X–ray Refinement of Crystal Form II," *J. Mol. Biol., 180*:301–329 (1984).

Wlodawer, A., et al., "Comparison of Two Highly Refined Structures of Bovine Pancreatic Trypsin Inhibitor," *J. Mol. Biol., 193*:145–56 (1987).

Wun, T.–C., et al., "Cloning and Characterization of a cDNA Coding for the Lipoprotein–associated Coagulation Inhibitor Shows That It Consists of Three Tandem Kunitz–type Inhibitory Domains," *J. Biol. Chem., 263*(13):6001–6004 (1988).

Debiopharm Brochure "Engineered Protein Inhibitor of Human Neutrophil Elastase EPI–hNE4 (DX–890)" Dated Oct. 2004, printed from www.debio.com/e/pdf/fiche_epi_hne4_e.pdf.

Delacourt et al. "Protection against acute lung injury by intravenous or intratracheal pretreatment with EPI–HNE–4, a new potent neutrophil elastase inhibitor." Am J Respir Cell Mol Biol. Mar. 2002;26(3):290–7.

Donnelly et al. (2003) "Therapy for chronic obstructive pulmonary disease in the 21$^{st}$ century" *Drugs* 63:1973–98.

Gebhard W, Schreitmuller T, Vetr, H, Wachter E, Hochstrasser K. Complementary DNA and deduced amino acid sequences of procine alpha 1–microglobulin and bikunin. FEBS Lett. Aug. 20, 1990;269(1):32–6.

Kido et al. "Protease–sepcificity of Kunitz inhibitor domain of Alzheimer's diseae amyloid protein precursor." Biochem Biophys Res Commun. Mar. 16, 1990;167(2):716–21.

Markland et al. Keystone Symposium on Structural and Molecular Biology of Protease Function and Inhibition, Santa Fe, New Mexico, USA, Mar. 5–12, 1994, Journal of Cellular Biochemistry Supplement O (18d). 1994. p. 157.

Markland W et al., "Selection for protease inhibitors using bacteriophage display." Methods Enzymol. 1996;267:28–51.

Nakamura T, Hirai T, Tokunaga F, Kawabata S, Iwanaga S. Purification and amino acid sequence of Kunitz–type protease inhibitor found in the hemocytes of horseshoe crab (*Tachypleus tridentatus*). J Biochem (Tokyo). May 1987;101(5):1297–306.

Roberts BL et al., "Protease inhibitor display M13 phage: selection of high–affinity neutrophil elastase inhibitors." Gene. Nov. 2, 1992;121(1):9–15.

Scheidig et al., "Crystal structures of bovine chymotrypsin and trypsin complexed to the inhibitor domain of Alzheimer's amyloid beta–protein precursor (APPI) and basic pancreatic trypsin inhibitor (BPTI): engineering of inhibitors with altered specificities." Protein Sci. Sep. 1997;6(9):1806–24.

Wark et al. (2002) DX–890, *iDRUGS,* 5:586–9.

Xu et al. "The crystal structure of bikunin from the inter–alpha–inhibitor complex: a serine protease inhibitor with two Kunitz domains." J Mol Biol. Mar. 13, 1998;276(5):955–66.

GENBANK : P05067.Amyloid beta A4 p . . . [gi:112927] sequence updated: Nov. 1, 1991 (unverified date).

GENBANK P04366 AMBP Protein Precursor [gi 2507586] sequence updated: Feb. 1, 1994 (unverified date).

GENBANK P10280. Kunitz–type protease inhibitor 5 II (gi:124810) sequence updated: Feb. 1, 1991 (unverified date).

GENBANK P00978 AMBP Protein Precursor [gi 2506821] sequence updated: Nov. 1, 1997 (unverified date).

GENBANK P16044 Proteinase inhibitor [gi 124074] sequence updated: Apr. 1, 1990 (unverified date).

GENBANK P00994 Isoinhibitor K [gi 124926] sequence updated: Jul. 21, 1986 (unverified date).

GENBANK P13371 Inter–alpha–trypsin inhibitor [gi 124019] sequence updated: Jan 1, 1990 (unverified date).

* cited by examiner

SEQUENCE LISTING

<160> NUMBER OF SEQ ID NOS: 84

<210> SEQ ID NO 1
<211> LENGTH: 5
<212> TYPE: PRT
<213> ORGANISM: Artificial Sequence
<220> FEATURE:

-continued

```
<223> OTHER INFORMATION: Synthetic linker peptide

<400> SEQUENCE: 1

Gly Gly Gly Gly Ser
 1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic linker peptide

<400> SEQUENCE: 2

Gly Gly Gly Ser
 1

<210> SEQ ID NO 3
<211> LENGTH: 65
<212> TYPE: PRT
<213> ORGANISM: Artificial Sequence
<220> FEATURE:
<223> OTHER INFORMATION: Kunitz domain
<220> FEATURE:
<221> NAME/KEY: VARIANT
<222> LOCATION: 1-4, 6-14, 16-33, 35, 36, 38-41, 43-51, 53-57, 59-61,
      63-65
<223> OTHER INFORMATION: May be any amino acid
<220> FEATURE:
<221> NAME/KEY: VARIANT
<222> LOCATION: (1)...(4)
<223> OTHER INFORMATION: This region may comprise 0 to 4 amino acids
<220> FEATURE:
<221> NAME/KEY: VARIANT
<222> LOCATION: (6)...(14)
<223> OTHER INFORMATION: This region may comprise 8 or 9 amino acids
<220> FEATURE:
<221> NAME/KEY: VARIANT
<222> LOCATION: (16)...(34)
<223> OTHER INFORMATION: This region may comprise 16, 17, 18 or 19 amino
      acids
<220> FEATURE:
<221> NAME/KEY: VARIANT
<222> LOCATION: 37, 52
<223> OTHER INFORMATION: Phe or Tyr
<220> FEATURE:
<221> NAME/KEY: VARIANT
<222> LOCATION: (43)...(57)
<223> OTHER INFORMATION: This region may comprise 12, 13, 14 or 15 amino
      acids
<220> FEATURE:
<221> NAME/KEY: VARIANT
<222> LOCATION: (63)...(65)
<223> OTHER INFORMATION: This region may comprise 0 to 3 amino acids
<220> FEATURE:
<221> NAME/KEY: VARIANT
<222> LOCATION: (57)...(57)
<223> OTHER INFORMATION: May be cysteine
<220> FEATURE:
<221> NAME/KEY: VARIANT
<222> LOCATION: (60)...(61)
<223> OTHER INFORMATION: May be cysteine
<220> FEATURE:
<221> NAME/KEY: VARIANT
<222> LOCATION: (65)...(65)
<223> OTHER INFORMATION: May be cysteine

<400> SEQUENCE: 3

Xaa Xaa Xaa Xaa Cys Xaa Xaa Xaa Xaa Xaa Xaa Xaa Xaa Cys Xaa
 1               5                  10                  15

Xaa Xaa Xaa Xaa Xaa Xaa Xaa Xaa Xaa Xaa Xaa Xaa Xaa Xaa Xaa
             20                  25                  30
```

```
Xaa Cys Xaa Xaa Xaa Xaa Xaa Xaa Cys Xaa Xaa Xaa Xaa Xaa
        35                  40                  45

Xaa Xaa Xaa Xaa Xaa Xaa Xaa Xaa Cys Xaa Xaa Xaa Cys Xaa Xaa
        50                  55                  60

Xaa
65

<210> SEQ ID NO 4
<211> LENGTH: 58
<212> TYPE: PRT
<213> ORGANISM: Homo sapiens

<400> SEQUENCE: 4

Val Arg Glu Val Cys Ser Glu Gln Ala Glu Thr Gly Pro Cys Arg Ala
  1               5                  10                  15

Met Ile Ser Arg Trp Tyr Phe Asp Val Thr Glu Gly Lys Cys Ala Pro
                 20                  25                  30

Phe Phe Tyr Gly Gly Cys Gly Gly Asn Arg Asn Asn Phe Asp Thr Glu
             35                  40                  45

Glu Tyr Cys Met Ala Val Cys Gly Ser Ala
         50                  55

<210> SEQ ID NO 5
<211> LENGTH: 58
<212> TYPE: PRT
<213> ORGANISM: Homo sapiens

<400> SEQUENCE: 5

Lys Gln Asp Val Cys Glu Met Pro Lys Glu Thr Gly Pro Cys Leu Ala
  1               5                  10                  15

Tyr Phe Leu His Trp Trp Tyr Asp Lys Lys Asp Asn Thr Cys Ser Met
                 20                  25                  30

Phe Val Tyr Gly Gly Cys Gln Gly Asn Asn Asn Phe Gln Ser Lys
             35                  40                  45

Ala Asn Cys Leu Asn Thr Cys Lys Asn Lys
         50                  55

<210> SEQ ID NO 6
<211> LENGTH: 58
<212> TYPE: PRT
<213> ORGANISM: Homo sapiens

<400> SEQUENCE: 6

Val Lys Ala Val Cys Ser Gln Glu Ala Met Thr Gly Pro Cys Arg Ala
  1               5                  10                  15

Val Met Pro Arg Trp Tyr Phe Asp Leu Ser Lys Gly Lys Cys Val Arg
                 20                  25                  30

Phe Ile Tyr Gly Gly Cys Gly Gly Asn Arg Asn Asn Phe Glu Ser Glu
             35                  40                  45

Asp Tyr Cys Met Ala Val Cys Lys Ala Met
         50                  55

<210> SEQ ID NO 7
<211> LENGTH: 58
<212> TYPE: PRT
<213> ORGANISM: Homo sapiens

<400> SEQUENCE: 7

Lys Glu Asp Ser Cys Gln Leu Gly Tyr Ser Ala Gly Pro Cys Met Gly
  1               5                  10                  15
```

-continued

```
Met Thr Ser Arg Tyr Phe Tyr Asn Gly Thr Ser Met Ala Cys Glu Thr
             20                  25                  30

Phe Gln Tyr Gly Gly Cys Met Gly Asn Gly Asn Asn Phe Val Thr Glu
             35                  40                  45

Lys Glu Cys Leu Gln Thr Cys Arg Thr Val
 50                  55

<210> SEQ ID NO 8
<211> LENGTH: 58
<212> TYPE: PRT
<213> ORGANISM: Homo sapiens

<400> SEQUENCE: 8

Thr Val Ala Ala Cys Asn Leu Pro Ile Val Arg Gly Pro Cys Arg Ala
  1               5                  10                  15

Phe Ile Gln Leu Trp Ala Phe Asp Ala Val Lys Gly Lys Cys Val Leu
             20                  25                  30

Phe Pro Tyr Gly Gly Cys Gln Gly Asn Gly Asn Lys Phe Tyr Ser Glu
             35                  40                  45

Lys Glu Cys Arg Glu Tyr Cys Gly Val Pro
 50                  55

<210> SEQ ID NO 9
<211> LENGTH: 59
<212> TYPE: PRT
<213> ORGANISM: Homo sapiens

<400> SEQUENCE: 9

Met His Ser Phe Cys Ala Phe Lys Ala Asp Asp Gly Pro Cys Lys Ala
  1               5                  10                  15

Ile Met Lys Arg Phe Phe Phe Asn Ile Phe Thr Arg Gln Cys Glu Glu
             20                  25                  30

Phe Ile Tyr Gly Gly Cys Glu Gly Asn Gln Asn Arg Phe Glu Ser Leu
             35                  40                  45

Glu Glu Cys Lys Lys Met Cys Thr Arg Asp Asn
 50                  55

<210> SEQ ID NO 10
<211> LENGTH: 58
<212> TYPE: PRT
<213> ORGANISM: Homo sapiens

<400> SEQUENCE: 10

Lys Pro Asp Phe Cys Phe Leu Glu Glu Asp Pro Gly Ile Cys Arg Gly
  1               5                  10                  15

Tyr Ile Thr Arg Tyr Phe Tyr Asn Asn Gln Thr Lys Gln Cys Glu Arg
             20                  25                  30

Phe Lys Tyr Gly Gly Cys Leu Gly Asn Met Asn Asn Phe Glu Thr Leu
             35                  40                  45

Glu Glu Cys Lys Asn Ile Cys Glu Asp Gly
 50                  55

<210> SEQ ID NO 11
<211> LENGTH: 58
<212> TYPE: PRT
<213> ORGANISM: Homo sapiens

<400> SEQUENCE: 11

Gly Pro Ser Trp Cys Leu Thr Pro Ala Asp Arg Gly Leu Cys Arg Ala
```

```
                1               5                  10                 15
Asn Glu Asn Arg Phe Tyr Tyr Asn Ser Val Ile Gly Lys Cys Arg Pro
                    20                 25                 30

Phe Lys Tyr Ser Gly Cys Gly Gly Asn Glu Asn Asn Phe Thr Ser Lys
            35                  40                 45

Gln Glu Cys Leu Arg Ala Cys Lys Lys Gly
        50                  55
```

<210> SEQ ID NO 12
<211> LENGTH: 58
<212> TYPE: PRT
<213> ORGANISM: Homo sapiens

<400> SEQUENCE: 12

```
Asn Ala Glu Ile Cys Leu Leu Pro Leu Asp Tyr Gly Pro Cys Arg Ala
1               5                   10                  15

Leu Leu Leu Arg Tyr Tyr Tyr Asp Arg Tyr Thr Gln Ser Cys Arg Gln
                20                  25                  30

Phe Leu Tyr Gly Gly Cys Glu Gly Asn Ala Asn Asn Phe Tyr Thr Trp
            35                  40                  45

Glu Ala Cys Asp Asp Ala Cys Trp Arg Ile
        50                  55
```

<210> SEQ ID NO 13
<211> LENGTH: 58
<212> TYPE: PRT
<213> ORGANISM: Homo sapiens

<400> SEQUENCE: 13

```
Val Pro Lys Val Cys Arg Leu Gln Val Val Asp Asp Gln Cys Glu Gly
1               5                   10                  15

Ser Thr Glu Lys Tyr Phe Phe Asn Leu Ser Ser Met Thr Cys Glu Lys
                20                  25                  30

Phe Phe Ser Gly Gly Cys His Arg Asn Arg Asn Arg Phe Pro Asp Glu
            35                  40                  45

Ala Thr Cys Met Gly Phe Cys Ala Pro Lys
        50                  55
```

<210> SEQ ID NO 14
<211> LENGTH: 58
<212> TYPE: PRT
<213> ORGANISM: Homo sapiens

<400> SEQUENCE: 14

```
Ile Pro Ser Phe Cys Tyr Ser Pro Lys Asp Glu Gly Leu Cys Ser Ala
1               5                   10                  15

Asn Val Thr Arg Tyr Tyr Phe Asn Pro Arg Tyr Arg Thr Cys Asp Ala
                20                  25                  30

Phe Thr Tyr Thr Gly Cys Gly Gly Asn Asp Asn Asn Phe Val Ser Arg
            35                  40                  45

Glu Asp Cys Lys Arg Ala Cys Ala Lys Ala
        50                  55
```

<210> SEQ ID NO 15
<211> LENGTH: 58
<212> TYPE: PRT
<213> ORGANISM: Homo sapiens

<400> SEQUENCE: 15

```
Thr Glu Asp Tyr Cys Leu Ala Ser Asn Lys Val Gly Arg Cys Arg Gly
1               5                   10                  15

Ser Phe Pro Arg Trp Tyr Asp Pro Thr Glu Gln Ile Cys Lys Ser
            20                  25                  30

Phe Val Tyr Gly Gly Cys Leu Gly Asn Lys Asn Asn Tyr Leu Arg Glu
        35                  40                  45

Glu Glu Cys Ile Leu Ala Cys Arg Gly Val
    50                  55
```

<210> SEQ ID NO 16
<211> LENGTH: 58
<212> TYPE: PRT
<213> ORGANISM: Homo sapiens

<400> SEQUENCE: 16

```
Asp Lys Gly His Cys Val Asp Leu Pro Asp Thr Gly Leu Cys Lys Glu
1               5                   10                  15

Ser Ile Pro Arg Trp Tyr Tyr Asn Pro Phe Ser Glu His Cys Ala Arg
            20                  25                  30

Phe Thr Tyr Gly Gly Cys Tyr Gly Asn Lys Asn Asn Phe Glu Glu Glu
        35                  40                  45

Gln Gln Cys Leu Glu Ser Cys Arg Gly Ile
    50                  55
```

<210> SEQ ID NO 17
<211> LENGTH: 58
<212> TYPE: PRT
<213> ORGANISM: Homo sapiens

<400> SEQUENCE: 17

```
Ile His Asp Phe Cys Leu Val Ser Lys Val Val Gly Arg Cys Arg Ala
1               5                   10                  15

Ser Met Pro Arg Trp Trp Tyr Asn Val Thr Asp Gly Ser Cys Gln Leu
            20                  25                  30

Phe Val Tyr Gly Gly Cys Asp Gly Asn Ser Asn Asn Tyr Leu Thr Lys
        35                  40                  45

Glu Glu Cys Leu Lys Lys Cys Ala Thr Val
    50                  55
```

<210> SEQ ID NO 18
<211> LENGTH: 585
<212> TYPE: PRT
<213> ORGANISM: Homo sapiens

<400> SEQUENCE: 18

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
```

-continued

```
                100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Lys Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
```

```
Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Arg Ala Ala Leu Gly Leu
            580                 585

<210> SEQ ID NO 19
<211> LENGTH: 58
<212> TYPE: PRT
<213> ORGANISM: Homo sapiens

<400> SEQUENCE: 19

Tyr Glu Glu Tyr Cys Thr Ala Asn Ala Val Thr Gly Pro Cys Arg Ala
1               5                   10                  15

Ser Phe Pro Arg Trp Tyr Phe Asp Val Glu Arg Asn Ser Cys Asn Asn
                20                  25                  30

Phe Ile Tyr Gly Gly Cys Arg Gly Asn Lys Asn Ser Tyr Arg Ser Glu
            35                  40                  45

Glu Ala Cys Met Leu Arg Cys Phe Arg Gln
50                  55

<210> SEQ ID NO 20
<211> LENGTH: 58
<212> TYPE: PRT
<213> ORGANISM: Homo sapiens

<400> SEQUENCE: 20

Thr Val Ala Ala Cys Asn Leu Pro Val Ile Arg Gly Pro Cys Arg Ala
1               5                   10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Tyr Ser Glu
            35                  40                  45

Lys Glu Cys Arg Glu Tyr Cys Gly Val Pro
50                  55

<210> SEQ ID NO 21
<211> LENGTH: 58
<212> TYPE: PRT
<213> ORGANISM: Homo sapiens

<400> SEQUENCE: 21

Leu Pro Asn Val Cys Ala Phe Pro Met Glu Lys Gly Pro Cys Gln Thr
1               5                   10                  15

Tyr Met Thr Arg Trp Phe Phe Asn Phe Glu Thr Gly Glu Cys Glu Leu
                20                  25                  30

Phe Ala Tyr Gly Gly Cys Gly Gly Asn Ser Asn Asn Phe Leu Arg Lys
            35                  40                  45

Glu Lys Cys Glu Lys Phe Cys Lys Phe Thr
50                  55

<210> SEQ ID NO 22
<211> LENGTH: 58
<212> TYPE: PRT
<213> ORGANISM: Homo sapiens
```

```
-continued

<400> SEQUENCE: 22

Ser Asp Asp Pro Cys Ser Leu Pro Leu Asp Glu Gly Ser Cys Thr Ala
1               5                   10                  15

Tyr Thr Leu Arg Trp Tyr His Arg Ala Val Thr Glu Ala Cys His Pro
            20                  25                  30

Phe Val Tyr Gly Gly Cys Gly Gly Asn Ala Asn Arg Phe Gly Thr Arg
        35                  40                  45

Glu Ala Cys Glu Arg Arg Cys Pro Pro Arg
    50                  55

<210> SEQ ID NO 23
<211> LENGTH: 61
<212> TYPE: PRT
<213> ORGANISM: Homo sapiens

<400> SEQUENCE: 23

Glu Asp Asp Pro Cys Ser Leu Pro Leu Asp Glu Gly Ser Cys Thr Ala
1               5                   10                  15

Tyr Thr Leu Arg Trp Tyr His Arg Ala Val Thr Gly Ser Thr Glu Ala
            20                  25                  30

Cys His Pro Phe Val Tyr Gly Gly Cys Gly Gly Asn Ala Asn Arg Phe
        35                  40                  45

Gly Thr Arg Glu Ala Cys Glu Arg Arg Cys Pro Pro Arg
    50                  55                  60

<210> SEQ ID NO 24
<211> LENGTH: 58
<212> TYPE: PRT
<213> ORGANISM: Homo sapiens

<400> SEQUENCE: 24

Glu Thr Asp Ile Cys Lys Leu Pro Lys Asp Glu Gly Thr Cys Arg Asp
1               5                   10                  15

Phe Ile Leu Lys Trp Tyr Tyr Asp Pro Asn Thr Lys Ser Cys Ala Arg
            20                  25                  30

Phe Trp Tyr Gly Gly Cys Gly Gly Asn Glu Asn Lys Phe Gly Ser Gln
        35                  40                  45

Lys Glu Cys Glu Lys Val Cys Ala Pro Val
    50                  55

<210> SEQ ID NO 25
<211> LENGTH: 58
<212> TYPE: PRT
<213> ORGANISM: Homo sapiens

<400> SEQUENCE: 25

Phe Gln Glu Pro Cys Met Leu Pro Val Arg His Gly Asn Cys Asn His
1               5                   10                  15

Glu Ala Gln Arg Trp His Phe Asp Phe Lys Asn Tyr Arg Cys Thr Pro
            20                  25                  30

Phe Lys Tyr Arg Gly Cys Glu Gly Asn Ala Asn Asn Phe Leu Asn Glu
        35                  40                  45

Asp Ala Cys Arg Thr Ala Cys Met Leu Ile
    50                  55

<210> SEQ ID NO 26
<211> LENGTH: 17
<212> TYPE: PRT
<213> ORGANISM: Artificial Sequence
```

```
<220> FEATURE:
<223> OTHER INFORMATION: Stanniocalcin signal sequence

<400> SEQUENCE: 26

Met Leu Gln Asn Ser Ala Val Leu Leu Leu Val Ile Ser Ala Ser
 1               5                  10                  15

Ala

<210> SEQ ID NO 27
<211> LENGTH: 22
<212> TYPE: PRT
<213> ORGANISM: Artificial Sequence
<220> FEATURE:
<223> OTHER INFORMATION: Consensus signal sequence

<400> SEQUENCE: 27

Met Pro Thr Trp Ala Trp Trp Leu Phe Leu Val Leu Leu Ala Leu
 1               5                  10                  15

Trp Ala Pro Ala Arg Gly
            20

<210> SEQ ID NO 28
<211> LENGTH: 14
<212> TYPE: DNA
<213> ORGANISM: Artificial Sequence
<220> FEATURE:
<223> OTHER INFORMATION: Polypeptide linker sequence

<400> SEQUENCE: 28
ggsggsggsg gsgg                                                          14

<210> SEQ ID NO 29
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 29
ttaggcttag gtggttctgg tggttccggt ggttctggtg gatccggtgg ttaata           56

<210> SEQ ID NO 30
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 30
agcttattaa ccaccggatc caccagaacc accggaacca ccagaaccac ctaagcc         57

<210> SEQ ID NO 31
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 31
gatctttgga taagagagac gctcacaagt ccgaagtcgc tcaccggt                    48

<210> SEQ ID NO 32
<211> LENGTH: 50
<212> TYPE: DNA
<213> ORGANISM: Artificial Sequence
```

```
<220> FEATURE:
<223> OTHER INFORMATION: Synthetic oligonucleotide

<400> SEQUENCE: 32
ccttgaaccg gtgagcgact tcggacttgt gagcgtctct cttatccaaa            50

<210> SEQ ID NO 33
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 33
gatctttgga taagagagac gctcacaagt ccgaagtcgc tcatcgat              48

<210> SEQ ID NO 34
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 34
ccttgaatcg atgagcgact tcggacttgt gagcgtctct cttatccaaa            50

<210> SEQ ID NO 35
<211> LENGTH: 86
<212> TYPE: DNA
<213> ORGANISM: Artificial Sequence
<220> FEATURE:
<223> OTHER INFORMATION: Synthetic oligonucleotide

<400> SEQUENCE: 35
tcaaggacct aggtgaggaa aacttcaagg ctttggtctt gatcgctttc gctcaatact    60
tgcaacaatg tccattcgaa gatcac                                        86

<210> SEQ ID NO 36
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 36
gtgatcttcg aatggacatt gttgcaagta ttgagcgaaa gcgatcaaga ccaaagcctt    60
gaagttttcc tcacctaggt                                               80

<210> SEQ ID NO 37
<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 37
gatctttgga taagagaggt ggatccggtg gttccggtgg ttctggtggt tccggtggtg    60
acgctcacaa gtccgaagtc gctca                                         85

<210> SEQ ID NO 38
<211> LENGTH: 85
<212> TYPE: DNA
<213> ORGANISM: Artificial Sequence
<220> FEATURE:
```

-continued

<223> OTHER INFORMATION: Synthetic oligonucleotide

<400> SEQUENCE: 38
ccggtgagcg acttcggact tgtgagcgtc accaccggaa ccaccagaac caccggaacc    60
accggatcca cctctcttat ccaaa                                          85

<210> SEQ ID NO 39
<211> LENGTH: 60
<212> TYPE: PRT
<213> ORGANISM: Artificial Sequence
<220> FEATURE:
<223> OTHER INFORMATION: Synthetic DPI-14 peptide

<400> SEQUENCE: 39

Glu Ala Val Arg Glu Val Cys Ser Glu Gln Ala Glu Thr Gly Pro Cys
 1               5                  10                  15

Ile Ala Phe Phe Pro Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala
    50                  55                  60

<210> SEQ ID NO 40
<211> LENGTH: 56
<212> TYPE: PRT
<213> ORGANISM: Artificial Sequence
<220> FEATURE:
<223> OTHER INFORMATION: Polypeptide sequence

<400> SEQUENCE: 40

Glu Ala Cys Asn Leu Pro Ile Val Arg Gly Pro Cys Ile Ala Phe Phe
 1               5                  10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55

<210> SEQ ID NO 41
<211> LENGTH: 4
<212> TYPE: PRT
<213> ORGANISM: Artificial Sequence
<220> FEATURE:
<223> OTHER INFORMATION: Synthetic peptide

<400> SEQUENCE: 41

Ala Ala Pro Val
 1

<210> SEQ ID NO 42
<211> LENGTH: 3000
<212> TYPE: DNA
<213> ORGANISM: Artificial Sequence
<220> FEATURE:
<223> OTHER INFORMATION: Albumin fusion expression plasmid

<400> SEQUENCE: 42
gcggccgccc gtaatgcggt atcgtgaaag cgaaaaaaaa actaacagta gataagacag    60
atagacagat agagatggac gagaaacagg ggggagaaa aggggaaaag agaaggaaag   120

| | |
|---|---|
| aaagactcat ctatcgcaga taagacaatc aaccctcatg gcgcctccaa ccaccatccg | 180 |
| cactagggac caagcgctcg caccgttagc aacgcttgac tcacaaacca actgccggct | 240 |
| gaaagagctt gtgcaatggg agtgccaatt caaaggagcc gaatacgtct gctcgccttt | 300 |
| taagaggctt tttgaacact gcattgcacc cgacaaatca gccactaact acgaggtcac | 360 |
| ggacacatat accaatagtt aaaaattaca tatactctat atagcacagt agtgtgataa | 420 |
| ataaaaaatt ttgccaagac ttttttaaac tgcacccgac agatcaggtc tgtgcctact | 480 |
| atgcacttat gcccggggtc ccgggaggag aaaaaacgag ggctgggaaa tgtccgtgga | 540 |
| cttaaaacgc tccgggttag cagagtagca gggctttcgg ctttggaaat ttaggtgact | 600 |
| tgttgaaaaa gcaaaatttg ggctcagtaa tgccactgca gtggcttatc acgccaggac | 660 |
| tgcgggagtg gcggggcaa acacacccgc gataaagagc gcgatgaata taaaaggggg | 720 |
| ccaatgttac gtcccgttat attggagttc ttcccataca aacttaagag tccaattagc | 780 |
| ttcatcgcca ataaaaaaac aagcttaacc taattctaac aagcaaagat gaagtgggtt | 840 |
| ttcatcgtct ccatttttgtt cttgttctcc tctgcttact ctagatcttt ggataagaga | 900 |
| gacgctcaca agtccgaagt cgctcaccgg ttcaaggacc taggtgagga aaacttcaag | 960 |
| gctttggtct tgatcgcttt cgctcaatac ttgcaacaat gtccattcga agatcacgtc | 1020 |
| aagttggtca acgaagttac cgaattcgct aagacttgtg ttgctgacga atctgctgaa | 1080 |
| aactgtgaca gtccttgca caccttgttc ggtgataagt tgtgtactgt tgctaccttg | 1140 |
| agagaaacct acggtgaaat ggctgactgt tgtgctaagc aagaaccaga agaaacgaa | 1200 |
| tgtttcttgc aacacaagga cgacaaccca aacttgccaa gattggttag accagaagtt | 1260 |
| gacgtcatgt gtactgcttt ccacgacaac gaagaaacct tcttgaagaa gtacttgtac | 1320 |
| gaaattgcta aagacacccc atacttctac gctccagaat tgttgttctt cgctaagaga | 1380 |
| tacaaggctg ctttcaccga atgttgtcaa gctgctgata aggctgcttg tttgttgcca | 1440 |
| aagttggatg aattgagaga cgaaggtaag gcttcttccg ctaagcaaag attgaagtgt | 1500 |
| gcttccttgc aaaagttcgg tgaaagagct ttcaaggctt gggctgtcgc tagattgtct | 1560 |
| caaagattcc caaaggctga attcgctgaa gttctaagt tggttactga cttgactaag | 1620 |
| gttcacactg aatgttgtca cggtgacttg ttggaatgtg ctgatgacag agctgacttg | 1680 |
| gctaagtaca tctgtgaaaa ccaagactct atctcttcca agttgaagga atgttgtgaa | 1740 |
| aagccattgt tggaaaagtc tcactgtatt gctgaagttg aaaacgatga aatgccagct | 1800 |
| gacttgccat cttttggctgc tgacttcgtt gaatctaagg acgtttgtaa gaactacgct | 1860 |
| gaagctaagg acgtcttctt gggtatgttc ttgtacgaat acgctagaag acacccagac | 1920 |
| tactccgttg tcttgttgtt gagattggct aagacctacg aaactacctt ggaaaagtgt | 1980 |
| tgtgctgctg ctgacccaca cgaatgttac gctaaggttt tcgatgaatt caagccattg | 2040 |
| gtcgaagaac cacaaaactt gatcaagcaa aactgtgaat tgttcgaaca attgggtgaa | 2100 |
| tacaagttcc aaaacgcttt gttggttaga tacactaaga aggtcccaca agtctccacc | 2160 |
| ccaactttgg ttgaagtctc tagaaacttg ggtaaggtcg gttctaagtg ttgtaagcac | 2220 |
| ccagaagcta agagaatgcc atgtgctgaa gattacttgt ccgtcgtttt gaaccaattg | 2280 |
| tgtgttttgc acgaaaagac cccagtctct gatagagtca ccaagtgttg tactgaatct | 2340 |
| ttggttaaca agagaccatg tttctctgct ttggaagtcg acgaaactta cgttccaaag | 2400 |
| gaattcaacg ctgaaacttt caccttccac gctgatatct gtaccttgtc cgaaaaggaa | 2460 |
| agacaaatta agaagcaaac tgctttggtt gaattggtca agcacaagcc aaaggctact | 2520 |

```
aaggaacaat tgaaggctgt catggatgat ttcgctgctt tcgttgaaaa gtgttgtaag    2580
gctgatgata aggaaacttg tttcgctgaa gaaggtaaga agttggtcgc tgcttcccaa    2640
gctgccttag gcttataata agcttaattc ttatgattta tgatttttat tattaaataa    2700
gttataaaaa aaataagtgt atacaaattt taaagtgact cttaggtttt aaaacgaaaa    2760
ttcttattct tgagtaactc tttcctgtag gtcaggttgc tttctcaggt atagcatgag    2820
gtcgctctta ttgaccacac ctctaccggc atgccgagca aatgcctgca aatcgctccc    2880
catttcaccc aattgtagat atgctaactc cagcaatgag ttgatgaatc tcggtgtgta    2940
ttttatgtcc tcagaggaca acacctgttg taatcgttct tccacacgga tcgcggccgc    3000
```

<210> SEQ ID NO 43
<211> LENGTH: 3084
<212> TYPE: DNA
<213> ORGANISM: Artificial Sequence
<220> FEATURE:
<223> OTHER INFORMATION: NotI Expression Cassette containing Polypeptide
      spacer

<400> SEQUENCE: 43

```
gcggccgccc gtaatgcggt atcgtgaaag cgaaaaaaaa actaacagta gataagacag      60
atagacagat agagatggac gagaaacagg ggggagaaa  aggggaaaag agaaggaaag     120
aaagactcat ctatcgcaga taagacaatc aaccctcatg gcgcctccaa ccaccatccg     180
cactagggac caagcgctcg caccgttagc aacgcttgac tcacaaacca actgccggct     240
gaaagagctt gtgcaatggg agtgccaatt caaggagcc  gaatacgtct gctcgccttt     300
taagaggctt tttgaacact gcattgcacc cgacaaatca gccactaact acgaggtcac     360
ggacacatat accaatagtt aaaaattaca tatactctat atagcacagt agtgtgataa     420
ataaaaaatt ttgccaagac ttttttaaac tgcacccgac agatcaggtc tgtgcctact     480
atgcacttat gcccggggtc ccgggaggag aaaaaacgag ggctgggaaa tgtccgtgga     540
ctttaaacgc tccgggttag cagagtagca gggctttcgg cttttgaaat ttaggtgact     600
tgttgaaaaa gcaaaatttg ggctcagtaa tgccactgca gtggcttatc acgccaggac     660
tgcgggagtg gcgggggcaa acacacccgc gataaagagc gcgatgaata taaaaggggg     720
ccaatgttac gtcccgttat attggagttc ttcccataca aacttaagag tccaattagc     780
ttcatcgcca ataaaaaaac aagcttaacc taattctaac aagcaaagat gaagtgggtt     840 tcatcgtct  ccattttgtt cttgttctcc tctgcttact ctagatcttt ggataagaga     900
ggtggatccg gtggttccgg tggttctggt ggttccggtg gtgacgctca caagtccgaa     960
gtcgctcacc ggttcaagga cctaggtgag gaaaacttca aggctttggt cttgatcgct    1020
ttcgctcaat acttgcaaca atgtccattc gaagatcacg tcaagttggt caacgaagtt    1080
accgaattcg ctaagacttg tgttgctgac gaatctgctg aaaactgtga caagtccttg    1140
cacaccttgt tcggtgataa gttgtgtact gttgctacct tgagagaaac ctacggtgaa    1200
atggctgact gttgtgctaa gcaagaacca gaaagaaacg aatgtttctt gcaacacaag    1260
gacgacaacc caaacttgcc aagattggtt agaccagaag ttgacgtcat gtgtactgct    1320
ttccacgaca cgaagaaac  cttcttgaag aagtacttgt acgaaattgc tagaagacac    1380
ccatacttct acgctccaga attgttgttc ttcgctaaga gatacaaggc tgctttcacc    1440
gaatgttgtc aagctgctga taaggctgct tgtttgttgc caaagttgga tgaattgaga    1500
gacgaaggta aggcttcttc cgctaagcaa agattgaagt gtgcttcctt gcaaaagttc    1560
```

```
ggtgaaagag ctttcaaggc ttgggctgtc gctagattgt ctcaaagatt cccaaaggct    1620
gaattcgctg aagtttctaa gttggttact gacttgacta aggttcacac tgaatgttgt    1680
cacggtgact tgttgaatg tgctgatgac agagctgact tggctaagta catctgtgaa     1740
aaccaagact ctatctcttc aagttgaag gaatgttgtg aaaagccatt gttggaaaag     1800
tctcactgta ttgctgaagt tgaaaacgat gaaatgccag ctgacttgcc atctttggct    1860
gctgacttcg ttgaatctaa ggacgtttgt aagaactacg ctgaagctaa ggacgtcttc    1920
ttgggtatgt tcttgtacga atacgctaga agacacccag actactccgt tgtcttgttg    1980
ttgagattgg ctaagaccta cgaaactacc ttggaaaagt gttgtgctgc tgctgaccca    2040
cacgaatgtt acgctaaggt tttcgatgaa ttcaagccat ggtcgaaga accacaaaac     2100 ttgatcaagc aaaactgtga attgttcgaa caattgggtg aatacaagtt ccaaaacgct    2160
ttgttggtta gatacactaa gaaggtccca caagtctcca ccccaacttt ggttgaagtc    2220
tctagaaact tgggtaaggt cggttctaag tgttgtaagc acccagaagc taagagaatg    2280
ccatgtgctg aagattactt gtccgtcgtt ttgaaccaat gtgtgttt gcacgaaaag      2340 accccagtct ctgatagagt caccaagtgt tgtactgaat ctttggttaa cagaagacca    2400
tgtttctctg ctttggaagt cgacgaaact tacgttccaa aggaattcaa cgctgaaact    2460
ttcaccttcc acgctgatat ctgtaccttg tccgaaaagg aaagacaaat taagaagcaa    2520
actgctttgg ttgaattggt caagcacaag ccaaaggcta ctaaggaaca attgaaggct    2580
gtcatggatg atttcgctgc tttcgttgaa agtgttgta aggctgatga taggaaact     2640 tgtttcgctg aagaaggtaa gaagttggtc gctgcttccc aagctgcctt aggcttaggt    2700
ggttctggtg gttccggagg ttctggtggt accggtggtt aataagctta attcttatga    2760
tttatgattt ttattattaa ataagttata aaaaaaataa gtgtatacaa attttaaagt    2820
gactcttagg ttttaaaacg aaaattctta ttcttgagta actctttcct gtaggtcagg    2880
ttgctttctc aggtatagca tgaggtcgct cttattgacc acacctctac cggcatgccg    2940
agcaaatgcc tgcaaatcgc tccccatttc acccaattgt agatatgcta actccagcaa    3000
tgagttgatg aatctcggtg tgtattttat gtcctcagag acaacacct gttgtaatcg     3060 ttcttccaca cggatcgcgg ccgc                                           3084
```

<210> SEQ ID NO 44
<211> LENGTH: 3444
<212> TYPE: DNA
<213> ORGANISM: Artificial Sequence
<220> FEATURE:
<223> OTHER INFORMATION: DPI-14-(GGS)4 GG-rHA-(GGS)4-GG-DX-890 DNA
      sequence

<400> SEQUENCE: 44

```
gcggccgccc gtaatgcggt atcgtgaaag cgaaaaaaaa actaacagta gataagacag    60
atagacagat agagatggac gagaaacagg gggggagaaa aggggaaaag agaaggaaag   120
aaagactcat ctatcgcaga taagacaatc aaccctcatg gcgcctccaa ccaccatccg   180
cactagggac caagcgctcg caccgttagc aacgcttgac tcacaaacca actgccggct   240
gaaagagctt gtgcaatggg agtgccaatt caaggagcc gaatacgtct gctcgccttt    300
taagaggctt tttgaacact gcattgcacc cgacaaatca gccactaact acgaggtcac   360
ggacacatat accaatagtt aaaaattaca tatactctat atagcacagt agtgtgataa   420
ataaaaaatt ttgccaagac tttttttaaac tgcacccgac agatcaggtc tgtgcctact   480
```

```
atgcacttat gcccggggtc ccgggaggag aaaaaacgag ggctgggaaa tgtccgtgga    540
ctttaaacgc tccggggttag cagagtagca gggctttcgg ctttggaaat ttaggtgact    600
tgttgaaaaa gcaaaatttg ggctcagtaa tgccactgca gtggcttatc acgccaggac    660
tgcgggagtg gcgggggcaa acacacccgc gataaagagc gcgatgaata taaaagggg     720
ccaatgttac gtcccgttat attggagttc ttcccataca aacttaagag tccaattagc    780
ttcatcgcca ataaaaaaac aagcttaacc taattctaac aagcaaagat gaagtgggtt    840
ttcatcgtct ccatttttgtt cttgttctcc tctgcttact ctagatcttt ggataagaga    900
gaagctgtta gagaagtttg ttctgaacaa gctgaaactg gtccatgtat tgctttcttc    960
ccaagatggt acttcgatgt tactgaaggt aagtgcgcgc cattcttcta cggtggttgt   1020
ggtggtaaca gaaacaactt cgatactgaa gaatactgta tggctgtttg tggttctgct   1080
ggtggatccg gtggttccgg tggttctggt ggttccggtg gtgacgctca caagtccgaa   1140
gtcgctcacc ggttcaagga cctaggtgag gaaaacttca aggctttggt cttgatcgct   1200
ttcgctcaat acttgcaaca atgtccattc gaagatcacg tcaagttggt caacgaagtt   1260
accgaattcg ctaagacttg tgttgctgac gaatctgctg aaaactgtga caagtccttg   1320
cacaccttgt tcggtgataa gttgtgtact gttgctacct tgagagaaac ctacggtgaa   1380
atggctgact gttgtgctaa gcaagaacca gaaagaaacg aatgtttctt gcaacacaag   1440
gacgacaacc caaacttgcc aagattggtt agaccagaag ttgacgtcat gtgtactgct   1500
ttccacgaca acgaagaaac cttcttgaag aagtacttgt acgaaattgc tagaagacac   1560
ccatacttct acgctccaga attgttgttc ttcgctaaga gatacaaggc tgctttcacc   1620
gaatgttgtc aagctgctga taaggctgct tgtttgttgc caaagttgga tgaattgaga   1680
gacgaaggta aggcttcttc cgctaagcaa agattgaagt gtgcttcctt gcaaaagttc   1740
ggtgaaagag ctttcaaggc ttgggctgtc gctagattgt ctcaaagatt cccaaaggct   1800
gaattcgctg aagtttctaa gttggttact gacttgacta aggttcacac tgaatgttgt   1860
cacggtgact gtggaatg tgctgatgac agagctgact ggctaagta catctgtgaa   1920
aaccaagact ctatctcttc caagttgaag gaatgttgtg aaaagccatt gttggaaaag   1980
tctcactgta ttgctgaagt tgaaaacgat gaaatgccag ctgacttgcc atctttggct   2040
gctgacttcg ttgaatctaa ggacgttgt aagaactacg ctgaagctaa ggacgtcttc   2100
ttgggtatgt tcttgtacga atacgctaga agacacccag actactccgt tgtcttgttg   2160
ttgagattgg ctaagaccta cgaaactacc ttggaaagt gttgtgctgc tgctgaccca   2220
cacgaatgtt acgctaaggt tttcgatgaa ttcaagccat ggtcgaaga accacaaaac   2280
ttgatcaagc aaaactgtga attgttcgaa caattgggtg aatacaagtt ccaaaacgct   2340
ttgttggtta gatacactaa gaaggtccca caagtctcca ccccaacttt ggttgaagtc   2400
tctagaaact tgggtaaggt cggttctaag tgttgtaagc acccagaagc taagagaatg   2460
ccatgtgctg aagattactt gtccgtcgtt ttgaaccaat gtgtgtttt gcacgaaaag   2520
accccagtct ctgatagagt caccaagtgt tgtactgaat ctttggttaa cagaagacca   2580
tgtttctctg ctttggaagt cgacgaaact tacgttccaa aggaattcaa cgctgaaact   2640
ttcaccttcc acgctgatat ctgtaccttg tccgaaaagg aaagacaaat taagaagcaa   2700
actgctttgg ttgaattggt caagcacaag ccaaaggcta ctaaggaaca attgaaggct   2760
gtcatggatg atttcgctgc tttcgttgaa aagtgttgta aggctgatga taaggaaact   2820
```

```
tgtttcgctg aagaaggtaa gaagttggtc gctgcttccc aagctgcctt aggcttaggt    2880
ggttctggtg gttccggagg tagtggtggc tccggtggtg aggcttgcaa tcttcctatc    2940
gtccgtggcc cttgcatcgc cttttttcct cgttgggcct ttgacgccgt caaaggcaaa    3000
tgcgtccttt ttccttacgg cggttgccag ggcaatggca ataaatttta tagcgagaaa    3060
gagtgccgtg agtattgcgg cgtcccttaa taaggtacct aataagctta attcttatga    3120
tttatgattt ttattattaa ataagttata aaaaaaataa gtgtatacaa attttaaagt    3180
gactcttagg ttttaaaacg aaaattctta ttcttgagta actctttcct gtaggtcagg    3240
ttgctttctc aggtatagca tgaggtcgct cttattgacc acacctctac ggcatgccg    3300 agcaaatgcc tgcaaatcgc tccccatttc acccaattgt agatatgcta actccagcaa    3360
tgagttgatg aatctcggtg tgtattttat gtcctcagag gacaacacct gttgtaatcg    3420
ttcttccaca cggatcgcgg ccgc                                            3444
```

<210> SEQ ID NO 45
<211> LENGTH: 753
<212> TYPE: PRT
<213> ORGANISM: Artificial Sequence
<220> FEATURE:
<223> OTHER INFORMATION: Translation product of DPI-14-(GGS)4
      GG-rHA-(GGS)4-GG-DX-890 DNA sequence

<400> SEQUENCE: 45

```
Met Lys Trp Val Phe Ile Val Ser Ile Leu Phe Leu Phe Ser Ser Ala
 1               5                  10                  15

Tyr Ser Arg Ser Leu Asp Lys Arg Glu Ala Val Arg Glu Val Cys Ser
            20                  25                  30

Glu Gln Ala Glu Thr Gly Pro Cys Ile Ala Phe Phe Pro Arg Trp Tyr
        35                  40                  45

Phe Asp Val Thr Glu Gly Lys Cys Ala Pro Phe Phe Tyr Gly Gly Cys
    50                  55                  60

Gly Gly Asn Arg Asn Asn Phe Asp Thr Glu Glu Tyr Cys Met Ala Val
65                  70                  75                  80

Cys Gly Ser Ala Gly Ser Gly Gly Ser Gly Gly Ser Gly Gly Ser
                85                  90                  95

Gly Gly Asp Ala His Lys Ser Glu Val Ala His Arg Phe Lys Asp Leu
            100                 105                 110

Gly Glu Glu Asn Phe Lys Ala Leu Val Leu Ile Ala Phe Ala Gln Tyr
        115                 120                 125

Leu Gln Gln Cys Pro Phe Glu Asp His Val Lys Leu Val Asn Glu Val
    130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                165                 170                 175

Thr Leu Arg Glu Thr Tyr Gly Glu Met Ala Asp Cys Cys Ala Lys Gln
            180                 185                 190

Glu Pro Glu Arg Asn Glu Cys Phe Leu Gln His Lys Asp Asp Asn Pro
        195                 200                 205

Asn Leu Pro Arg Leu Val Arg Pro Glu Val Asp Val Met Cys Thr Ala
    210                 215                 220

Phe His Asp Asn Glu Glu Thr Phe Leu Lys Lys Tyr Leu Tyr Glu Ile
225                 230                 235                 240

Ala Arg Arg His Pro Tyr Phe Tyr Ala Pro Glu Leu Leu Phe Phe Ala
```

-continued

```
                245                 250                 255
Lys Arg Tyr Lys Ala Ala Phe Thr Glu Cys Cys Gln Ala Ala Asp Lys
            260                 265                 270
Ala Ala Cys Leu Leu Pro Lys Leu Asp Glu Leu Arg Asp Glu Gly Lys
            275                 280                 285
Ala Ser Ser Ala Lys Gln Arg Leu Lys Cys Ala Ser Leu Gln Lys Phe
            290                 295                 300
Gly Glu Arg Ala Phe Lys Ala Trp Ala Val Ala Arg Leu Ser Gln Arg
305                 310                 315                 320
Phe Pro Lys Ala Glu Phe Ala Glu Val Ser Lys Leu Val Thr Asp Leu
                325                 330                 335
Thr Lys Val His Thr Glu Cys Cys His Gly Asp Leu Leu Glu Cys Ala
            340                 345                 350
Asp Asp Arg Ala Asp Leu Ala Lys Tyr Ile Cys Glu Asn Gln Asp Ser
            355                 360                 365
Ile Ser Ser Lys Leu Lys Glu Cys Cys Glu Lys Pro Leu Leu Glu Lys
            370                 375                 380
Ser His Cys Ile Ala Glu Val Glu Asn Asp Glu Met Pro Ala Asp Leu
385                 390                 395                 400
Pro Ser Leu Ala Ala Asp Phe Val Glu Ser Lys Asp Val Cys Lys Asn
                405                 410                 415
Tyr Ala Glu Ala Lys Asp Val Phe Leu Gly Met Phe Leu Tyr Glu Tyr
            420                 425                 430
Ala Arg Arg His Pro Asp Tyr Ser Val Val Leu Leu Leu Arg Leu Ala
            435                 440                 445
Lys Thr Tyr Glu Thr Thr Leu Glu Lys Cys Cys Ala Ala Ala Asp Pro
450                 455                 460
His Glu Cys Tyr Ala Lys Val Phe Asp Glu Phe Lys Pro Leu Val Glu
465                 470                 475                 480
Glu Pro Gln Asn Leu Ile Lys Gln Asn Cys Glu Leu Phe Glu Gln Leu
                485                 490                 495
Gly Glu Tyr Lys Phe Gln Asn Ala Leu Leu Val Arg Tyr Thr Lys Lys
            500                 505                 510
Val Pro Gln Val Ser Thr Pro Thr Leu Val Glu Val Ser Arg Asn Leu
            515                 520                 525
Gly Lys Val Gly Ser Lys Cys Cys Lys His Pro Glu Ala Lys Arg Met
            530                 535                 540
Pro Cys Ala Glu Asp Tyr Leu Ser Val Val Leu Asn Gln Leu Cys Val
545                 550                 555                 560
Leu His Glu Lys Thr Pro Val Ser Asp Arg Val Thr Lys Cys Cys Thr
                565                 570                 575
Glu Ser Leu Val Asn Arg Arg Pro Cys Phe Ser Ala Leu Glu Val Asp
            580                 585                 590
Glu Thr Tyr Val Pro Lys Glu Phe Asn Ala Glu Thr Phe Thr Phe His
            595                 600                 605
Ala Asp Ile Cys Thr Leu Ser Glu Lys Glu Arg Gln Ile Lys Lys Gln
            610                 615                 620
Thr Ala Leu Val Glu Leu Val Lys His Lys Pro Lys Ala Thr Lys Glu
625                 630                 635                 640
Gln Leu Lys Ala Val Met Asp Asp Phe Ala Ala Phe Val Glu Lys Cys
                645                 650                 655
Cys Lys Ala Asp Asp Lys Glu Thr Cys Phe Ala Glu Glu Gly Lys Lys
            660                 665                 670
```

```
Leu Val Ala Ala Ser Gln Ala Ala Leu Gly Leu Gly Gly Ser Gly Gly
        675                 680                 685

Ser Gly Gly Ser Gly Gly Ser Gly Gly Glu Ala Cys Asn Leu Pro Ile
        690                 695                 700

Val Arg Gly Pro Cys Ile Ala Phe Phe Pro Arg Trp Ala Phe Asp Ala
705                 710                 715                 720

Val Lys Gly Lys Cys Val Leu Phe Pro Tyr Gly Gly Cys Gln Gly Asn
                725                 730                 735

Gly Asn Lys Phe Tyr Ser Glu Lys Glu Cys Arg Glu Tyr Cys Gly Val
            740                 745                 750

Pro

<210> SEQ ID NO 46
<211> LENGTH: 729
<212> TYPE: PRT
<213> ORGANISM: Artificial Sequence
<220> FEATURE:
<223> OTHER INFORMATION: Secreted product

<400> SEQUENCE: 46

Glu Ala Val Arg Glu Val Cys Ser Glu Gln Ala Glu Thr Gly Pro Cys
1               5                   10                  15

Ile Ala Phe Phe Pro Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Gly Gly Ser Gly
        50                  55                  60

Gly Ser Gly Gly Ser Gly Gly Ser Gly Gly Asp Ala His Lys Ser Glu
65                  70                  75                  80

Val Ala His Arg Phe Lys Asp Leu Gly Glu Glu Asn Phe Lys Ala Leu
                85                  90                  95

Val Leu Ile Ala Phe Ala Gln Tyr Leu Gln Gln Cys Pro Phe Glu Asp
                100                 105                 110

His Val Lys Leu Val Asn Glu Val Thr Glu Phe Ala Lys Thr Cys Val
            115                 120                 125

Ala Asp Glu Ser Ala Glu Asn Cys Asp Lys Ser Leu His Thr Leu Phe
130                 135                 140

Gly Asp Lys Leu Cys Thr Val Ala Thr Leu Arg Glu Thr Tyr Gly Glu
145                 150                 155                 160

Met Ala Asp Cys Cys Ala Lys Gln Glu Pro Glu Arg Asn Glu Cys Phe
                165                 170                 175

Leu Gln His Lys Asp Asp Asn Pro Asn Leu Pro Arg Leu Val Arg Pro
                180                 185                 190

Glu Val Asp Val Met Cys Thr Ala Phe His Asp Asn Glu Glu Thr Phe
            195                 200                 205

Leu Lys Lys Tyr Leu Tyr Glu Ile Ala Arg Arg His Pro Tyr Phe Tyr
        210                 215                 220

Ala Pro Glu Leu Leu Phe Phe Ala Lys Arg Tyr Lys Ala Ala Phe Thr
225                 230                 235                 240

Glu Cys Cys Gln Ala Ala Asp Lys Ala Ala Cys Leu Leu Pro Lys Leu
                245                 250                 255

Asp Glu Leu Arg Asp Glu Gly Lys Ala Ser Ser Ala Lys Gln Arg Leu
                260                 265                 270
```

-continued

```
Lys Cys Ala Ser Leu Gln Lys Phe Gly Glu Arg Ala Phe Lys Ala Trp
            275                 280                 285
Ala Val Ala Arg Leu Ser Gln Arg Phe Pro Lys Ala Glu Phe Ala Glu
        290                 295                 300
Val Ser Lys Leu Val Thr Asp Leu Thr Lys Val His Thr Glu Cys Cys
305                 310                 315                 320
His Gly Asp Leu Leu Glu Cys Ala Asp Asp Arg Ala Asp Leu Ala Lys
                325                 330                 335
Tyr Ile Cys Glu Asn Gln Asp Ser Ile Ser Ser Lys Leu Lys Glu Cys
            340                 345                 350
Cys Glu Lys Pro Leu Leu Glu Lys Ser His Cys Ile Ala Glu Val Glu
        355                 360                 365
Asn Asp Glu Met Pro Ala Asp Leu Pro Ser Leu Ala Ala Asp Phe Val
370                 375                 380
Glu Ser Lys Asp Val Cys Lys Asn Tyr Ala Glu Ala Lys Asp Val Phe
385                 390                 395                 400
Leu Gly Met Phe Leu Tyr Glu Tyr Ala Arg Arg His Pro Asp Tyr Ser
                405                 410                 415
Val Val Leu Leu Leu Arg Leu Ala Lys Thr Tyr Glu Thr Thr Leu Glu
            420                 425                 430
Lys Cys Cys Ala Ala Ala Asp Pro His Glu Cys Tyr Ala Lys Val Phe
        435                 440                 445
Asp Glu Phe Lys Pro Leu Val Glu Glu Pro Gln Asn Leu Ile Lys Gln
        450                 455                 460
Asn Cys Glu Leu Phe Glu Gln Leu Gly Glu Tyr Lys Phe Gln Asn Ala
465                 470                 475                 480
Leu Leu Val Arg Tyr Thr Lys Lys Val Pro Gln Val Ser Thr Pro Thr
                485                 490                 495
Leu Val Glu Val Ser Arg Asn Leu Gly Lys Val Gly Ser Lys Cys Cys
            500                 505                 510
Lys His Pro Glu Ala Lys Arg Met Pro Cys Ala Glu Asp Tyr Leu Ser
        515                 520                 525
Val Val Leu Asn Gln Leu Cys Val Leu His Glu Lys Thr Pro Val Ser
        530                 535                 540
Asp Arg Val Thr Lys Cys Cys Thr Glu Ser Leu Val Asn Arg Arg Pro
545                 550                 555                 560
Cys Phe Ser Ala Leu Glu Val Asp Glu Thr Tyr Val Pro Lys Glu Phe
                565                 570                 575
Asn Ala Glu Thr Phe Thr Phe His Ala Asp Ile Cys Thr Leu Ser Glu
            580                 585                 590
Lys Glu Arg Gln Ile Lys Lys Gln Thr Ala Leu Val Glu Leu Val Lys
        595                 600                 605
His Lys Pro Lys Ala Thr Lys Glu Gln Leu Lys Ala Val Met Asp Asp
        610                 615                 620
Phe Ala Ala Phe Val Glu Lys Cys Cys Lys Ala Asp Asp Lys Glu Thr
625                 630                 635                 640
Cys Phe Ala Glu Glu Gly Lys Lys Leu Val Ala Ala Ser Gln Ala Ala
                645                 650                 655
Leu Gly Leu Gly Gly Ser Gly Gly Ser Gly Gly Ser Gly Gly Ser Gly
            660                 665                 670
Gly Glu Ala Cys Asn Leu Pro Ile Val Arg Gly Pro Cys Ile Ala Phe
        675                 680                 685
Phe Pro Arg Trp Ala Phe Asp Ala Val Lys Gly Lys Cys Val Leu Phe
```

-continued

```
            690              695              700
Pro Tyr Gly Gly Cys Gln Gly Asn Gly Asn Lys Phe Tyr Ser Glu Lys
705                  710              715                  720

Glu Cys Arg Glu Tyr Cys Gly Val Pro
                725
```

<210> SEQ ID NO 47
<211> LENGTH: 60
<212> TYPE: PRT
<213> ORGANISM: Artificial Sequence
<220> FEATURE:
<223> OTHER INFORMATION: DX-1000 Kunitz domain peptide

<400> SEQUENCE: 47

```
Glu Ala Met His Ser Phe Cys Ala Phe Lys Ala Glu Thr Gly Pro Cys
1               5                  10                  15

Arg Ala Arg Phe Asp Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu
        35                  40                  45

Ser Leu Glu Glu Cys Lys Lys Met Cys Thr Arg Asp
    50                  55                  60
```

<210> SEQ ID NO 48
<211> LENGTH: 60
<212> TYPE: PRT
<213> ORGANISM: Artificial Sequence
<220> FEATURE:
<223> OTHER INFORMATION: DX-88 Kunitz domain peptide

<400> SEQUENCE: 48

```
Glu Ala Met His Ser Phe Cys Ala Phe Lys Ala Asp Asp Gly Pro Cys
1               5                  10                  15

Arg Ala Ala His Pro Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu
        35                  40                  45

Ser Leu Glu Glu Cys Lys Lys Met Cys Thr Arg Asp
    50                  55                  60
```

<210> SEQ ID NO 49
<211> LENGTH: 207
<212> TYPE: DNA
<213> ORGANISM: Artificial Sequence
<220> FEATURE:
<223> OTHER INFORMATION: DNA sequence of the N-Terminal BglII-BamHI
      DPI-14
      cDNA

<400> SEQUENCE: 49

```
agatctttgg ataagagaga agctgttaga gaagtttgtt ctgaacaagc tgaaactggt      60
ccatgtattg ctttcttccc aagatggtac ttcgatgtta ctgaaggtaa gtgcgcgcca     120
ttcttctacg gtggttgtgg tggtaacaga aacaacttcg atactgaaga atactgtatg     180
gctgtttgtg gttctgctgg tggatcc                                         207
```

<210> SEQ ID NO 50
<211> LENGTH: 202
<212> TYPE: DNA
<213> ORGANISM: Artificial Sequence
<220> FEATURE:
<223> OTHER INFORMATION: DNA sequence of the C-Terminal BamHI-HindIII DPI-14 cDNA

<400> SEQUENCE: 50

| | | | | |
|---|---|---|---|---|
| ggatccggtg | gtgaagctgt | tagagaagtt | tgttctgaac | aagctgaaac tggtccatgt | 60 |
| attgctttct | tcccaagatg | gtacttcgat | gttactgaag | gtaagtgcgc gccattcttc | 120 |
| tacggtggtt | gtggtggtaa | cagaaacaac | ttcgatactg | aagaatactg tatggctgtt | 180 |
| tgtggttctg | cttaataagc | tt | | | 202 |

<210> SEQ ID NO 51
<211> LENGTH: 1977
<212> TYPE: DNA
<213> ORGANISM: Artificial Sequence
<220> FEATURE:
<223> OTHER INFORMATION: DNA sequence of the N-Terminal
     DPI-14-(GGS)4GG-albumin fusion coding region

<400> SEQUENCE: 51

| | | | | | |
|---|---|---|---|---|---|
| gaagctgtta | gagaagtttg | ttctgaacaa | gctgaaactg | gtccatgtat tgctttcttc | 60 |
| ccaagatggt | acttcgatgt | tactgaaggt | aagtgcgcgc | cattcttcta cggtggttgt | 120 |
| ggtggtaaca | gaaacaactt | cgatactgaa | gaatactgta | tggctgtttg tggttctgct | 180 |
| ggtggatccg | gtggttccgg | tggttctggt | ggttccggtg | gtgacgctca caagtccgaa | 240 |
| gtcgctcacc | ggttcaagga | cctaggtgag | gaaaacttca | aggcttttggt cttgatcgct | 300 |
| ttcgctcaat | acttgcaaca | atgtccattc | gaagatcacg | tcaagttggt caacgaagtt | 360 |
| accgaattcg | ctaagacttg | tgttgctgac | gaatctgctg | aaaactgtga caagtccttg | 420 |
| cacaccttgt | tcggtgataa | gttgtgtact | gttgctacct | tgagagaaac ctacggtgaa | 480 |
| atggctgact | gttgtgctaa | gcaagaacca | gaaagaaacg | aatgtttctt gcaacacaag | 540 |
| gacgacaacc | caaacttgcc | aagattggtt | agaccagaag | ttgacgtcat gtgtactgct | 600 |
| ttccacgaca | acgaagaaac | cttcttgaag | aagtacttgt | acgaaattgc tagaagacac | 660 |
| ccatacttct | acgctccaga | attgttgttc | ttcgctaaga | gatacaaggc tgctttcacc | 720 |
| gaatgttgtc | aagctgctga | taaggctgct | gttttgttgc | aaagttggat gaattgaga | 780 |
| gacgaaggta | aggcttcttc | cgctaagcaa | agattgaagt | gtgcttcctt gcaaaagttc | 840 |
| ggtgaaagag | ctttcaaggc | ttgggctgtc | gctagattgt | ctcaaagatt cccaaaggct | 900 |
| gaattcgctg | aagtttctaa | gttggttact | gacttgacta | aggttcacac tgaatgttgt | 960 |
| cacggtgact | tgttggaatg | tgctgatgac | agagctgact | ggctaagta catctgtgaa | 1020 |
| aaccaagact | ctatctcttc | caagttgaag | gaatgttgtg | aaaagccatt gttggaaaag | 1080 |
| tctcactgta | ttgctgaagt | tgaaaacgat | gaaatgccag | ctgacttgcc atctttggct | 1140 |
| gctgacttcg | ttgaatctaa | ggacgtttgt | aagaactacg | ctgaagctaa ggacgtcttc | 1200 |
| ttgggtatgt | tcttgtacga | atacgctaga | agacacccag | actactccgt tgtcttgttg | 1260 |
| ttgagattgg | ctaagaccta | cgaaactacc | ttggaaaagt | gttgtgctgc tgctgaccca | 1320 |
| cacgaatgtt | acgctaaggt | tttcgatgaa | ttcaagccat | tggtcgaaga ccacaaaaac | 1380 |
| ttgatcaagc | aaaactgtga | attgttcgaa | caattgggtg | aatacaagtt ccaaaacgct | 1440 |
| ttgttggtta | gatacactaa | gaaggtccca | caagtctcca | ccccaacttt ggttgaagtc | 1500 |
| tctagaaact | tgggtaaggt | cggttctaag | tgttgtaagc | acccagaagc taagagaatg | 1560 |
| ccatgtgctg | aagattactt | gtccgtcgtt | ttgaaccaat | gtgtgttttt gcacgaaaag | 1620 |
| accccagtct | ctgatagagt | caccaagtgt | tgtactgaat | ctttggttaa cagaagacca | 1680 |

```
tgtttctctg ctttggaagt cgacgaaact tacgttccaa aggaattcaa cgctgaaact    1740
ttcaccttcc acgctgatat ctgtaccttg tccgaaaagg aaagacaaat taagaagcaa    1800
actgctttgg ttgaattggt caagcacaag ccaaaggcta ctaaggaaca attgaaggct    1860
gtcatggatg atttcgctgc tttcgttgaa aagtgttgta aggctgatga taaggaaact    1920
tgtttcgctg aagaaggtaa gaagttggtc gctgcttccc aagctgcttt gggtttg      1977
```

<210> SEQ ID NO 52
<211> LENGTH: 659
<212> TYPE: PRT
<213> ORGANISM: Artificial Sequence
<220> FEATURE:
<223> OTHER INFORMATION: Amino acid sequence of the N-Terminal
      DPI-14-(GGS)4GG-albumin fusion protein

<400> SEQUENCE: 52

```
Glu Ala Val Arg Glu Val Cys Ser Glu Gln Ala Glu Thr Gly Pro Cys
 1               5                  10                  15

Ile Ala Phe Phe Pro Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Gly Gly Ser Gly
        50                  55                  60

Gly Ser Gly Gly Ser Gly Gly Ser Gly Gly Asp Ala His Lys Ser Glu
 65                  70                  75                  80

Val Ala His Arg Phe Lys Asp Leu Gly Glu Glu Asn Phe Lys Ala Leu
                 85                  90                  95

Val Leu Ile Ala Phe Ala Gln Tyr Leu Gln Gln Cys Pro Phe Glu Asp
            100                 105                 110

His Val Lys Leu Val Asn Glu Val Thr Glu Phe Ala Lys Thr Cys Val
        115                 120                 125

Ala Asp Glu Ser Ala Glu Asn Cys Asp Lys Ser Leu His Thr Leu Phe
    130                 135                 140

Gly Asp Lys Leu Cys Thr Val Ala Thr Leu Arg Glu Thr Tyr Gly Glu
145                 150                 155                 160

Met Ala Asp Cys Cys Ala Lys Gln Glu Pro Glu Arg Asn Glu Cys Phe
                165                 170                 175

Leu Gln His Lys Asp Asp Asn Pro Asn Leu Pro Arg Leu Val Arg Pro
            180                 185                 190

Glu Val Asp Val Met Cys Thr Ala Phe His Asp Asn Glu Glu Thr Phe
        195                 200                 205

Leu Lys Lys Tyr Leu Tyr Glu Ile Ala Arg Arg His Pro Tyr Phe Tyr
    210                 215                 220

Ala Pro Glu Leu Leu Phe Phe Ala Lys Arg Tyr Lys Ala Ala Phe Thr
225                 230                 235                 240

Glu Cys Cys Gln Ala Ala Asp Lys Ala Ala Cys Leu Leu Pro Lys Leu
                245                 250                 255

Asp Glu Leu Arg Asp Glu Gly Lys Ala Ser Ser Ala Lys Gln Arg Leu
            260                 265                 270

Lys Cys Ala Ser Leu Gln Lys Phe Gly Glu Arg Ala Phe Lys Ala Trp
        275                 280                 285

Ala Val Ala Arg Leu Ser Gln Arg Phe Pro Lys Ala Glu Phe Ala Glu
    290                 295                 300

Val Ser Lys Leu Val Thr Asp Leu Thr Lys Val His Thr Glu Cys Cys
```

His Gly Asp Leu Leu Glu Cys Ala Asp Asp Arg Ala Asp Leu Ala Lys
305                 310                 315                 320
                325                 330                 335

Tyr Ile Cys Glu Asn Gln Asp Ser Ile Ser Ser Lys Leu Lys Glu Cys
                340                 345                 350

Cys Glu Lys Pro Leu Leu Glu Lys Ser His Cys Ile Ala Glu Val Glu
                355                 360                 365

Asn Asp Glu Met Pro Ala Asp Leu Pro Ser Leu Ala Ala Asp Phe Val
                370                 375                 380

Glu Ser Lys Asp Val Cys Lys Asn Tyr Ala Glu Ala Lys Asp Val Phe
385                 390                 395                 400

Leu Gly Met Phe Leu Tyr Glu Tyr Ala Arg Arg His Pro Asp Tyr Ser
                405                 410                 415

Val Val Leu Leu Leu Arg Leu Ala Lys Thr Tyr Glu Thr Thr Leu Glu
                420                 425                 430

Lys Cys Cys Ala Ala Ala Asp Pro His Glu Cys Tyr Ala Lys Val Phe
                435                 440                 445

Asp Glu Phe Lys Pro Leu Val Glu Glu Pro Gln Asn Leu Ile Lys Gln
450                 455                 460

Asn Cys Glu Leu Phe Glu Gln Leu Gly Glu Tyr Lys Phe Gln Asn Ala
465                 470                 475                 480

Leu Leu Val Arg Tyr Thr Lys Lys Val Pro Gln Val Ser Thr Pro Thr
                485                 490                 495

Leu Val Glu Val Ser Arg Asn Leu Gly Lys Val Gly Ser Lys Cys Cys
                500                 505                 510

Lys His Pro Glu Ala Lys Arg Met Pro Cys Ala Glu Asp Tyr Leu Ser
                515                 520                 525

Val Val Leu Asn Gln Leu Cys Val Leu His Glu Lys Thr Pro Val Ser
                530                 535                 540

Asp Arg Val Thr Lys Cys Cys Thr Glu Ser Leu Val Asn Arg Arg Pro
545                 550                 555                 560

Cys Phe Ser Ala Leu Glu Val Asp Glu Thr Tyr Val Pro Lys Glu Phe
                565                 570                 575

Asn Ala Glu Thr Phe Thr Phe His Ala Asp Ile Cys Thr Leu Ser Glu
                580                 585                 590

Lys Glu Arg Gln Ile Lys Lys Gln Thr Ala Leu Val Glu Leu Val Lys
                595                 600                 605

His Lys Pro Lys Ala Thr Lys Glu Gln Leu Lys Ala Val Met Asp Asp
                610                 615                 620

Phe Ala Ala Phe Val Glu Lys Cys Cys Lys Ala Asp Asp Lys Glu Thr
625                 630                 635                 640

Cys Phe Ala Glu Glu Gly Lys Lys Leu Val Ala Ala Ser Gln Ala Ala
                645                 650                 655

Leu Gly Leu

<210> SEQ ID NO 53
<211> LENGTH: 1977
<212> TYPE: DNA
<213> ORGANISM: Artificial Sequence
<220> FEATURE:
<223> OTHER INFORMATION: DNA sequence of the C-terminal
      albumin-(GGS)4GG-DPI-14 fusion coding region

<400> SEQUENCE: 53
gatgcacaca agagtgaggt tgctcatcgg tttaaagatt tgggagaaga aaatttcaaa      60

```
gccttggtgt tgattgcctt tgctcagtat cttcagcagt gtccatttga agatcatgta      120
aaattagtga atgaagtaac tgaatttgca aaaacatgtg ttgctgatga gtcagctgaa      180
aattgtgaca atcacttca tacccttttt ggagacaaat tatgcacagt tgcaactctt       240
cgtgaaacct atggtgaaat ggctgactgc tgtgcaaaac aagaacctga gagaaatgaa      300
tgcttcttgc aacacaaaga tgacaaccca aacctccccc gattggtgag accagaggtt      360
gatgtgatgt gcactgcttt tcatgacaat aagagacat ttttgaaaaa atacttatat       420
gaaattgcca aagacatcc ttactttat gccccggaac tccttttctt tgctaaaagg        480
tataaagctg cttttacaga atgttgccaa gctgctgata aagctgcctg cctgttgcca      540
aagctcgatg aacttcggga tgaagggaag gcttcgtctg ccaaacagag actcaagtgt      600
gccagtctcc aaaaatttgg agaaagagct ttcaaagcat gggcagtagc tcgcctgagc      660
cagagatttc ccaaagctga gtttgcagaa gtttccaagt tagtgacaga tcttaccaaa      720
gtccacacgg aatgctgcca tggagatctg cttgaatgtg ctgatgacag ggcggacctt     780
gccaagtata tctgtgaaaa tcaagattcg atctccagta aactgaagga atgctgtgaa      840
aaacctctgt ggaaaaatc ccactgcatt gccgaagtgg aaaatgatga gatgcctgct       900
gacttgcctt cattagctgc tgattttgtt gaaagtaagg atgtttgcaa aaactatgct      960
gaggcaaagg atgtcttcct gggcatgttt ttgtatgaat atgcaagaag gcatcctgat     1020
tactctgtcg tgctgctgct gagacttgcc aagacatatg aaaccactct agagaagtgc    1080
tgtgccgctg cagatcctca tgaatgctat gccaaagtgt tcgatgaatt taaacctctt    1140
gtggaagagc ctcagaattt aatcaaacaa aattgtgagc tttttgagca gcttggagag    1200
tacaaattcc agaatgcgct attagttcgt tacaccaaga aagtaccca gtgtcaact      1260 ccaactcttg tagaggtctc aagaaaccta ggaaaagtgg gcagcaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg atgaaacata cgttcccaaa    1500
gagtttaatg ctgaaacatt caccttccat gcagatatat gcacactttc tgagaaggag    1560
agacaaatca gaaacaaac tgcacttgtt gagctcgtga acacaagcc caaggcaaca     1620 aaagagcaac tgaaagctgt tatggatgat ttcgcagctt ttgtagagaa gtgctgcaag    1680
gctgacgata aggagacctg cttttgccgag gagggtaaaa aacttgttgc tgcaagtcaa    1740
gctgccttag gcttaggtgg ttctggtggt tccggtggtt ctggtggatc cggtggtgaa    1800
gctgttagag aagtttgttc tgaacaagct gaaactggtc catgtattgc tttcttccca    1860
agatggtact cgatgttac tgaaggtaag tgcgcgccat tcttctacgg tggttgtggt    1920
ggtaacagaa acaacttcga tactgaagaa tactgtatgg ctgtttgtgg ttctgct      1977
```

<210> SEQ ID NO 54
<211> LENGTH: 659
<212> TYPE: PRT
<213> ORGANISM: Artificial Sequence
<220> FEATURE:
<223> OTHER INFORMATION: Amino acid sequence of the C-Terminal albumin-(GGS)4GG-DPI-14 fusion protein

<400> SEQUENCE: 54

```
Asp Ala His Lys Ser Glu Val Ala His Arg Phe Lys Asp Leu Gly Glu
 1               5                  10                  15
```

```
Glu Asn Phe Lys Ala Leu Val Leu Ile Ala Phe Ala Gln Tyr Leu Gln
             20                  25                  30

Gln Cys Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
```

```
            435                 440                 445
Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Ser Gly Ser Gly
                580                 585                 590

Gly Ser Gly Gly Ser Gly Gly Glu Ala Val Arg Glu Val Cys Ser Glu
            595                 600                 605

Gln Ala Glu Thr Gly Pro Cys Ile Ala Phe Phe Pro Arg Trp Tyr Phe
        610                 615                 620

Asp Val Thr Glu Gly Lys Cys Ala Pro Phe Phe Tyr Gly Gly Cys Gly
625                 630                 635                 640

Gly Asn Arg Asn Asn Phe Asp Thr Glu Glu Tyr Cys Met Ala Val Cys
                645                 650                 655

Gly Ser Ala

<210> SEQ ID NO 55
<211> LENGTH: 202
<212> TYPE: DNA
<213> ORGANISM: Artificial Sequence
<220> FEATURE:
<223> OTHER INFORMATION: DNA sequence of the C-Terminal BamHI-HindIII
      DX-1000 cDNA

<400> SEQUENCE: 55
ggatccggtg gtgaggctat gcattccttc tgcgccttca aggctgagac tggtccttgt      60
agagctaggt tcgaccgttg gttcttcaac atcttcacgc gtcagtgcga ggaattcatt     120
tacggtggtt gtgaaggtaa ccagaaccgg ttcgaatctc tagaggaatg taagaagatg     180
tgcactcgtg actaataagc tt                                              202

<210> SEQ ID NO 56
<211> LENGTH: 195
<212> TYPE: DNA
<213> ORGANISM: Artificial Sequence
<220> FEATURE:
<223> OTHER INFORMATION: DNA sequence of the N-Terminal BglII-BamHI
      DX-890
      cDNA

<400> SEQUENCE: 56
agatctttgg ataagagaga agcctgtaac ttgccaattg ttagaggtcc atgtattgct      60
ttcttcccaa gatgggcttt cgatgctgtt aagggtaagt gtgttttgtt cccatatggt     120
ggttgtcaag gtaacggtaa caagttctac tctgaaaagg aatgtagaga atactgtggt     180
```

```
gttccaggtg gatcc                                                      195

<210> SEQ ID NO 57
<211> LENGTH: 190
<212> TYPE: DNA
<213> ORGANISM: Artificial Sequence
<220> FEATURE:
<223> OTHER INFORMATION: DNA sequence of the C-Terminal BamHI-HindIII
      DX-890 cDNA

<400> SEQUENCE: 57
ggatccggtg gtgaagcctg taacttgcca attgttagag gtccatgtat tgctttcttc    60
ccaagatggg ctttcgatgc tgttaagggt aagtgtgttt tgttcccata tggtggttgt   120
caaggtaacg gtaacaagtt ctactctgaa aggaatgtga gaatactg tggtgttcca     180 taataagctt                                                          190

<210> SEQ ID NO 58
<211> LENGTH: 1965
<212> TYPE: DNA
<213> ORGANISM: Artificial Sequence
<220> FEATURE:
<223> OTHER INFORMATION: DNA sequence of the N-Terminal
      DX-890-(GGS)4GG-albumin fusion coding region

<400> SEQUENCE: 58
gaagcctgta acttgccaat tgttagaggt ccatgtattg ctttcttccc aagatgggct    60
ttcgatgctg ttaagggtaa gtgtgttttg ttcccatatg gtggttgtca aggtaacggt   120
aacaagttct actctgaaaa ggaatgtaga gaatactgtg gtgttccagg tggatccggt   180
ggttccggtg gttctggtgg ttccggtggt gacgctcaca gtccgaagt cgctcaccgg    240 ttcaaggacc taggtgagga aaacttcaag gctttggtct tgatcgcttt cgctcaatac   300
ttgcaacaat gtccattcga agatcacgtc aagttggtca acgaagttac cgaattcgct   360
aagacttgtg ttgctgacga atctgctgaa actgtgaca agtccttgca caccttgttc    420
ggtgataagt tgtgtactgt tgctaccttg agagaaacct acggtgaaat ggctgactgt   480
tgtgctaagc aagaaccaga agaaacgaa tgtttcttgc aacacaagga cgacaaccca    540
aacttgccaa gattggttag accagaagtt gacgtcatgt gtactgcttt ccacgacaac   600
gaagaaacct tcttgaagaa gtacttgtac gaaattgcta agacaccc atacttctac     660 gctccagaat tgttgttctt cgctaagaga tacaaggctg cttttcaccga atgttgtcaa    720 gctgctgata aggctgcttg tttgttgcca aagttggatg aattgagaga cgaaggtaag   780
gcttcttccg ctaagcaaag attgaagtgt gcttccttgc aaaagttcgg tgaaagagct    840
ttcaaggctt gggctgtcgc tagattgtct caaagattcc caaggctga attcgctgaa    900 gtttctaagt tggttactga cttgactaag gttcacactg aatgttgtca cggtgacttg    960
ttggaatgtg ctgatgacag agctgacttg gctaagtaca tctgtgaaaa ccaagactct   1020
atctcttcca gttgaagga atgttgtgaa aagccattgt ggaaaagtc tcactgtatt    1080 gctgaagttg aaaacgatga atgccagct gacttgccat ctttggctgc tgacttcgtt    1140
gaatctaagg acgtttgtaa gaactacgct gaagctaagg acgtcttctt gggtatgttc    1200
ttgtacgaat acgctagaag acacccagac tactccgttg tcttgttgtt gagattggct   1260
aagacctacg aaactacctt ggaaaagtgt tgtgctgctg ctgacccaca cgaatgttac   1320
gctaaggttt tcgatgaatt caagccattg gtcgaagaac cacaaaactt gatcaagcaa   1380
```

-continued

```
aactgtgaat tgttcgaaca attgggtgaa tacaagttcc aaaacgcttt gttggttaga      1440
tacactaaga aggtcccaca agtctccacc ccaactttgg ttgaagtctc tagaaacttg      1500
ggtaaggtcg gttctaagtg ttgtaagcac ccagaagcta agagaatgcc atgtgctgaa      1560
gattacttgt ccgtcgtttt gaaccaattg tgtgttttgc acgaaaagac cccagtctct      1620
gatagagtca ccaagtgttg tactgaatct ttggttaaca aagaccatg tttctctgct       1680 ttggaagtcg acgaaactta cgttccaaag gaattcaacg ctgaaacttt caccttccac      1740
gctgatatct gtaccttgtc cgaaaaggaa agacaaatta agaagcaaac tgctttggtt      1800
gaattggtca agcacaagcc aaaggctact aaggaacaat tgaaggctgt catggatgat      1860
ttcgctgctt tcgttgaaaa gtgttgtaag gctgatgata aggaaacttg tttcgctgaa      1920
gaaggtaaga agttggtcgc tgcttcccaa gctgctttgg gtttg                     1965
```

<210> SEQ ID NO 59
<211> LENGTH: 655
<212> TYPE: PRT
<213> ORGANISM: Artificial Sequence
<220> FEATURE:
<223> OTHER INFORMATION: Amino acid sequence of the N-terminal
      DX-890-(GGS)4GG-albumin fusion protein

<400> SEQUENCE: 59

```
Glu Ala Cys Asn Leu Pro Ile Val Arg Gly Pro Cys Ile Ala Phe Phe
 1               5                  10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro Gly Gly Ser Gly Gly Ser Gly Gly
    50                  55                  60

Ser Gly Gly Ser Gly Gly Asp Ala His Lys Ser Glu Val Ala His Arg
65                  70                  75                  80

Phe Lys Asp Leu Gly Glu Glu Asn Phe Lys Ala Leu Val Leu Ile Ala
                85                  90                  95

Phe Ala Gln Tyr Leu Gln Gln Cys Pro Phe Glu Asp His Val Lys Leu
            100                 105                 110

Val Asn Glu Val Thr Glu Phe Ala Lys Thr Cys Val Ala Asp Glu Ser
        115                 120                 125

Ala Glu Asn Cys Asp Lys Ser Leu His Thr Leu Phe Gly Asp Lys Leu
    130                 135                 140

Cys Thr Val Ala Thr Leu Arg Glu Thr Tyr Gly Glu Met Ala Asp Cys
145                 150                 155                 160

Cys Ala Lys Gln Glu Pro Glu Arg Asn Glu Cys Phe Leu Gln His Lys
                165                 170                 175

Asp Asp Asn Pro Asn Leu Pro Arg Leu Val Arg Pro Glu Val Asp Val
            180                 185                 190

Met Cys Thr Ala Phe His Asp Asn Glu Glu Thr Phe Leu Lys Lys Tyr
        195                 200                 205

Leu Tyr Glu Ile Ala Arg Arg His Pro Tyr Phe Tyr Ala Pro Glu Leu
    210                 215                 220

Leu Phe Phe Ala Lys Arg Tyr Lys Ala Ala Phe Thr Glu Cys Cys Gln
225                 230                 235                 240

Ala Ala Asp Lys Ala Ala Cys Leu Leu Pro Lys Leu Asp Glu Leu Arg
                245                 250                 255
```

```
Asp Glu Gly Lys Ala Ser Ser Ala Lys Gln Arg Leu Lys Cys Ala Ser
            260                 265                 270

Leu Gln Lys Phe Gly Glu Arg Ala Phe Lys Ala Trp Ala Val Ala Arg
        275                 280                 285

Leu Ser Gln Arg Phe Pro Lys Ala Glu Phe Ala Glu Val Ser Lys Leu
    290                 295                 300

Val Thr Asp Leu Thr Lys Val His Thr Glu Cys Cys His Gly Asp Leu
305                 310                 315                 320

Leu Glu Cys Ala Asp Asp Arg Ala Asp Leu Ala Lys Tyr Ile Cys Glu
                325                 330                 335

Asn Gln Asp Ser Ile Ser Ser Lys Leu Lys Glu Cys Cys Glu Lys Pro
            340                 345                 350

Leu Leu Glu Lys Ser His Cys Ile Ala Glu Val Glu Asn Asp Glu Met
        355                 360                 365

Pro Ala Asp Leu Pro Ser Leu Ala Ala Asp Phe Val Glu Ser Lys Asp
    370                 375                 380

Val Cys Lys Asn Tyr Ala Glu Ala Lys Asp Val Phe Leu Gly Met Phe
385                 390                 395                 400

Leu Tyr Glu Tyr Ala Arg Arg His Pro Asp Tyr Ser Val Val Leu Leu
                405                 410                 415

Leu Arg Leu Ala Lys Thr Tyr Glu Thr Thr Leu Glu Lys Cys Cys Ala
            420                 425                 430

Ala Ala Asp Pro His Glu Cys Tyr Ala Lys Val Phe Asp Glu Phe Lys
        435                 440                 445

Pro Leu Val Glu Glu Pro Gln Asn Leu Ile Lys Gln Asn Cys Glu Leu
    450                 455                 460

Phe Glu Gln Leu Gly Glu Tyr Lys Phe Gln Asn Ala Leu Leu Val Arg
465                 470                 475                 480

Tyr Thr Lys Lys Val Pro Gln Val Ser Thr Pro Thr Leu Val Glu Val
                485                 490                 495

Ser Arg Asn Leu Gly Lys Val Gly Ser Lys Cys Cys Lys His Pro Glu
            500                 505                 510

Ala Lys Arg Met Pro Cys Ala Glu Asp Tyr Leu Ser Val Val Leu Asn
        515                 520                 525

Gln Leu Cys Val Leu His Glu Lys Thr Pro Val Ser Asp Arg Val Thr
    530                 535                 540

Lys Cys Cys Thr Glu Ser Leu Val Asn Arg Arg Pro Cys Phe Ser Ala
545                 550                 555                 560

Leu Glu Val Asp Glu Thr Tyr Val Pro Lys Glu Phe Asn Ala Glu Thr
                565                 570                 575

Phe Thr Phe His Ala Asp Ile Cys Thr Leu Ser Glu Lys Glu Arg Gln
            580                 585                 590

Ile Lys Lys Gln Thr Ala Leu Val Glu Leu Val Lys His Lys Pro Lys
        595                 600                 605

Ala Thr Lys Glu Gln Leu Lys Ala Val Met Asp Asp Phe Ala Ala Phe
    610                 615                 620

Val Glu Lys Cys Cys Lys Ala Asp Asp Lys Glu Thr Cys Phe Ala Glu
625                 630                 635                 640

Glu Gly Lys Lys Leu Val Ala Ala Ser Gln Ala Ala Leu Gly Leu
                645                 650                 655

<210> SEQ ID NO 60
<211> LENGTH: 1965
<212> TYPE: DNA
```

<213> ORGANISM: Artificial Sequence
<220> FEATURE:
<223> OTHER INFORMATION: DNA sequence of the C-terminal
    albumin-(GGS)4GG-DX-890 fusion coding region

<400> SEQUENCE: 60

| | | | | | |
|---|---|---|---|---|---|
| gatgcacaca | agagtgaggt | tgctcatcgg | tttaaagatt | tgggagaaga | aaatttcaaa | 60 |
| gccttggtgt | tgattgcctt | tgctcagtat | cttcagcagt | gtccatttga | agatcatgta | 120 |
| aaattagtga | atgaagtaac | tgaatttgca | aaaacatgtg | ttgctgatga | gtcagctgaa | 180 |
| aattgtgaca | atcacttca | tacccttttt | ggagacaaat | tatgcacagt | tgcaactctt | 240 |
| cgtgaaacct | atggtgaaat | ggctgactgc | tgtgcaaaac | aagaacctga | gagaaatgaa | 300 |
| tgcttcttgc | aacacaaaga | tgacaaccca | acctccccc | gattggtgag | accagaggtt | 360 |
| gatgtgatgt | gcactgcttt | tcatgacaat | gaagagacat | ttttgaaaaa | atacttatat | 420 |
| gaaattgcca | agacatcc | ttactttat | gccccggaac | tccttttctt | tgctaaaagg | 480 |
| tataaagctg | cttttacaga | atgttgccaa | gctgctgata | agctgcctg | cctgttgcca | 540 |
| aagctcgatg | aacttcggga | tgaagggaag | gcttcgtctg | ccaaacagag | actcaagtgt | 600 |
| gccagtctcc | aaaaatttgg | agaaagagct | ttcaaagcat | gggcagtagc | tcgcctgagc | 660 |
| cagagatttc | ccaaagctga | gtttgcagaa | gtttccaagt | tagtgacaga | tcttaccaaa | 720 |
| gtccacacgg | aatgctgcca | tggagatctg | cttgaatgtg | ctgatgacag | ggcggacctt | 780 |
| gccaagtata | tctgtgaaaa | tcaagattcg | atctccagta | aactgaagga | atgctgtgaa | 840 |
| aaacctctgt | tggaaaaatc | ccactgcatt | gccgaagtgg | aaaatgatga | gatgcctgct | 900 |
| gacttgcctt | cattagctgc | tgatttttgtt | gaaagtaagg | atgtttgcaa | aaactatgct | 960 |
| gaggcaaagg | atgtcttcct | gggcatgttt | ttgtatgaat | atgcaagaag | gcatcctgat | 1020 |
| tactctgtcg | tgctgctgct | gagacttgcc | aagacatatg | aaaccactct | agagaagtgc | 1080 |
| tgtgccgctg | cagatcctca | tgaatgctat | gccaaagtgt | tcgatgaatt | taaacctctt | 1140 |
| gtggaagagc | tcagaatttt | aatcaaacaa | aattgtgagc | ttttgagca | gcttggagag | 1200 |
| tacaaattcc | agaatgcgct | attagttcgt | tacaccaaga | aagtaccca | agtgtcaact | 1260 |
| ccaactcttg | tagaggtctc | aagaaaccta | ggaaaagtgg | gcagcaaatg | ttgtaaacat | 1320 |
| cctgaagcaa | aaagaatgcc | ctgtgcagaa | gactatctat | ccgtggtcct | gaaccagtta | 1380 |
| tgtgtgttgc | atgagaaaac | gccagtaagt | gacagagtca | ccaaatgctg | cacagaatcc | 1440 |
| ttggtgaaca | ggcgaccatg | cttttcagct | ctggaagtcg | atgaaacata | cgttcccaaa | 1500 |
| gagtttaatg | ctgaaacatt | caccttccat | gcagatatat | gcacactttc | tgagaaggag | 1560 |
| agacaaatca | agaaacaaac | tgcacttgtt | gagctcgtga | acacaagcc | caaggcaaca | 1620 |
| aaagagcaac | tgaaagctgt | tatggatgat | ttcgcagctt | ttgtagagaa | gtgctgcaag | 1680 |
| gctgacgata | aggagacctg | cttttgccgag | gagggtaaaa | aacttgttgc | tgcaagtcaa | 1740 |
| gctgccttag | gcttaggtgg | ttctggtggt | tccggtggtt | ctggtggatc | cggtggtgaa | 1800 |
| gcctgtaact | tgccaattgt | tagaggtcca | tgtattgctt | tcttcccaag | atgggctttc | 1860 |
| gatgctgtta | agggtaagtg | tgttttgttc | ccatatggtg | gttgtcaagg | taacggtaac | 1920 |
| aagttctact | ctgaaaagga | atgtagagaa | tactgtggtg | ttcca | 1965 |

<210> SEQ ID NO 61
<211> LENGTH: 655
<212> TYPE: PRT
<213> ORGANISM: Artificial Sequence
<220> FEATURE:

-continued

<223> OTHER INFORMATION: Amino acid sequence of the C-terminal
      albumin-(GGS)4GG-DX-890 fusion protein

<400> SEQUENCE: 61

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400
```

```
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Ser Gly Ser Gly
            580                 585                 590

Gly Ser Gly Gly Ser Gly Gly Glu Ala Cys Asn Leu Pro Ile Val Arg
    595                 600                 605

Gly Pro Cys Ile Ala Phe Phe Pro Arg Trp Ala Phe Asp Ala Val Lys
            610                 615                 620

Gly Lys Cys Val Leu Phe Pro Tyr Gly Gly Cys Gln Gly Asn Gly Asn
625                 630                 635                 640

Lys Phe Tyr Ser Glu Lys Glu Cys Arg Glu Tyr Cys Gly Val Pro
                645                 650                 655

<210> SEQ ID NO 62
<211> LENGTH: 207
<212> TYPE: DNA
<213> ORGANISM: Artificial Sequence
<220> FEATURE:
<223> OTHER INFORMATION: DNA sequence of the N-terminal BglII-BamHI
      DX-88
      cDNA

<400> SEQUENCE: 62
agatctttgg ataagagaga agctatgcac tctttctgtg ctttcaaggc tgacgacggt    60
ccgtgcagag ctgctcaccc aagatggttc ttcaacatct tcacgcgaca atgcgaggag   120
ttcatctacg gtggttgtga gggtaaccaa aacagattcg agtctctaga ggagtgtaag   180
aagatgtgta ctagagacgg tggatcc                                       207

<210> SEQ ID NO 63
<211> LENGTH: 1977
<212> TYPE: DNA
<213> ORGANISM: Artificial Sequence
<220> FEATURE:
<223> OTHER INFORMATION: DNA sequence of the N-terminal
      DX-88-(GGS)4GG-albumin fusion coding region

<400> SEQUENCE: 63
```

-continued

```
gaagctatgc actctttctg tgctttcaag gctgacgacg gtccgtgcag agctgctcac      60
ccaagatggt tcttcaacat cttcacgcga caatgcgagg agttcatcta cggtggttgt     120
gagggtaacc aaaacagatt cgagtctcta gaggagtgta agaagatgtg tactagagac     180
ggtggatccg gtggttccgg tggttctggt ggttccggtg gtgacgctca agtccgaa      240 gtcgctcacc ggtcaagga cctaggtgag gaaaacttca aggctttggt cttgatcgct     300
ttcgctcaat acttgcaaca atgtccattc gaagatcacg tcaagttggt caacgaagtt     360
accgaattcg ctaagacttg tgttgctgac gaatctgctg aaactgtga caagtccttg     420 cacaccttgt tcggtgataa gttgtgtact gttgctacct tgagagaaac ctacggtgaa     480
atggctgact gttgtgctaa gcaagaacca gaaagaaacg aatgtttctt gcaacacaag     540
gacgacaacc caaacttgcc aagattggtt agaccagaag ttgacgtcat gtgtactgct     600
ttccacgaca cgaagaaac cttcttgaag aagtacttgt acgaaattgc tagaagacac     660
ccatacttct acgctccaga attgttgttc ttcgctaaga gatacaaggc tgctttcacc     720
gaatgttgtc aagctgctga taaggctgct tgtttgttgc caaagttgga tgaattgaga     780
gacgaaggta aggcttcttc cgctaagcaa agattgaagt gtgcttcctt gcaaaagttc     840
ggtgaaagag ctttcaaggc ttgggctgtc gctagattgt ctcaaagatt cccaaaggct     900
gaattcgctg aagtttctaa gttggttact gacttgacta aggttcacac tgaatgttgt     960
cacggtgact tgttggaatg tgctgatgac agagctgact tggctaagta catctgtgaa    1020
aaccaagact ctatctcttc caagttgaag gaatgttgtg aaaagccatt gttggaaaag    1080
tctcactgta ttgctgaagt tgaaaacgat gaaatgccag ctgacttgcc atctttggct    1140
gctgacttcg ttgaatctaa ggacgtttgt aagaactacg ctgaagctaa ggacgtcttc    1200
ttgggtatgt tcttgtacga atacgctaga agacacccag actactccgt tgtcttgttg    1260
ttgagattgg ctaagaccta cgaaactacc ttggaaaagt gttgtgctgc tgctgaccca    1320
cacgaatgtt acgctaaggt tttcgatgaa ttcaagccat tggtcgaaga accacaaaac    1380
ttgatcaagc aaaactgtga attgttcgaa caattgggtg aatacaagtt ccaaaacgct    1440
ttgttggtta gatacactaa gaaggtccca caagtctcca ccccaacttt ggttgaagtc    1500
tctagaaact tgggtaaggt cggttctaag tgttgtaagc acccgaagc taagagaatg    1560 ccatgtgctg aagattactt gtccgtcgtt ttgaaccaat gtgtgttttt gcacgaaaag    1620 acccagtct ctgatagagt caccaagtgt tgtactgaat ctttggttaa cagaagacca    1680
tgtttctctg ctttggaagt cgacgaaact tacgttccaa aggaattcaa cgctgaaact    1740 ttcacccttcc acgctgatat ctgtaccttg tccgaaaagg aaagacaaat taagaagcaa    1800
actgctttgg ttgaattggt caagcacaag ccaaaggcta ctaaggaaca attgaaggct    1860
gtcatggatg atttcgctgc tttcgttgaa agtgttgta aggctgatga taaggaaact    1920
tgtttcgctg aagaaggtaa gaagttggtc gctgcttccc aagctgcttt gggtttg      1977
```

<210> SEQ ID NO 64
<211> LENGTH: 617
<212> TYPE: PRT
<213> ORGANISM: Artificial Sequence
<220> FEATURE:
<223> OTHER INFORMATION: Amino acid sequence of DX-88::HSA

<400> SEQUENCE: 64

Glu Ala Met His Ser Phe Cys Ala Phe Lys Ala Asp Asp Gly Pro Cys
1               5                   10                  15

-continued

```
Arg Ala Ala His Pro Arg Trp Phe Phe Asn Ile Phe Thr Arg Gln Cys
             20                  25                  30

Glu Glu Phe Ile Tyr Gly Gly Cys Glu Gly Asn Gln Asn Arg Phe Glu
             35                  40                  45

Ser Leu Glu Glu Cys Lys Lys Met Cys Thr Arg Asp Gly Gly Ser Gly
     50                  55                  60

Gly Ser Gly Gly Ser Gly Gly Ser Gly Gly Asp Ala His Lys Ser Glu
65                  70                  75                  80

Val Ala His Arg Phe Lys Asp Leu Gly Glu Glu Asn Phe Lys Ala Leu
                 85                  90                  95

Val Leu Ile Ala Phe Ala Gln Tyr Leu Gln Gln Cys Pro Phe Glu Asp
                100                 105                 110

His Val Lys Leu Val Asn Glu Val Thr Glu Phe Ala Lys Thr Cys Val
                115                 120                 125

Ala Asp Glu Ser Ala Glu Asn Cys Asp Lys Ser Leu His Thr Leu Phe
            130                 135                 140

Gly Asp Lys Leu Cys Thr Val Ala Thr Leu Arg Glu Thr Tyr Gly Glu
145                 150                 155                 160

Met Ala Asp Cys Cys Ala Lys Gln Glu Pro Glu Arg Asn Glu Cys Phe
                165                 170                 175

Leu Gln His Lys Asp Asp Asn Pro Asn Leu Pro Arg Leu Val Arg Pro
                180                 185                 190

Glu Val Asp Val Met Cys Thr Ala Phe His Asp Asn Glu Glu Thr Phe
            195                 200                 205

Leu Lys Lys Tyr Leu Tyr Glu Ile Ala Arg Arg His Pro Tyr Phe Tyr
    210                 215                 220

Ala Pro Glu Leu Leu Phe Phe Ala Lys Arg Tyr Lys Ala Ala Phe Thr
225                 230                 235                 240

Glu Cys Cys Gln Ala Ala Asp Lys Ala Ala Cys Leu Leu Pro Lys Leu
                245                 250                 255

Asp Glu Leu Arg Asp Glu Gly Lys Ala Ser Ser Ala Lys Gln Arg Leu
            260                 265                 270

Lys Cys Ala Ser Leu Gln Lys Phe Gly Glu Arg Ala Phe Lys Ala Trp
    275                 280                 285

Ala Val Ala Arg Leu Ser Gln Arg Phe Pro Lys Ala Glu Phe Ala Glu
            290                 295                 300

Val Ser Lys Leu Val Thr Asp Leu Thr Lys Val His Thr Glu Cys Cys
305                 310                 315                 320

His Gly Asp Leu Leu Glu Cys Ala Asp Asp Arg Ala Asp Leu Ala Lys
                325                 330                 335

Tyr Ile Cys Glu Asn Gln Asp Ser Ile Ser Ser Lys Leu Lys Glu Cys
            340                 345                 350

Cys Glu Lys Pro Leu Leu Glu Lys Ser His Cys Ile Ala Glu Val Glu
        355                 360                 365

Asn Asp Glu Met Pro Ala Asp Leu Pro Ser Leu Ala Ala Asp Phe Val
370                 375                 380

Glu Ser Lys Asp Val Cys Lys Asn Tyr Ala Glu Ala Lys Asp Val Phe
385                 390                 395                 400

Leu Gly Met Phe Leu Tyr Glu Tyr Ala Arg Arg His Pro Asp Tyr Ser
                405                 410                 415

Val Val Leu Leu Leu Arg Leu Ala Lys Thr Tyr Glu Thr Thr Leu Glu
            420                 425                 430
```

-continued

```
Lys Cys Cys Ala Ala Ala Asp Pro His Glu Cys Tyr Ala Lys Val Phe
        435                 440                 445

Asp Glu Phe Lys Pro Leu Val Glu Glu Pro Gln Asn Leu Ile Lys Gln
    450                 455                 460

Asn Cys Glu Leu Phe Glu Gln Leu Gly Tyr Lys Phe Gln Asn Ala
465                 470                 475                 480

Leu Leu Val Arg Tyr Thr Lys Lys Val Pro Gln Val Ser Thr Pro Thr
                485                 490                 495

Leu Val Glu Val Ser Arg Asn Leu Gly Lys Val Gly Ser Lys Cys Cys
            500                 505                 510

Lys His Pro Glu Ala Lys Arg Met Pro Cys Ala Glu Asp Tyr Leu Ser
        515                 520                 525

Val Val Leu Asn Gln Leu Cys Val Leu His Glu Lys Thr Pro Val Ser
    530                 535                 540

Asp Arg Val Thr Lys Cys Cys Thr Glu Ser Leu Val Asn Arg Arg Pro
545                 550                 555                 560

Cys Phe Ser Ala Leu Glu Val Asp Glu Thr Tyr Val Pro Lys Glu Phe
                565                 570                 575

Asn Ala Glu Thr Phe Thr Phe His Ala Asp Ile Cys Thr Leu Ser Glu
            580                 585                 590

Lys Glu Arg Gln Ile Lys Lys Gln Thr Ala Leu Val Glu Leu Val Lys
        595                 600                 605

His Lys Pro Lys Ala Thr Lys Glu His
    610                 615

<210> SEQ ID NO 65
<211> LENGTH: 202
<212> TYPE: DNA
<213> ORGANISM: Artificial Sequence
<220> FEATURE:
<223> OTHER INFORMATION: DNA sequence of the C-terminal BamHI-HindIII
      DX-88
      cDNA

<400> SEQUENCE: 65
ggatccggtg gtgaagctat gcactctttc tgtgctttca aggctgacga cggtccgtgc      60
agagctgctc acccaagatg gttcttcaac atcttcacgc gacaatgcga ggagttcatc     120
tacggtggtt gtgagggtaa ccaaaacaga ttcgagtctc tagaggagtg taagaagatg     180
tgtactagag actaataagc tt                                              202

<210> SEQ ID NO 66
<211> LENGTH: 1977
<212> TYPE: DNA
<213> ORGANISM: Artificial Sequence
<220> FEATURE:
<223> OTHER INFORMATION: HSA::(GGS)4GG::DX-88

<400> SEQUENCE: 66
gatgcacaca agagtgaggt tgctcatcgg tttaaagatt gggagaaga aatttcaaa       60 gccttggtgt tgattgcctt tgctcagtat cttcagcagt gtccatttga agatcatgta    120
aaattagtga atgaagtaac tgaatttgca aaaacatgtg ttgctgatga gtcagctgaa    180
aattgtgaca atcacttca tacccttttt ggagacaaat tatgcacagt tgcaactctt    240
cgtgaaacct atggtgaaat ggctgactgc tgtgcaaaac aagaacctga gaaatgaa    300 tgcttcttgc aacacaaaga tgacaaccca aacctccccc gattggtgag accagaggtt    360
gatgtgatgt gcactgcttt tcatgacaat gaagagacat ttttgaaaaa atacttatat    420
```

-continued

```
gaaattgcca agaagacatcc ttacttttat gccccggaac tccttttctt tgctaaaagg    480
tataaagctg cttttacaga atgttgccaa gctgctgata aagctgcctg cctgttgcca    540
aagctcgatg aacttcggga tgaagggaag gcttcgtctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg cttgaatgtg ctgatgacag ggcggacctt    780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc ctcagaattt aatcaaacaa aattgtgagc tttttgagca gcttggagag   1200
tacaaattcc agaatgcgct attagttcgt tacaccaaga aagtaccccca agtgtcaact   1260 ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg cttttcagct ctggaagtcg atgaaacata cgttcccaaa   1500
gagtttaatg ctgaaacatt caccttccat gcagatatat gcacactttc tgagaaggag   1560
agacaaatca gaaacaaac tgcacttgtt gagctcgtga acacaagcc caaggcaaca   1620 aaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
gctgccttag gcttaggtgg ttctggtggt tccggtggtt ctggtggatc cggtggtgaa   1800
gctatgcact ctttctgtgc tttcaaggct gacgacggtc cgtgcagagc tgctcaccca   1860
agatggttct tcaacatctt cacgcgacaa tgcgaggagt tcatctacgg tggttgtgag   1920
ggtaaccaaa acagattcga gtctctagag gagtgtaaga agatgtgtac tagagac      1977
```

<210> SEQ ID NO 67
<211> LENGTH: 659
<212> TYPE: PRT
<213> ORGANISM: Artificial Sequence
<220> FEATURE:
<223> OTHER INFORMATION: Amino acid sequence encoded by
      HSA::(GGS)4GG::DX-88

<400> SEQUENCE: 67

```
Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80
```

-continued

```
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
```

-continued

```
                500             505             510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
        530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Gly Gly Ser Gly Ser Gly
            580                 585                 590
Gly Ser Gly Gly Ser Gly Gly Glu Ala Met His Ser Phe Cys Ala Phe
        595                 600                 605
Lys Ala Asp Asp Gly Pro Cys Arg Ala Ala His Pro Arg Trp Phe Phe
    610                 615                 620
Asn Ile Phe Thr Arg Gln Cys Glu Glu Phe Ile Tyr Gly Gly Cys Glu
625                 630                 635                 640
Gly Asn Gln Asn Arg Phe Glu Ser Leu Glu Glu Cys Lys Lys Met Cys
                645                 650                 655
Thr Arg Asp
```

<210> SEQ ID NO 68
<211> LENGTH: 3087
<212> TYPE: DNA
<213> ORGANISM: Artificial Sequence
<220> FEATURE:
<223> OTHER INFORMATION: NotI cassette of pDB2300X1 with 2xGS linkers

<400> SEQUENCE: 68

```
gcggccgccc gtaatgcggt atcgtgaaag cgaaaaaaaa actaacagta gataagacag      60
atagacagat agagatggac gagaaacagg gggggagaaa aggggaaaag agaaggaaag     120
aaagactcat ctatcgcaga taagacaatc aaccctcatg gcgcctccaa ccaccatccg     180
cactagggac caagcgctcg caccgttagc aacgcttgac tcacaaacca actgccggct     240
gaaagagctt gtgcaatggg agtgccaatt caaggagcc gaatacgtct gctcgccttt      300
taagaggctt tttgaacact gcattgcacc cgacaaatca gccactaact acgaggtcac     360
ggacacatat accaatagtt aaaaattaca tatactctat atagcacagt agtgtgataa     420
ataaaaaatt ttgccaagac ttttttaaac tgcacccgac agatcaggtc tgtgcctact     480
atgcacttat gcccggggtc ccgggaggag aaaaaacgag ggctgggaaa tgtccgtgga     540
ctttaaacgc tccgggttag cagagtagca gggctttcgg cttttgaaat ttaggtgact     600
tgttgaaaaa gcaaaatttg ggctcagtaa tgccactgca gtggcttatc acgccaggac     660
tgcgggagtg gcggggcaa acacacccgc gataaagagc gcgatgaata taaaagggggg    720
ccaatgttac gtcccgttat attggagttc ttcccataca aacttaagag tccaattagc     780
ttcatcgcca ataaaaaaac aagcttaacc taattctaac aagcaaagat gaagtgggtt     840
ttcatcgtct ccatttttgtt cttgttctcc tctgcttact ctagatcttt ggataagaga     900
ggtggatccg gtggttccgg tggttctggt ggttccggtg gtgacgctca caagtccgaa     960
gtcgctcacc ggttcaagga cctaggtgag gaaaacttca aggctttggt cttgatcgct    1020
ttcgctcaat acttgcaaca atgtccattc gaagatcacg tcaagttggt caacgaagtt    1080
accgaattcg ctaagacttg tgttgctgac gaatctgctg aaaactgtga caagtccttg    1140
```

```
cacaccttgt tcggtgataa gttgtgtact gttgctacct tgagagaaac ctacggtgaa    1200
atggctgact gttgtgctaa gcaagaacca gaaagaaacg aatgtttctt gcaacacaag    1260
gacgacaacc caaacttgcc aagattggtt agaccagaag ttgacgtcat gtgtactgct    1320
ttccacgaca acgaagaaac cttcttgaag aagtacttgt acgaaattgc tagaagacac    1380
ccatacttct acgctccaga attgttgttc ttcgctaaga gatacaaggc tgctttcacc    1440
gaatgttgtc aagctgctga taaggctgct tgtttgttgc caaagttgga tgaattgaga    1500
gacgaaggta aggcttcttc cgctaagcaa agattgaagt gtgcttcctt gcaaaagttc    1560
ggtgaaagag ctttcaaggc ttgggctgtc gctagattgc tcaaagatt cccaaaggct    1620 gaattcgctg aagtttctaa gttggttact gacttgacta aggttcacac tgaatgttgt    1680
cacggtgact gttggaatg tgctgatgac agagctgact ggctaagta catctgtgaa    1740 aaccaagact ctatctcttc caagttgaag gaatgttgtg aaaagccatt gttggaaaag    1800
tctcactgta ttgctgaagt tgaaaacgat gaaatgccag ctgacttgcc atctttggct    1860
gctgacttcg ttgaatctaa ggacgtttgt aagaactacg ctgaagctaa ggacgtcttc    1920
ttgggtatgt tcttgtacga atacgctaga agacacccag actactccgt tgtcttgttg    1980
ttgagattgg ctaagaccta cgaaactacc ttggaaaagt gttgtgctgc tgctgaccca    2040
cacgaatgtt acgctaaggt tttcgatgaa ttcaagccat ggtcgaaga ccacaaaaac    2100 ttgatcaagc aaaactgtga attgttcgaa caattgggtg aatacaagtt ccaaaacgct    2160
ttgttggtta gatacactaa gaaggtccca caagtctcca ccccaacttt ggttgaagtc    2220
tctagaaact tgggtaaggt cggttctaag tgttgtaagc acccagaagc taagagaatg    2280
ccatgtgctg aagattactt gtccgtcgtt ttgaaccaat gtgtgttt gcacgaaaag    2340 accccagtct ctgatagagt caccaagtgt tgtactgaat ctttggttaa cagaagacca    2400
tgtttctctg ctttggaagt cgacgaaact tacgttccaa aggaattcaa cgctgaaact    2460
ttcaccttcc acgctgatat ctgtaccttg tccgaaaagg aaagacaaat taagaagcaa    2520
actgctttgg ttgaattggt caagcacaag ccaaaggcta ctaaggaaca attgaaggct    2580
gtcatggatg atttcgctgc tttcgttgaa agtgttgta aggctgatga taaggaaact    2640
tgtttcgctg aagaaggtaa gaagttggtc gctgcttccc aagctgcctt aggcttaggt    2700
ggttctggtg gttccggtgg ttccggaggt tccggtggta cctaataagc ttaattctta    2760
tgatttatga ttttttattat taaataagtt ataaaaaaaa taagtgtata caaatttttaa   2820 agtgactctt aggttttaaa acgaaaattc ttattcttga gtaactcttt cctgtaggtc    2880
aggttgcttt ctcaggtata gcatgaggtc gctcttattg accacacctc taccggcatg    2940
ccgagcaaat gcctgcaaat cgctcccat ttcacccaat gtagatatg ctaactccag    3000 caatgagttg atgaatctcg gtgtgtattt tatgtcctca gaggacaaca cctgttgtaa    3060
tcgttcttcc acacggatcg cggccgc                                       3087
```

<210> SEQ ID NO 69
<211> LENGTH: 638
<212> TYPE: PRT
<213> ORGANISM: Artificial Sequence
<220> FEATURE:
<223> OTHER INFORMATION: Amino acid sequence encoded by NotI cassette of pDB2300X1 with 2xGS linkers

<400> SEQUENCE: 69

```
        Met Lys Trp Val Phe Ile Val Ser Ile Leu Phe Leu Phe Ser Ser Ala
  1               5                  10                  15
```

```
Tyr Ser Arg Ser Leu Asp Lys Arg Gly Gly Ser Gly Gly
                20                  25                  30
Ser Gly Gly Ser Gly Gly Asp Ala His Lys Ser Glu Val Ala His Arg
         35                  40                  45
Phe Lys Asp Leu Gly Glu Glu Asn Phe Lys Ala Leu Val Leu Ile Ala
     50                  55                  60
Phe Ala Gln Tyr Leu Gln Gln Cys Pro Phe Glu Asp His Val Lys Leu
 65                  70                  75                  80
Val Asn Glu Val Thr Glu Phe Ala Lys Thr Cys Val Ala Asp Glu Ser
                 85                  90                  95
Ala Glu Asn Cys Asp Lys Ser Leu His Thr Leu Phe Gly Asp Lys Leu
            100                 105                 110
Cys Thr Val Ala Thr Leu Arg Glu Thr Tyr Gly Glu Met Ala Asp Cys
            115                 120                 125
Cys Ala Lys Gln Glu Pro Glu Arg Asn Glu Cys Phe Leu Gln His Lys
        130                 135                 140
Asp Asp Asn Pro Asn Leu Pro Arg Leu Val Arg Pro Glu Val Asp Val
145                 150                 155                 160
Met Cys Thr Ala Phe His Asp Asn Glu Glu Thr Phe Leu Lys Lys Tyr
                165                 170                 175
Leu Tyr Glu Ile Ala Arg Arg His Pro Tyr Phe Tyr Ala Pro Glu Leu
            180                 185                 190
Leu Phe Phe Ala Lys Arg Tyr Lys Ala Ala Phe Thr Glu Cys Cys Gln
            195                 200                 205
Ala Ala Asp Lys Ala Ala Cys Leu Leu Pro Lys Leu Asp Glu Leu Arg
        210                 215                 220
Asp Glu Gly Lys Ala Ser Ser Ala Lys Gln Arg Leu Lys Cys Ala Ser
225                 230                 235                 240
Leu Gln Lys Phe Gly Glu Arg Ala Phe Lys Ala Trp Ala Val Ala Arg
                245                 250                 255
Leu Ser Gln Arg Phe Pro Lys Ala Glu Phe Ala Glu Val Ser Lys Leu
            260                 265                 270
Val Thr Asp Leu Thr Lys Val His Thr Glu Cys Cys His Gly Asp Leu
            275                 280                 285
Leu Glu Cys Ala Asp Asp Arg Ala Asp Leu Ala Lys Tyr Ile Cys Glu
        290                 295                 300
Asn Gln Asp Ser Ile Ser Ser Lys Leu Lys Glu Cys Cys Glu Lys Pro
305                 310                 315                 320
Leu Leu Glu Lys Ser His Cys Ile Ala Glu Val Glu Asn Asp Glu Met
                325                 330                 335
Pro Ala Asp Leu Pro Ser Leu Ala Ala Asp Phe Val Glu Ser Lys Asp
            340                 345                 350
Val Cys Lys Asn Tyr Ala Glu Ala Lys Asp Val Phe Leu Gly Met Phe
            355                 360                 365
Leu Tyr Glu Tyr Ala Arg Arg His Pro Asp Tyr Ser Val Val Leu Leu
        370                 375                 380
Leu Arg Leu Ala Lys Thr Tyr Glu Thr Thr Leu Glu Lys Cys Cys Ala
385                 390                 395                 400
Ala Ala Asp Pro His Glu Cys Tyr Ala Lys Val Phe Asp Glu Phe Lys
                405                 410                 415
Pro Leu Val Glu Glu Pro Gln Asn Leu Ile Lys Gln Asn Cys Glu Leu
            420                 425                 430
Phe Glu Gln Leu Gly Glu Tyr Lys Phe Gln Asn Ala Leu Leu Val Arg
```

```
                435                 440                 445
Tyr Thr Lys Lys Val Pro Gln Val Ser Thr Pro Thr Leu Val Glu Val
        450                 455                 460
Ser Arg Asn Leu Gly Lys Val Gly Ser Lys Cys Cys Lys His Pro Glu
465                 470                 475                 480
Ala Lys Arg Met Pro Cys Ala Glu Asp Tyr Leu Ser Val Val Leu Asn
                485                 490                 495
Gln Leu Cys Val Leu His Glu Lys Thr Pro Val Ser Asp Arg Val Thr
        500                 505                 510
Lys Cys Cys Thr Glu Ser Leu Val Asn Arg Arg Pro Cys Phe Ser Ala
        515                 520                 525
Leu Glu Val Asp Glu Thr Tyr Val Pro Lys Glu Phe Asn Ala Glu Thr
        530                 535                 540
Phe Thr Phe His Ala Asp Ile Cys Thr Leu Ser Glu Lys Glu Arg Gln
545                 550                 555                 560
Ile Lys Lys Gln Thr Ala Leu Val Glu Leu Val Lys His Lys Pro Lys
                565                 570                 575
Ala Thr Lys Glu Gln Leu Lys Ala Val Met Asp Asp Phe Ala Ala Phe
                580                 585                 590
Val Glu Lys Cys Cys Lys Ala Asp Asp Lys Glu Thr Cys Phe Ala Glu
                595                 600                 605
Glu Gly Lys Lys Leu Val Ala Ala Ser Gln Ala Ala Leu Gly Leu Gly
        610                 615                 620
Gly Ser Gly Gly Ser Gly Gly Ser Gly Gly Ser Gly Gly Thr
625                 630                 635

<210> SEQ ID NO 70
<211> LENGTH: 3255
<212> TYPE: DNA
<213> ORGANISM: Artificial Sequence
<220> FEATURE:
<223> OTHER INFORMATION: NotI cassette of pDB2300X2 with DX890 (Nterm)
      and
      Cterm linker ready for second DX890

<400> SEQUENCE: 70
gcggccgccc gtaatgcggt atcgtgaaag cgaaaaaaaa actaacagta gataagacag      60
atagacagat agagatggac gagaaacagg gggggagaaa agggggaaag agaaggaaag     120
aaagactcat ctatcgcaga taagacaatc aaccctcatg gcgcctccaa ccaccatccg     180
cactagggac caagcgctcg caccgttagc aacgcttgac tcacaaacca actgccggct     240
gaaagagctt gtgcaatggg agtgccaatt caaggagcc gaatacgtct gctcgccttt     300
taagaggctt tttgaacact gcattgcacc cgacaaatca gccactaact acgaggtcac     360
ggacacatat accaatagtt aaaaattaca tatactctat atagcacagt agtgtgataa     420
ataaaaaatt ttgccaagac ttttttaaac tgcacccgac agatcaggtc tgtgcctact     480
atgcacttat gcccgggtc ccgggaggag aaaaaacgag ggctgggaaa tgtccgtgga     540 cttaaacgc tccgggttag cagagtagca gggctttcgg ctttggaaat ttaggtgact     600
tgttgaaaaa gcaaaatttg ggctcagtaa tgccactgca gtggcttatc acgccaggac     660
tgcgggagtg gcgggggcaa acacacccgc gataaagagc gcgatgaata taaaaggggg     720
ccaatgttac gtcccgttat attggagttc ttcccataca aacttaagag tccaattagc     780
ttcatcgcca ataaaaaaac aagcttaacc taattctaac aagcaaagat gaagtgggtt     840
```

-continued

| | |
|---|---|
| ttcatcgtct ccattttgtt cttgttctcc tctgcttact ctagatcttt ggataagaga | 900 |
| gaagcctgta acttgccaat tgttagaggt ccatgtattg ctttcttccc aagatgggct | 960 |
| ttcgatgctg ttaagggtaa gtgtgttttg ttcccatatg gtggttgtca aggtaacggt | 1020 |
| aacaagttct actctgaaaa ggaatgtaga gaatactgtg gtgttccagg tggatccggt | 1080 |
| ggttccggtg gttctggtgg ttccggtggt gacgctcaca agtccgaagt cgctcaccgg | 1140 |
| ttcaaggacc taggtgagga aaacttcaag gctttggtct tgatcgcttt cgctcaatac | 1200 |
| ttgcaacaat gtccattcga agatcacgtc aagttggtca acgaagttac cgaattcgct | 1260 |
| aagacttgtg ttgctgacga atctgctgaa aactgtgaca agtccttgca caccttgttc | 1320 |
| ggtgataagt tgtgtactgt tgctaccttg agagaaacct acggtgaaat ggctgactgt | 1380 |
| tgtgctaagc aagaaccaga aagaaacgaa tgtttcttgc aacacaagga cgacaaccca | 1440 |
| aacttgccaa gattggttag accagaagtt gacgtcatgt gtactgcttt ccacgacaac | 1500 |
| gaagaaacct tcttgaagaa gtacttgtac gaaattgcta aagacaccc atacttctac | 1560 |
| gctccagaat tgttgttctt cgctaagaga tacaaggctg ctttcaccga atgttgtcaa | 1620 |
| gctgctgata aggctgcttg tttgttgcca aagttggatg aattgagaga cgaaggtaag | 1680 |
| gcttcttccg ctaagcaaag attgaagtgt gcttccttgc aaaagttcgg tgaaagagct | 1740 |
| ttcaaggctt gggctgtcgc tagattgtct caaagattcc caaaggctga attcgctgaa | 1800 |
| gtttctaagt tggttactga cttgactaag gttcacactg aatgttgtca cggtgacttg | 1860 |
| ttggaatgtg ctgatgacag agctgacttg gctaagtaca tctgtgaaaa ccaagactct | 1920 |
| atctcttcca gttgaagga atgttgtgaa aagccattgt tggaaaagtc tcactgtatt | 1980 |
| gctgaagttg aaaacgatga aatgccagct gacttgccat cttggctgc tgacttcgtt | 2040 |
| gaatctaagg acgtttgtaa gaactacgct gaagctaagg acgtcttctt gggtatgttc | 2100 |
| ttgtacgaat acgctagaag acacccgac tactccgttg tcttgttgtt gagattggct | 2160 |
| aagacctacg aaaactacctt ggaaaagtgt tgtgctgctg ctgacccaca cgaatgttac | 2220 |
| gctaaggttt tcgatgaatt caagccattg gtcgaagaac cacaaaactt gatcaagcaa | 2280 |
| aactgtgaat tgttcgaaca attgggtgaa tacaagttcc aaaacgcttt gttggttaga | 2340 |
| tacactaaga aggtcccaca agtctccacc ccaactttgg ttgaagtctc tagaaacttg | 2400 |
| ggtaaggtcg gttctaagtg ttgtaagcac ccagaagcta agagaatgcc atgtgctgaa | 2460 |
| gattacttgt ccgtcgtttt gaaccaattg tgtgttttgc acgaaaagac cccagtctct | 2520 |
| gatagagtca ccaagtgttg tactgaatct ttggttaaca gaagaccatg tttctctgct | 2580 |
| ttggaagtcg acgaaactta cgttccaaag gaattcaacg ctgaaacttt caccttccac | 2640 |
| gctgatatct gtaccttgtc cgaaaaggaa agacaaatta gaagcaaac tgctttggtt | 2700 |
| gaattggtca agcacaagcc aaaggctact aaggaacaat tgaaggctgt catggatgat | 2760 |
| ttcgctgctt tcgttgaaaa gtgttgtaag gctgatgata ggaaacttg tttcgctgaa | 2820 |
| gaaggtaaga agttggtcgc tgcttcccaa gctgccttag gcttaggtgg ttctggtggt | 2880 |
| tccggtggtt ccggaggttc cggtggtacc taataagctt aattcttatg atttatgatt | 2940 |
| tttattatta aataagttat aaaaaaaata agtgtataca aattttaaag tgactcttag | 3000 |
| gttttaaaac gaaattcttt attcttgagt aactctttcc tgtaggtcag gttgctttct | 3060 |
| caggtatagc atgaggtcgc tcttattgac cacacctcta ccggcatgcc gagcaaatgc | 3120 |
| ctgcaaatcg ctccccatt cacccaattg tagatatgct aactccagca atgagttgat | 3180 |
| gaatctcggt gtgtatttta tgtcctcaga ggacaacacc tgttgtaatc gttcttccac | 3240 |

```
acggatcgcg gccgc                                              3255
```

<210> SEQ ID NO 71
<211> LENGTH: 694
<212> TYPE: PRT
<213> ORGANISM: Artificial Sequence
<220> FEATURE:
<223> OTHER INFORMATION: Amino acid sequence encoded by NotI cassette of
      pDB2300X2 with DX890 (Nterm) and Cterm linker
      ready for second DX890

<400> SEQUENCE: 71

```
Met Lys Trp Val Phe Ile Val Ser Ile Leu Phe Leu Phe Ser Ser Ala
1               5                   10                  15

Tyr Ser Arg Ser Leu Asp Lys Arg Glu Ala Cys Asn Leu Pro Ile Val
            20                  25                  30

Arg Gly Pro Cys Ile Ala Phe Phe Pro Arg Trp Ala Phe Asp Ala Val
        35                  40                  45

Lys Gly Lys Cys Val Leu Phe Pro Tyr Gly Gly Cys Gln Gly Asn Gly
    50                  55                  60

Asn Lys Phe Tyr Ser Glu Lys Glu Cys Arg Glu Tyr Cys Gly Val Pro
65                  70                  75                  80

Gly Gly Ser Gly Gly Ser Gly Gly Ser Gly Gly Ser Gly Gly Asp Ala
                85                  90                  95

His Lys Ser Glu Val Ala His Arg Phe Lys Asp Leu Gly Glu Glu Asn
            100                 105                 110

Phe Lys Ala Leu Val Leu Ile Ala Phe Ala Gln Tyr Leu Gln Gln Cys
        115                 120                 125

Pro Phe Glu Asp His Val Lys Leu Val Asn Glu Val Thr Glu Phe Ala
    130                 135                 140

Lys Thr Cys Val Ala Asp Glu Ser Ala Glu Asn Cys Asp Lys Ser Leu
145                 150                 155                 160

His Thr Leu Phe Gly Asp Lys Leu Cys Thr Val Ala Thr Leu Arg Glu
                165                 170                 175

Thr Tyr Gly Glu Met Ala Asp Cys Cys Ala Lys Gln Glu Pro Glu Arg
            180                 185                 190

Asn Glu Cys Phe Leu Gln His Lys Asp Asp Asn Pro Asn Leu Pro Arg
        195                 200                 205

Leu Val Arg Pro Glu Val Asp Val Met Cys Thr Ala Phe His Asp Asn
    210                 215                 220

Glu Glu Thr Phe Leu Lys Lys Tyr Leu Tyr Glu Ile Ala Arg Arg His
225                 230                 235                 240

Pro Tyr Phe Tyr Ala Pro Glu Leu Leu Phe Phe Ala Lys Arg Tyr Lys
                245                 250                 255

Ala Ala Phe Thr Glu Cys Cys Gln Ala Ala Asp Lys Ala Ala Cys Leu
            260                 265                 270

Leu Pro Lys Leu Asp Glu Leu Arg Asp Glu Gly Lys Ala Ser Ser Ala
        275                 280                 285

Lys Gln Arg Leu Lys Cys Ala Ser Leu Gln Lys Phe Gly Glu Arg Ala
    290                 295                 300

Phe Lys Ala Trp Ala Val Ala Arg Leu Ser Gln Arg Phe Pro Lys Ala
305                 310                 315                 320

Glu Phe Ala Glu Val Ser Lys Leu Val Thr Asp Leu Thr Lys Val His
                325                 330                 335

Thr Glu Cys Cys His Gly Asp Leu Leu Glu Cys Ala Asp Asp Arg Ala
```

340                 345                 350
Asp Leu Ala Lys Tyr Ile Cys Glu Asn Gln Asp Ser Ile Ser Ser Lys
            355                 360                 365

Leu Lys Glu Cys Cys Glu Lys Pro Leu Leu Glu Lys Ser His Cys Ile
        370                 375                 380

Ala Glu Val Glu Asn Asp Glu Met Pro Ala Asp Leu Pro Ser Leu Ala
385                 390                 395                 400

Ala Asp Phe Val Glu Ser Lys Asp Val Cys Lys Asn Tyr Ala Glu Ala
                    405                 410                 415

Lys Asp Val Phe Leu Gly Met Phe Leu Tyr Glu Tyr Ala Arg Arg His
                420                 425                 430

Pro Asp Tyr Ser Val Val Leu Leu Arg Leu Ala Lys Thr Tyr Glu
            435                 440                 445

Thr Thr Leu Glu Lys Cys Cys Ala Ala Ala Asp Pro His Glu Cys Tyr
        450                 455                 460

Ala Lys Val Phe Asp Glu Phe Lys Pro Leu Val Glu Glu Pro Gln Asn
465                 470                 475                 480

Leu Ile Lys Gln Asn Cys Glu Leu Phe Glu Gln Leu Gly Glu Tyr Lys
                    485                 490                 495

Phe Gln Asn Ala Leu Leu Val Arg Tyr Thr Lys Lys Val Pro Gln Val
                500                 505                 510

Ser Thr Pro Thr Leu Val Glu Val Ser Arg Asn Leu Gly Lys Val Gly
            515                 520                 525

Ser Lys Cys Cys Lys His Pro Glu Ala Lys Arg Met Pro Cys Ala Glu
        530                 535                 540

Asp Tyr Leu Ser Val Val Leu Asn Gln Leu Cys Val Leu His Glu Lys
545                 550                 555                 560

Thr Pro Val Ser Asp Arg Val Thr Lys Cys Cys Thr Glu Ser Leu Val
                    565                 570                 575

Asn Arg Arg Pro Cys Phe Ser Ala Leu Glu Val Asp Glu Thr Tyr Val
                580                 585                 590

Pro Lys Glu Phe Asn Ala Glu Thr Phe Thr Phe His Ala Asp Ile Cys
            595                 600                 605

Thr Leu Ser Glu Lys Glu Arg Gln Ile Lys Lys Gln Thr Ala Leu Val
        610                 615                 620

Glu Leu Val Lys His Lys Pro Lys Ala Thr Lys Glu Gln Leu Lys Ala
625                 630                 635                 640

Val Met Asp Asp Phe Ala Ala Phe Val Glu Lys Cys Cys Lys Ala Asp
                    645                 650                 655

Asp Lys Glu Thr Cys Phe Ala Glu Gly Lys Lys Leu Val Ala Ala
                660                 665                 670

Ser Gln Ala Ala Leu Gly Leu Gly Gly Ser Gly Ser Gly Gly Ser
            675                 680                 685

Gly Gly Ser Gly Gly Thr
        690

<210> SEQ ID NO 72
<211> LENGTH: 207
<212> TYPE: DNA
<213> ORGANISM: Artificial Sequence
<220> FEATURE:
<223> OTHER INFORMATION: DNA to insert at BspEI/KpnI site for 2nd
      encoding
      of DX-890

<400> SEQUENCE: 72

-continued

```
tccggaggta gtggtggctc cggtggtgag gcttgcaatc ttcctatcgt ccgtggccct      60
tgcatcgcct ttttcctcg ttgggccttt gacgccgtca aaggcaaatg cgtccttttt     120
ccttacggcg gttgccaggg caatggcaat aaattttata gcgagaaaga gtgccgtgag    180
tattgcggcg tcccttaata aggtacc                                         207
```

<210> SEQ ID NO 73
<211> LENGTH: 3440
<212> TYPE: DNA
<213> ORGANISM: Artificial Sequence
<220> FEATURE:
<223> OTHER INFORMATION: DNA sequence of NotI cassette of pDB2300X3 with 2
      x DX-890

<400> SEQUENCE: 73

```
gcggccgccc gtaatgcggt atcgtgaaag cgaaaaaaaa actaacagta gataagacag      60
atagacagat agagatggac gagaaacagg gggggagaaa aggggaaaag agaaggaaag    120
aaagactcat ctatcgcaga taagacaatc aaccctcatg cgcctccaa ccaccatccg     180 cactagggac caagcgctcg caccgttagc aacgcttgac tcacaaacca actgccggct    240
gaaagagctt gtgcaatggg agtgccaatt caaaggagcc gaatacgtct gctcgccttt    300
taagaggctt tttgaacact gcattgcacc cgacaaatca gccactaact acgaggtcac    360
ggacacatat accaatagtt aaaaattaca tatactctat atagcacagt agtgtgataa    420
ataaaaaatt ttgccaagac ttttttaaac tgcacccgac agatcaggtc tgtgcctact    480
atgcacttat gcccggggtc ccggaggag aaaaaacgag ggctgggaaa tgtccgtgga    540
cttaaaacgc tccgggttag cagagtagca gggcttcgg ctttggaaat ttaggtgact    600
tgttgaaaaa gcaaaatttg ggctcagtaa tgccactgca gtggcttatc acgccaggac    660
tgcgggagtg gcggggcaa acacacccgc gataaagagc gcgatgaata taaaagggg     720 ccaatgttac gtcccgttat attggagttc ttcccataca aacttaagag tccaattagc    780
ttcatcgcca ataaaaaaac aagcttaacc taattctaac aagcaaagat gaagtgggtt    840
ttcatcgtct ccattttgtt cttgttctcc tctgcttact ctagatcttt ggataagaga    900
gaagcctgta acttgccaat tgttagaggt ccatgtattg ctttcttccc aagatgggct    960
ttcgatgctg ttaagggtaa gtgtgttttg ttcccatatg gtggttgtca aggtaacggt   1020
aacaagttct actctgaaaa ggaatgtaga gaatactgtg gtgttccagg tggatccggt   1080
ggttccggtg gttctggtgg ttccggtggt gacgctcaca gtccgaagt cgctcaccgg   1140 ttcaaggacc taggtgagga aaacttcaag gctttggtct tgatcgcttt cgctcaatac   1200
ttgcaacaat gtccattcga agatcacgtc aagttggtca acgaagttac cgaattcgct   1260
aagacttgtg ttgctgacga atctgctgaa actgtgaca agtccttgca caccttgttc   1320
ggtgataagt tgtgtactgt tgctaccttg agagaaacct acggtgaaat ggctgactgt   1380
tgtgctaagc aagaaccaga agaaacgaa tgtttcttgc aacacaagga cgacaaccca   1440
aacttgccaa gattggttag accagaagtt gacgtcatgt gtactgcttt ccacgacaac   1500
gaagaaacct tcttgaagaa gtacttgtac gaaattgcta aagacacccc atacttctac   1560
gctccagaat tgttgttctt cgctaagaga tacaaggctg ctttcaccga atgttgtcaa   1620
gctgctgata aggctgcttg ttttgttgcca agttggatg aattgagaga cgaaggtaag   1680
gcttcttccg ctaagcaaag attgaagtgt gcttccttgc aaaagttcgg tgaaagagct   1740
```

-continued

```
ttcaaggctt gggctgtcgc tagattgtct caaagattcc caaaggctga attcgctgaa     1800
gtttctaagt tggttactga cttgactaag gttcacactg aatgttgtca cggtgacttg     1860
ttggaatgtg ctgatgacag agctgacttg gctaagtaca tctgtgaaaa ccaagactct     1920
atctcttcca agttgaagga atgttgtgaa aagccattgt tggaaaagtc tcactgtatt     1980
gctgaagttg aaaacgatga aatgccagct gacttgccat cttttggctgc tgacttcgtt     2040 gaatctaagg acgtttgtaa gaactacgct gaagctaagg acgtcttctt gggtatgttc     2100
ttgtacgaat acgctagaag acacccagac tactccgttg tcttgttgtt gagattggct     2160
aagacctacg aaactacctt ggaaaagtgt tgtgctgctg ctgacccaca cgaatgttac     2220
gctaaggttt tcgatgaatt caagccattg gtcgaagaac cacaaaactt gatcaagcaa     2280
aactgtgaat tgttcgaaca attgggtgaa tacaagttcc aaaacgcttt gttggttaga     2340
tacactaaga aggtcccaca agtctccacc ccaactttgg ttgaagtctc tagaaacttg     2400
ggtaaggtcg ttctaagtg ttgtaagcac ccagaagcta agagaatgcc atgtgctgaa     2460
gattacttgt ccgtcgtttt gaaccaattg tgtgttttgc acgaaaagac cccagtctct     2520
gatagagtca ccaagtgttg tactgaatct ttggttaaca gaagaccatg tttctctgct     2580
ttggaagtcg acgaaactta cgttccaaag gaattcaacg ctgaaacttt caccttccac     2640
gctgatatct gtaccttgtc cgaaaaggaa agacaaatta gaagcaaac tgctttggtt     2700 gaattggtca agcacaagcc aaaggctact aaggaacaat gaaggctgt catggatgat     2760 ttcgctgctt tcgttgaaaa gtgttgtaag gctgatgata aggaaacttg tttcgctgaa     2820
gaaggtaaga agttggtcgc tgcttcccaa gctgccttag gcttaggtgg ttctggtggt     2880
tccggtggtt ccggaggtag tggtggctcc ggtggtgagg cttgcaatct tcctatcgtc     2940 cgtggcccttt gcatcgcctt ttttcctcgt tgggcctttg acgccgtcaa aggcaaatgc     3000 gtccttttc cttacggcgg ttgccagggc aatggcaata aatttatag cgagaaagag     3060 tgccgtgagt attgcggcgt cccttaataa ggtacctaat aagcttaatt cttatgatt     3120 atgattttta ttattaaata agttataaaa aaataagtg tatacaaatt ttaaaggact     3180
cttaggtttt aaaacgaaaa ttcttattct tgagtaactc tttcctgtag gtcaggttgc     3240
tttctcaggt atagcatgag gtcgctctta ttgaccacac ctctaccggc atgccgagca     3300
aatgcctgca aatcgctccc catttcaccc aattgtagat atgctaactc cagcaatgag     3360
ttgatgaatc tcggtgtgta ttttatgtcc tcagaggaca cacctgttg taatcgttct     3420 tccacacgga tcgcggccgc                                                 3440
```

<210> SEQ ID NO 74
<211> LENGTH: 752
<212> TYPE: PRT
<213> ORGANISM: Artificial Sequence
<220> FEATURE:
<223> OTHER INFORMATION: Amino acid sequence of NotI cassette of
    pDB2300X3
    with 2 x DX-890

<400> SEQUENCE: 74

```
Met Lys Trp Val Phe Ile Val Ser Ile Leu Phe Leu Phe Ser Ser Ala
  1               5                  10                  15

Tyr Ser Arg Ser Leu Asp Lys Arg Glu Ala Cys Asn Leu Pro Ile Val
                 20                  25                  30

Arg Gly Pro Cys Ile Ala Phe Phe Pro Arg Trp Ala Phe Asp Ala Val
             35                  40                  45
```

-continued

```
Lys Gly Lys Cys Val Leu Phe Pro Tyr Gly Gly Cys Gln Gly Asn Gly
 50                  55                  60

Asn Lys Phe Tyr Ser Glu Lys Glu Cys Arg Glu Tyr Cys Gly Val Pro
 65                  70                  75                  80

Gly Gly Ser Gly Gly Ser Gly Gly Ser Gly Gly Ser Gly Gly Asp Ala
                 85                  90                  95

His Lys Ser Glu Val Ala His Arg Phe Lys Asp Leu Gly Glu Glu Asn
                100                 105                 110

Phe Lys Ala Leu Val Leu Ile Ala Phe Ala Gln Tyr Leu Gln Gln Cys
                115                 120                 125

Pro Phe Glu Asp His Val Lys Leu Val Asn Glu Val Thr Glu Phe Ala
    130                 135                 140

Lys Thr Cys Val Ala Asp Glu Ser Ala Glu Asn Cys Asp Lys Ser Leu
145                 150                 155                 160

His Thr Leu Phe Gly Asp Lys Leu Cys Thr Val Ala Thr Leu Arg Glu
                165                 170                 175

Thr Tyr Gly Glu Met Ala Asp Cys Cys Ala Lys Gln Glu Pro Glu Arg
                180                 185                 190

Asn Glu Cys Phe Leu Gln His Lys Asp Asp Asn Pro Asn Leu Pro Arg
            195                 200                 205

Leu Val Arg Pro Glu Val Asp Val Met Cys Thr Ala Phe His Asp Asn
    210                 215                 220

Glu Glu Thr Phe Leu Lys Lys Tyr Leu Tyr Glu Ile Ala Arg Arg His
225                 230                 235                 240

Pro Tyr Phe Tyr Ala Pro Glu Leu Leu Phe Phe Ala Lys Arg Tyr Lys
                245                 250                 255

Ala Ala Phe Thr Glu Cys Cys Gln Ala Ala Asp Lys Ala Ala Cys Leu
                260                 265                 270

Leu Pro Lys Leu Asp Glu Leu Arg Asp Glu Gly Lys Ala Ser Ser Ala
            275                 280                 285

Lys Gln Arg Leu Lys Cys Ala Ser Leu Gln Lys Phe Gly Glu Arg Ala
    290                 295                 300

Phe Lys Ala Trp Ala Val Ala Arg Leu Ser Gln Arg Phe Pro Lys Ala
305                 310                 315                 320

Glu Phe Ala Glu Val Ser Lys Leu Val Thr Asp Leu Thr Lys Val His
                325                 330                 335

Thr Glu Cys Cys His Gly Asp Leu Leu Glu Cys Ala Asp Asp Arg Ala
                340                 345                 350

Asp Leu Ala Lys Tyr Ile Cys Glu Asn Gln Asp Ser Ile Ser Ser Lys
            355                 360                 365

Leu Lys Glu Cys Cys Glu Lys Pro Leu Leu Glu Lys Ser His Cys Ile
    370                 375                 380

Ala Glu Val Glu Asn Asp Glu Met Pro Ala Asp Leu Pro Ser Leu Ala
385                 390                 395                 400

Ala Asp Phe Val Glu Ser Lys Asp Val Cys Lys Asn Tyr Ala Glu Ala
                405                 410                 415

Lys Asp Val Phe Leu Gly Met Phe Leu Tyr Glu Tyr Ala Arg Arg His
                420                 425                 430

Pro Asp Tyr Ser Val Val Leu Leu Leu Arg Leu Ala Lys Thr Tyr Glu
            435                 440                 445

Thr Thr Leu Glu Lys Cys Cys Ala Ala Ala Asp Pro His Glu Cys Tyr
    450                 455                 460

Ala Lys Val Phe Asp Glu Phe Lys Pro Leu Val Glu Glu Pro Gln Asn
```

-continued

```
                465                 470                 475                 480
Leu Ile Lys Gln Asn Cys Glu Leu Phe Glu Gln Leu Gly Glu Tyr Lys
                    485                 490                 495
Phe Gln Asn Ala Leu Leu Val Arg Tyr Thr Lys Lys Val Pro Gln Val
                500                 505                 510
Ser Thr Pro Thr Leu Val Glu Val Ser Arg Asn Leu Gly Lys Val Gly
            515                 520                 525
Ser Lys Cys Cys Lys His Pro Glu Ala Lys Arg Met Pro Cys Ala Glu
        530                 535                 540
Asp Tyr Leu Ser Val Val Leu Asn Gln Leu Cys Val Leu His Glu Lys
545                 550                 555                 560
Thr Pro Val Ser Asp Arg Val Thr Lys Cys Cys Thr Glu Ser Leu Val
                565                 570                 575
Asn Arg Arg Pro Cys Phe Ser Ala Leu Glu Val Asp Glu Thr Tyr Val
            580                 585                 590
Pro Lys Glu Phe Asn Ala Glu Thr Phe Thr Phe His Ala Asp Ile Cys
        595                 600                 605
Thr Leu Ser Glu Lys Glu Arg Gln Ile Lys Lys Gln Thr Ala Leu Val
    610                 615                 620
Glu Leu Val Lys His Lys Pro Lys Ala Thr Lys Glu Gln Leu Lys Ala
625                 630                 635                 640
Val Met Asp Asp Phe Ala Ala Phe Val Glu Lys Cys Cys Lys Ala Asp
                645                 650                 655
Asp Lys Glu Thr Cys Phe Ala Glu Glu Gly Lys Lys Leu Val Ala Ala
            660                 665                 670
Ser Gln Ala Ala Leu Gly Leu Gly Gly Ser Gly Gly Ser Gly Gly Ser
        675                 680                 685
Gly Gly Ser Gly Gly Ser Gly Gly Glu Ala Cys Asn Leu Pro Ile Val
    690                 695                 700
Arg Gly Pro Cys Ile Ala Phe Phe Pro Arg Trp Ala Phe Asp Ala Val
705                 710                 715                 720
Lys Gly Lys Cys Val Leu Phe Pro Tyr Gly Gly Cys Gln Gly Asn Gly
                725                 730                 735
Asn Lys Phe Tyr Ser Glu Lys Glu Cys Arg Glu Tyr Cys Gly Val Pro
            740                 745                 750

<210> SEQ ID NO 75
<211> LENGTH: 728
<212> TYPE: PRT
<213> ORGANISM: Artificial Sequence
<220> FEATURE:
<223> OTHER INFORMATION: Amino acid sequence of
      DX-890::(GGS)4GG::HA::(GGS)4GG::DX890

<400> SEQUENCE: 75

Glu Ala Cys Asn Leu Pro Ile Val Arg Gly Pro Cys Ile Ala Phe Phe
1               5                   10                  15
Pro Arg Trp Ala Phe Asp Ala Val Lys Gly Lys Cys Val Leu Phe Pro
            20                  25                  30
Tyr Gly Gly Cys Gln Gly Asn Gly Asn Lys Phe Tyr Ser Glu Lys Glu
        35                  40                  45
Cys Arg Glu Tyr Cys Gly Val Pro Gly Ser Gly Gly Ser Gly Gly
    50                  55                  60
Ser Gly Gly Ser Gly Gly Asp Ala His Lys Ser Glu Val Ala His Arg
65                  70                  75                  80
```

-continued

Phe Lys Asp Leu Gly Glu Glu Asn Phe Lys Ala Leu Val Leu Ile Ala
                85                  90                  95

Phe Ala Gln Tyr Leu Gln Gln Cys Pro Phe Glu Asp His Val Lys Leu
            100                 105                 110

Val Asn Glu Val Thr Glu Phe Ala Lys Thr Cys Val Ala Asp Glu Ser
            115                 120                 125

Ala Glu Asn Cys Asp Lys Ser Leu His Thr Leu Phe Gly Asp Lys Leu
130                 135                 140

Cys Thr Val Ala Thr Leu Arg Glu Thr Tyr Gly Glu Met Ala Asp Cys
145                 150                 155                 160

Cys Ala Lys Gln Glu Pro Glu Arg Asn Glu Cys Phe Leu Gln His Lys
                165                 170                 175

Asp Asp Asn Pro Asn Leu Pro Arg Leu Val Arg Pro Glu Val Asp Val
            180                 185                 190

Met Cys Thr Ala Phe His Asp Asn Glu Glu Thr Phe Leu Lys Lys Tyr
            195                 200                 205

Leu Tyr Glu Ile Ala Arg Arg His Pro Tyr Phe Tyr Ala Pro Glu Leu
        210                 215                 220

Leu Phe Phe Ala Lys Arg Tyr Lys Ala Ala Phe Thr Glu Cys Cys Gln
225                 230                 235                 240

Ala Ala Asp Lys Ala Ala Cys Leu Leu Pro Lys Leu Asp Glu Leu Arg
                245                 250                 255

Asp Glu Gly Lys Ala Ser Ser Ala Lys Gln Arg Leu Lys Cys Ala Ser
            260                 265                 270

Leu Gln Lys Phe Gly Glu Arg Ala Phe Lys Ala Trp Ala Val Ala Arg
        275                 280                 285

Leu Ser Gln Arg Phe Pro Lys Ala Glu Phe Ala Glu Val Ser Lys Leu
        290                 295                 300

Val Thr Asp Leu Thr Lys Val His Thr Glu Cys Cys His Gly Asp Leu
305                 310                 315                 320

Leu Glu Cys Ala Asp Asp Arg Ala Asp Leu Ala Lys Tyr Ile Cys Glu
                325                 330                 335

Asn Gln Asp Ser Ile Ser Ser Lys Leu Lys Glu Cys Cys Glu Lys Pro
            340                 345                 350

Leu Leu Glu Lys Ser His Cys Ile Ala Glu Val Glu Asn Asp Glu Met
        355                 360                 365

Pro Ala Asp Leu Pro Ser Leu Ala Ala Asp Phe Val Glu Ser Lys Asp
        370                 375                 380

Val Cys Lys Asn Tyr Ala Glu Ala Lys Asp Val Phe Leu Gly Met Phe
385                 390                 395                 400

Leu Tyr Glu Tyr Ala Arg Arg His Pro Asp Tyr Ser Val Val Leu Leu
                405                 410                 415

Leu Arg Leu Ala Lys Thr Tyr Glu Thr Thr Leu Glu Lys Cys Cys Ala
            420                 425                 430

Ala Ala Asp Pro His Glu Cys Tyr Ala Lys Val Phe Asp Glu Phe Lys
        435                 440                 445

Pro Leu Val Glu Glu Pro Gln Asn Leu Ile Lys Gln Asn Cys Glu Leu
        450                 455                 460

Phe Glu Gln Leu Gly Glu Tyr Lys Phe Gln Asn Ala Leu Leu Val Arg
465                 470                 475                 480

Tyr Thr Lys Lys Val Pro Gln Val Ser Thr Pro Thr Leu Val Glu Val
                485                 490                 495

Ser Arg Asn Leu Gly Lys Val Gly Ser Lys Cys Cys Lys His Pro Glu

```
                          500                 505                 510
Ala Lys Arg Met Pro Cys Ala Glu Asp Tyr Leu Ser Val Val Leu Asn
            515                 520                 525

Gln Leu Cys Val Leu His Glu Lys Thr Pro Val Ser Asp Arg Val Thr
        530                 535                 540

Lys Cys Cys Thr Glu Ser Leu Val Asn Arg Arg Pro Cys Phe Ser Ala
545                 550                 555                 560

Leu Glu Val Asp Glu Thr Tyr Val Pro Lys Glu Phe Asn Ala Glu Thr
                565                 570                 575

Phe Thr Phe His Ala Asp Ile Cys Thr Leu Ser Glu Lys Glu Arg Gln
            580                 585                 590

Ile Lys Lys Gln Thr Ala Leu Val Glu Leu Val Lys His Lys Pro Lys
        595                 600                 605

Ala Thr Lys Glu Gln Leu Lys Ala Val Met Asp Asp Phe Ala Ala Phe
610                 615                 620

Val Glu Lys Cys Cys Lys Ala Asp Asp Lys Glu Thr Cys Phe Ala Glu
625                 630                 635                 640

Glu Gly Lys Lys Leu Val Ala Ala Ser Gln Ala Ala Leu Gly Leu Gly
                645                 650                 655

Gly Ser Gly Gly Ser Gly Gly Ser Gly Gly Ser Gly Gly Ser Gly Gly
            660                 665                 670

Glu Ala Cys Asn Leu Pro Ile Val Arg Gly Pro Cys Ile Ala Phe Phe
        675                 680                 685

Pro Arg Trp Ala Phe Asp Ala Val Lys Gly Lys Cys Val Leu Phe Pro
        690                 695                 700

Tyr Gly Gly Cys Gln Gly Asn Gly Asn Lys Phe Tyr Ser Glu Lys Glu
705                 710                 715                 720

Cys Arg Glu Tyr Cys Gly Val Pro
                725
```

<210> SEQ ID NO 76
<211> LENGTH: 204
<212> TYPE: DNA
<213> ORGANISM: Artificial Sequence
<220> FEATURE:
<223> OTHER INFORMATION: DNA sequence of the N-terminal BglII-BamHI
      DX-1000
      cDNA

<400> SEQUENCE: 76

```
agatctttgg ataagagaga ggctatgcat tccttctgcg ccttcaaggc tgagactggt      60
ccttgtagag ctaggttcga ccgttggttc ttcaacatct tcacgcgtca gtgcgaggaa    120
ttcatttacg gtggttgtga aggtaaccag aaccggttcg aatctctaga ggaatgtaag    180
aagatgtgca ctcgtgacgg atcc                                            204
```

<210> SEQ ID NO 77
<211> LENGTH: 617
<212> TYPE: PRT
<213> ORGANISM: Artificial Sequence
<220> FEATURE:
<223> OTHER INFORMATION: Amino acid sequence of DX-1000::(GGS)4GG::HA

<400> SEQUENCE: 77

```
Glu Ala Met His Ser Phe Cys Ala Phe Lys Ala Glu Thr Gly Pro Cys
1               5                   10                  15

Arg Ala Arg Phe Asp Arg Trp Phe Phe Asn Ile Phe Thr Arg Gln Cys
            20                  25                  30
```

```
Glu Glu Phe Ile Tyr Gly Gly Cys Glu Gly Asn Gln Asn Arg Phe Glu
                35                  40                  45
Ser Leu Glu Glu Cys Lys Lys Met Cys Thr Arg Asp Gly Gly Ser Gly
 50                  55                  60
Gly Ser Gly Gly Ser Gly Ser Gly Gly Asp Ala His Lys Ser Glu
 65                  70                  75                  80
Val Ala His Arg Phe Lys Asp Leu Gly Glu Glu Asn Phe Lys Ala Leu
                85                  90                  95
Val Leu Ile Ala Phe Ala Gln Tyr Leu Gln Gln Cys Pro Phe Glu Asp
                100                 105                 110
His Val Lys Leu Val Asn Glu Val Thr Glu Phe Ala Lys Thr Cys Val
                115                 120                 125
Ala Asp Glu Ser Ala Glu Asn Cys Asp Lys Ser Leu His Thr Leu Phe
 130                 135                 140
Gly Asp Lys Leu Cys Thr Val Ala Thr Leu Arg Glu Thr Tyr Gly Glu
 145                 150                 155                 160
Met Ala Asp Cys Cys Ala Lys Gln Glu Pro Glu Arg Asn Glu Cys Phe
                165                 170                 175
Leu Gln His Lys Asp Asp Asn Pro Asn Leu Pro Arg Leu Val Arg Pro
                180                 185                 190
Glu Val Asp Val Met Cys Thr Ala Phe His Asp Asn Glu Glu Thr Phe
                195                 200                 205
Leu Lys Lys Tyr Leu Tyr Glu Ile Ala Arg Arg His Pro Tyr Phe Tyr
                210                 215                 220
Ala Pro Glu Leu Leu Phe Phe Ala Lys Arg Tyr Lys Ala Ala Phe Thr
 225                 230                 235                 240
Glu Cys Cys Gln Ala Ala Asp Lys Ala Ala Cys Leu Leu Pro Lys Leu
                245                 250                 255
Asp Glu Leu Arg Asp Glu Gly Lys Ala Ser Ser Ala Lys Gln Arg Leu
                260                 265                 270
Lys Cys Ala Ser Leu Gln Lys Phe Gly Glu Arg Ala Phe Lys Ala Trp
                275                 280                 285
Ala Val Ala Arg Leu Ser Gln Arg Phe Pro Lys Ala Glu Phe Ala Glu
 290                 295                 300
Val Ser Lys Leu Val Thr Asp Leu Thr Lys Val His Thr Glu Cys Cys
 305                 310                 315                 320
His Gly Asp Leu Leu Glu Cys Ala Asp Asp Arg Ala Asp Leu Ala Lys
                325                 330                 335
Tyr Ile Cys Glu Asn Gln Asp Ser Ile Ser Ser Lys Leu Lys Glu Cys
                340                 345                 350
Cys Glu Lys Pro Leu Leu Glu Lys Ser His Cys Ile Ala Glu Val Glu
                355                 360                 365
Asn Asp Glu Met Pro Ala Asp Leu Pro Ser Leu Ala Ala Asp Phe Val
                370                 375                 380
Glu Ser Lys Asp Val Cys Lys Asn Tyr Ala Glu Ala Lys Asp Val Phe
 385                 390                 395                 400
Leu Gly Met Phe Leu Tyr Glu Tyr Ala Arg Arg His Pro Asp Tyr Ser
                405                 410                 415
Val Val Leu Leu Leu Arg Leu Ala Lys Thr Tyr Glu Thr Thr Leu Glu
                420                 425                 430
Lys Cys Cys Ala Ala Ala Asp Pro His Glu Cys Tyr Ala Lys Val Phe
 435                 440                 445
```

Asp Glu Phe Lys Pro Leu Val Glu Pro Gln Asn Leu Ile Lys Gln
             450                 455                 460

Asn Cys Glu Leu Phe Glu Gln Leu Gly Glu Tyr Lys Phe Gln Asn Ala
465                 470                 475                 480

Leu Leu Val Arg Tyr Thr Lys Lys Val Pro Gln Val Ser Thr Pro Thr
                485                 490                 495

Leu Val Glu Val Ser Arg Asn Leu Gly Lys Val Gly Ser Lys Cys Cys
            500                 505                 510

Lys His Pro Glu Ala Lys Arg Met Pro Cys Ala Glu Asp Tyr Leu Ser
        515                 520                 525

Val Val Leu Asn Gln Leu Cys Val Leu His Glu Lys Thr Pro Val Ser
    530                 535                 540

Asp Arg Val Thr Lys Cys Cys Thr Glu Ser Leu Val Asn Arg Arg Pro
545                 550                 555                 560

Cys Phe Ser Ala Leu Glu Val Asp Glu Thr Tyr Val Pro Lys Glu Phe
                565                 570                 575

Asn Ala Glu Thr Phe Thr Phe His Ala Asp Ile Cys Thr Leu Ser Glu
            580                 585                 590

Lys Glu Arg Gln Ile Lys Lys Gln Thr Ala Leu Val Glu Leu Val Lys
        595                 600                 605

His Lys Pro Lys Ala Thr Lys Glu His
    610                 615

<210> SEQ ID NO 78
<211> LENGTH: 222
<212> TYPE: DNA
<213> ORGANISM: Artificial Sequence
<220> FEATURE:
<223> OTHER INFORMATION: DNA sequence of N-terminal BspEI-KpnI DX-88
      cDNA-2nd encoding

<400> SEQUENCE: 78
tccggaggta gtggtggctc cggtggtgag gccatgcatt ctttctgtgc tttcaaggct        60
gacgacggtc cgtgcagagc tgctcaccca agatggttct tcaacatctt cacgcgacaa       120
tgcgaggagt tcatctacgg tggttgtgag ggtaaccaaa acagattcga gtctctagag       180
gagtgtaaga gatgtgtac tagagacggt taataaggta cc                           222

<210> SEQ ID NO 79
<211> LENGTH: 617
<212> TYPE: PRT
<213> ORGANISM: Artificial Sequence
<220> FEATURE:
<223> OTHER INFORMATION: Amino acid sequence of DPI14::HSA

<400> SEQUENCE: 79

Glu Ala Val Arg Glu Val Cys Ser Glu Gln Ala Glu Thr Gly Pro Cys
1               5                  10                  15

Ile Ala Phe Phe Pro Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Gly Gly Ser Gly
        50                  55                  60

Gly Ser Gly Gly Ser Gly Gly Ser Gly Gly Asp Ala His Lys Ser Glu
65                  70                  75                  80

Val Ala His Arg Phe Lys Asp Leu Gly Glu Glu Asn Phe Lys Ala Leu
                85                  90                  95

-continued

Val Leu Ile Ala Phe Ala Gln Tyr Leu Gln Gln Cys Pro Phe Glu Asp
            100                 105                 110

His Val Lys Leu Val Asn Glu Val Thr Glu Phe Ala Lys Thr Cys Val
            115                 120                 125

Ala Asp Glu Ser Ala Glu Asn Cys Asp Lys Ser Leu His Thr Leu Phe
            130                 135                 140

Gly Asp Lys Leu Cys Thr Val Ala Thr Leu Arg Glu Thr Tyr Gly Glu
145                 150                 155                 160

Met Ala Asp Cys Cys Ala Lys Gln Glu Pro Glu Arg Asn Glu Cys Phe
                165                 170                 175

Leu Gln His Lys Asp Asp Asn Pro Asn Leu Pro Arg Leu Val Arg Pro
            180                 185                 190

Glu Val Asp Val Met Cys Thr Ala Phe His Asp Asn Glu Glu Thr Phe
            195                 200                 205

Leu Lys Lys Tyr Leu Tyr Glu Ile Ala Arg Arg His Pro Tyr Phe Tyr
            210                 215                 220

Ala Pro Glu Leu Leu Phe Phe Ala Lys Arg Tyr Lys Ala Ala Phe Thr
225                 230                 235                 240

Glu Cys Cys Gln Ala Ala Asp Lys Ala Ala Cys Leu Leu Pro Lys Leu
                245                 250                 255

Asp Glu Leu Arg Asp Glu Gly Lys Ala Ser Ser Ala Lys Gln Arg Leu
            260                 265                 270

Lys Cys Ala Ser Leu Gln Lys Phe Gly Glu Arg Ala Phe Lys Ala Trp
            275                 280                 285

Ala Val Ala Arg Leu Ser Gln Arg Phe Pro Lys Ala Glu Phe Ala Glu
            290                 295                 300

Val Ser Lys Leu Val Thr Asp Leu Thr Lys Val His Thr Glu Cys Cys
305                 310                 315                 320

His Gly Asp Leu Leu Glu Cys Ala Asp Asp Arg Ala Asp Leu Ala Lys
                325                 330                 335

Tyr Ile Cys Glu Asn Gln Asp Ser Ile Ser Ser Lys Leu Lys Glu Cys
            340                 345                 350

Cys Glu Lys Pro Leu Leu Glu Lys Ser His Cys Ile Ala Glu Val Glu
            355                 360                 365

Asn Asp Glu Met Pro Ala Asp Leu Pro Ser Leu Ala Ala Asp Phe Val
            370                 375                 380

Glu Ser Lys Asp Val Cys Lys Asn Tyr Ala Glu Ala Lys Asp Val Phe
385                 390                 395                 400

Leu Gly Met Phe Leu Tyr Glu Tyr Ala Arg Arg His Pro Asp Tyr Ser
                405                 410                 415

Val Val Leu Leu Leu Arg Leu Ala Lys Thr Tyr Glu Thr Thr Leu Glu
            420                 425                 430

Lys Cys Cys Ala Ala Ala Asp Pro His Glu Cys Tyr Ala Lys Val Phe
            435                 440                 445

Asp Glu Phe Lys Pro Leu Val Glu Glu Pro Gln Asn Leu Ile Lys Gln
    450                 455                 460

Asn Cys Glu Leu Phe Glu Gln Leu Gly Glu Tyr Lys Phe Gln Asn Ala
465                 470                 475                 480

Leu Leu Val Arg Tyr Thr Lys Lys Val Pro Gln Val Ser Thr Pro Thr
                485                 490                 495

Leu Val Glu Val Ser Arg Asn Leu Gly Lys Val Gly Ser Lys Cys Cys
            500                 505                 510

```
Lys His Pro Glu Ala Lys Arg Met Pro Cys Ala Glu Asp Tyr Leu Ser
        515                 520                 525

Val Val Leu Asn Gln Leu Cys Val Leu His Glu Lys Thr Pro Val Ser
        530                 535                 540

Asp Arg Val Thr Lys Cys Cys Thr Glu Ser Leu Val Asn Arg Arg Pro
545                 550                 555                 560

Cys Phe Ser Ala Leu Glu Val Asp Glu Thr Tyr Val Pro Lys Glu Phe
                565                 570                 575

Asn Ala Glu Thr Phe Thr Phe His Ala Asp Ile Cys Thr Leu Ser Glu
            580                 585                 590

Lys Glu Arg Gln Ile Lys Lys Gln Thr Ala Leu Val Glu Leu Val Lys
        595                 600                 605

His Lys Pro Lys Ala Thr Lys Glu His
    610                 615

<210> SEQ ID NO 80
<211> LENGTH: 12
<212> TYPE: DNA
<213> ORGANISM: Artificial Sequence
<220> FEATURE:
<223> OTHER INFORMATION: Illustrative oligonucleotide
<220> FEATURE:
<221> NAME/KEY: misc_feature
<222> LOCATION: 4, 5, 6, 7, 8, 9
<223> OTHER INFORMATION: n = A,T,C or G

<400> SEQUENCE: 80
gcannnnnnt cg                                                         12

<210> SEQ ID NO 81
<211> LENGTH: 11
<212> TYPE: DNA
<213> ORGANISM: Artificial Sequence
<220> FEATURE:
<223> OTHER INFORMATION: Illustrative oligonucleotide
<220> FEATURE:
<221> NAME/KEY: misc_feature
<222> LOCATION: 4, 5, 6, 7, 8
<223> OTHER INFORMATION: n = A,T,C or G

<400> SEQUENCE: 81
ccannnnntg g                                                          11

<210> SEQ ID NO 82
<211> LENGTH: 10
<212> TYPE: DNA
<213> ORGANISM: Artificial Sequence
<220> FEATURE:
<223> OTHER INFORMATION: Illustrative oligonucleotide
<220> FEATURE:
<221> NAME/KEY: misc_feature
<222> LOCATION: 7, 8, 9, 10
<223> OTHER INFORMATION: n = A,T,C or G

<400> SEQUENCE: 82 ctcttcnnnn                                                            10

<210> SEQ ID NO 83
<211> LENGTH: 15
<212> TYPE: DNA
<213> ORGANISM: Artificial Sequence
<220> FEATURE:
<223> OTHER INFORMATION: Illustrative oligonucleotide
<220> FEATURE:
<221> NAME/KEY: misc_feature
<222> LOCATION: 4, 5, 6, 7, 8, 9, 10, 11, 12
```

-continued

```
<223> OTHER INFORMATION: n = A,T,C or G

<400> SEQUENCE: 83
ccannnnnnn nntgg                                              15

<210> SEQ ID NO 84
<211> LENGTH: 10
<212> TYPE: DNA
<213> ORGANISM: Artificial Sequence
<220> FEATURE:
<223> OTHER INFORMATION: Illustrative oligonucleotide
<220> FEATURE:
<221> NAME/KEY: misc_feature
<222> LOCATION: 4, 5, 6, 7
<223> OTHER INFORMATION: n = A,T,C or G

<400> SEQUENCE: 84 gacnnnngtc                                                    10
```

KUNITZ DOMAIN PEPTIDES

FIELD OF THE INVENTION

The invention relates to the fields of Kunitz domain peptides and albumin fusion proteins. More specifically, the invention relates to Kunitz domain peptides and albumin fusion proteins for treating, preventing, or ameliorating a disease or disorder.

BACKGROUND OF THE INVENTION

A Kunitz domain is a folding domain of approximately 51–64 residues which forms a central anti-parallel beta sheet and a short C-terminal helix (see e.g., U.S. Pat. No. 6,087,473, which is hereby incorporated by reference in its entirety). This characteristic domain comprises six cysteine residues that form three disulfide bonds, resulting in a double-loop structure. Between the N-terminal region and the first beta strand resides the active inhibitory binding loop. This binding loop is disulfide bonded through the P2 $C_{14}$ residue to the hairpin loop formed between the last two beta strands. Isolated Kunitz domains from a variety of proteinase inhibitors have been shown to have inhibitory activity (e.g., Petersen et al., Eur. J. Biochem. 125:310–316, 1996; Wagner et al., Biochem. Biophys. Res. Comm. 186:1138–1145, 1992; Dennis et al., J. Biol. Chem. 270:25411–25417, 1995).

Linked Kunitz domains also have been shown to have inhibitory activity, as discussed, for example, in U.S. Pat. No. 6,087,473. Proteinase inhibitors comprising one or more Kunitz domains include tissue factor pathway inhibitor (TFPI), tissue factor pathway inhibitor 2 (TFPI-2), amyloid β-protein precursor (AβPP), aprotinin, and placental bikunin. TFPI, an extrinsic pathway inhibitor and a natural anticoagulant, contains three tandemly linked Kunitz inhibitor domains. The amino-terminal Kunitz domain inhibits factor VIIa, plasmin, and cathepsin G; the second domain inhibits factor Xa, trypsin, and chymotrypsin; and the third domain has no known activity (Petersen et al., ibid.).

The inhibitory activity of Kunitz domain peptides towards serine proteases has been demonstrated in several previous studies. The following subsections discuss studies of the inhibition of serine proteases, such as plasma kallikrein, plasmin, and neutrophil elastase by Kunitz Domain peptides.

Plasma Kallikrein Inhibitors

Kallikreins are serine proteases found in both tissues and plasma [see, for example, U.S. Pat. No. 6,333,402 to Markland, which is hereby incorporated by reference in its entirety]. Plasma kallikrein is involved in contact-activated (intrinsic pathway) coagulation, fibrinolysis, hypotension, and inflammation [See Bhoola, K. D., C. D. Figueroa, and K. Worthy, Pharmacological Reviews (1992) 44(1)1–80]. These effects of kallikrein are mediated through the activities of three distinct physiological substrates:

i) Factor XII (coagulation),
ii) Pro-urokinase/plasminogen (fibrinolysis), and
iii) Kininogens (hypotension and inflammation).

Kallikrein cleavage of kininogens results in the production of kinins, small highly potent bioactive peptides. The kinins act through cell surface receptors, designated BK-1 and BK-2, present on a variety of cell types including endothelia, epithelia, smooth muscle, neural, glandular and hematopoietic. Intracellular heterotrimeric G-proteins link the kinin receptors to second messenger pathways including nitric oxide, adenyl cyclase, phospholipase $A_2$ and phospholipase C. Among the significant physiological activities of kinins are: (i) increased vascular permeability; (ii) vasodilation; (iii) bronchospasm; and (iv) pain induction. Thus, kinins mediate the life-threatening vascular shock and edema associated with bacteremia (sepsis) or trauma, the edema and airway hyperreactivity of asthma, and both inflammatory and neurogenic pain associated with tissue injury. The consequences of inappropriate plasma kallikrein activity and resultant kinin production are dramatically illustrated in patients with hereditary angioedema (HAE). HAE is due to a genetic deficiency of C1-inhibitor, the principal endogenous inhibitor of plasma kallikrein. Symptoms of HAE include edema of the skin, subcutaneous tissues and gastrointestinal tract, and abdominal pain and vomiting. Nearly one-third of HAE patients die by suffocation due to edema of the larynx and upper respiratory tract. Kallikrein is secreted as a zymogen (prekallikrein) that circulates as an inactive molecule until activated by a proteolytic event. [Genebank entry P03952 shows Human Plasma Prekallikrein.]

An important inhibitor of plasma kallikrein (pKA) in vivo is the C1 inhibitor; (see Schmaier, et al. in "Contact Activation and Its Abnormalities", Chapter 2 in Hemostasis and Thrombosis, Colman, R W, J Hirsh, V J Marder, and E W Salzman, Editors, Second Edition, 1987, J. B. Lippincott Company, Philadelphia, Pa., pp.27–28). C1 is a serpin and forms an irreversible or nearly irreversible complex with pKA. Although bovine pancreatic trypsin inhibitor (also known as BPTI, aprotinin, or Trasylol™) was initially thought to be a strong pKA inhibitor with $K_i$=320 pM [Auerswald, E.-A., D. Hoerlein, G. Reinhardt, W. Schroder, and E. Schnabel, Bio. Chem. Hoppe-Seyler, (1988), 369 (Supplement):27–35], a more recent report [Berndt, et al., Biochemistry, 32:4564–70, 1993] indicates that its $K_i$ for plasma Kallikrein is 30 nM (i.e., 30,000 pM). The G36S mutant had a $K_i$ of over 500 nM.

Markland et al. [U.S. Pat. Nos. 6,333,402; 5,994,125; 6,057,287; and 5,795,865; each reference hereby incorporated by reference in its entirety] claim a number of derivatives having high affinity and specificity in inhibiting human plasma kallikrein. One of these proteins is being tested in human patients who have HAE. Although early indications are that the compound is safe and effective, the duration of effect is shorter than desired.

Plasmin Inhibitors

Plasmin is a serine protease derived from plasminogen. The catalytic domain of plasmin (or "CatDom") cuts peptide bonds, particularly after arginine residues and to a lesser extent after lysines and is highly homologous to trypsin, chymotrypsin, kallikrein, and many other serine proteases. Most of the specificity of plasmin derives from the kringles' binding of fibrin (Lucas et al., J Biological Chem (1983) 258(7)4249–56.; Varadi & Patthy, Biochemistry (1983) 22:2440–2446.; and Varadi & Patthy, Biochemistry (1984) 23:2108–2112.). On activation, the bond between $ARG_{561}$–$Val_{562}$ is cut, allowing the newly free amino terminus to form a salt bridge. The kringles remain, nevertheless, attached to the CatDom through two disulfides (Colman, R W, J Hirsh, V J Marder, and E W Salzman, Editors, Hemostasis and Thrombosis, Second Edition, 1987, J. B. Lippincott Company, Philadelphia, Pa., Bobbins, 1987, supra.

The agent mainly responsible for fibrinolysis is plasmin the activated form of plasminogen. Many substances can activate plasminogen, including activated Hageman factor, streptokinase, urokinase (uPA), tissue-type plasminogen activator (tPA), and plasma kallikrein (pKA). pKA is both an activator of the zymogen form of urokinase and a direct plasminogen activator.

Plasmin is undetectable in normal circulating blood, but plasminogen, the zymogen, is present at about 3 $\mu$M. An additional, unmeasured amount of plasminogen is bound to fibrin and other components of the extracellular matrix and cell surfaces. Normal blood contains the physiological inhibitor of plasmin, $\alpha_2$-plasmin inhibitor ($\alpha_2$-PI), at about 2 $\mu$M. Plasmin and $\alpha_2$-PI form a 1:1 complex. Matrix or cell bound-plasmin is relatively inaccessible to inhibition by $\alpha_2$-PI. Thus, activation of plasmin can exceed the neutralizing capacity of $\alpha_2$-PI causing a profibrinolytic state.

Plasmin, once formed:
i) degrades fibrin clots, sometimes prematurely;
ii) digests fibrinogen (the building material of clots) impairing hemostasis by causing formation of friable, easily lysed clots from the degradation products, and inhibition of platelet adhesion/aggregation by the fibrinogen degradation products;
iii) interacts directly with platelets to cleave glycoproteins Ib and IIb/IIIa preventing adhesion to injured endothelium in areas of high shear blood flow and impairing the aggregation response needed for platelet plug formation (Adelman et al., Blood (1986) 68(6)1280–1284.);
iv) proteolytically inactivates enzymes in the extrinsic coagulation pathway further promoting a prolytic state. Robbins (Robbins, Chapter 21 of Hemostasis and Thrombosis, Colman, R. W., J. Hirsh, V. J. Marder, and E. W. Salzman, Editors, Second Edition, 1987, J. B. Lippincott Company, Philadelphia, Pa.) reviewed the plasminogen-plasmin system in detail. This publication (i.e., Colman, R. W., J Hirsh, V. J. Marder, and E. W. Salzman, Editors, Hemostasis and Thrombosis, Second Edition, 1987, J. B. Lippincott Company, Philadelphia, Pa.) is hereby incorporated by reference.

Fibrinolysis and Fibrinogenolysis

Inappropriate fibrinolysis and fibrinogenolysis leading to excessive bleeding is a frequent complication of surgical procedures that require extracorporeal circulation, such as cardiopulmonary bypass, and is also encountered in thrombolytic therapy and organ transplantation, particularly liver. Other clinical conditions characterized by high incidence of bleeding diathesis include liver cirrhosis, amyloidosis, acute promyelocytic leukemia, and solid tumors. Restoration of hemostasis requires infusion of plasma and/or plasma products, which risks immunological reaction and exposure to pathogens, e.g. hepatitis virus and HIV.

Very high blood loss can resist resolution even with massive infusion. When judged life-threatening, the hemorrhage is treated with antifibrinolytics such as c-amino caproic acid (See Hoover et al., Biochemistry (1993) 32:10936–43) (EACA), tranexarnic acid, or aprotinin (Neuhaus et al., Lancet (1989) 2(8668)924–5). EACA and tranexamic acid only prevent plasmin from binding fibrin by binding the kringles, thus leaving plasmin as a free protease in plasma. BPTI is a direct inhibitor of plasmin and is the most effective of these agents. Due to the potential for thrombotic complications, renal toxicity and, in the case of BPTI, immmunogenicity, these agents are used with caution and usually reserved as a "last resort" (Putterman, Acta Chir Scand (1989) 155(6–7)367). All three of the antifibrinolytic agents lack target specificity and affinity and interact with tissues and organs through uncharacterized metabolic pathways. The large doses required due to low affinity, side effects due to lack of specificity and potential for immune reaction and organ/tissue toxicity augment against use of these antifibrinolytics prophylactically to prevent bleeding or as a routine postoperative therapy to avoid or reduce transfusion therapy. Thus, there is a need for a safe antifibrinolytic. The essential attributes of such an agent are:

i) Neutralization of relevant target fibrinolytic enzyme(s);
ii) High affinity binding to target enzymes to minimize dose;
iii) High specificity for target, to reduce side effects; and
iv) High degree of similarity to human protein to minimize potential immunogenicity and organ/tissue toxicity.

All of the fibrinolytic enzymes that are candidate targets for inhibition by an efficacious antifibrinolytic are chymotrypin-homologous serine proteases.

Excessive Bleeding

Excessive bleeding can result from deficient coagulation activity, elevated fibrinolytic activity, or a combination of the two conditions. In most bleeding diatheses one must control the activity of plasmin. The clinically beneficial effect of BPTI in reducing blood loss is thought to result from its inhibition of plasmin ($K_i$~0.3 nM) or of plasma kallikrein ($K_i$~100 nM) or both enzymes.

Gardell [Toxicol. Pathol. (1993) 21(2)190–8] has reviewed currently-used thrombolytics, and has stated that, although thrombolytic agents (e.g. tPA) do open blood vessels, excessive bleeding is a serious safety issue. Although tPA and streptokinase have short plasma half lives, the plasmin they activate remains in the system for a long time and, as stated, the system is potentially deficient in plasmin inhibitors. Thus, excessive activation of plasminogen can lead to a dangerous inability to clot and injurious or fatal hemorrhage. A potent, highly specific plasmin inhibitor would be useful in such cases.

BPTI is a potent plasmin inhibitor. However, it has been found that it is sufficiently antigenic that second uses require skin testing. Furthermore, the doses of BPTI required to control bleeding are quite high and the mechanism of action is not clear. Some say that BPTI acts on plasmin while others say that it acts by inhibiting plasma kallikrein. Fraedrich et al. [Thorac Cardiovasc Surg (1989) 37(2)89–91] report that doses of about 840 mg of BPTI to 80 open-heart surgery patients reduced blood loss by almost half and the mean amount transfused was decreased by 74%. Miles Inc. has recently introduced Trasylol™ in the U.S. for reduction of bleeding in surgery [see Miles product brochure on Trasylol™, which is hereby incorporated by reference]. Lohmann and Marshal [Refract Corneal Surg (1993) 9(4) 300–2] suggest that plasmin inhibitors may be useful in controlling bleeding in surgery of the eye. Sheridan et al. [Dis Colon Rectum (1989) 32(6)505–8] reports that BPTI may be useful in limiting bleeding in colonic surgery.

A plasmin inhibitor that is approximately as potent as BPTI or more potent but that is almost identical to a human protein domain offers similar therapeutic potential but poses less potential for antigenicity.

Angiogenesis:

Plasmin is the key enzyme in angiogenesis. O'Reilly et al. [Cell (1994) 79:315–328] reports that a 38 kDa fragment of plasmin (lacking the catalytic domain) is a potent inhibitor of metastasis, indicating that inhibition of plasmin could be useful in blocking metastasis of tumors [Fidler & Ellis, Cell (1994) 79:185–188; See also Ellis et al., Ann NY Acad Sci (1992) 667:13–31; O'Reilly et al., Fidler & Ellis, and Ellis et al. are hereby incorporated by reference].

Neutrophil Elastase Inhibition

Cystic Fibrosis is a hereditary, autosomal recessive disorder affecting pulmonary, gastrointestinal, and reproductive systems. With a prevalence of 80,000 worldwide, the incidence of CF is estimated at 1 in 3500 [Cystic Fibrosis Foundation, *Patient Registry* 1998 *Annual Data Report*, Bethesda, Md., September 1999]. The genetic defect in CF was described in 1989 as the loss of a single phenylalanine at position 508 (ΔF508), resulting in a faulty cystic fibrosis transmembrane conductance regulator protein (CFTR) which inhibits the reabsorption of Cl⁻ (and hence Na⁺ and water) [Rommens, J. M., et al., "Identification of the cystic fibrosis gene: chromosome walking and jumping," *Science* 245:1059, 1989; Riordan, J. R., et al., "Identification of the cystic fibrosis gene: cloning and complementary DNA," *Science* 245:1066, 1989; Kerem, B., et al., "Identification of the cystic fibrosis gene: genetic analysis, *Science* 245:1073, 1989]. Mutations other than ΔF508 have been found in CFTR and may cause CF. Desiccated mucus then plugs many of the passageways in the respiratory, gastrointestinal, and reproductive systems.

More than 75% of the mortality from CF is due to respiratory complications [Cystic Fibrosis Foundation, *Patient Registry* 1998 *Annual Data Report*, Bethesda, Md., September 1999]. Although disease of the pancreas, liver, and intestine is present in CF individuals before birth, the CF lung is normal at birth and until the onset of infection and inflammation. Then, defective Cl⁻ reabsorption in the CF lung leads to desiccated airway secretions by drawing sodium out of the airways, with water following passively. Desiccated secretions may then interfere with mucociliary clearance by trapping bacteria in an environment well suited to colonization with distinctive microbial pathogens [Reynolds, H. Y., et al., "Mucoid *Pseudomonas aeruginosa*: a sign of cystic fibrosis in young adults with chronic pulmonary disease," *J.A.M.A.* 236:2190, 1976]. The ensuing lung infection and inflammation recruits and activates neutrophils which release neutrophil elastase (NE). The neutrophil-dominated inflammation on the respiratory epithelial surface results in a chronic epithelial burden of neutrophil elastase. Endogenous antiprotease is rapidly overwhelmed by an excess of NE in the CF lung. In addition, NE stimulates the production of pro-inflammatory mediators and cleaves complement receptors and IgG, thereby crippling host defense mechanisms preventing further bacterial colonization [Tosi, M. F., et al., "Neutrophil elastase cleaves C3bi on opsonized Pseudomonas as well as CR1 on neutrophils to create a functionally important opsonin receptor mismatch," *J. Clin. Invest.* 86:300, 1990]. The infection thereby becomes persistent, and the massive ongoing inflammation and excessive levels of NE destroy the airway epithelium, leading to bronchiectasis, and the progressive loss of pulmonary function and death.

One therapeutic approach in patients with CF is the eradication of CF pathogens by systemic antimicrobials such as tobramycin and ciprofloxin. While these specific antimicrobial agents have been shown to be effective in clearing infection and improving pulmonary function, antibiotic resistance to tobramycin and ciprofloxin is reported in 7.5% and 9.6% of CF patients respectively [Cystic Fibrosis Foundation, *Patient Registry* 1998 *Annual Data Report*, Bethesda, Md., September 1999]. As the use of these antimicrobials for CF increases in patients of whom 60% are infected with *P. aeruginosa* and 41% with *S. aureus*, drug resistance selection pressure has increased.

Pulmonary function also has been a therapeutic target in patients with CF. Pulmozyme® (domase alfa), a recombinant human deoxyribonuclease which reduces mucus viscoelasticity by hydrolyzing DNA in sputum, has been shown in clinical studies to increase $FEV_1$ and FVC after 8 days of treatment. This change last for six months, and is accompanied by a reduction in the use of intravenous antibiotics [Fuchs, H. L., et al., "Effect of aerosolized recombinant human Dnase on exacerbations of respiratory symptoms and on pulmonary function in patients with cystic fibrosis," *N. Engl. J. Med.,* 331:637–642, 1994].

Another therapeutic approach is to use a protease inhibitor to ablate the direct effect of NE on elastase degradation and its sequelae. Neutralization of excess NE can restore normal homeostatic balance which protects the extracellular lung matrix. Normalized antiprotease activity in the lung preserves elastin, reduces mucus viscosity through reduction of the neutrophil response, and preserves of pulmonary function, thus reducing mortality in CF. In addition, the restoration of complement-mediated phagocytosis can enable the immune system to clear bacterial pathogens, resulting in reduction of the incidence, duration, and severity of pulmonary infection. For example, in a rat model of CF, after seven days of treatment with $alpha_1$ antitrypsin reduced bacterial counts to 0.2±0.4, compared to 85±21 in the placebo group [Cantin, A. and Woods, D, "Aerosolized Prolastin Suppresses Bacterial Proliferation in a Model of Chronic *Pseudomonas aeruginosa* Lung Infection" *Am J Respir Crit Care Med* 160:1130–1136, 1999]

SUMMARY OF THE INVENTION

The invention includes a polypeptide having the following sequece:

EAVREVCSEQAETGPCIAFFPRWYFDVTEGKCAP (SEQ ID NO:39)
FFYGGCGGNRNNFDTEEYCMAVCGSA;

a method of using the polypeptide to inhibit human neutrophil elastase; and method of using the polypeptide to treat cystic fibrosis or a cystic fibrosis-related disease or disorder.

The invention relates to proteins comprising Kunitz domain peptides fused to albumin. These fusion proteins are herein collectively referred to as "albumin fusion proteins of the invention." These fusion proteins of the invention exhibit extended in vivo half-life and/or extended or therapeutic activity in solution.

The invention encompasses therapeutic albumin fusion proteins, compositions, pharmaceutical compositions, formulations and kits. The invention also encompasses nucleic acid molecules encoding the albumin fusion proteins of the invention, as well as vectors containing these nucleic acids, host cells transformed with these nucleic acids and vectors, and methods of making the albumin fusion proteins of the invention using these nucleic acids, vectors, and/or host cells.

An object of the invention is to provide an albumin fusion protein comprising a Kunitz domain peptide or a fragment or variant thereof, and albumin, or a fragment or variant thereof. Suitable Kunitz domain peptides for use in such albumin fusion proteins include DX-890, DX-88, DX-1000, and DPI-14. The Kunitz domain peptide portion optionally may be separated from the albumin portion by a linker. Another object of the invention is to provide compositions and methods involving albumin fusion proteins for inhibiting serine proteases, non-limiting examples of which include plasma kallikrein, plasmin and neutrophil elastase.

Another aspect of the invention is to provide an albumin fusion protein comprising at least two Kunitz domain peptides or fragments or variants thereof, wherein at least one of the Kunitz domain peptide or fragment or variant has a functional activity, such as inhibiting plasmin, kallikrein, or human neutrophil elastase.

Yet another aspect of this invention is to provide an albumin fusion protein comprising a Kunitz domain peptide, or a fragment or variant thereof, and albumin, or a fragment or variant thereof, wherein the albumin has an albumin activity that prolongs the in vivo half-life of a Kunitz domain peptide, such as DX-890, DX-88, DX-1000, and DPI-14, or a fragment or variant thereof, compared to the in vivo half-life of the Kunitz domain peptide or a fragment or variant thereof in an unfused state.

Yet another aspect of this invention is to provide an albumin fusion protein comprising a Kunitz domain peptide, or a fragment or variant thereof, and albumin, or a fragment of variant thereof, wherein the albumin fusion protein of the invention has increased solubility at physiological pH.

One aspect of the invention is to provide an albumin fusion protein comprising a Kunitz domain peptide, or fragment or variant thereof, and albumin, or fragment or variant thereof, wherein the Kunitz domain peptide, or fragment or variant thereof, is fused to the N-terminus of albumin or to the N-terminus of the fragment or variant of albumin. Alternatively, this invention also provides an albumin fusion protein comprising a Kunitz domain peptide, or fragment or variant thereof, and albumin, or fragment or variant thereof, wherein the Kunitz domain peptide, or fragment or variant thereof, is fused to the C-terminus of albumin or to the C-terminus of the fragment or variant of albumin.

This invention provides a composition comprising an albumin fusion protein and a pharmaceutically acceptable carrier. Another object of the invention is to provide a method of treating a patient with cystic fibrosis, a cystic fibrosis-related disease or disorder, or a disease or disorder that can be modulated by a Kunitz domain peptide comprising DX-890 and/or DPI-14. The method comprises the step of administering an effective amount of the albumin fusion protein comprising a Kunitz domain peptide that comprises DX-890 and/or DPI-14, or fragment or variant thereof, and albumin, or fragment or variant thereof.

Another object of this invention is to provide a method of treating a patient with hereditary angioedema, a hereditary angioedema-related disease or disorder, or a disease that is modulated by a Kunitz domain peptide such as DX-88. The method comprises the step of administering an effective amount of the albumin fusion protein, wherein the albumin fusion protein comprises a Kunitz domain peptide comprising DX-88, or fragment or variant thereof, and albumin, or fragment or variant thereof.

An object of this invention is to provide a method of treating a patient with cancer, a cancer-related disease, bleeding, or disease that is modulated by a Kunitz domain peptide such as DX-1000. The method comprises the step of administering an effective amount of the albumin fusion protein, wherein the albumin fusion protein comprises a Kunitz domain peptide comprising DX-1000, or fragment or variant thereof, and albumin, or fragment or variant thereof.

Another object of the invention is to provide a nucleic acid molecule comprising a polynucleotide sequence encoding an albumin fusion protein, as well as a vector that comprises such a nucleic acid molecule.

The invention also provides a method for manufacturing a albumin fusion protein, wherein the method comprises:
(a) providing a nucleic acid comprising a nucleotide sequence encoding the albumin fusion protein expressible in an organism;
(b) expressing the nucleic acid in the organism to form an albumin fusion protein; and
(c) purifying the albumin fusion protein.

DETAILED DESCRIPTION OF THE INVENTION

Figure 1:
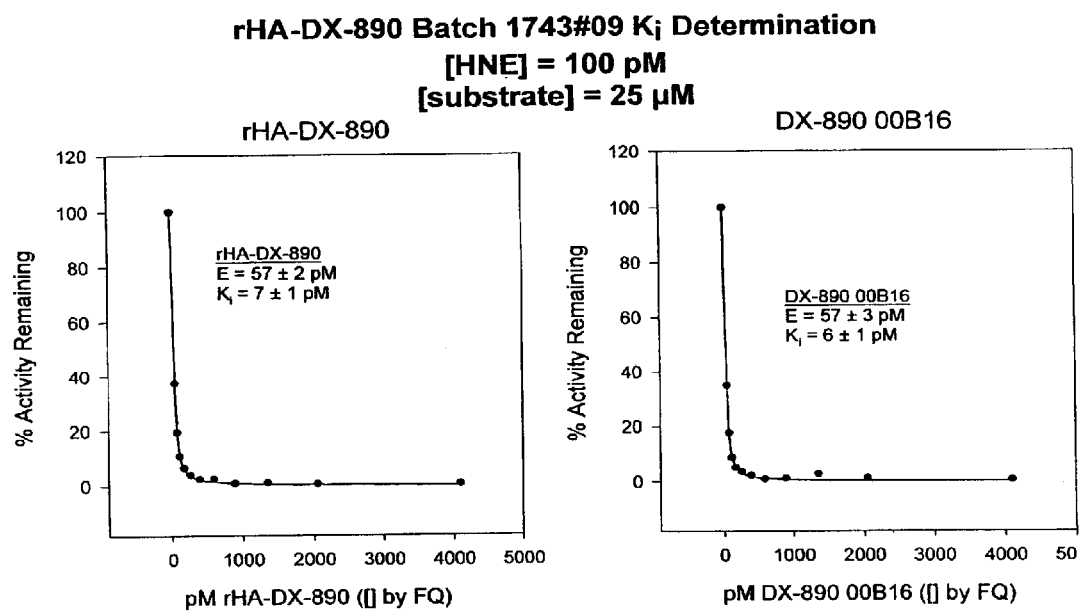
FIG. 1: $K_i$ measurements of DX-890 and the DX-890-HSA fusion.

The present invention relates to albumin-fused Kunitz domain peptides. The present invention also relates to bifunctional (or multifunctional) fusion proteins in which albumin is coupled to two (or more) Kunitz domain peptides, optionally different Kunitz domain peptides. Such bifunctional (or multifunctional) fusion proteins having different Kunitz domain peptides are expected to have an improved drug resistance profile as compared to an albumin fusion protein comprising only one type of Kunitz domain peptide. Some conditions may require inhibition of two or more proteases and fusion of multiple Kunitz domains allows one compound to be used for inhibition of the two or more proteases. Alternatively, one can fuse two or more Kunitz domains, each directed to the same protease so that the inhibitor activity per gram is increased. A useful form of an inhibitor having two Kunitz domains is $K_1::SA::K_2$, where $K_1$ and $K_2$ are the Kunitz domains and SA is serum albumin or a substantial portion thereof. Such bifunctional (or multifunctional) fusion proteins may also exhibit synergistic effects, as compared to an albumin fusion protein comprising only one type of Kunitz domain peptide. Furthermore, chemical entities may be covalently attached to the fusion proteins of the invention to enhance a biological activity or to modulate a biological activity.

The albumin fusion proteins of the present invention are expected to prolong the half-life of the Kunitz domain peptide in vivo. The in vitro or in vivo half-life of said albumin-fused peptide is extended 2-fold, or 5-fold, or more, over the half-life of the peptide lacking the linked albumin. Furthermore, due at least in part to the increased half-life of the peptide, the albumin fusion proteins of the present invention are expected to reduce the frequency of the dosing schedule of the therapeutic peptide. The dosing schedule frequency is reduced by at least one-quarter or by at least one-half, as compared to the frequency of the dosing schedule of the therapeutic peptide lacking the linked albumin.

The albumin fusion proteins of the present invention prolong the shelf life of the peptide, and/or stabilize the peptide and/or its activity in solution (or in a pharmaceutical composition) in vitro and/or in vivo. These albumin fusion proteins, which may be therapeutic agents, are expected to reduce the need to formulate protein solutions with large excesses of carrier proteins (such as albumin, unfused) to prevent loss of proteins due to factors such as nonspecific binding.

The present invention also encompasses nucleic acid molecules encoding the albumin fusion proteins as well as vectors containing these nucleic acids, host cells transformed with these nucleic acids vectors, and methods of making the albumin fusion proteins of the invention using these nucleic acids, vectors, and/or host cells. The present invention further includes transgenic organisms modified to contain the nucleic acid molecules of the invention, optionally modified to express the albumin fusion proteins encoded by the nucleic acid molecules.

Albumin

The terms, human serum albumin (HSA) and human albumin (HA) are used interchangeably herein. The terms, "albumin" and "serum albumin" are broader, and encompass human serum albumin (and fragments and variants thereof) as well as albumin from other species (and fragments and variants thereof).

As used herein, "albumin" refers collectively to albumin protein or amino acid sequence, or an albumin fragment or variant, having one or more functional activities (e.g., biological activities) of albumin. In particular, "albumin" refers to human albumin or fragments thereof (see EP 201 239, EP 322 094 WO 97/24445, WO95/23857) especially the mature form of human albumin as shown in SEQ ID NO:18 herein and in Table 1 and SEQ ID NO:18 of U.S. Provisional Application Ser. No. 60/355,547 and WO 01/79480 or albumin from other vertebrates or fragments thereof, or analogs or variants of these molecules or fragments thereof.

The human serum albumin protein used in the albumin fusion proteins of the invention contains one or both of the following sets of point mutations with reference to SEQ ID NO:18: Leu-407 to Ala, Leu-408 to Val, Val-409 to Ala, and Arg-410 to Ala; or Arg-410 to Ala, Lys-413 to Gln, and Lys-414 to Gln (see, e.g., International Publication No. WO95/23857, hereby incorporated in its entirety by reference herein). In some embodiments, albumin fusion proteins of the invention that contain one or both of above-described sets of point mutations have improved stability/resistance to yeast Yap3p proteolytic cleavage, allowing increased production of recombinant albumin fusion proteins expressed in yeast host cells.

As used herein, a portion of albumin sufficient to prolong or extend the in vivo half-life, therapeutic activity, or shelf-life of the Therapeutic protein refers to a portion of albumin sufficient in length or structure to stabilize, prolong or extend the in vivo half-life, therapeutic activity or shelf life of the Therapeutic protein portion of the albumin fusion protein compared to the in vivo half-life, therapeutic activity, or shelf-life of the Therapeutic protein in the non-fusion state. The albumin portion of the albumin fusion proteins may comprise the full length of the HA sequence as described above, or may include one or more fragments thereof that are capable of stabilizing or prolonging the therapeutic activity. Such fragments may be of 10 or more amino acids in length or may include about 15, 20, 25, 30, 50, or more contiguous amino acids from the HA sequence or may include part or all of specific domains of HA.

The albumin portion of the albumin fusion proteins of the invention may be a variant of normal HA. The Therapeutic protein portion of the albumin fusion proteins of the invention may also be variants of the Therapeutic proteins as described herein. The term "variants" includes insertions, deletions and substitutions, either conservative or non-conservative, where such changes do not substantially alter one or more of the oncotic, useful ligand-binding and non-immunogenic properties of albumin, or the active site, or active domain which confers the therapeutic activities of the Therapeutic proteins.

In particular, the albumin fusion proteins of the invention may include naturally occurring polymorphic variants of human albumin and fragments of human albumin, for example those fragments disclosed in EP 322 094 (namely HA (Pn), where n is 369 to 419). The albumin may be derived from any vertebrate, especially any mammal, for example human, cow, sheep, or pig. Non-mammalian albumins include, but are not limited to, hen and salmon. The albumin portion of the albumin fusion protein may be from a different animal than the Therapeutic protein portion.

Generally speaking, an HA fragment or variant will be at least 100 amino acids long, for example, at least 150 amino acids long. The HA variant may consist of or alternatively comprise at least one whole domain of HA, for example domains 1 (amino acids 1–194 of SEQ ID NO:18), 2 (amino acids 195–387 of SEQ ID NO:18), 3 (amino acids 388–585 of SEQ ID NO:18), 1+2 (1–387 of SEQ ID NO:18), 2+3 (195–585 of SEQ ID NO:18) or 1+3 (amino acids 1–194 of SEQ ID NO:18+amino acids 388–585 of SEQ ID NO:18). Each domain is itself made up of two homologous subdomains namely 1–105, 120–194, 195–291, 316–387, 388–491 and 512–585, with flexible inter-subdomain linker regions comprising residues Lys106 to Glu119, Glu292 to Val 315 and Glu492 to Ala511.

The albumin portion of an albumin fusion protein of the invention may comprise at least one subdomain or domain of HA or conservative modifications thereof. If the fusion is based on subdomains, some or all of the adjacent linker may optionally be used to link to the Therapeutic protein moiety.

Albumin Fusion Proteins

The present invention relates generally to albumin fusion proteins and methods of treating, preventing, or ameliorating diseases or disorders. As used herein, "albumin fusion protein" refers to a protein formed by the fusion of at least one molecule of albumin (or a fragment or variant thereof) to at least one molecule of a Therapeutic protein (or fragment or variant thereof). An albumin fusion protein of the invention comprises at least a fragment or variant of a Therapeutic protein and at least a fragment or variant of human serum albumin, which are associated with one another, such as by genetic fusion (i.e., the albumin fusion protein is generated by translation of a nucleic acid in which a polynucleotide encoding all or a portion of a Therapeutic protein is joined in-frame with a polynucleotide encoding all or a portion of albumin) to one another. The Therapeutic protein and albumin protein, once part of the albumin fusion protein, may be referred to as a "portion", "region", or "moiety" of the albumin fusion protein.

In one embodiment, the invention provides an albumin fusion protein comprising, or alternatively consisting of, a Therapeutic protein and a serum albumin protein. In other embodiments, the invention provides an albumin fusion protein comprising, or alternatively consisting of, a biologically active and/or therapeutically active fragment of a Therapeutic protein and a serum albumin protein. In other embodiments, the invention provides an albumin fusion protein comprising, or alternatively consisting of, a biologically active and/or therapeutically active variant of a Therapeutic protein and a serum albumin protein. In some embodiments, the serum albumin protein component of the albumin fusion protein is the mature portion of serum albumin.

In further embodiments, the invention provides an albumin fusion protein comprising, or alternatively consisting of, a Therapeutic protein, and a biologically active and/or therapeutically active fragment of serum albumin. In further embodiments, the invention provides an albumin fusion protein comprising, or alternatively consisting of, a Therapeutic protein and a biologically active and/or therapeutically active variant of serum albumin. In certain embodiments, the Therapeutic protein portion of the albumin fusion protein is the mature portion of the Therapeutic protein.

In further embodiments, the invention provides an albumin fusion protein comprising, or alternatively consisting of, a biologically active and/or therapeutically active fragment or variant of a Therapeutic protein and a biologically active and/or therapeutically active fragment or variant of serum albumin. In some embodiments, the invention provides an albumin fusion protein comprising, or alternatively consisting of, the mature portion of a Therapeutic protein and the mature portion of serum albumin.

The albumin fusion protein comprises HA as the N-terminal portion, and a Therapeutic protein as the C-terminal portion. Alternatively, an albumin fusion protein comprising HA as the C-terminal portion, and a Therapeutic protein as the N-terminal portion may also be used.

In other embodiments, the albumin fusion protein has a Therapeutic protein fused to both the N-terminus and the C-terminus of albumin. In one embodiment, the Therapeutic proteins fused at the N- and C-termini are the same Therapeutic proteins. In another embodiment, the Therapeutic proteins fused at the N- and C-termini are different Therapeutic proteins. In yet another embodiment, the Therapeutic proteins fused at the N- and C-termini are different Therapeutic proteins which may be used to treat or prevent the same disease, disorder, or condition. In some embodiments, the Therapeutic proteins fused at the N- and C-termini are different Therapeutic proteins which may be used to treat or prevent diseases or disorders which are known in the art to commonly occur in patients simultaneously.

In addition to albumin fusion protein in which the albumin portion is fused N-terminal and/or C-terminal of the Therapeutic protein portion, albumin fusion proteins of the invention may also be produced by inserting the Therapeutic protein or peptide of interest into an internal region of HA. For instance, within the protein sequence of the HA molecule a number of loops or turns exist between the end and beginning of α-helices, which are stabilized by disulphide bonds. The loops, as determined from the crystal structure of HA (PDB identifiers 1AO6, 1BJ5, 1BKE, 1BM0, 1E7E to 1E7I and 1UOR) for the most part extend away from the body of the molecule. These loops are useful for the insertion, or internal fusion, of therapeutically active peptides, particularly those requiring a secondary structure to be functional, or Therapeutic proteins, to essentially generate an albumin molecule with specific biological activity.

Loops in human albumin structure into which peptides or polypeptides may be inserted to generate albumin fusion proteins of the invention include: Val54-Asn61, Thr76-Asp89, Ala92-Glu100, Gln170-Ala176, His247-Glu252, Glu266-Glu277, Glu280-His288, Ala362-Glu368, Lys439-Pro447, Val462-Lys475, Thr478-Pro486, and Lys560-Thr566. In other embodiments, peptides or polypeptides are inserted into the Val54-Asn61, Gln170-Ala176, and/or Lys560-Thr566 loops of mature human albumin (Table 1) (SEQ ID NO:18).

The Therapeutic protein to be inserted may be derived from any source, including phage display and synthetic peptide libraries screened for specific biological activity or from the active portions of a molecule with the desired function. Additionally, random peptide libraries comprising Kunitz domain peptides that are candidates for use as a Therapeutic protein may be generated within particular loops or by insertions of such randomized peptides into particular loops of the HA molecule and in which many (e.g. $5 \times 10^9$) combinations of amino acids are represented.

Such library(s) could be generated on HA or domain fragments of HA by one of the following methods:

(a) randomized mutation of amino acids within one or more peptide loops of HA or HA domain fragments. Either one, more than one or all the residues within a loop could be mutated in this manner;

(b) replacement of, or insertion into one or more loops of HA or HA domain fragments (i.e., internal fusion) of a randomized peptide(s) of length $X_n$ (where X is an amino acid and n is the number of residues;

(c) N-, C- or N- and C-terminal peptide/protein fusions in addition to (a) and/or (b).

The HA or HA domain fragment may also be made multifunctional by grafting the peptides derived from different screens of different loops against different targets into the same HA or HA domain fragment.

Non-limiting examples of peptides inserted into a loop of human serum albumin are DX-890 (an inhibitor of human neutrophil elastase), DPI-14 (an inhibitor of human neutrophil elastase), DX-88 peptide (an inhibitor of human plasma kallikrein, Table 2), and DX-1000 (an inhibitor of human plasmin, Table 2) or peptide fragments or peptide variants thereof. More particularly, the invention encompasses albumin fusion proteins which comprise peptide fragments or peptide variants at least 7 at least 8, at least 9, at least 10, at least 11, at least 12, at least 13, at least 14, at least 15, at least 20, at least 25, at least 30, at least 35, or at least 40 amino acids in length inserted into a loop of human serum albumin. The invention also encompasses albumin fusion proteins which comprise peptide fragments or peptide variants at least 7 at least 8, at least 9, at least 10, at least 11, at least 12, at least 13, at least 14, at least 15, at least 20, at least 25, at least 30, at least 35, or at least 40 amino acids fused to the N-terminus of human serum albumin. The invention also encompasses albumin fusion proteins which comprise peptide fragments or peptide variants at least 7 at least 8, at least 9, at least 10, at least 11, at least 12, at least 13, at least 14, at least 15, at least 20, at least 25, at least 30, at least 35, or at least 40 amino acids fused to the C-terminus of human serum albumin.

Generally, the albumin fusion proteins of the invention may have one HA-derived region and one Therapeutic protein-derived region. Multiple regions of each protein, however, may be used to make an albumin fusion protein of the invention. Similarly, more than one Therapeutic protein may be used to make an albumin fusion protein of the invention. For instance, a Therapeutic protein may be fused to both the N- and C-terminal ends of the HA. In such a configuration, the Therapeutic protein portions may be the same or different Therapeutic protein molecules. The structure of bifunctional albumin fusion proteins may be represented as: X-HA-Y or Y-HA-X or X-Y-HA or HA-X-Y or HA-X-Y-HA or HA-Y-X-HA or HA-X—X-HA or HA-Y—Y-HA or HA-X-HA-Y or X-HA-Y-HA or multiple combinations or inserting X and/or Y within the HA sequence at any location.

Additional embodiments that involve a therapeutic protein "X", such as a Kunitz domain, and a therapeutic peptide "Y" involve separating HA into parts 1 and 2. The fusion proteins of the invention could have the forms: X-HA(part1)-Y-HA(part2) and HA(part1)-Y-HA(part2)-X. Additional embodiments involve two therapeutic protein domains "X" and "Z" and a therapeutic peptide "Y" leading to fusion proteins of the forms: X-HA(part1)-Y-HA(part2)-Z and Z-HA(part1)-Y-HA(part2)-X.

Bi- or multi-functional albumin fusion proteins may be prepared in various ratios depending on function, half-life, etc.

Bi- or multi-functional albumin fusion proteins may also be prepared to target the Therapeutic protein portion of a fusion to a target organ or cell type via protein or peptide at the opposite terminus of HA.

As an alternative to the fusion of known therapeutic molecules, the peptides could be obtained by screening libraries constructed as fusions to the N- , C- or N- and C-termini of HA, or domain fragment of HA, of typically 6, 8, 12, 20 or 25 or $X_n$ (where X is an amino acid (aa) and n equals the number of residues) randomized amino acids, and in which all possible combinations of amino acids were allowed. A particular advantage of this approach is that the peptides may be selected in situ on the HA molecule and the properties of the peptide would therefore be as selected for rather than, potentially, modified as might be the case for a peptide derived by any other method then being attached to HA. Such selection is not needed for attachment of well-folded domains, such as Kunitz domains, at the ends of HA. Selection in-situ is likely to be important for peptides that have no disulfides or a single disulfide loop.

Additionally, the albumin fusion proteins of the invention may include a linker peptide between the fused portions to provide greater physical separation between the moieties and thus maximize the accessibility of the Therapeutic protein portion, for instance, for binding to its cognate receptor. The linker peptide may consist of amino acids such that it is flexible or more rigid.

Therefore, as described above, the albumin fusion proteins of the invention may have the following formula R2-R1; R1-R2; R2-R1-R2; R2-L-R1-L-R2; R1-L-R2; R2-L-R1; or R1-L-R2-L-R1, wherein R1 is at least one Therapeutic protein, peptide or polypeptide sequence (including fragments or variants thereof), and not necessarily the same Therapeutic protein, L is a linker and R2 is a serum albumin sequence (including fragments or variants thereof). Exemplary linkers include $(GGGGS)_N$ (SEQ ID No.: 1) or $(GGGS)_N$ (SEQ ID No.: 2) or $(GGS)_N$, wherein N is an integer greater than or equal to 1 and wherein G represents glycine and S represents serine.

In certain embodiments, albumin fusion proteins of the invention comprising a Therapeutic protein have extended shelf life or in vivo half-life or therapeutic activity compared to the shelf life or in vivo half-life or therapeutic activity of the same Therapeutic protein when not fused to albumin. Shelf-life typically refers to the time period over which the therapeutic activity of a Therapeutic protein in solution or in some other storage formulation, is stable without undue loss of therapeutic activity. Many of the Therapeutic proteins are highly labile in their unfused state. As described below, the typical shelf-life of these Therapeutic proteins is markedly prolonged upon incorporation into the albumin fusion protein of the invention.

Albumin fusion proteins of the invention with "prolonged" or "extended" shelf-life exhibit greater therapeutic activity relative to a standard that has been subjected to the same storage and handling conditions. The standard may be the unfused full-length Therapeutic protein. When the Therapeutic protein portion of the albumin fusion protein is an analog, a variant, or is otherwise altered or does not include the complete sequence for that protein, the prolongation of therapeutic activity may alternatively be compared to the unfused equivalent of that analog, variant, altered peptide or incomplete sequence. As an example, an albumin fusion protein of the invention may retain greater than about 100% of the therapeutic activity, or greater than about 105%, 110%, 120%, 130%, 150% or 200% of the therapeutic activity of a standard when subjected to the same storage and handling conditions as the standard when compared at a given time point. However, it is noted that the therapeutic activity depends on the Therapeutic protein's stability, and may be below 100%.

Shelf-life may also be assessed in terms of therapeutic activity remaining after storage, normalized to therapeutic activity when storage began. Albumin fusion proteins of the invention with prolonged or extended shelf-life as exhibited by prolonged or extended therapeutic activity may retain greater than about 50% of the therapeutic activity, about 60%, 70%, 80%, or 90% or more of the therapeutic activity of the equivalent unfused Therapeutic protein when subjected to the same conditions.

Albumin fusion proteins of the invention exhibit greater solubility relative to the non-fused Therapeutic protein standard that has been subjected to the same storage and handling conditions.

Therapeutic Proteins

As stated above, an albumin fusion protein of the invention comprises at least a fragment or variant of a Therapeutic protein and at least a fragment or variant of human serum albumin, which are associated with one another by genetic fusion.

As used herein, "Therapeutic protein" refers to a Kunitz domain peptide, non-limiting examples of which include DX-890, DPI-14, DX-88 or DX-1000, or fragments or variants thereof, having one or more therapeutic and/or biological activities. A Kunitz domain is a folding domain of approximately 51–64 residues which forms a central anti-parallel beta sheet and a short C-terminal helix. This characteristic domain comprises six cysteine residues that form three disulfide bonds, resulting in a double-loop structure. Between the N-terminal region and the first beta strand resides the active inhibitory binding loop. This binding loop is disulfide bonded through the P2 $C_{14}$ residue to the hairpin loop formed between the last two beta strands.

A Kunitz domain is a polypeptide of from about 51 AAs to about 64 AAs of the form:

$X_1X_2X_3X_4C_5X_6X_7X_8X_9X_{9a}X_{10}X_{11}X_{12}X_{13}C_{14}$ (SEQ ID No. 3)

$X_{15}X_{16}X_{17}X_{18}X_{19}X_{20}X_{21}X_{22}X_{23}X_{24}X_{25}X_{26}$ $X_{26a}X_{26b}X_{26c}X_{27}X_{28}X_{29}C_{30}X_{31}X_{32}X_{33}X_{34}$ $X_{35}X_{36}X_{37}C_{38}X_{39}X_{40}X_{41}X_{42}X_{42a}X_{42b}X_{42c}$ $X_{43}X_{44}X_{45}X_{46}X_{47}X_{48}X_{49}X_{50}C_{51}X_{52}X_{53}X_{54}$ $C_{55}X_{56}X_{57}X_{58}$

Disulfides are formed between $C_5$ and $C_{55}$, $C_{14}$ and $C_{38}$, and $C_{30}$ and $C_{51}$. The $C_{14}$–$C_{38}$ disulfide is always seen in natural Kunitz domains, but may be removed in artificial Kunitz domains. If $C_{14}$ is changed to another amino-acid type, then $C_{38}$ is also changed to a non-cysteine and vice versa. Any polypeptide may be fused to the amino terminus. $X_1$–$X_4$ may comprise zero to four amino acids. $X_6$–$X_{13}$ may comprise 8 or 9 amino acids. If $X_{9a}$ is absent, then $X_{12}$ is Gly. Each of $X_{26a}$, $X_{26b}$, and $X_{26c}$ may be absent; that is, $X_{15}$–$C_{30}$ may comprise 16, 17, 18, or 19 amino acids. $X_{33}$ is Phe or Tyr. $X_{39}$–$X_{50}$ may comprise 12, 13, 14, or 15 amino acids; that is, each of $X_{42a}$, $X_{42b}$, and $X_{42c}$ may be absent. $X_{45}$ is Phe or Tyr. $X_{56}$–$X_{58}$ may comprise zero to three amino acids. Additional cysteines may occur at positions 50, 53, 54 or 58. Any polypeptide may be fused to the carboxy terminus. Table 3 shows the amino-acid sequences of 21 known human Kunitz domains.

TABLE 3

Amino acid sequences of 21 known human Kunitz domains

| Domain | Protein | Amino Acid Sequence | Accession |
|---|---|---|---|
| single | A4 (amyloid precursor PTN) | VREVCSEQAETGPCRAMISRWYFDVTEGK CAPFFYGGCGGNRNNFDTEEYCMAVCGSA SEQ ID No.: 4 | SP: A4_HUMAN A#P05067 |
| single | embl loCus HS461P17 = "CAB37" | KQDVCEMPKETGPCLAYFLHWWYDKKDNT CSMFVYGGCQGNNNNFQSKANCLNTCKNK SEQ ID No.: 5 | (CAB37635; g4467797) |
| single | Amyloid-like PTN 2 | VKAVCSQEAMTGPCRAVMPRWYFDLSKGK CVRFIYGGCGGNRNNFESEDYCMAVCKAM SEQ ID No.: 6 | Loc: 1703344; S41082 g1082207 & g1703344 & g477608 |
| K1 | ITI | KEDSCQLGYSAGPCMGMTSRYFYNGTSMA CETFQYGGCMGNGNNFVTEKECLQTCRTV SEQ ID No.: 7 | SP: HC_HUMAN A#P02760 (HI-8e) = gi\|223133 |
| K2 | ITI | TVAACNLPIVRGPCRAFIQLWAFDAVKGK CVLFPYGGCQGNGNKFYSEKECREYCGVP SEQ ID No.: 8 | SP: HC_HUMAN A#P02760 (HI-8e) = gi\|223133 |
| K1 | TFPI-1 = LACI | MHSFCAFKADDGPCKAIMKRFFFNIFTRQ CEEFIYGGCEGNQNRFESLEECKKMCTRD N SEQ ID No.: 9 (corrected May 14, 2000) | SP: LACI_HUMAN, A#P10646 gim\|14667 |
| K2 | TFPI-1 | KPDFCFLEEDPGICRGYITRYFYNNQTKQ CERFKYGGCLGNMNNFETLEECKNICEDG SEQ ID No.: 10 | SP: LACI_HUMAN, A#P10646 gim\|14667 |
| K3 | TFPI-1 | GPSWCLTPADRGLCRANENRFYYNSVIGK CRPFKYSGCGGNENNFTSKQECLRACKKG SEQ ID No.: 11 | SP: LACI_HUMAN, A#P10646 gim\|14667 |
| K1 | TFPI-2 | NAEICLLPLDYGPCRALLLRYYYDRYTQS CRQFLYGGCEGNANNFYTWEACDDACWRI SEQ ID No.: 12 | Specher &al. PNAS 91: 3353–3357 (1994) |
| K2 | TFPI-2 | VPKVCRLQVVDDQCEGSTEKYFFNLSSMT CEKFFSGGCHRNRNRFPDEATCMGFCAPK SEQ ID No.: 13 | Specher &al, PNAS 91: 3353ff (1994) |
| K3 | TFPI-2 | IPSFCYSPKDEGLCSANVTRYYFNPRYRT CDAFTYTGCGGNDNNFVSREDCKRACAKA SEQ ID No.: 14 | Specher &al, PNAS 91: 3353ff (1994) |
| K1 | Hepatocyte GF activator inhib type 1 | TEDYCLASNKVGRCRGSFPRWYYDPTEQI CKSFVYGGCLGNKNNYLREEECILACRGV SEQ ID No.: 15 | Locus 2924601 |
| K2 | Hepatocyte GF activator inhib type 1 | DKGHCVDLPDTGLCKESIPRWYYNPFSEH CARFTYGGCYGNKNNFEEEQQCLESCRGI SEQ ID No.: 16 | Locus 2924601 |
| K1 | hepatocyte GF activator inhib. type 2 | IHDFCLVSKVVGRCRASMPRWWYNVTDGS CQLFVYGGCDGNSNNYLTKEECLKKCATV SEQ ID No.: 17 | LOC. 2924620 |
| K2 | hepatocyte GF activator inhib. type2 | YEEYCTANAVTGPCRASFPRWYPDVERNS CNNFIYGGCRGNKNSYRSEEACMLRCFRQ SEQ ID No.: 19 | LOC. 2924620 |
| Single | PRF | TVAACNLPVIRGPCRAFIQLWAFDAVKGK CVLFPYGGCQGNGNKFYSEKECREYCGVP SEQ ID No.: 20 | gi\|223132 Name: 0511271A |
| Single | HKI B9 domain | LPNVCAFPMEKGPCQTYMTRWFFNPETGE CELFAYGGCGGNSNNFLRKEKCEKFCKFT SEQ ID No. : 21 | gi\|579567 WO93/14123-A; g542925 |
| Single | Collagen α1 (VII) | SDDPCSLPLDEGSCTAYTLRWYHRAVTEA CHPFVYGGCGGNANRFGTREACERRCPPR SEQ ID No.: 22 | NCBI: gi\|543915 |

TABLE 3-continued

| Amino acid sequences of 21 known human Kunitz domains | | | |
|---|---|---|---|
| Domain | Protein | Amino Acid Sequence | Accession |
| Single | collagen alpha 1 (VII) | EDDPCSLPLDEGSCTAYTLRWYHRAVTGS TEACHPFVYGGCGGNANRFGTREACERRC PPR SEQ ID No.: 23 | g627406–A54849 GI: 627406 |
| Single | collagen ∀3 | ETDICKLPKDEGTCRDFILKWYYDPNTKS CARFWYGGCGGNENKFGSQKECEKVCAPV SEQ ID No.: 24 | NCBI Seq ID: 512802 W093/14119-A. 2193976 (Xray) |
| single | Chromosome 20 ptn "Chrome20" | FQEPCMLPVRHGNCNHEAQRWHFDFKNYR CTPFKYRGCEGNANNFLNEDACRTACMLI SEQ ID No.: 25 | CAB37634 PID g7024350 |

Any of the domains in Table 1 could be engineered to have a specific biological effect (such as inhibiting a particular protease) and be fused to HA. Thus an albumin fusion protein of the invention may contain at least a fragment or variant of a Therapeutic protein. Variants include mutants, analogs, and mimetics, as well as homologs, including the endogenous or naturally occurring correlates.

By a polypeptide displaying a "therapeutic activity" or a protein that is "therapeutically active" is meant a polypeptide that possesses one or more known biological and/or therapeutic activities associated with a Therapeutic protein such as one or more of the Therapeutic proteins described herein or otherwise known in the art. As a non-limiting example, a "Therapeutic protein" is a protein that is useful to treat, prevent or ameliorate a disease, condition or disorder.

As used herein, "therapeutic activity" or "activity" may refer to an activity whose effect is consistent with a desirable therapeutic outcome in humans, or to desired effects in non-human mammals or in other species or organisms. Therapeutic activity may be measured in vivo or in vitro. For example, a desirable effect may be assayed in cell culture. Such in vitro or cell culture assays are commonly available for many Therapeutic proteins as described in the art.

Examples of useful assays include, but are not limited to, those described in references and publications of Table 4, specifically incorporated by reference herein, and those described in the Examples herein. The activity exhibited by the fusion proteins of the invention may be measured, for example, by easily performed in vitro assays, such as those described herein. Using these assays, such parameters as the relative biological and/or therapeutic activity that the fusion proteins exhibit as compared to the Therapeutic protein (or fragment or variant thereof) when it is not fused to albumin can be determined.

Therapeutic proteins corresponding to a Therapeutic protein portion of an albumin fusion protein of the invention may be modified by the attachment of one or more oligosaccharide groups. The modification, referred to as glycosylation, can dramatically affect the physical properties of proteins and can be important in protein stability, secretion, and localization. Such modifications are described in detail in U.S. Provisional Application Ser. No. 60/355,547 and WO 01/79480, which are incorporated herein by reference.

Therapeutic proteins corresponding to a Therapeutic protein portion of an albumin fusion protein of the invention, as well as analogs and variants thereof, may be modified so that glycosylation at one or more sites is altered as a result of manipulation(s) of their nucleic acid sequence, by the host cell in which they are expressed, or due to other conditions of their expression. For example, glycosylation isomers may be produced by abolishing or introducing glycosylation sites, e.g., by substitution or deletion of amino acid residues, such as substitution of glutamine for asparagine, or unglycosylated recombinant proteins may be produced by expressing the proteins in host cells that will not glycosylate them, e.g. in *E. coli* or glycosylation-deficient yeast. Examples of these approaches are described in more detail in U.S. Provisional Application Ser. No. 60/355,547 and WO 01/79480, which are incorporated by reference, and are known in the art.

Table 4 provides a non-exhaustive list of Therapeutic proteins that correspond to a Therapeutic protein portion of an albumin fusion protein of the invention. The "Therapeutic Protein X" column discloses Therapeutic protein molecules followed by parentheses containing scientific and brand names that comprise, or alternatively consist of, that Therapeutic protein molecule or a fragment or variant thereof. "Therapeutic protein X" as used herein may refer either to an individual Therapeutic protein molecule (as defined by the amino acid sequence obtainable from the CAS and Genbank accession numbers), or to the entire group of Therapeutic proteins associated with a given Therapeutic protein molecule disclosed in this column. The information associated with each of these entries are each incorporated by reference in their entireties, particularly with respect to the amino acid sequences described therein. The "PCT/Patent Reference" column provides U.S. patent numbers, or PCT International Publication Numbers corresponding to patents and/or published patent applications that describe the Therapeutic protein molecule. Each of the patents and/or published patent applications cited in the "PCT/Patent Reference" column are herein incorporated by reference in their entireties. In particular, the amino acid sequences of the specified polypeptide set forth in the sequence listing of each cited "PCT/Patent Reference", the variants of these amino acid sequences (mutations, fragments, etc.) set forth, for example, in the detailed description of each cited "PCT/Patent Reference", the therapeutic indications set forth, for example, in the detailed description of each cited "PCT/Patent Reference", and the activity assays for the specified polypeptide set forth in the detailed description, and more particularly, the examples of each cited "PCT/Patent Reference" are incorporated herein by reference. The "Biological activity" column describes Biological activities associated with the Therapeutic protein molecule. Each of the references cited in the "Relevant Publications" column are herein incorporated by reference in their entireties, particularly with respect to the description of the respective activity assay described in the reference (see Methods section, for example) for assaying the corresponding biological activity. The "Preferred Indication Y" column describes disease, disorders, and/or conditions that may be treated, prevented, diagnosed, or ameliorated by Therapeutic protein X or an albumin fusion protein of the invention comprising a Therapeutic protein X portion.

TABLE 4

A List of Selected Therapeutic Proteins

| Therapeutic Protein X | PCT/Patent Reference | Biological Activity | Relevant Publications | Preferred Indication Y |
|---|---|---|---|---|
| DX-890, DPI14 | U.S. Pat. No. 5,663,143, SEQ ID NO: 20 = DX-890 | Inhibition of human neutrophil elastase, $K_i \sim 5$ pM. | Rusckowski et al. (2000) J. Nuclear Medicine 41: 363–74 | Emphysema, Cystic fibrosis COPD, Bronchitis, Pulmonary Hypertension, Acute respiratory distress syndrome, Interstitial lung disease, Asthma, Smoke intoxication, Bronchopulmonary dysplasia, Pneumonia, Thermal Injury, Lung transplant rejection. |
| DX-88 | U.S. Pat. Nos. 6,333,402; 5,994,125; 6,057,287; and 5,795,865 | Inhibition of human plasma kallikrein | Markland et al. Biochemistry 35(24): 8058–67, 1996. Ley et al. (1996) Mol Divers 2(1–2) 119–24. | HAE |
| DX-1000 | U.S. Pat. Nos. 6,010,880; 6,071,723; and 6,103,499 | Inhibits human plasmin | Markland et al. Biochemistry 35(24): 8045–57, 1996. Ley et al. (1996) Mol Divers 2 (1–2) 119–24. | Bleeding, cancer. |

In various embodiments, the albumin fusion proteins of the invention are capable of a therapeutic activity and/or biologic activity corresponding to the therapeutic activity and/or biologic activity of the Therapeutic protein corresponding to the Therapeutic protein portion of the albumin fusion protein listed in the corresponding row of Table 4. (See, e.g., the "Biological Activity" and "Therapeutic Protein X" columns of Table 4.) In other embodiments, the therapeutically active protein portions of the albumin fusion proteins of the invention are fragments or variants of the reference sequence and are capable of the therapeutic activity and/or biologic activity of the corresponding Therapeutic protein disclosed in "Biological Activity" column of Table 4.

Polypeptide and Polynucleotide Fragments and Variants

Fragments

The present invention is further directed to fragments of the Therapeutic proteins described in Table 4, albumin proteins, and/or albumin fusion proteins of the invention.

Even if deletion of one or more amino acids from the N-terminus of a protein results in modification or loss of one or more biological functions of the Therapeutic protein, albumin protein, and/or albumin fusion protein, other Therapeutic activities and/or functional activities (e.g., biological activities, ability to multimerize, ability to bind a ligand) may still be retained. For example, the ability of polypeptides with N-terminal deletions to induce and/or bind to antibodies which recognize the complete or mature forms of the polypeptides generally will be retained when less than the majority of the residues of the complete polypeptide are removed from the N-terminus. Whether a particular polypeptide lacking N-terminal residues of a complete polypeptide retains such immunologic activities can readily be determined by routine methods described herein and otherwise known in the art. It is not unlikely that a mutein with a large number of deleted N-terminal amino acid residues may retain some biological or immunogenic activities. In fact, peptides composed of as few as six amino acid residues may often evoke an immune response.

Accordingly, fragments of a Therapeutic protein corresponding to a Therapeutic protein portion of an albumin fusion protein of the invention, include the full length protein as well as polypeptides having one or more residues deleted from the amino terminus of the amino acid sequence of the reference polypeptide (e.g., a Therapeutic protein as disclosed in Table 4). Polynucleotides encoding these polypeptides are also encompassed by the invention.

In addition, fragments of serum albumin polypeptides corresponding to an albumin protein portion of an albumin fusion protein of the invention, include the full length protein as well as polypeptides having one or more residues deleted from the amino terminus of the amino acid sequence of the reference polypeptide (i.e., serum albumin). Polynucleotides encoding these polypeptides are also encompassed by the invention.

Moreover, fragments of albumin fusion proteins of the invention include the full-length albumin fusion protein as well as polypeptides having one or more residues deleted from the amino terminus of the albumin fusion protein. Polynucleotides encoding these polypeptides are also encompassed by the invention.

Also as mentioned above, even if deletion of one or more amino acids from the N-terminus or C-terminus of a reference polypeptide (e.g., a Therapeutic protein and/or serum albumin protein) results in modification or loss of one or more biological functions of the protein, other functional activities (e.g., biological activities, ability to multimerize, ability to bind a ligand) and/or Therapeutic activities may still be retained. For example the ability of polypeptides with C-terminal deletions to induce and/or bind to antibodies which recognize the complete or mature forms of the polypeptide generally will be retained when less than the majority of the residues of the complete or mature polypeptide are removed from the C-terminus. Whether a particular polypeptide lacking N-terminal and/or C-terminal residues of a reference polypeptide retains Therapeutic activity can readily be determined by routine methods described herein and/or otherwise known in the art.

The present invention further provides polypeptides having one or more residues deleted from the carboxy terminus of the amino acid sequence of a Therapeutic protein corresponding to a Therapeutic protein portion of an albumin fusion protein of the invention (e.g., a Therapeutic protein referred to in Table 4). Polynucleotides encoding these polypeptides are also encompassed by the invention.

In addition, the present invention provides polypeptides having one or more residues deleted from the carboxy terminus of the amino acid sequence of an albumin protein corresponding to an albumin protein portion of an albumin fusion protein of the invention (e.g., serum albumin). Polynucleotides encoding these polypeptides are also encompassed by the invention.

Moreover, the present invention provides polypeptides having one or more residues deleted from the carboxy terminus of an albumin fusion protein of the invention. Polynucleotides encoding these polypeptides are also encompassed by the invention.

In addition, any of the above described N- or C-terminal deletions can be combined to produce a N- and C-terminal deleted reference polypeptide (e.g., a Therapeutic protein referred to in Table 4, or serum albumin (e.g., SEQ ID NO:18, Table 1), or an albumin fusion protein of the invention). The invention also provides polypeptides having one or more amino acids deleted from both the amino and the carboxyl termini. Polynucleotides encoding these polypeptides are also encompassed by the invention.

The present application is also directed to proteins containing polypeptides at least 60%, 80%, 85%, 90%, 95%, 96%, 97%, 98% or 99% identical to a reference polypeptide sequence (e.g., a Therapeutic protein, serum albumin protein or an albumin fusion protein of the invention) set forth herein, or fragments thereof. In some embodiments, the application is directed to proteins comprising polypeptides at least 80%, 85%, 90%, 95%, 96%, 97%, 98% or 99% identical to reference polypeptides having the amino acid sequence of N- and C-terminal deletions as described above. Polynucleotides encoding these polypeptides are also encompassed by the invention.

Other polypeptide fragments of the invention are fragments comprising, or alternatively, consisting of, an amino acid sequence that displays a Therapeutic activity and/or functional activity (e.g. biological activity) of the polypeptide sequence of the Therapeutic protein or serum albumin protein of which the amino acid sequence is a fragment.

Other polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Variants

"Variant" refers to a polynucleotide or nucleic acid differing from a reference nucleic acid or polypeptide, but retaining essential properties thereof. Generally, variants are overall closely similar, and, in many regions, identical to the reference nucleic acid or polypeptide.

As used herein, "variant", refers to a Therapeutic protein portion of an albumin fusion protein of the invention, albumin portion of an albumin fusion protein of the invention, or albumin fusion protein differing in sequence from a Therapeutic protein (e.g., see "Therapeutic Protein X" column of Table 4), albumin protein, and/or albumin fusion protein of the invention, respectively, but retaining at least one functional and/or therapeutic property thereof (e.g., a therapeutic activity and/or biological activity as disclosed in the "Biological Activity" column of Table 4) as described elsewhere herein or otherwise known in the art. Generally, variants are overall very similar, and, in many regions, identical to the amino acid sequence of the Therapeutic protein corresponding to a Therapeutic protein portion of an albumin fusion protein of the invention, albumin protein corresponding to an albumin protein portion of an albumin fusion protein of the invention, and/or albumin fusion protein of the invention. Nucleic acids encoding these variants are also encompassed by the invention.

The present invention is also directed to proteins which comprise, or alternatively consist of, an amino acid sequence which is at least 60%, 80%, 85%, 90%, 95%, 96%, 97%, 98%, 99% or 100%, identical to, for example, the amino acid sequence of a Therapeutic protein corresponding to a Therapeutic protein portion of an albumin fusion protein of the invention (e.g., an amino acid sequence disclosed in a reference in Table 4, or fragments or variants thereof), albumin proteins (e.g., Table 1) or fragments or variants thereof) corresponding to an albumin protein portion of an albumin fusion protein of the invention, and/or albumin fusion proteins of the invention. Fragments of these polypeptides are also provided (e.g., those fragments described herein). Further polypeptides encompassed by the invention are polypeptides encoded by polynucleotides which hybridize to the complement of a nucleic acid molecule encoding an amino acid sequence of the invention under stringent hybridization conditions (e.g., hybridization to filter bound DNA in 6× Sodium chloride/Sodium citrate (SSC) at about 45 degrees Celsius, followed by one or more washes in 0.2×SSC, 0.1% SDS at about 50–65 degrees Celsius), under highly stringent conditions (e.g., hybridization to filter bound DNA in 6× sodium chloride/Sodium citrate (SSC) at about 45 degrees Celsius, followed by one or more washes in 0.1×SSC, 0.2% SDS at about 68 degrees Celsius), or under other stringent hybridization conditions which are known to those of skill in the art (see, for example, Ausubel, F. M. et al., eds., 1989 *Current protocol in Molecular Biology*, Green publishing associates, Inc., and John Wiley & Sons Inc., New York, at pages 6.3.1–6.3.6 and 2.10.3). Polynucleotides encoding these polypeptides are also encompassed by the invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least 60%, 80%, 85%, 90%, 95%, 96%, 97%, 98% or 99% identical to, for instance, the amino acid sequence of an albumin fusion protein of the invention or a fragment thereof (such as the Therapeutic protein portion of the albumin fusion protein or the albumin portion of the albumin fusion protein), can be determined conventionally using known computer programs. Such programs and methods of using them are described, e.g., in U.S. Provisional Application Ser. No. 60/355,547 and WO 01/79480 (pp. 41–43), which are incorporated by reference herein, and are well known in the art.

The polynucleotide variants of the invention may contain alterations in the coding regions, non-coding regions, or both. Polynucleotide variants include those containing alterations which produce silent substitutions, additions, or deletions, but do not alter the properties or activities of the encoded polypeptide. Such nucleotide variants may be produced by silent substitutions due to the degeneracy of the genetic code. Polypeptide variants include those in which less than 50, less than 40, less than 30, less than 20, less than 10, or 5–50, 5–25, 5–10, 1–5, or 1–2 amino acids are substituted, deleted, or added in any combination. Polynucleotide variants can be produced for a variety of reasons, e.g., to optimize codon expression for a particular host (change codons in the human mRNA to those preferred by a microbial host, such as, yeast or E. coli).

In another embodiment, a polynucleotide encoding an albumin portion of an albumin fusion protein of the invention is optimized for expression in yeast or mammalian cells. In yet another embodiment, a polynucleotide encoding a Therapeutic protein portion of an albumin fusion protein of the invention is optimized for expression in yeast or mammalian cells. In still another embodiment, a polynucleotide encoding an albumin fusion protein of the invention is optimized for expression in yeast or mammalian cells.

In an alternative embodiment, a codon optimized polynucleotide encoding a Therapeutic protein portion of an albumin fusion protein of the invention does not hybridize to the wild type polynucleotide encoding the Therapeutic protein under stringent hybridization conditions as described herein. In a further embodiment, a codon optimized polynucleotide encoding an albumin portion of an albumin fusion protein of the invention does not hybridize to the wild type polynucleotide encoding the albumin protein under stringent hybridization conditions as described herein. In another embodiment, a codon optimized polynucleotide encoding an albumin fusion protein of the invention does not hybridize to the wild type polynucleotide encoding the Therapeutic protein portion or the albumin protein portion under stringent hybridization conditions as described herein.

In an additional embodiment, polynucleotides encoding a Therapeutic protein portion of an albumin fusion protein of the invention do not comprise, or alternatively consist of, the naturally occurring sequence of that Therapeutic protein. In a further embodiment, polynucleotides encoding an albumin protein portion of an albumin fusion protein of the invention do not comprise, or alternatively consist of, the naturally occurring sequence of albumin protein. In an alternative embodiment, polynucleotides encoding an albumin fusion protein of the invention do not comprise, or alternatively consist of, the naturally occurring sequence of a Therapeutic protein portion or the albumin protein portion.

In an additional embodiment, the Therapeutic protein may be selected from a random peptide library by biopanning, as there will be no naturally occurring wild type polynucleotide.

Naturally occurring variants are called "allelic variants," and refer to one of several alternate forms of a gene occupying a given locus on a chromosome of an organism. (Genes II, Lewin, B., ed., John Wiley & Sons, New York (1985)). These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids may be deleted from the N-terminus or C-terminus of the polypeptide of the present invention without substantial loss of biological function. See, e.g., Ron et al. (J. Biol. Chem. 268: 2984–2988 (1993) (KGF variants) and Dobeli et al., J. Biotechnology 7:199–216 (1988) (interferon gamma variants).

Moreover, ample evidence demonstrates that variants often retain a biological activity similar to that of the naturally occurring protein (e.g. Gayle and coworkers (J. Biol. Chem. 268:22105–22111 (1993) (IL-1a variants)). Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which have a functional activity (e.g., biological activity and/or therapeutic activity). In further embodiments the invention provides variants of albumin fusion proteins that have a functional activity (e.g., biological activity and/or therapeutic activity, such as that disclosed in the "Biological Activity" column in Table 4) that corresponds to one or more biological and/or therapeutic activities of the Therapeutic protein corresponding to the Therapeutic protein portion of the albumin fusion protein. Such variants include deletions, insertions, inversions, repeats, and substitutions selected according to general rules known in the art so as have little effect on activity.

In other embodiments, the variants of the invention have conservative substitutions. By "conservative substitutions" is intended swaps within groups such as replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Guidance concerning how to make phenotypically silent amino acid substitutions is provided, for example, in Bowie et al., "Deciphering the Message in Protein Sequences: Tolerance to Amino Acid Substitutions," Science 247:1306–1310 (1990), wherein the authors indicate that there are two main strategies for studying the tolerance of an amino acid sequence to change.

As the authors state, proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly. Besides conservative amino acid substitution, variants of the present invention include (i) polypeptides containing substitutions of one or more of the non-conserved amino acid residues, where the substituted amino acid residues may or may not be one encoded by the genetic code, or (ii) polypeptides containing substitutions of one or more of the amino acid residues having a substituent group, or (iii) polypeptides which have been fused with or chemically conjugated to another compound, such as a compound to increase the stability and/or solubility of the polypeptide (for example, polyethylene glycol), (iv) polypeptide containing additional amino acids, such as, for example, an IgG Fc fusion region peptide. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. See Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).

In specific embodiments, the polypeptides of the invention comprise, or alternatively, consist of, fragments or variants of the amino acid sequence of a Therapeutic protein described herein and/or human serum albumin, and/or albumin fusion protein of the invention, wherein the fragments or variants have 1–5, 5–10, 5–25, 5–50, 10–50 or 50–150, amino acid residue additions, substitutions, and/or deletions when compared to the reference amino acid sequence. In certain embodiments, the amino acid substitutions are conservative. Nucleic acids encoding these polypeptides are also encompassed by the invention.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination.

Furthermore, chemical entities may be covalently attached to the albumin fusion proteins to enhance or modulate a specific functional or biological activity such as by methods disclosed in Current Opinions in Biotechnology, 10:324 (1999).

Furthermore, targeting entities may be covalently attached to the albumin fusion proteins of the invention to target a specific functional or biological activity to certain cell or stage specific types, tissue types or anatomical structures. By directing albumin fusion proteins of the invention the action of the agent may be localized. Further, such targeting may enable the dosage of the albumin fusion proteins of the invention required to be reduced since, by accumulating the albumin fusion proteins of the invention at the required site, a higher localized concentration may be achieved. Albumin fusion proteins of the invention can be conjugated with a targeting portion by use of cross-linking agents as well as by recombinant DNA techniques whereby the nucleotide sequence encoding the albumin fusion proteins of the invention, or a functional portion of it, is cloned adjacent to the nucleotide sequence of the ligand when the ligand is a protein, and the conjugate expressed as a fusion protein.

Additional post-translational modifications encompassed by the invention include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of procaryotic host cell expression. The albumin fusion proteins may also be modified with a detectable label, such as an enzymatic, fluorescent, isotopic or affinity label to allow for detection and isolation of the protein. Examples of such modifications are given, e.g., in U.S. Provisional Application Ser. No. 60/355,547 and in WO 01/79480 (pp. 105–106), which are incorporated by reference herein, and are well known in the art.

Functional Activity

"A polypeptide having functional activity" refers to a polypeptide capable of displaying one or more known functional activities associated with the full-length, pro-protein, and/or mature form of a Therapeutic protein. Such functional activities include, but are not limited to, biological activity, enzyme inhibition, antigenicity [ability to bind to an anti-polypeptide antibody or compete with a polypeptide for binding], immunogenicity (ability to generate an antibody which binds to a specific polypeptide of the invention), ability to form multimers with polypeptides of the invention, and ability to bind to a receptor or ligand for a polypeptide.

"A polypeptide having biological activity" refers to a polypeptide exhibiting activity similar to, but not necessarily identical to, an activity of a Therapeutic protein of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention.

In other embodiments, an albumin fusion protein of the invention has at least one biological and/or therapeutic activity associated with the Therapeutic protein (or fragment or variant thereof) when it is not fused to albumin.

The albumin fusion proteins of the invention can be assayed for functional activity (e.g., biological activity) using or routinely modifying assays known in the art, as well as assays described herein. Specifically, albumin fusion proteins may be assayed for functional activity (e.g., biological activity or therapeutic activity) using the assay referenced in the "Relevant Publications" column of Table 4. Additionally, one of skill in the art may routinely assay fragments of a Therapeutic protein corresponding to a Therapeutic protein portion of an albumin fusion protein of the invention, for activity using assays referenced in its corresponding row of Table 4. Further, one of skill in the art may routinely assay fragments of an albumin protein corresponding to an albumin protein portion of an albumin fusion protein of the invention, for activity using assays known in the art and/or as described in the Examples section below.

In addition, assays described herein (see Examples and Table 4) and otherwise known in the art may routinely be applied to measure the ability of albumin fusion proteins of the present invention and fragments, variants and derivatives thereof to elicit biological activity and/or Therapeutic activity (either in vitro or in vivo) related to either the Therapeutic protein portion and/or albumin portion of the albumin fusion protein of the present invention. Other methods will be known to the skilled artisan and are within the scope of the invention.

Expression of Fusion Proteins

The albumin fusion proteins of the invention may be produced as recombinant molecules by secretion from yeast, a microorganism such as a bacterium, or a human or animal cell line. Optionally, the polypeptide is secreted from the host cells.

For expression of the albumin fusion proteins exemplified herein, yeast strains disrupted of the HSP150 gene as exemplified in WO 95/33833, or yeast strains disrupted of the PMT1 gene as exemplified in WO 00/44772 [rHA process] (serving to reduce/eliminate O-linked glycosylation of the albumin fusions), or yeast strains disrupted of the YAP3 gene as exemplified in WO 95/23857 were successfully used, in combination with the yeast PRB1 promoter, the HSA/MFα-1 fusion leader sequence exemplified in WO 90/01063, the yeast ADH1 terminator, the LEU2 selection marker and the disintegration vector pSAC35 exemplified in U.S. Pat. No. 5,637,504.

Other yeast strains, promoters, leader sequences, terminators, markers and vectors which are expected to be useful in the invention are described in U.S. Provisional Application Serial No. 60/355,547 and in WO 01/74980 (pp. 94–99), which are incorporated herein by reference, and are well known in the art.

The present invention also includes a cell, optionally a yeast cell transformed to express an albumin fusion protein of the invention. In addition to the transformed host cells themselves, the present invention also contemplates a culture of those cells, optionally a monoclonal (clonally homogeneous) culture, or a culture derived from a monoclonal culture, in a nutrient medium. If the polypeptide is secreted, the medium will contain the polypeptide, with the cells, or without the cells if they have been filtered or centrifuged away. Many expression systems are known and may be used, including bacteria (for example E. coli and Bacillus subtilis), yeasts (for example Saccharomyces cerevisiae, Kluyveromyces lactis and Pichia pastoris), filamentous fungi (for example Aspergillus), plant cells, animal cells and insect cells.

The desired protein is produced in conventional ways, for example from a coding sequence inserted in the host chromosome or on a free plasmid. The yeasts are transformed with a coding sequence for the desired protein in any of the usual ways, for example electroporation. Methods for transformation of yeast by electroporation are disclosed in Becker & Guarente (1990) Methods Enzymol. 194, 182.

Successfully transformed cells, i.e., cells that contain a DNA construct of the present invention, can be identified by well known techniques. For example, cells resulting from the introduction of an expression construct can be grown to produce the desired polypeptide. Cells can be harvested and lysed and their DNA content examined for the presence of the DNA using a method such as that described by Southern (1975) J. Mol. Biol. 98, 503 or Berent et al. (1985) Biotech. 3, 208. Alternatively, the presence of the protein in the supernatant can be detected using antibodies.

Useful yeast plasmid vectors include pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413–416 are Yeast Centromere plasmids (YCps).

Vectors for making albumin fusion proteins for expression in yeast include pPPC0005, pScCHSA, pScNHSA, and pC4:HSA which were deposited on Apr. 11, 2001 at the American Type Culture Collection, 10801 University Boulevard, Manassas, Va. 20110–2209 and which are described in Provisional Application Ser. No. 60/355,547 and WO 01/79480, which are incorporated by reference herein.

Another vector which is expected to be useful for expressing an albumin fusion protein in yeast is the pSAC35 vector which is described in Sleep et al., BioTechnology 8:42 (1990), which is hereby incorporated by reference in its entirety. The plasmid pSAC35 is of the disintegration class of vector described in U.S. Pat. No. 5,637,504.

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion, is treated with bacteriophage T4 DNA polymerase or E. coli DNA polymerase I, enzymes that remove protruding, γ-single-stranded termini with their 3' 5'-exonucleolytic activities, and fill in recessed 3'-ends with their polymerizing activities. The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of commercial sources.

A desirable way to modify the DNA in accordance with the invention, if, for example, HA variants are to be prepared, is to use the polymerase chain reaction as disclosed by Saiki et al. (1988) *Science* 239, 487–491. In this method the DNA to be enzymatically amplified is flanked by two specific oligonucleotide primers which themselves become incorporated into the amplified DNA. The specific primers may contain restriction endonuclease recognition sites which can be used for cloning into expression vectors using methods known in the art.

Exemplary genera of yeast contemplated to be useful in the practice of the present invention as hosts for expressing the albumin fusion proteins are *Pichia* (formerly classified as *Hansenula*), *Saccharomyces, Kluyveromyces, Aspergillus, Candida, Torulopsis, Torulaspora, Schizosaccharomyces, Citeromyces, Pachysolen, Zygosaccharomyces, Debaromyces, Trichoderma, Cephalosporium, Humicola, Mucor, Neurospora, Yarrowia, Metschunikowia, Rhodosporidium, Leucosporidium, Botryoascus, Sporidiobolus, Endomycopsis*, and the like. Genera include those selected from the group consisting of *Saccharomyces, Schizosaccharomyces, Kluyveromyces, Pichia* and *Torulaspora*. Examples of *Saccharomyces* spp. are *S. cerevisiae, S. italicus* and *S. rouxii*. Examples of other species, and methods of transforming them, are described in U.S. Provisional Application Ser. No. 60/355,547 and WO 01/79480 (pp. 97–98), which are incorporated herein by reference.

Methods for the transformation of *S. cerevisiae* are taught generally in EP 251 744, EP 258 067 and WO 90/01063, all of which are incorporated herein by reference.

Suitable promoters for *S. cerevisiae* include those associated with the PGK1 gene, GAL1 or GAL10 genes, CYCI, PHO5, TRPI, ADHI, ADH2, the genes for glyceraldehyde-3-phosphate dehydrogenase, hexokinase, pyruvate decarboxylase, phosphofructokinase, triose phosphate isomerase, phosphoglucose isomerase, glucokinase, alpha-mating factor pheromone, [a mating factor pheromone], the PRBI promoter, the GUT2 promoter, the GPDI promoter, and hybrid promoters involving hybrids of parts of 5' regulatory regions with parts of 5' regulatory regions of other promoters or with upstream activation sites (e.g. the promoter of EP-A-258 067).

Convenient regulatable promoters for use in *Schizosaccharomyces pombe* are the thiamine-repressible promoter from the nmt gene as described by Maundrell (1990) *J. Biol. Chem.* 265, 10857–10864 and the glucose repressible jbpl gene promoter as described by Hoffman & Winston (1990) *Genetics* 124, 807–816.

Methods of transforming *Pichia* for expression of foreign genes are taught in, for example, Cregg et al. (1993), and various Phillips patents (e.g. U.S. Pat. No. 4,857,467, incorporated herein by reference), and *Pichia* expression kits are commercially available from Invitrogen BV, Leek, Netherlands, and Invitrogen Corp., San Diego, Calif. Suitable promoters include AOXI and AOX2. Gleeson et al. (1986) *J. Gen. Microbiol.* 132, 3459–3465 include information on *Hansenula* vectors and transformation, suitable promoters being MOXI and FMD1; whilst EP 361 991, Fleer et al. (1991) and other publications from Rhone-Poulenc Rorer teach how to express foreign proteins in *Kluyveromyces* spp.

The transcription termination signal may be the 3' flanking sequence of a eukaryotic gene which contains proper signals for transcription termination and polyadenylation. Suitable 3' flanking sequences may, for example, be those of the gene naturally linked to the expression control sequence used, i.e. may correspond to the promoter. Alternatively, they may be different in which case the termination signal of the *S. cerevisiae* ADHI gene is optionally used.

The desired albumin fusion protein may be initially expressed with a secretion leader sequence, which may be any leader effective in the yeast chosen. Leaders useful in *S. cerevisiae* include that from the mating factor α polypeptide (MF α-1) and the hybrid leaders of EP-A-387 319. Such leaders (or signals) are cleaved by the yeast before the mature albumin is released into the surrounding medium. Further such leaders include those of *S. cerevisiae* invertase (SUC2) disclosed in JP 62-096086 (granted as 911036516), acid phosphatase (PH05), the pre-sequence of MFα-1, 0 glucanase (BGL2) and killer toxin; *S. diastaticus* glucoamylase II; *S. carlsbergensis* α-galactosidase (MEL1); *K. lactis* killer toxin; and *Candida glucoamylase*.

Additional Methods of Recombinant and Synthetic Production of Albumin Fusion Proteins The present invention includes polynucleotides encoding albumin fusion proteins of this invention, as well as vectors, host cells and organisms containing these polynucleotides. The present invention also includes methods of producing albumin fusion proteins of the invention by synthetic and recombinant techniques. The polynucleotides, vectors, host cells, and organisms may be isolated and purified by methods known in the art.

A vector useful in the invention may be, for example, a phage, plasmid, cosmid, mini-chromosome, viral or retroviral vector.

The vectors which can be utilized to clone and/or express polynucleotides of the invention are vectors which are capable of replicating and/or expressing the polynucleotides in the host cell in which the polynucleotides are desired to be replicated and/or expressed. In general, the polynucleotides and/or vectors can be utilized in any cell, either eukaryotic or prokaryotic, including mammalian cells (e.g., human (e.g., HeLa), monkey (e.g., Cos), rabbit (e.g., rabbit reticulocytes), rat, hamster (e.g., CHO, NSO and baby hamster kidney cells) or mouse cells (e.g., L cells), plant cells, yeast cells, insect cells or bacterial cells (e.g., *E. coli*). See, e.g., F. Ausubel et al., *Current Protocols in Molecular Biology*, Greene Publishing Associates and Wiley-Interscience (1992) and Sambrook et al. (1989) for examples of appropriate vectors for various types of host cells. Note, however, that when a retroviral vector that is replication defective is used, viral propagation generally will occur only in complementing host cells.

The host cells containing these polynucleotides can be used to express large amounts of the protein useful in, for example, pharmaceuticals, diagnostic reagents, vaccines and therapeutics. The protein may be isolated and purified by methods known in the art or described herein.

The polynucleotides encoding albumin fusion proteins of the invention may be joined to a vector containing a selectable marker for propagation in a host. Generally, a plasmid vector may be introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter compatible with the host cell in which the polynucleotide is to be expressed. The promoter may be a strong promoter and/or an inducible promoter.

Examples of promoters include the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs may include a translation initiating codon at the beginning and a termination codon (TAA, TGA or TAG) appropriately positioned at the end of the polypeptide to be translated.

As indicated, the expression vectors may include at least one selectable marker. Such markers include dihydrofolate reductase, G418, glutamine synthase, or neomycin resistance for eukaryotic cell culture, and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, NSO, 293, and Bowes melanoma cells; and plant cells. Appropriate culture mediums and conditions for the above-described host cells are known in the art.

In one embodiment, polynucleotides encoding an albumin fusion protein of the invention may be fused to signal sequences which will direct the localization of a protein of the invention to particular compartments of a prokaryotic or eukaryotic cell and/or direct the secretion of a protein of the invention from a prokaryotic or eukaryotic cell. For example, in *E. coli*, one may wish to direct the expression of the protein to the periplasmic space. Examples of signal sequences or proteins (or fragments thereof) to which the albumin fusion proteins of the invention may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit, and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, polynucleotides albumin fusion proteins of the invention may be fused to the pelB pectate lyase signal sequence to increase the efficiency of expression and purification of such polypeptides in Gram-negative bacteria. See, U.S. Pat. Nos. 5,576,195 and 5,846,818, the contents of which are herein incorporated by reference in their entireties.

Examples of signal peptides that may be fused to an albumin fusion protein of the invention in order to direct its secretion in mammalian cells include, but are not limited to, the MPIF-1 signal sequence (e.g., amino acids 1–21 of GenBank Accession number AAB51134), the stanniocalcin signal sequence (MLQNSAVLLLLVISASA, SEQ ID No.: 26, and a consensus signal sequence (MPTWAWWLFLVLLLALWAPARG, SEQ ID No.: 27. A suitable signal sequence that may be used in conjunction with baculoviral expression systems is the gp67 signal sequence (e.g., amino acids 1–19 of GenBank Accession Number AAA72759).

Vectors which use glutamine synthase (GS) or DHFR as the selectable markers can be amplified in the presence of the drugs methionine sulphoximine or methotrexate, respectively. An advantage of glutamine synthase based vectors is the availability of cell lines (e.g., the murine myeloma cell line, NSO) which are glutamine synthase negative. Glutamine synthase expression systems can also function in glutamine synthase expressing cells (e.g., Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657, which are hereby incorporated in their entireties by reference herein. Additionally, glutamine synthase expression vectors can be obtained from Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are herein incorporated by reference.

The present invention also relates to host cells containing vector constructs, such as those described herein, and additionally encompasses host cells containing nucleotide sequences of the invention that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. A host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the nucleic acids and nucleic acid constructs of the invention into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., the coding sequence corresponding to a Therapeutic protein may be replaced with an albumin fusion protein corresponding to the Therapeutic protein), and/or to include genetic material (e.g., heterologous polynucleotide sequences such as for example, an albumin fusion protein of the invention corresponding to the Therapeutic protein may be included). The genetic material operably associated with the endogenous polynucleotide may activate, alter, and/or amplify endogenous polynucleotides.

In addition, techniques known in the art may be used to operably associate heterologous polynucleotides (e.g., polynucleotides encoding an albumin protein, or a fragment or variant thereof) and/or heterologous control regions (e.g., promoter and/or enhancer) with endogenous polynucleotide sequences encoding a Therapeutic protein via homologous recombination (see, e.g., U.S. Pat. No. 5,641,670, issued Jun. 24, 1997; International Publication Number WO 96/29411; International Publication Number WO 94/12650; Koller et al., *Proc. Natl. Acad. Sci. USA* 86:8932–8935 (1989); and Zijlstra et al., *Nature* 342:435–438 (1989), the disclosures of each of which are incorporated by reference in their entireties).

Advantageously, albumin fusion proteins of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, hydrophobic charge interaction chromatography and lectin chromatography. In some embodiments, high performance liquid chromatography ("HPLC") may be employed for purification. In some cases, therapeutic proteins have low solubility or are soluble only in low or high pH or only in high or low salt. Fusion of therapeutic proteins to HSA is likely to improve the solubility characteristics of the therapeutic protein.

In some embodiments albumin fusion proteins of the invention are purified using one or more Chromatography methods listed above. In other embodiments, albumin fusion proteins of the invention are purified using one or more of the following Chromatography columns, Q sepharose FF column, SP Sepharose FF column, Q Sepharose High Performance Column, Blue Sepharose FF column, Blue Column, Phenyl Sepharose FF column, DEAE Sepharose FF, or Methyl Column.

Additionally, albumin fusion proteins of the invention may be purified using the process described in International Publication No. WO 00/44772 which is herein incorporated by reference in its entirety. One of skill in the art could easily modify the process described therein for use in the purification of albumin fusion proteins of the invention.

Albumin fusion proteins of the present invention may be recovered from products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, albumin fusion proteins of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

Albumin fusion proteins of the invention and antibodies that bind a Therapeutic protein or fragments or variants thereof can be fused to marker sequences, such as a peptide to facilitate purification. In one embodiment, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "FLAG" tag.

Further, an albumin fusion protein of the invention may be conjugated to a therapeutic moiety such as a cytotoxin, e.g., a cytostatic or cytocidal agent, a therapeutic agent or a radioactive metal ion, e.g., alpha-emitters such as, for example, 213Bi. Examples of such agents are given in U.S. Provisional Application Ser. No. 60/355,547 and in WO 01/79480 (p. 107), which are incorporated herein by reference.

Albumin fusion proteins may also be attached to solid supports, which are particularly useful for immunoassays or purification of polypeptides that are bound by, that bind to, or associate with albumin fusion proteins of the invention. Such solid supports include, but are not limited to, glass, cellulose, polyacrylamide, nylon, polystyrene, polyvinyl chloride or polypropylene.

Also provided by the invention are chemically modified derivatives of the albumin fusion proteins of the invention which may provide additional advantages such as increased solubility, stability and circulating time of the polypeptide, or decreased immunogenicity (see U.S. Pat. No. 4,179,337). Examples involving the use of polyethylene glycol are given in WO 01/79480 (pp. 109–111), which are incorporated by reference herein.

The presence and quantity of albumin fusion proteins of the invention may be determined using ELISA, a well known immunoassay known in the art.

Uses of the Polypeptides

Each of the polypeptides identified herein can be used in numerous ways. The following description should be considered exemplary and utilizes known techniques.

The albumin fusion proteins of the present invention are useful for treatment, prevention and/or prognosis of various disorders in mammals, preferably humans. Such disorders include, but are not limited to, those described herein under the heading "Biological Activity" in Table 4. For example, the albumin fusion proteins of the present invention may be used as inhibitors of serine proteases, plasmin, human neutrophil elastase and/or kallikrein.

Albumin fusion proteins can also be used to assay levels of polypeptides in a biological sample. For example, radiolabeled albumin fusion proteins of the invention could be used for imaging of polypeptides in a body. Examples of assays are given, e.g., in U.S. Provisional Application Ser. No. 60/355,547 and WO 0179480 (pp. 112–122), which are incorporated herein by reference, and are well known in the art. Labels or markers for in vivo imaging of protein include, but are not limited to, those detectable by X-radiography, nuclear magnetic resonance (NMR), electron spin relaxation (ESR), positron emission tomography (PET), or computer tomography (CT). For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the albumin fusion protein by labeling of nutrients given to a cell line expressing the albumin fusion protein of the invention.

An albumin fusion protein which has been labeled with an appropriate detectable imaging moiety, such as a radioisotope (for example, $^{131}I$, $^{112}In$, $^{99m}Tc$, ($^{131}I$, $^{125}I$, $^{123}I$, $^{121}I$), carbon ($^{14}C$), sulfur ($^{35}S$), tritium ($^3H$), indium ($^{115}In$, $^{113m}In$, $^{112}In$, $^{111}In$), and technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$, $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}Tc$. The labeled albumin fusion protein will then preferentially accumulate at locations in the body (e.g., organs, cells, extracellular spaces or matrices) where one or more receptors, ligands or substrates (corresponding to that of the Therapeutic protein used to make the albumin fusion protein of the invention) are located. Alternatively, in the case where the albumin fusion protein comprises at least a fragment or variant of a Therapeutic antibody, the labeled albumin fusion protein will then preferentially accumulate at the locations in the body (e.g., organs, cells, extracellular spaces or matrices) where the polypeptides/epitopes corresponding to those bound by the Therapeutic antibody (used to make the albumin fusion protein of the invention) are located. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)). The protocols described therein could easily be modified by one of skill in the art for use with the albumin fusion proteins of the invention.

Albumin fusion proteins of the invention can also be used to raise antibodies, which in turn may be used to measure protein expression of the Therapeutic protein, albumin protein, and/or the albumin fusion protein of the invention from a recombinant cell, as a way of assessing transformation of the host cell, or in a biological sample. Moreover, the albumin fusion proteins of the present invention can be used to test the biological activities described herein.

Transgenic Organisms

Transgenic organisms that express the albumin fusion proteins of the invention are also included in the invention. Transgenic organisms are genetically modified organisms into which recombinant, exogenous or cloned genetic material has been transferred. Such genetic material is often referred to as a transgene. The nucleic acid sequence of the transgene may include one or more transcriptional regulatory sequences and other nucleic acid sequences such as introns, that may be necessary for optimal expression and secretion of the encoded protein. The transgene may be designed to direct the expression of the encoded protein in a manner that facilitates its recovery from the organism or from a product produced by the organism, e.g. from the milk, blood, urine, eggs, hair or seeds of the organism. The transgene may consist of nucleic acid sequences derived from the genome of the same species or of a different species than the species of the target animal. The transgene may be integrated either at a locus of a genome where that particular nucleic acid sequence is not otherwise normally found or at the normal locus for the transgene.

The term "germ cell line transgenic organism" refers to a transgenic organism in which the genetic alteration or genetic information was introduced into a germ line cell, thereby conferring the ability of the transgenic organism to transfer the genetic information to offspring. If such offspring in fact possess some or all of that alteration or genetic information, then they too are transgenic organisms. The alteration or genetic information may be foreign to the species of organism to which the recipient belongs, foreign only to the particular individual recipient, or may be genetic information already possessed by the recipient. In the last case, the altered or introduced gene may be expressed differently than the native gene.

A transgenic organism may be a transgenic human, animal or plant. Transgenics can be produced by a variety of different methods including transfection, electroporation, microinjection, gene targeting in embryonic stem cells and recombinant viral and retroviral infection (see, e.g., U.S. Pat. No. 4,736,866; U.S. Pat. No. 5,602,307; Mullins et al. (1993) Hypertension 22(4):630–633; Brenin et al. (1997) Surg. Oncol. 6(2)99–110; Tuan (ed.), *Recombinant Gene Expression Protocols*, Methods in Molecular Biology No. 62, Humana Press (1997)). The method of introduction of nucleic acid fragments into recombination competent mammalian cells can be by any method which favors co-transformation of multiple nucleic acid molecules. Detailed procedures for producing transgenic animals are readily available to one skilled in the art, including the disclosures in U.S. Pat. No. 5,489,743 and U.S. Pat. No. 5,602,307. Additional information is given in U.S. Provisional Application Ser. No. 60/355,547 and WO 01/79480 (pp. 151–162), which are incorporated by reference herein.

Gene Therapy

Constructs encoding albumin fusion proteins of the invention can be used as a part of a gene therapy protocol to deliver therapeutically effective doses of the albumin fusion protein. One approach for in vivo introduction of nucleic acid into a cell is by use of a viral vector containing nucleic acid, encoding an albumin fusion protein of the invention. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid. The extended plasma half-life of the described albumin fusion proteins may even compensate for a potentially low expression level.

Retrovirus vectors and adeno-associated virus vectors can be used as a recombinant gene delivery system for the transfer of exogenous nucleic acid molecules encoding albumin fusion proteins in vivo. These vectors provide efficient delivery of nucleic acids into cells, and the transferred nucleic acids are stably integrated into the chromosomal DNA of the host. Examples of such vectors, methods of using them, and their advantages, as well as non-viral delivery methods are described in detail in U.S. Provisional Application Ser. No. 60/355,547 and WO 01/79480 (pp. 151–153), which are incorporated by reference herein.

Gene delivery systems for a gene encoding an albumin fusion protein of the invention can be introduced into a patient by any of a number of methods. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by Stereotactic injection (e.g. Chen et al. (1994) PNAS 91: 3054–3057). The pharmaceutical preparation of the gene therapy construct can consist essentially of the gene delivery system in an acceptable diluent, or can comprise a slow release matrix in which the gene delivery vehicle is imbedded. Where the albumin fusion protein can be produced intact from recombinant cells, e.g. retroviral vectors, the pharmaceutical preparation can comprise one or more cells which produce the albumin fusion protein. Additional gene therapy methods are described in U.S. Provisional Application Ser. No. 60/355,547 and in WO 01/79480 (pp. 153–162), which are incorporated herein by reference.

Pharmaceutical or Therapeutic Compositions

The albumin fusion proteins of the invention or formulations thereof may be administered by any conventional method including parenteral (e.g. subcutaneous or intramuscular) injection or intravenous infusion. The treatment may consist of a single dose or a plurality of doses over a period of time. Furthermore, the dose, or plurality of doses, is administered less frequently than for the Therapeutic Protein which is not fused to albumin.

While it is possible for an albumin fusion protein of the invention to be administered alone, it is desirable to present it as a pharmaceutical formulation, together with one or more acceptable carriers. The carrier(s) must be "acceptable" in the sense of being compatible with the albumin fusion protein and not deleterious to the recipients thereof. Typically, the carriers will be water or saline which will be sterile and pyrogen free. Albumin fusion proteins of the invention are particularly well suited to formulation in aqueous carriers such as sterile pyrogen free water, saline or other isotonic solutions because of their extended shelf-life in solution. For instance, pharmaceutical compositions of the invention may be formulated well in advance in aqueous form, for instance, weeks or months or longer time periods before being dispensed.

Formulations containing the albumin fusion protein may be prepared taking into account the extended shelf-life of the albumin fusion protein in aqueous formulations. As discussed above, the shelf-life of many of these Therapeutic proteins are markedly increased or prolonged after fusion to HA.

In instances where aerosol administration is appropriate, the albumin fusion proteins of the invention can be formulated as aerosols using standard procedures. The term "aerosol" includes any gas-borne suspended phase of an albumin fusion protein of the instant invention which is capable of being inhaled into the bronchioles or nasal passages. Specifically, aerosol includes a gas-borne suspension of droplets of an albumin fusion protein of the instant invention, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example.

The formulations may conveniently be presented in unit dosage form and may be prepared by any of the methods well known in the art of pharmacy. Such methods include the step of bringing into association the albumin fusion protein with the carrier that constitutes one or more accessory ingredients. In general the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation appropriate for the intended recipient; and aqueous and non-aqueous sterile suspensions which may include suspending agents and thickening agents. The formulations may be presented in unit-dose or multi-dose containers, for example sealed ampules, vials or syringes, and may be stored in a freeze-dried (lyophilised) condition requiring only the addition of the sterile liquid carrier, for example water for injections, immediately prior to use. Extemporaneous injection solutions and suspensions may be prepared from sterile powders. Dosage formulations may contain the Therapeutic protein portion at a lower molar concentration or lower dosage compared to the non-fused standard formulation for the Therapeutic protein given the extended serum half-life exhibited by many of the albumin fusion proteins of the invention.

As an example, when an albumin fusion protein of the invention comprises one or more of the Therapeutic protein regions, the dosage form can be calculated on the basis of the potency of the albumin fusion protein relative to the potency of the Therapeutic protein, while taking into account the prolonged serum half-life and shelf-life of the albumin fusion proteins compared to that of the native Therapeutic protein. For example, in an albumin fusion protein consisting of a full length HA fused to a full length Therapeutic protein, an equivalent dose in terms of units would represent a greater weight of agent but the dosage frequency can be reduced.

Formulations or compositions of the invention may be packaged together with, or included in a kit with, instructions or a package insert referring to the extended shelf-life of the albumin fusion protein component. For instance, such instructions or package inserts may address recommended storage conditions, such as time, temperature and light, taking into account the extended or prolonged shelf-life of the albumin fusion proteins of the invention. Such instructions or package inserts may also address the particular advantages of the albumin fusion proteins of the inventions, such as the ease of storage for formulations that may require use in the field, outside of controlled hospital, clinic or office conditions. As described above, formulations of the invention may be in aqueous form and may be stored under less than ideal circumstances without significant loss of therapeutic activity.

The invention also provides methods of treatment and/or prevention of diseases or disorders (such as, for example, any one or more of the diseases or disorders disclosed herein) by administration to a subject of an effective amount of an albumin fusion protein of the invention or a polynucleotide encoding an albumin fusion protein of the invention ("albumin fusion polynucleotide") in a pharmaceutically acceptable carrier.

Effective dosages of the albumin fusion protein and/or polynucleotide of the invention to be administered may be determined through procedures well known to those in the art which address such parameters as biological half-life, bioavailability, and toxicity, including using data from routine in vitro and in vivo studies such as those described in the references in Table 4, using methods well known to those skilled in the art.

The albumin fusion protein and/or polynucleotide will be formulated and dosed in a fashion consistent with good medical practice, taking into account the clinical condition of the individual patient (especially the side effects of treatment with the albumin fusion protein and/or polynucleotide alone), the site of delivery, the method of administration, the scheduling of administration, and other factors known to practitioners. The "effective amount" for purposes herein is thus determined by such considerations.

For example, determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Albumin fusion proteins and polynucleotides of the present invention can be administered to any animal, preferably to mammals and birds. Preferred mammals include humans, dogs, cats, mice, rats, rabbits sheep, cattle, horses and pigs, with humans being particularly preferred.

As a general proposition, the albumin fusion protein of the invention will be dosed lower or administered less frequently than the unfused Therapeutic peptide. A therapeutically effective dose may refer to that amount of the compound sufficient to result in amelioration of symptoms, disease stabilization, a prolongation of survival in a patient, or improvement in the quality of life.

Albumin fusion proteins and/or polynucleotides can be are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Albumin fusion proteins and/or polynucleotides of the invention are also suitably administered by sustained-release systems, such as those described in U.S. Provisional Application Ser. No. 60/355,547 and WO 01/79480 (pp. 129–130), which are incorporated by reference herein.

For parenteral administration, in one embodiment, the albumin fusion protein and/or polynucleotide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation optionally does not include oxidizing agents and other compounds that are known to be deleterious to the Therapeutic.

The albumin fusion proteins and/or polynucleotides of the invention may be administered alone or in combination with other therapeutic agents. Albumin fusion protein and/or polynucleotide agents that may be administered in combination with the albumin fusion proteins and/or polynucleotides of the invention, include but not limited to, chemotherapeutic agents, antibiotics, steroidal and non-steroidal anti-inflammatories, conventional immunotherapeutic agents, and/or therapeutic treatments as described in U.S. Provisional Application Ser. No. 60/355,547 and WO 01/79480 (pp. 132–151) which are incorporated by reference herein. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

Pharmaceutical compositions suitable for use in the present invention include compositions wherein the active ingredients are contained in an effective amount to achieve its intended purpose.

The invention also provides a pharmaceutical pack or kit comprising one or more containers filled with one or more of the ingredients of the pharmaceutical compositions comprising albumin fusion proteins of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

With this general description of the invention, it is believed that one of ordinary skill in the art can, using the preceding description and the following illustrative examples, make and utilize the alterations detected in the present invention and practice the claimed methods. The following working examples therefore, specifically point out different embodiments of the present invention, and are not to be construed as limiting in any way the remainder of the disclosure.

EXAMPLES

Example 1

Construction of N-Terminal and C-Terminal Albumin-(GGS)$_4$GG Linker Cloning Vectors The recombinant albumin expression vectors pDB2243 and pDB2244 have been described previously in patent application WO 00/44772. The recombinant albumin expression vectors pAYE645 and pAYE646 have been described previously in UK patent application 0217033.0. Plasmid pDB2243 was modified to introduce a DNA sequence encoding the 14 amino acid polypeptide linker N-GGSGGSGGSGGSGG-C ((GGS)$_4$GG, "N" and "C" denote the orientation of the polypeptide sequence) (SEQ ID No.: 28) at the C-terminal end of the albumin polypeptide in such a way to subsequently enable another polypeptide chain to be inserted C-terminal to the (GGS)$_4$GG linker to produce a C-terminal albumin fusion in the general configuration, albumin-(GGS)$_4$GG-polypeptide. Similarly, plasmid pAYE645 was modified to introduce a DNA sequence encoding the (GGS)$_4$GG polypeptide linker at the N-terminal end of the albumin polypeptide in such a way to subsequently enable another polypeptide chain to be inserted N-terminal to the (GGS)$_4$GG linker to produce an N-terminal albumin fusion in the general configuration of polypeptide-(GGS)$_4$GG-albumin.

Plasmid pDB2243, described by Sleep, D., et al. (1991) Bio/Technology 9, 183–187 and in patent application WO 00/44772 which contained the yeast PRB1 promoter and the yeast ADH1 terminator providing appropriate transcription promoter and transcription terminator sequences. Plasmid pDB2243 was digested to completion with BamHI, the recessed ends were blunt ended with T4 DNA polymerase and dNTPs, and finally religated to generate plasmid pDB2566.

A double stranded synthetic oligonucleotide linker Bsu36I/HindIII linker was synthesized by annealing the synthetic oligonucleotides JH033A and JH033B.

JH033A
5-TTAGGCTTAGGTGGTTCTGGTGGTTCCGGTGG (SEQ ID No.: 29)

TTCTGGTGGATCCGGTGGTTAATA-3'

JH033B
5'-AGCTTATTAACCACCGGATCCACCAGAACCA (SEQ ID No.: 30)

CCGGAACCACCAGAACCACCTAAGCC-3'

The annealed Bsu36I/HindIII linker was ligated into HindIII/Bsu36I cut pDB2566 to generate plasmid pDB2575X which comprised an albumin coding region with a (GGS)$_4$GG peptide linker at its C-terminal end.

Plasmid pAYE645 that contained the yeast PRB1 promoter and the yeast ADH1 terminator providing appropriate transcription promoter and transcription terminator sequences is described in UK patent application 0217033.0. Plasmid pAYE645 was digested to completion with the restriction enzyme AflII and partially digested with the restriction enzyme HindIII and the DNA fragment comprising the 3' end of the yeast PRB1 promoter and the rHA coding sequence was isolated. Plasmid pDB2241 described in patent application WO 00/44772, was digested with AflII/HindIII and the DNA fragment comprising the 5' end of the yeast PRB1 promoter and the yeast ADH1 terminator was isolated. The AflII/HindIII DNA fragment from pAYE645 was then cloned into the AflII/HindIII pDB2241 vector DNA fragment to create the plasmid pDB2302. Plasmid pDB2302 was digested to completion with PacI/XhoI and the 6.19 kb fragment isolated, the recessed ends were blunt ended with T4 DNA polymerase and dNTPs, and religated to generate plasmid pDB2465. Plasmid pDB2465 was linearized with ClaI, the recessed ends were blunt ended with T4 DNA polymerase and dNTPs, and religated to generate plasmid pDB2533. Plasmid pDB2533 was linearized with BlnI, the recessed ends were blunt ended with T4 DNA polymerase and dNTPs, and religated to generate plasmid pDB2534. Plasmid pDB2534 was digested to completion with BmgBI/BglII, the 6.96 kb DNA fragment isolated and ligated to one of two double stranded oligonucleotide linkers, VC053/VC054 and VC057/VC058 to create plasmid pDB2540, or VC055/VC056 and VC057/VC058 to create plasmid pDB2541.

VC053
5'-GATCTTTGGATAAGAGAGACGCTCACAAGTC (SEQ ID No.: 31)

CGAAGTCGCTCACCGGT-3'

VC054
5'-pCCTTGAACCGGTGAGCGACTTCGGACTTGT (SEQ ID No.: 32)

GAGCGTCTCTCTTATCCAAA-3'

VC055
5'-GATCTTTGGATAAGAGAGACGCTCACAAGTC (SEQ ID No.: 33)

CGAAGTCGCTCATCGAT-3'

VC056
5'-pCCTTGAATCGATGAGCGACTTCGGACTTGT (SEQ ID No.: 34)

GAGCGTCTCTCTTATCCAAA-3'

-continued

VC057
5'-pTCAAGGACCTAGGTGAGGAAAACTTCAAGG (SEQ ID No.: 35)

CTTTGGTCTTGATCGCTTTCGCTCAATACTTGCA

ACAATGTCCATTCGAAGATCAC-3'

VC058
5'-GTGATCTTCGAATGGACATTGTTGCAAGTAT (SEQ ID No.: 36)

TGAGCGAAAGCGATCAAGACCAAAGCCTTGAAGT

TTTCCTCACCTAGGT-3'

A double stranded synthetic oligonucleotide linker BglII/AgeI linker was synthesized by annealing the synthetic oligonucleotides JH035A and JH035B.

JH035A
5'-GATCTTTGGATAAGAGAGGTGGATCCGGTGG (SEQ ID No.: 37)

TTCCGGTGGTTCTGGTGGTTCCGGTGGTGACGCT

CACAAGTCCGAAGTGGCTCA-3'

JH035B
5'-CCGGTGAGCGACTTCGGACTTGTGAGCGTCA (SEQ ID No.: 38)

CCACCGGAACCACCAGAACCACCGGAACCACCGG

ATCCACCTCTCTTATCCAAA-3'

The annealed BglII/AgeI linker was ligated into BglII/AgeI cut pDB2540 to generate plasmid pDB2573X, which comprised an albumin coding region with a (GGS)$_4$GG peptide linker at its N-terminal end.

Example 2

Equilibrium Inhibition Constant for Unfused DPI-14

The amino acid sequence of DPI-14 is EAVREVCSEQA-ETGPCIAFFPRWYFDVTEGKCAPFFYG-GCGGNRNNFDTEEYCMAVCGSA (SEQ ID No.: 39). A DNA sequence was derived from this polypeptide sequence by the process of back-translation. The DPI-14 was expressed in *Pichia* and extracted from the fermentation broth supernatant using ion-exchange chromatography, hydrophobic interaction chromatography, and ultrafiltration. The equilibrium inhibition constant ($K_i$) for DPI-14 inhibition of human neutrophil elastase (HNE) was determined to be 15±2 pM, for [HNE]=57±7 pM. The $K_i$ measurement was performed using the methods set forth in Example 15.

Example 3

A Construction of N-Terminal and C-Terminal Albumin-DPI-14 Fusions

The DNA sequences were provided at the 5' or 3' end to encode bridging sequences between the DPI-14 coding region, the albumin coding region or the leader sequence as appropriate for N-terminal DPI-14-(GGS)$_4$GG-albumin or C-terminal albumin-(GGS)$_4$GG-DPI-14 fusions. An N-terminal BglII-BamHI DPI-14 cDNA (Table 5) and a C-terminal BamHI-HindIII DPI-14 cDNA (Table 6) were constructed from overlapping oligonucleotides.

Example 4

Construction of N-Terminal DPI-14-(GGS)$_4$GG-albumin Expression Plasmids

Plasmid pDB2573X was digested to completion with BglII and BamHI, the 6.21 kb DNA fragment was isolated and treated with calf intestinal phosphatase and then ligated with the 0.2 kb BglII/BamHI N terminal DPI-14 cDNA to create pDB2666. The DNA and amino acid sequence of the N-terminal DPI-14-(GGS)$_4$GG-albumin fusion are shown in Table 7 and Table 8, respectively. Appropriate yeast vector sequences were provide by a "disintegration" plasmid pSAC35 generally disclosed in EP-A-286 424 and described by Sleep, D., et al. (1991) Bio/Technology 9, 183–187. The NotI N-terminal DPI-14-(GGS)$_4$GG-rHA expression cassette was isolated from pDB2666, purified and ligated into NotI digested pSAC35 which had been treated with calf intestinal phosphatase, creating two plasmids; the first (pDB2679) contained the NotI expression cassette in the same expression orientation as LEU2, while the second (pDB2680) contained the NotI expression cassette in the opposite orientation to LEU2. Both pDB2679 and pDB2680 are good producers of the desired fusion protein.

Example 5

Construction of C-Terminal Albumin-(GGS)$_4$GG-DPI-14 Expression Plasmid

Plasmid pDB2575X was partially digested with HindIII and then digested to completion with BamHI. The desired 6.55 kb DNA fragment was isolated and ligated with the 0.2 kb BamHI/HindIII C terminal DPI-14 cDNA to create pDB2648. The DNA and amino acid sequence of the C-terminal albumin-(GGS)$_4$GG-DPI-14 fusion are shown in Table 9 and Table 10, respectively. Appropriate yeast vector sequences were provide by a "disintegration" plasmid pSAC35 generally disclosed in EP-A-286 424 and described by Sleep, D., et al. (1991) Bio/Technology 9, 183–187. The NotI C-terminal albumin-(GGS)$_4$GG-DPI-14 expression cassette was isolated from pDB2648, purified and ligated into NotI digested pSAC35 which had been treated with calf intestinal phosphatase, creating pDB2651 contained the NotI expression cassette in the same expression orientation as LEU2.

Example 6

Construction of C-Terminal Albumin-(GGS)$_4$GG-DX-1000 Expression Plasmid

Plasmid pDB2575X was partially digested with HindIII and then digested to completion with BamHI. The desired 6.55 kb DNA fragment was isolated and ligated with the 0.2 kb BamHI/HindIII C-terminal DX-1000 cDNA as shown in Table 11 to create pDB2648X-1000. Appropriate yeast vector sequences were provide by a "disintegration" plasmid pSAC35 generally disclosed in EP-A-286 424 and described by Sleep, D., et al. (1991) Bio/Technology 9, 183–187. The NotI C-terminal albumin-(GGS)$_4$GG-DX1000 expression cassette was isolated from pDB2648X-1000, purified and ligated into NotI digested pSAC35 which had been treated with calf intestinal phosphatase, creating pDB265 IX-1000 contained the NotI expression cassette in the same expression orientation as LEU2.

Example 7

Construction of N-Terminal and C-Terminal Albumin-DX-890 Fusions
Generation of the Basic Clone
The amino acid sequence of DX-890 is EACNLPIVRGP-CIAFFPRWAFDAVKGKCVLFPYGGC-QGNGNKFYSEKECREYCGVP (SEQ ID No.: 40). A DNA sequence was derived from this polypeptide sequence by the process of back-translation. The DNA sequences were provided at the 5' or 3' end to encode bridging sequences between the DX-890 coding region, the albumin coding region or the leader sequence as appropriate for N-terminal DX-890-(GGS)$_4$GG-albumin or C-terminal albumin-(GGS)$_4$GG-DX-890 fusions. An N-terminal BglII-BamHI DX-890 cDNA (Table 12) and a C-terminal BamHI-HindIII DX-890 cDNA (Table 13) were constructed from overlapping oligonucleotides.

Example 8

Construction of N-Terminal DX-890-(GGS)$_4$GG-Albumin Expression Plasmids

Plasmid pDB2573X was digested to completion with BglII and BamHI, the 6.21 kb DNA fragment was isolated and treated with calf intestinal phosphatase and then ligated with the 0.2 kb BglII/BamHI N terminal DX-890 cDNA to create pDB2683. The DNA and amino acid sequence of the N-terminal DX-890-(GGS)$_4$GG-albumin fusion are shown in Table 14 and Table 15, respectively. Appropriate yeast vector sequences were provide by a "disintegration" plasmid pSAC35 generally disclosed in EP-A-286 424 and described by Sleep, D., et al. (1991) Bio/Technology 9, 183–187. The NotI N-terminal DX-890-(GGS)$_4$GG-rHA expression cassette was isolated from pDB2683, purified and ligated into NotI digested pSAC35 which had been treated with calf intestinal phosphatase creating pDB2684 contained the NotI expression cassette in the opposite orientation to LEU2.

Example 9

Construction of C-Terminal Albumin-(GGS)$_4$GG-DX-890 Expression Plasmid

Plasmid pDB2575X was partially digested with HindIII and then digested to completion with BamHI. The desired 6.55 kb DNA fragment was isolated and ligated with the 0.2 kb BamHI/HindIII C terminal DX-890 cDNA to create pDB2649. The DNA and amino acid sequence of the C-terminal albumin-(GGS)$_4$GG-DX-890 fusion are shown in Table 16 and Table 17, respectively. Appropriate yeast vector sequences were provide by a "disintegration" plasmid pSAC35 generally disclosed in EP-A-286 424 and described by Sleep, D., et al. (1991) Bio/Technology 9, 183–187. The NotI C-terminal albumin-(GGS)$_4$GG-DX-890 expression cassette was isolated from pDB2649, purified and ligated into NotI digested pSAC35 which had been treated with calf intestinal phosphatase, creating two plasmids; the first pDB2652 contained the NotI expression cassette in the same expression orientation as LEU2, while the second pDB2653 contained the NotI expression cassette in the opposite orientation to LEU2.

Example 10

Fermentation to Produce a Fusion Protein

The DX-890-HSA fusion protein was expressed in fermentation culture as described in WO 00/44772. The DX-890-HSA fusion protein was purified from fermentation culture supernatant using the standard HA purification SP-FF (Pharmacia) conditions as described in WO 00/44772, except that an extra 200 mM NaCl was required in the elution buffer.

Example 11

Yeast Transformation and Culturing Conditions

Yeast strains disclosed in WO 95/23857, WO 95/33833 and WO 94/04687 were transformed to leucine prototrophy as described in Sleep D., et al. (2001) Yeast 18, 403–421. The transformants were patched out onto Buffered Minimal Medium (BMM, described by Kerry-Williams, S. M. et al. (1998) Yeast 14, 161–169) and incubated at 30° C. until grown sufficiently for further analysis.

Example 12

$K_i$ Measurement of DX-890 Samples

Equilibrium inhibition constants ($K_i$) for DX-890 or DX-890-HSA inhibition of HNE were determined according to the tight-binding inhibition model with formation of a reversible complex (1:1 stoichiometry). Inhibition of hNE was determined at 30° C. in 50 mM HEPES, pH 7.5, 150 mM NaCl, and 0.1% Triton X-100. All reactions (total volume=200 µL) were carried out in microtiter plates (Costar #3789). hNE was incubated with varying concentrations of added inhibitor for 24 hours. Residual enzymatic activities were determined from the relative rates of substrate hydrolysis. The hydrolysis reaction was initiated by addition of N-methoxysuccinyl-Ala-Ala-Pro-Val-7-aminomethylcoumarin (SEQ ID No.: 41) as substrate. Enzymatic cleavage of this substrate releases the methylcoumarin moiety with concomitant increase the sample fluorescence. The rate of substrate hydrolysis was monitored at an excitation of 360 nm and an emission of 460 nm. Plots of the percent remaining activity versus inhibitor concentration were fit by nonlinear regression analysis to Equation 1 to determine equilibrium dissociation constants.

$$\% A = 100 - \left( \frac{(I + E + K_i) - \sqrt{(I + E + K_i)^2 - 4 \cdot E \cdot I}}{2 \cdot E} \right) \cdot 100 \quad (1)$$

Where:
% A=percent activity
I=DX-890
E=HNE concentration
$K_i$=equilibrium inhibition constant The $K_i$ of native DX-890 was measured at the same time as a positive control. The $K_i$'s of DX-890 and DX-890-HSA fusion for human neutrophil elastase (HNE) were similar to each other (FIG. 1). Similar results were seen with the DX-890-HSA fusion in supernatant from a shake flask yeast culture or from a fermentor. Both supernatants were supplied by Aventis to Dyax. This result indicates that fusion to HSA does not affect the potency of DX-890 as an inhibitor of HNE.

Example 13

Fusions of DX-88 to N Terminus of HSA

DX-88 is a Kunitz domain derived from the first Kunitz domain of human LACI which inhibits human plasma kallikrein with $K_i$~40 pM. The serum half-time of DX-88 is not more than 1 hour. DX-88 is currently being tested in the clinic for treatment of hereditary angioedema (HAE). Initial data suggest that DX-88 is safe and effective. HAE is a condition in which attacks recur episodically and having a long-acting form would allow prophylactic treatment instead of reactive treatment.

A DNA sequence is available for DX-88, prepared for fusion to the N terminus of HA. The DNA sequences are provided at the 5' or 3' end to encode bridging sequences between the DX-88 coding region, the albumin coding region or the leader sequence as appropriate for N-terminal DX-88-(GGS)$_4$GG-albumin (Table 18).

Plasmid pDB2573X is digested to completion with BglII and BamHI, the 6.21 kb DNA fragment is isolated and treated with calf intestinal phosphatase and then ligated with the 0.2 kb BglII/BamHI N terminal DX-88 cDNA to create pDB2666-88. The DNA and amino acid sequence of the N-terminal DX-88-(GGS)$_4$GG-albumin fusion are shown in Table 19 and Table 20, respectively. Appropriate yeast vector sequences are provided by a "disintegration" plasmid pSAC35 generally disclosed in EP-A-286 424 and described by Sleep, D., et al. (1991) Bio/Technology 9, 183–187. The NotI N-terminal DX-88-(GGS)$_4$GG-rHA expression cassette is isolated from pDB2666-88, purified and ligated into NotI digested pSAC35 which had been treated with calf intestinal phosphatase, creating two plasmids; the first pDB2679-88 contains the NotI expression cassette in the same expression orientation as LEU2, while the second pDB2680-88 contains the NotI expression cassette in the opposite orientation to LEU2.

Example 14

Construction of C-Terminal Albumin-(GGS)$_4$GG-DX-88 Expression Plasmid

As in Example 5, Plasmid pDB2575X is partially digested with HindIII and then digested to completion with BamHI. The desired 6.55 kb DNA fragment is isolated and ligated with the 0.2 kb BamHI/HindIII C terminal DX-88 cDNA (Table 21) to create pDB2648-88. The DNA and amino acid sequence of the C-terminal albumin-(GGS)$_4$GG-DX-88 fusion are shown in Table 22 and Table 23, respectively. Appropriate yeast vector sequences are provide by a "disintegration" plasmid pSAC35 generally disclosed in EP-A-286 424 and described by Sleep, D., et al. (1991) Bio/Technology 9, 183–187. The NotI C-terminal albumin-(GGS)$_4$GG-DX-88 expression cassette is isolated from pDB2648-88, purified and ligated into NotI digested pSAC35 which is treated with calf intestinal phosphatase, creating pDB2651-88 contained the NotI expression cassette in the same expression orientation as LEU2.

Example 15

Pharmacokinetic Study in Mice

The DX-890-HSA fusion protein was expressed in fermentation culture as described in WO 00/44772. The DX-890-HSA fusion protein was purified from fermentation culture supernatant using the standard HA purification SP-FF (Pharmacia) conditions as described in WO 00/44772, except that an extra 200 mM NaCl was required in the elution buffer.

About 10 mg of rHA-DX-890 fusion was purified from the diafiltration retentate by SEC-HPLC and characterized by SCS-PAGE and RP-HPLC methods to be about 92% monomeric form. This material was used for subsequent $^{125}$I radiolabeling and in-vivo plasma clearance studies.

For studies using mice, animals were injected in the tail vein and 4 animals were sacrificed at approximately 0, 7, 15, 30 and 90 minutes, 4 h, 8 h, 16 h, 24 h after injection, less 4 time points for the native DX-890 because of its likely short half life. Time of injection and time of sampling were recorded. At sacrifice, samples of ~0.5 ml were collected into anticoagulant (0.02 ml EDTA). Cells were spun down and separated from plasma. Plasma was divided into two aliquots, one frozen and one stored at 4° C. for immediate analysis. Analysis included gamma counting of all samples. In addition, analysis was performed for two plasma samples (N=2) at each time point, i.e., 0, and 30 minutes, for $^{125}$I-DX-890, and 0, 30 minutes, and 24 h for the $^{125}$I-DX-890-HSA fusion. A SEC-HPLC Superose-12 column with an in-line radiation detector was used to analyze plasma fractions.

Figure 2:
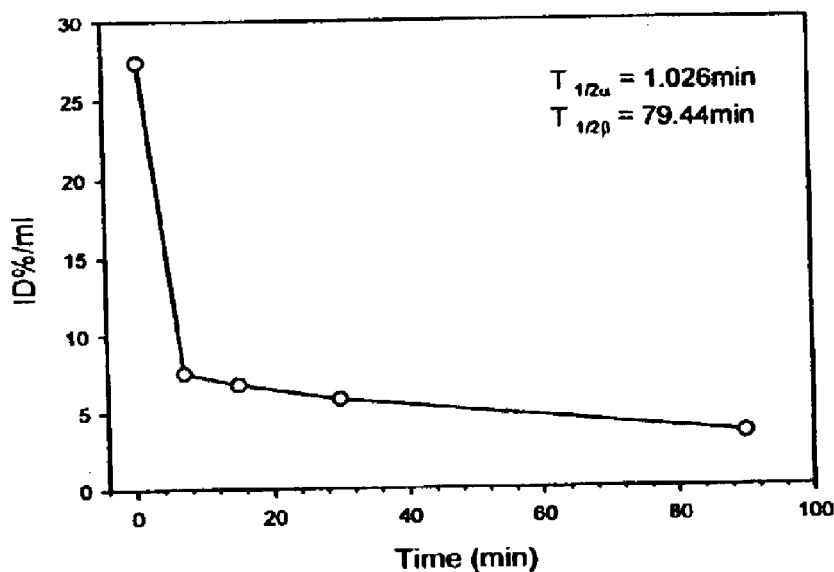
FIG. 2: Plasma clearance curves for $^{125}$I-DX-890 (top) and $^{125}$I-DX-890-HSA fusion (bottom).
Figure 2:
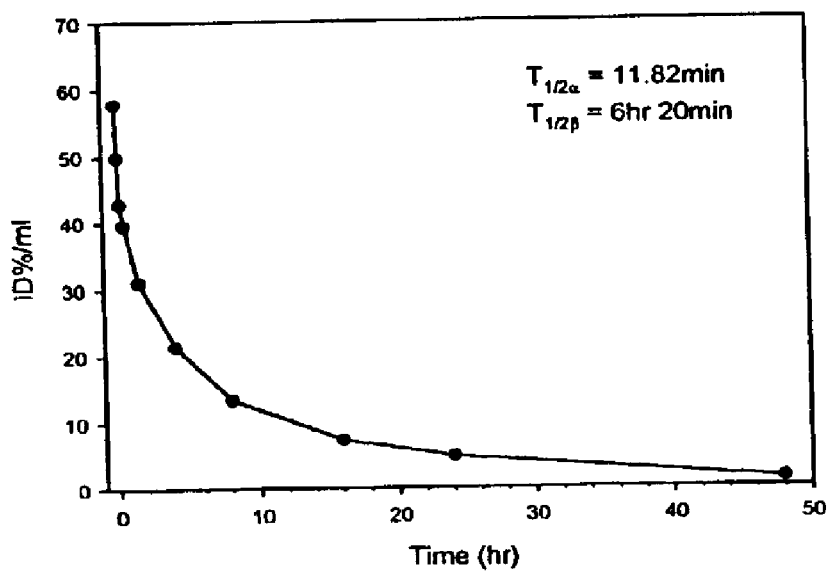
Figure 3:
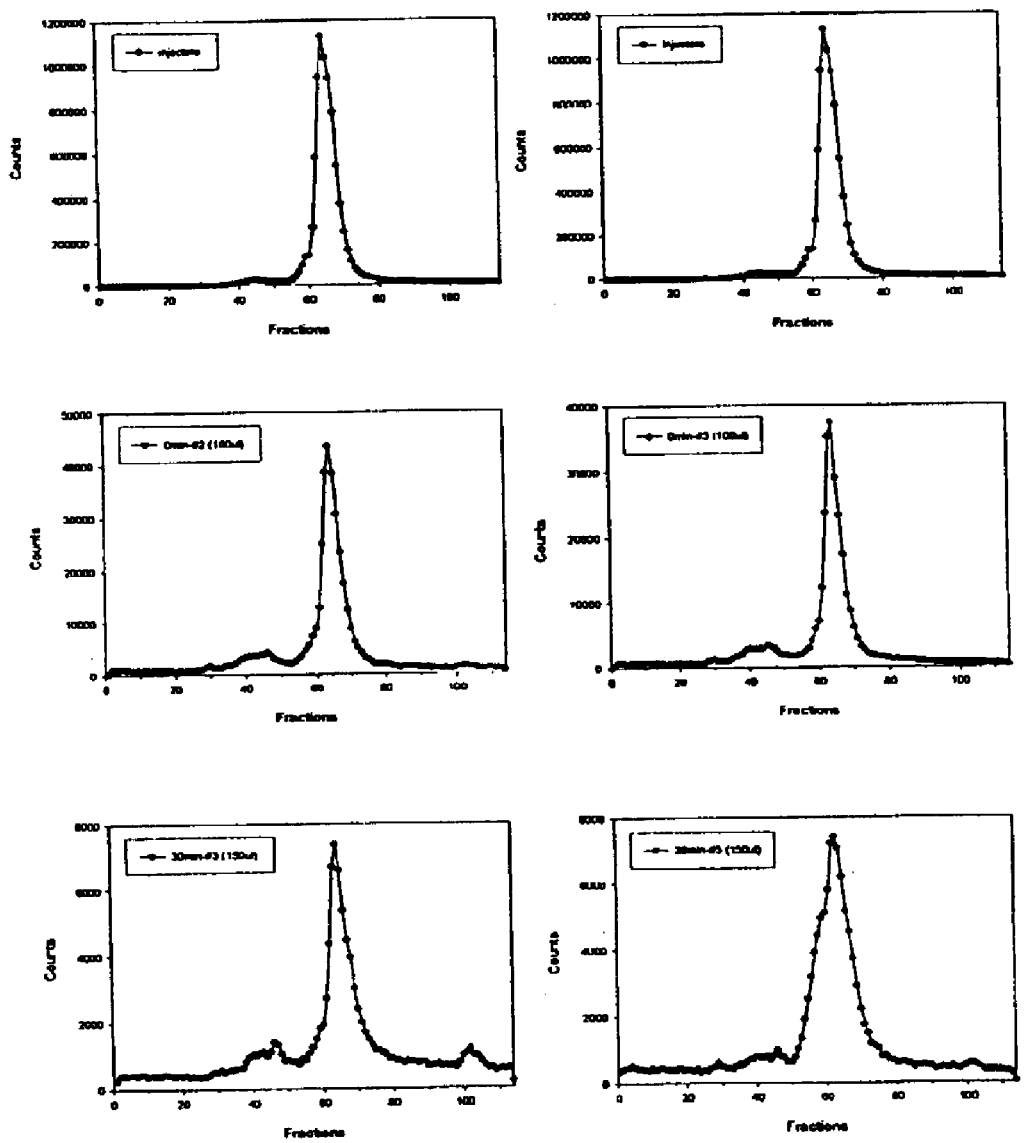
FIG. 3: $^{125}$I-DX890 in normal mouse plasma on SE-HPLC (Superose-12).
Figure 4:
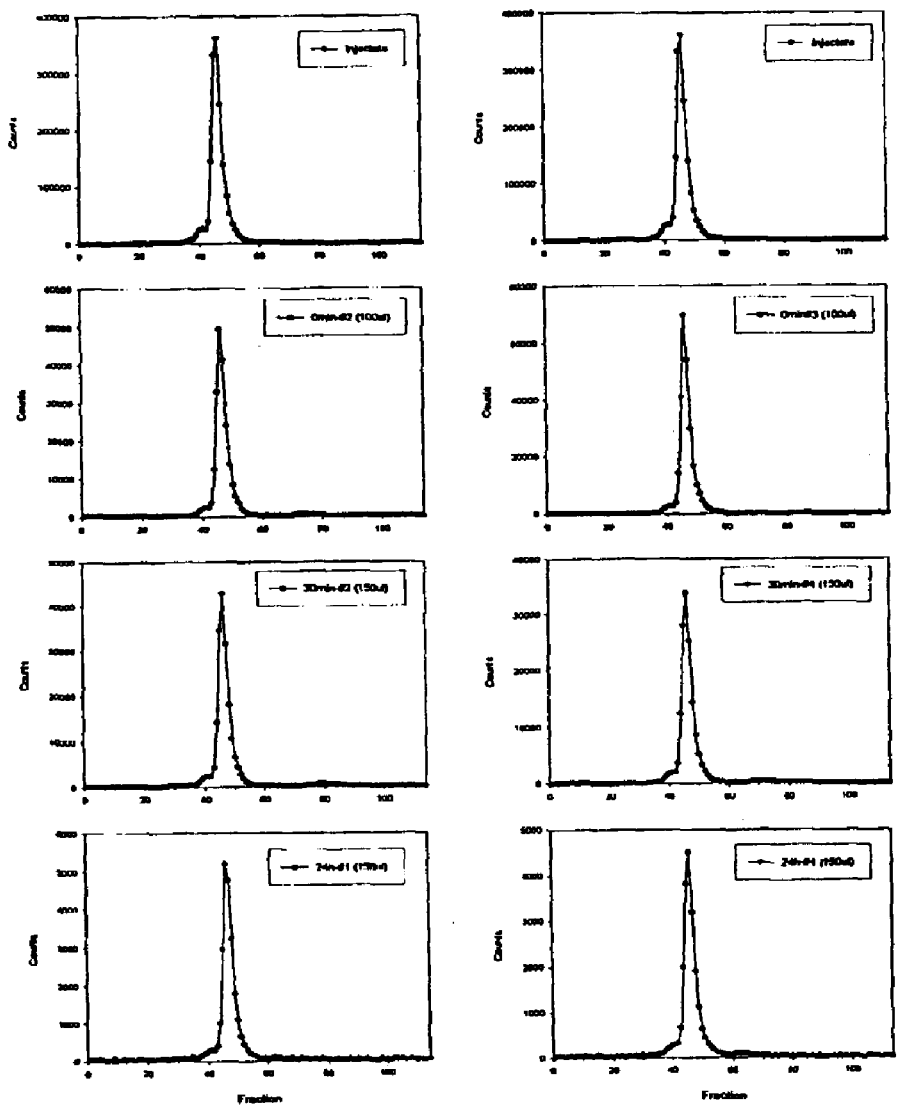
FIG. 4: SE-HPLC(Superose-12) Profiles of $^{125}$I-HAS-DX890 in normal mouse plasma.

The results show that fusing DX-890 to HSA dramatically improves its beta (elimination) half life by ~5× (FIG. 2). In addition, it appears that the DX-890-HSA-fusion is more stable in mouse plasma than DX-890 (FIGS. 3 and 4).

Example 16

Pharmacokinetic Study in Rabbits

Pharmacokinetic properties of DX-890 and DX-890-HSA were measured by iodinating the proteins and measuring clearance of the radiolabel from circulation in rabbits. The two DX-890 preparations were iodinated with iodine-125 using the iodogen method. After radiolabeling, the two labeled protein preparations were purified from unbound label by size exclusion chromatography (SEC). Fractions from the SEC column having the highest radioactivity were pooled. The purified, radiolabeled preparations were characterized for specific activity by scintillation counting and for purity by SEC using a Superose-12 column equipped with an in-line radiation detector.

New Zealand White rabbits (ca. 2.5 Kg) were used for clearance measurements, with one animal each used for of the two labeled protein preparations. The radiolabeled preparation was injected into the animal via an ear vein. One blood sample was collected per animal per time point with early time points at approximately 0, 7, 15, 30, and 90 minutes and later time points at 4, 8, 16, 24, 48, 72, 96, 144, 168, and 192 hours. Samples (about 0.5 ml) were collected into anticoagulant (EDTA) tubes. Cells were separated from the plasma/serum fraction by centrifugation. The plasma fraction was divided into two aliquots. One plasma aliquot was stored at −70° C. and the other aliquot was kept at 4° C. for immediate analyses. Sample analyses included radiation counting for clearance rate determinations and SEC chromatography for in vivo stability. The results of the rabbit clearance study are summarized in FIGS. 5 and 6 and in Table 24.

Figure 5:
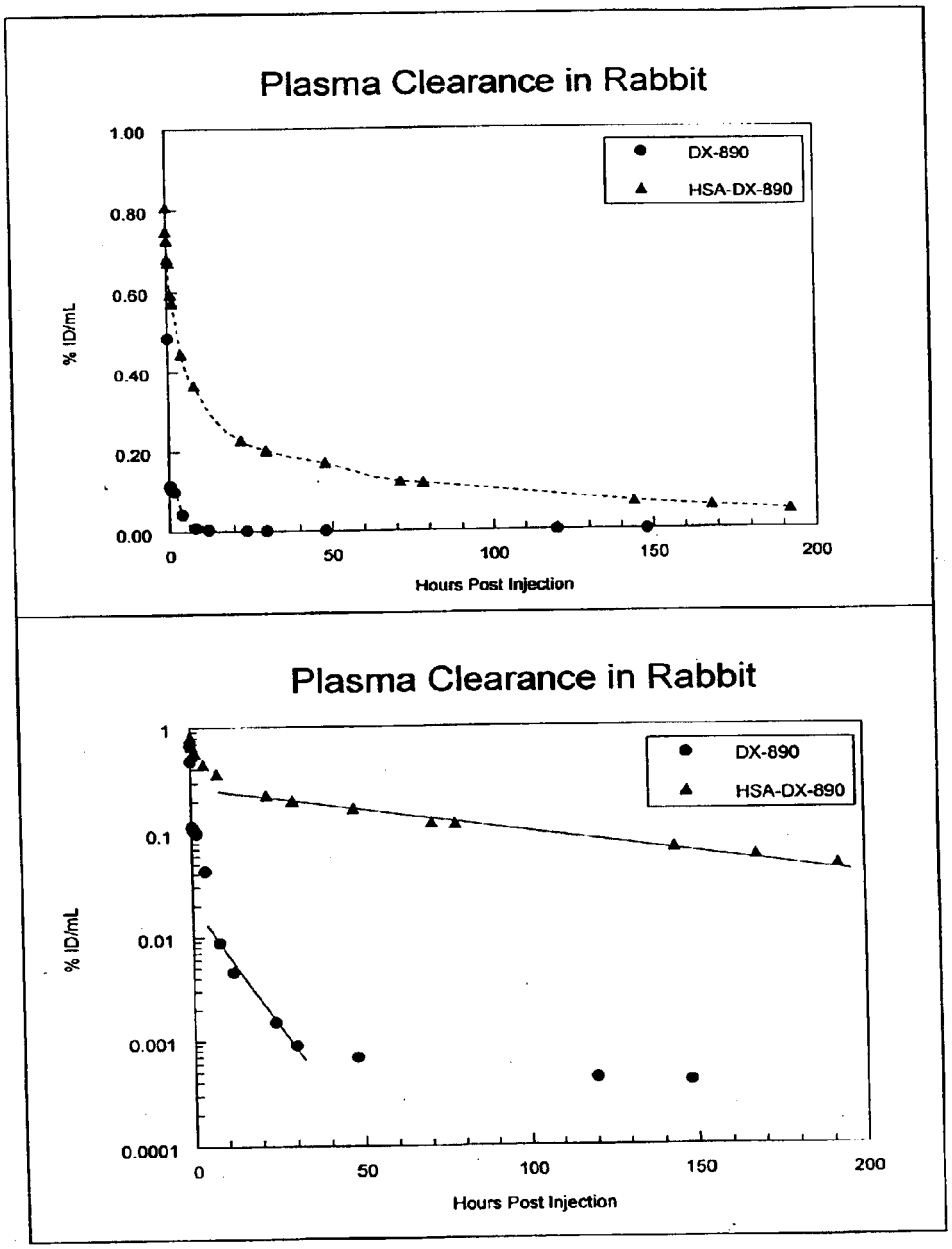
FIG. 5: Plasma Clearance of $^{125}$I Labeled DX-890 and HSA-DX-890 in Rabbits

The HSA-DX-890 fusion protein shows substantial improvements in in vivo circulation properties relative to those of the unmodified DX-890. Plasma clearance rates are greatly reduced for the fusion protein so that after a single day relative circulating levels of radiolabel are more than 100-fold higher for the HSA-DX-890 fusion than for the unmodified protein (FIG. 5). A simple bi-exponential fit to the data shows large increases in both the alpha and beta portions of the clearance curve (Table 24). In particular, the value for $T_{1/2\beta}$ is increased more than 20-fold, from about 165 min (2.75 hrs) for the unmodified protein to about 3500 min (~60 hrs, ~2.5 days) for the HSA-DX-890 fusion. In addition, the fraction of the total material involved in the slow clearance portion of the curve nearly doubles for the fusion protein relative to unmodified DX-890 (Table 24).

TABLE 24

Clearance Times in Rabbits

| Compound | Dose | | Clearance Times (min) | | | |
|---|---|---|---|---|---|---|
| | μgm | μCi | $T_{1/2\alpha}$ | % α | $T_{1/2\beta}$ | % β |
| DX-890 | 50 | 83 | 0.4 | 75 | 165 | 25 |
| HSA-DX-890 | 151 | 105 | 270 | 60 | 3500 | 40 |

Figure 6:
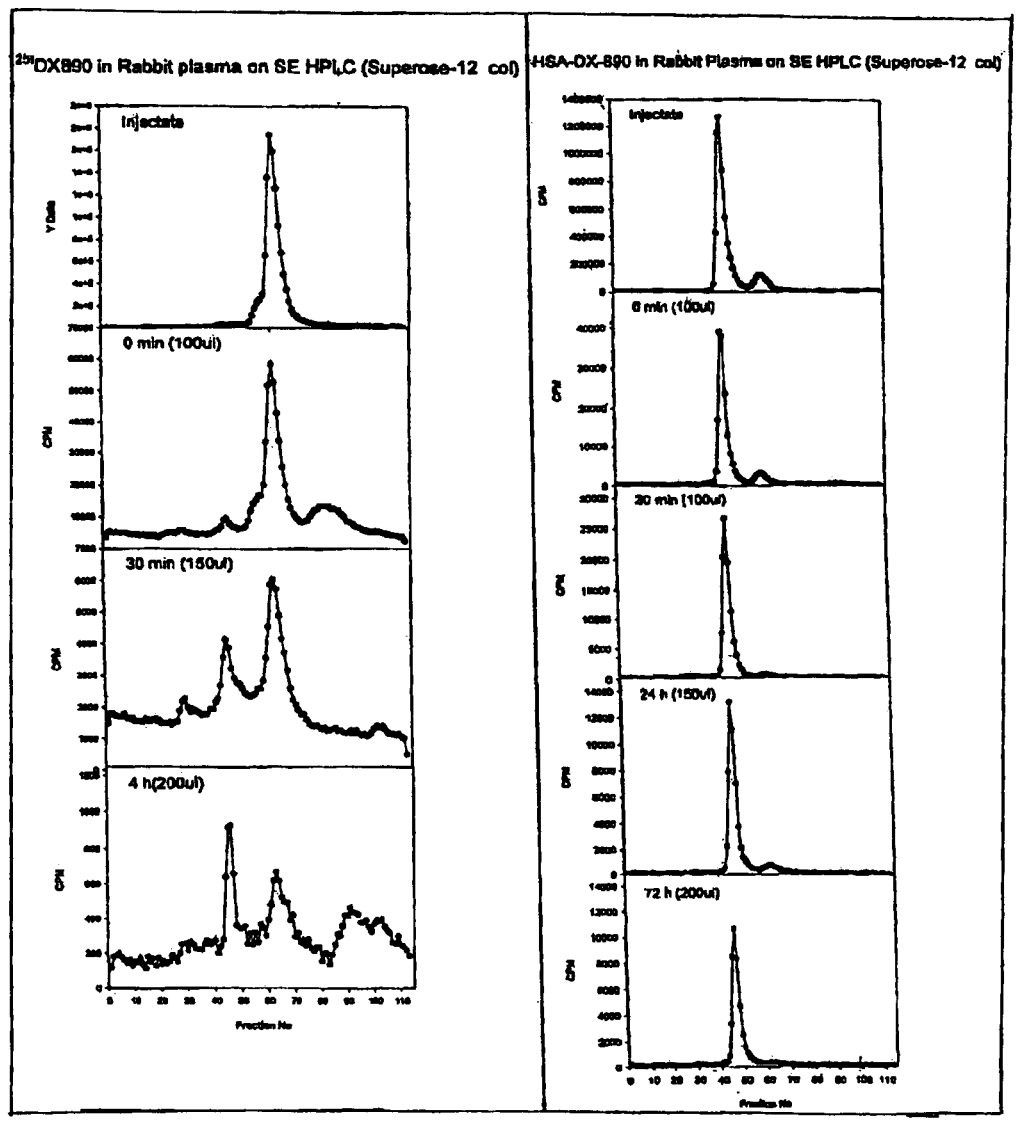
FIG. 6: SEC Analysis of Rabbit Plasma Samples

Finally, in vivo stability appears to be improved for the fusion protein relative to unmodified DX-890 (FIG. 6). SEC analysis of plasma from the rabbit injected with $^{125}$I-DX-890 (FIG. 6, Part A) shows a relatively rapid association of label with higher molecular weight plasma components (earlier eluting peaks). Further, the relative proportion of the total residual circulating label associated with the high molecular weight material increases as time post-injection increases (compare 30 min and 4 hour elution profiles). In contrast, SEC analyses of plasma samples from the rabbit injected with $^{125}$I-HSA-DX-890 (FIG. 6, Part B) shows that almost all of the circulating label is associated with the HSA-DX-890 peak seen in the injectate and that the label remains stably associated with this peak for at least 72 hours.

Example 17

A Vector for Making a Doubly Fused HSA

The vector pDB2300X1 is a modification of pDB2575X in which there is a BglII/BamHI cassette near the 5' terminus of the rHA gene and a BspEI/KpnI cassette near the 3' terminus. The NotI cassette that comprises this gene is shown in Table 25 showing the DNA, encoded AA sequence and useful restriction sites. In each line in Table 25, everything after an exclamation point is commentary, the DNA sequence is numbered and spaced to allow understand the design.

Example 18

Adding a First Instance of DX890 to pDB2300X1

The DNA shown in Table 12 is introduced into pDB2300X1 that has been cut with BglII and BamHI to make the new vector pDB2300X2. The DNA, encoded AA sequence and useful restriction sites of the NotI cassette of pDB2300X2 are shown in Table 26.

Example 19

Adding a Second Instance of DX890 to pDB2300X2

The DNA shown in Table 27 is introduced into pDB2300X2 that has been cut with BspEI and KpnI to make the new vector pDB2300X3. Although this DNA encodes the same AA sequence as does the DNA of Table 12, many codons have been changed to reduce the likelihood of recombination between the two DX890-encoding regions. The DNA, encoded AA sequence and useful restriction sites of this construct are shown in Table 28. The encoded AA sequence is shown in Table 29. This protein is expressed in the same manner as the other constructions of the present invention. The protein of Table 103, "Dx890-HA-Dx890", will have ~16% the HNE-neutralizing activity of DX890 but a much long serum life time. Thus area-under-the-curve for inhibition of HNE will be much higher than for naked DX890.

Example 20

DX1000::(GGS)₄GG::HSA

The DNA shown in Table 30 is introduced into pDB2573X which has been cut with BglII and BamHI to create pDX1000. The AA sequence of the encoded protein is shown in Table 31. Expression of this protein is essentially the same as for other HA fusions of the present invention.

Example 21

DX-88::(GGS)₄GG::HSA::(GGS)₄GG::DX-88

In a manner similar to the construction of a gene encoding DX-890-HSA-DX-890, the DNA of Table 18 is inserted into pDB2300X1 that has been cut with BglII and BamHI to make the new vector pDB2300X88a. The DNA shown in Table 32 is introduced into pDB2300X88a as a BspEI/KpnI fragment to create pDB2300X88b which contains two instances of DNA that encodes DX-88. The DNA in Table 32 is substantially different from the DNA in Table 18 so that recombination is unlikely.

Example 22

Multiple Albumin Fusions

The N-terminal fusion expression plasmid, pDB2540, as described herein, can be modified to introduce a unique Bsu36I at the C-terminal end; the new plasmid is named pDB2301X. The DNA sequence of the NotI expression cassette from pDB2301X is as follows:

```
                           pDB2540 + Bsu36I
        Not I                                                              (SEQ ID No.: 42)
      1 GCGGCCGCcc gtaatgcggt atcgtgaaag cgaaaaaaaa actaacagta gataagacag 61 atagacagat agagatggac gagaaacagg gggggagaaa aggggaaaag agaaggaaag NarI
    121 aaagactcat ctatcgcaga taagacaatc aaccctcatG GCGCCtccaa ccaccatccg 181 cactagggac caagcgctcg caccgttagc aacgcttgac tcacaaacca actgccggct 241 gaaagagctt gtgcaatggg agtgccaatt caaggagcc gaatacgtct gctcgccttt 301 taagaggctt tttgaacact gcattgcacc cgacaaatca gccactaact acgaggtcac 361 ggacacatat accaatagtt aaaaattaca tatactctat atagcacagt agtgtgataa 421 ataaaaaatt ttgccaagac ttttttaaac tgcacccgac agatcaggtc tgtgcctact 481 atgcacttat gcccggggtc ccgggaggag aaaaaacgag ggctgggaaa tgtccgtgga 541 ctttaaacgc tccgggttag cagagtagca gggctttcgg ctttggaaat ttaggtgact 601 tgttgaaaaa gcaaaatttg ggctcagtaa tgccactgca gtggcttatc acgccaggac 661 tgcgggagtg gcggggcaa acacacccgc gataaagagc gcgatgaata taaaaggggg 721 ccaatgttac gtcccgttat attggagttc ttcccataca aacttaagag tccaattagc HindIII
    781 ttcatcgcca ataaaaaaac AAGCTTaacc taattctaac aagcaaagat gaagtgggtt
                                                                   >>..........>

BglII
    841 ttcatcgtct ccattttgtt cttgttctcc tctgcttact ctAGATCTtt ggataagaga
        >...........................Fusion Leader........................>>

AgeI
    901 gacgctcaca agtccgaagt cgctcACCGG Ttcaaggacc taggtgagga aaacttcaag
        >>..................rHA synth. gene ..Continues to base 2655......>

961 gctttggtct tgatcgcttt cgctcaatac ttgcaacaat gtccattcga agatcacgtc 1021 aagttggtca acgaagttac cgaattcgct aagacttgtg ttgctgacga atctgctgaa 1081 aactgtgaca agtccttgca caccttgttc ggtgataagt tgtgtactgt tgctaccttg 1141 agagaaacct acggtgaaat ggctgactgt tgtgctaagc aagaaccaga aagaaacgaa 1201 tgtttcttgc aacacaagga cgacaaccca aacttgccaa gattggttag accagaagtt 1261 gacgtcatgt gtactgcttt ccacgacaac gaagaaacct tcttgaagaa gtacttgtac 1321 gaaattgcta agacaccc atacttctac gctccagaat tgttgttctt cgctaagaga 1381 tacaaggctg ctttccacga atgttgtcaa gctgctgata ggctgcttg tttgttgcca
```

-continued pDB2540 + Bsu36I

```
1441 aagttggatg aattgagaga cgaaggtaag gcttcttccg ctaagcaaag attgaagtgt 1501 gcttccttgc aaaagttcgg tgaaagagct ttcaaggctt gggctgtcgc tagattgtct 1561 caaagattcc caaaggctga attcgctgaa gtttctaagt tggttactga cttgactaag 1621 gttcacactg aatgttgtca cggtgacttg ttggaatgtg ctgatgacag agctgacttg 1681 gctaagtaca tctgtgaaaa ccaagactct atctcttcca agttgaagga atgttgtgaa 1741 aagccattgt tggaaaagtc tcactgtatt gctgaagttg aaaacgatga aatgccagct 1801 gacttgccat ctttggctgc tgacttcgtt gaatctaagg acgtttgtaa gaactacgct 1861 gaagctaagg acgtcttctt gggtatgttc ttgtacgaat acgctagaag cacccagac 1921 tactccgttg tcttgttgtt gagattggct aagacctacg aaactacctt ggaaaagtgt 1981 tgtgctgctg ctgacccaca cgaatgttac gctaaggttt tcgatgaatt caagccattg 2041 gtcgaagaac cacaaaactt gatcaagcaa aactgtgaat tgttcgaaca attgggtgaa 2101 tacaagttcc aaaacgcttt gttggttaga tacactaaga aggtcccaca agtctccacc 2161 ccaactttgg ttgaagtctc tagaaacttg ggtaaggtcg gttctaagtg ttgtaagcac 2221 ccagaagcta agagaatgcc atgtgctgaa gattacttgt ccgtcgtttt gaaccaattg 2281 tgtgttttgc acgaaaagac cccagtctct gatagagtca ccaagtgttg tactgaatct 2341 ttggttaaca gaagaccatg tttctctgct ttggaagtcg acgaaactta cgttccaaag EcoRV
2401 gaattcaacg ctgaaacttt caccttccac gctGATATCt gtaccttgtc cgaaaaggaa 2461 agacaaatta agaagcaaac tgctttggtt gaattggtca agcacaagcc aaaggctact 2521 aaggaacaat tgaaggctgt catggatgat ttcgctgctt tcgttgaaaa gtgttgtaag 2581 gctgatgata aggaaacttg tttcgctgaa gaaggtaaga agttggtcgc tgcttcccaa Bsu36I            HindIII
2641 gctgCCTTAG GcttataatA AGCTTaattc ttatgattta tgattttat tattaaataa
     >.............>>

2701 gttataaaaa aaataagtgt atacaaattt taaagtgact cttaggtttt aaaacgaaaa 2761 ttcttattct tgagtaactc tttcctgtag gtcaggttgc tttctcaggt atagcatgag SphI
2821 gtcgctctta ttgaccacac ctctaccgGC ATGCcgagca aatgcctgca aatcgctccc 2881 catttcaccc aattgtagat atgctaactc cagcaatgag ttgatgaatc tcggtgtgta NotI
2941 ttttatgtcc tcagaggaca cacctgttg taatcgttct tccacacgga tcGCGGCCGC
```

DNA encoding polypeptides can be inserted in between the BglII and AgeI sites to express an N-terminal albumin fusion, or between the Bsu36I and HindIII (not unique and so will require a partial HindIII digest) sites to express an C-terminal albumin fusion, or between both pairs of sites to make a co-N- and C-terminal albumin fusion.

Polypeptide spacers can be optionally incorporated. The DNA sequence of the NotI expression cassette from the modified pDB2540 is expected to be as follows:

pDB2540 + 2xGSlinkers

```
   Not I                                                      (SEQ ID No.: 43)
 1 GCGGCCGCcc gtaatgcggt atcgtgaaag cgaaaaaaaa actaacagta gataagacag 61 atagacagat agagatggac gagaaacagg gggggagaaa aggggaaaag agaaggaaag
```

-continued pDB2540 + 2xGSlinkers

```
                             NarI
 121 aaagactcat ctatcgcaga taagacaatc aaccctcatG GCGCCtccaa ccaccatccg 181 cactagggac caagcgctcg caccgttagc aacgcttgac tcacaaacca actgccggct 241 gaaagagctt gtgcaatggg agtgccaatt caaaggagcc gaatacgtct gctcgccttt 301 taagaggctt tttgaacact gcattgcacc cgacaaatca gccactaact acgaggtcac 361 ggacacatat accaatagtt aaaaattaca tatactctat atagcacagt agtgtgataa 421 ataaaaaatt ttgccaagac tttttttaaac tgcacccgac agatcaggtc tgtgcctact 481 atgcacttat gcccggggtc ccgggaggag aaaaaacgag ggctgggaaa tgtccgtgga 541 ctttaaacgc tccgggttag cagagtagca gggctttcgg cttggaaat ttaggtgact 601 tgttgaaaaa gcaaaatttg ggctcagtaa tgccactgca gtggcttatc acgccaggac 661 tgcgggagtg gcggggggcaa acacacccgc gataaagagc gcgatgaata taaaaggggg 721 ccaatgttac gtcccgttat attggagttc ttcccataca aacttaagag tccaattagc HindIII
 781 ttcatcgcca ataaaaaaac AAGCTTaacc taattctaac aagcaaagat gaagtgggtt
                                                    >>..........>

BglII
 841 ttcatcgtct ccatttttgtt cttgttctcc tctgcttact ctAGATCTtt ggataagaga
     >......................Fusion Leader......................>>

BamHI
 901 ggtGGATCCg gtggttccgg tggttctggt ggttccggtg gtgacgctca caagtccgaa
     >>..............GS linker.................>|>>......rHA........>

AgeI
 961 gtcgctcACC GGTtcaagga cctaggtgag gaaaacttca aggctttggt cttgatcgct
     >..............rHA synth. gene continues to base 2739..............>

1021 ttcgctcaat acttgcaaca atgtccattc gaagatcacg tcaagttggt caacgaagtt 1081 accgaattcg ctaagacttg tgttgctgac gaatctgctg aaaactgtga caagtccttg 1141 cacaccttgt tcggtgataa gttgtgtact gttgctacct tgagagaaac ctacggtgaa 1201 atggctgact gttgtgctaa gcaagaacca gaaagaaacg aatgtttctt gcaacacaag 1261 gacgacaacc caaacttgcc aagattggtt agaccagaag ttgacgtcat gtgtactgct 1321 ttccacgaca cgaagaaaac cttcttgaag aagtacttgt acgaaattgc tagaagacac 1381 ccatacttct acgctccaga attgttgttc ttcgctaaga gatacaaggc tgctttcacc 1441 gaatgttgtc aagctgctga taaggctgct tgtttgttgc caaagttgga tgaattgaga 1501 gacgaaggta aggcttcttc cgctaagcaa agattgaagt gtgcttcctt gcaaaagttc 1561 ggtgaaagag ctttcaaggc ttgggctgtc gctagattgt ctcaaagatt cccaaaggct 1621 gaattcgctg aagtttctaa gttggttact gacttgacta aggttcacac tgaatgttgt 1681 cacggtgact gttggaaatg tgctgatgac agagctgact ggctaagta catctgtgaa 1741 aaccaagact ctatctcttc caagttgaag gaatgttgtg aaaagccatt gttggaaaag 1801 tctcactgta ttgctgaagt tgaaaacgat gaaatgccag ctgacttgcc atctttggct 1861 gctgacttcg ttgaatctaa ggacgtttgt aagaactacg ctgaagctaa ggacgtcttc 1921 ttgggtatgt tcttgtacga atacgctaga agacacccag actactccgt tgtcttgttg 1981 ttgagattgg ctaagaccta cgaaactacc ttggaaaagt gttgtgctgc tgctgaccca 2041 cacgaatgtt acgctaaggt tttcgatgaa ttcaagccat ggtcgaaga accacaaaac 2101 ttgatcaagc aaaactgtga attgttcgaa caattgggtg aatacaagtt ccaaaacgct
```

```
                        pDB2540 + 2xGSlinkers
2161  ttgttggtta gatacactaa gaaggtccca caagtctcca ccccaactttt ggttgaagtc 2221  tctagaaact tgggtaaggt cggttctaag tgttgtaagc acccagaagc taagagaatg 2281  ccatgtgctg aagattactt gtccgtcgtt ttgaaccaat tgtgtgtttt gcacgaaaag 2341  accccagtct ctgatagagt caccaagtgt tgtactgaat ctttggttaa cagaagacca 2401  tgtttctctg ctttggaagt cgacgaaact tacgttccaa aggaattcaa cgctgaaact EcoRV
2461  ttcaccttcc acgctGATAT Ctgtaccttg tccgaaaagg aaagacaaat taagaagcaa 2521  actgctttgg ttgaattggt caagcacaag ccaaaggcta ctaaggaaca attgaaggct 2581  gtcatggatg atttcgctgc tttcgttgaa aagtgttgta aggctgatga taaggaaact Bsu36I
2641  tgtttcgctg aagaaggtaa gaagttggtc gctgcttccc aagctgCCTT AGGcttaggt
      >....................rHA synth. gene .....................>|>>>

BspEI            KpnI              HindIII
2701  ggttctggtg gtTCCGGAgg ttctggtGGT ACCggtggtt aatAAGCTTa attcttatga
      >..............GS linker..............>>

2761  tttatgattt ttattattaa ataagttata aaaaaaataa gtgtatacaa attttaaagt 2821  gactcttagg ttttaaaacg aaaattctta ttcttgagta actctttcct gtaggtcagg SphI
2881  ttgctttctc aggtatagca tgaggtcgct cttattgacc acacctctac cgGCATGCcg 2941  agcaaatgcc tgcaaatcgc tccccatttc acccaattgt agatatgcta actccagcaa 3001  tgagttgatg aatctcggtg tgtattttat gtcctcagag acaacacct gttgtaatcg NotI
3061  ttcttccaca cggatcGCGG CCGC
```

DNA encoding polypeptides can be inserted in between the BglII and BamHI sites to express an N-terminal albumin fusion, or between the unique BspEI and KpnI sites to express an C-terminal albumin fusion, or between both pairs of sites to make a co-N- and C-terminal albumin fusion. This is exemplified most simply by using the BglII-BamHI DPI-14 cDNA and the BamHI-HindIII DX-890 cDNA as described herein. By ligating these cDNAs into the appropriate site, a DPI-14-(GGS)$_4$GG-rHA-(GGS)$_4$GG-DX-890 fusion with the following DNA sequence would be constructed.

```
           Not I                                                          (SEQ ID No.: 44)
    1  GCGGCCGCcc gtaatgcggt atcgtgaaag cgaaaaaaaa actaacagta gataagacag 61  atagacagat agagatggac gagaaacagg gggggagaaa aggggaaaag agaaggaaag NarI
  121  aaagactcat ctatcgcaga taagacaatc aaccctcatG GCGCCtccaa ccaccatccg 181  cactagggac caagcgctcg caccgttagc aacgcttgac tcacaaacca actgccggct 241  gaaagagctt gtgcaatggg agtgccaatt caaggagcc gaatacgtct gctcgccttt 301  taagaggctt tttgaacact gcattgcacc cgacaaatca gccactaact acgaggtcac 361  ggacacatat accaatagtt aaaaattaca tatactctat atagcacagt agtgtgataa 421  ataaaaaatt ttgccaagac ttttttaaac tgcacccgac agatcaggtc tgtgcctact 481  atgcacttat gcccggggtc ccgggaggag aaaaaacgag ggctgggaaa tgtccgtgga 541  ctttaaacgc tccgggttag cagagtagca gggctttcgg ctttggaaat ttaggtgact 601  tgttgaaaaa gcaaaatttg ggctcagtaa tgccactgca gtggcttatc acgccaggac 661  tgcgggagtg gcgggggcaa acacacccgc gataaagagc gcgatgaata taaaaggggg
```

-continued

```
 721 ccaatgttac gtcccgttat attggagttc ttcccataca aacttaagag tccaattagc

HindIII
 781 ttcatcgcca ataaaaaaac AAGCTTaacc taattctaac aagcaaagat gaagtgggtt
                                 >>..........>

BglII
 841 ttcatcgtct ccatttttgtt cttgttctcc tctgcttact ctAGATCTtt ggataagaga
     >.....................Fusion Leader........................>>

901 gaagctgtta gagaagtttg ttctgaacaa gctgaaactg gtccatgtat tgctttcttc
     >>....................DPI-14 up to base 1080...................>

961 ccaagatggt acttcgatgt tactgaaggt aagtgcgcgc cattcttcta cggtggttgt 1021 ggtggtaaca gaaacaactt cgatactgaa gaatactgta tggctgtttg tggttctgct
     >..........................DPI-14............................>>

BamHI
1081 ggtGGATCCg gtggttccgg tggttctggt ggttccggtg gtgacgctca caagtccgaa
        >>...............GS linker.................>|>>...rHA synth gene.>

AgeI
1141 gtcgctcACC GGTtcaagga cctaggtgag gaaaacttca aggctttggt cttgatcgct
     >............rHA synth. gene continues to base 2877..............>

1201 ttcgctcaat acttgcaaca atgtccattc gaagatcacg tcaagttggt caacgaagtt 1261 accgaattcg ctaagacttg tgttgctgac gaatctctg aaaactgtga caagtccttg 1321 cacaccttgt tcggtgataa gttgtgtact gttgctacct gagagaaac ctacggtgaa 1381 atggctgact gttgtgctaa gcaagaacca gaaagaaacg aatgtttctt gcaacacaag 1441 gacgacaacc caaacttgcc aagattggtt agaccagaag ttgacgtcat gtgtactgct 1501 ttccacgaca acgaagaaac cttcttgaag aagtacttgt acgaaattgc tagaagacac 1561 ccatacttct acgctccaga attgttgttc ttcgctaaga gatacaaggc tgctttcacc 1621 gaatgttgtc aagctgctga taaggctgct tgtttgttgc caaagttgga tgaattgaga 1681 gacgaaggta aggcttcttc cgctaagcaa agattgaagt gtgcttcctt gcaaaagttc 1741 ggtgaaagag ctttcaaggc ttgggctgtc gctagattgt ctcaaagatt cccaaaggct 1801 gaattcgctg aagtttctaa gttggttact gacttgacta aggttcacac tgaatgttgt 1861 cacggtgact gttggaatg tgctgatgac agagctgact ggctaagta catctgtgaa 1921 aaccaagact ctatctcttc caagttgaag gaatgttgtg aaaagccatt gttggaaaag 1981 tctcactgta ttgctgaagt tgaaaacgat gaaatgccag ctgacttgcc atctttggct 2041 gctgacttcg ttgaatctaa ggacgttttgt aagaactacg ctgaagctaa ggacgtcttc 2101 ttgggtatgt tcttgtacga atacgctaga gacacccag actactccgt tgtcttgttg 2161 ttgagattgg ctaagaccta cgaaactacc ttggaaaagt gttgtgctgc tgctgaccca 2221 cacgaatgtt acgctaaggt tttcgatgaa ttcaagccat ggtcgaaga accacaaaac 2281 ttgatcaagc aaaactgtga attgttcgaa caattgggtg aatacaagtt ccaaaacgct 2341 ttgttggtta gatacactaa gaaggtccca caagtctcca ccccaactttt ggttgaagtc 2401 tctagaaact tgggtaaggt cggttctaag tgttgtaagc acccagaagc taagagaatg 2461 ccatgtgctg aagattactt gtccgtcgtt ttgaaccaat gtgtgttttt gcacgaaaag 2521 accccagtct ctgatagagt caccaagtgt gtactgaat ctttggttaa cagaagacca 2581 tgtttctctg ctttggaagt cgacgaaact tacgttccaa aggaattcaa cgctgaaact
```

-continued

```
2641 ttcaccttcc acgctGATAT CTgtaccttg tccgaaaagg aaagacaaat taagaagcaa 2701 actgctttgg ttgaattggt caagcacaag ccaaaggcta ctaaggaaca attgaaggct 2761 gtcatggatg atttcgctgc tttcgttgaa aagtgttgta aggctgatga taaggaaact Bsu36I
2821 tgtttcgctg aagaaggtaa gaagttggtc gctgcttccc aagctgCCTT AGGcttaggt
     >....................rHA synth. gene ......................>|>>>

BspEI
2881 ggttctggtg gtTCCGGAgg tagtggtggc tccggtggtg aggcttgcaa tcttcctatc
     Linker__________________________________>|--DX-890(second coding) -->

2941 gtccgtggcc cttgcatcgc ctttttttcct cgttgggcct ttgacgccgt caaaggcaaa 3001 tgcgtccttt ttccttacgg cggttgccag ggcaatggca ataaatttta tagcgagaaa 3061 gagtgccgtg agtattgcgg cgtcccttaa taaGGTACCL aatAAGCTTa attcttatga
     ----DX-890 (2nd coding)---->|

3121 tttatgattt ttattattaa ataagttata aaaaaaataa gtgtatacaa attttaaagt 3181 gactcttagg ttttaaaacg aaaattctta ttcttgagta actctttcct gtaggtcagg SphI
3241 ttgctttctc aggtatagca tgaggtcgct cttattgacc acacctctac cgGCATGCcg 3301 agcaaatgcc tgcaaatcgc tccccatttc acccaattgt agatatgcta actccagcaa 3361 tgagttgatg aatctcggtg tgtattttat gtcctcagag gacaacacct gttgtaatcg NotI
3421 ttcttccaca cggatcGCGG CCGC
```

The primary translation product of this DPI-14-$(GGS)_4$GG-rHA-$(GGS)_4$GG-DX-890 fusion is as follows. But as the first 24 amino acids constitute the fusion leader sequence, as described herein, the amino acid sequence of the secreted product are as follows:

```
  1 MKWVFIVSIL FLFSSAYSRS LDKREAVREV CSEQAETGPC IAFFPRWYFD (SEQ ID No.: 45)

51 VTEGKCAPFF YGGCGGNRNN FDTEEYCMAV CGSAGGSGGS GGSGGSGGDA

101 HKSEVAHRFK DLGEENFKAL VLIAFAQYLQ QCPFEDHVKL VNEVTEFAKT

151 CVADESAENC DKSLHTLFGD KLCTVATLRE TYGEMADCCA KQEPERNECF

201 LQHKDDNPNL PRLVRPEVDV MCTAFHDNEE TFLKKYLYEI ARRHPYFYAP

251 ELLFFAKRYK AAFTECCQAA DKAACLLPKL DELRDEGKAS SAKQRLKCAS

301 LQKFGERAFK AWAVARLSQR FPKAEFAEVS KLVTDLTKVH TECCHGDLLE

351 CADDRADLAK YICENQDSIS SKLKECCEKP LLEKSHCIAE VENDEMPADL

401 PSLAADFVES KDVCKNYAEA KDVFLGMFLY EYARRHPDYS VVLLLRLAKT

451 YETTLEKCCA AADPHECYAK VFDEFKPLVE EPQNLIKQNC ELFEQLGEYK

501 FQNALLVRYT KKVPQVSTPT LVEVSRNLGK VGSKCCKHPE AKRMPCAEDY

551 LSVVLNQLCV LHEKTPVSDR VTKCCTESLV NRRPCFSALE VDETYVPKEF

601 NAETFTFHAD ICTLSEKERQ IKKQTALVEL VKHKPKATKE QLKAVMDDFA

651 AFVEKCCKAD DKETCFAEEG KKLVAASQAA LGLGGSGGSG GSGGSGGEAC

701 NLPIVRGPCI AFFPRWAFDA VKGKCVLFPY GGCQGNGNKF YSEKECREYC

751 GVP
```

```
  1 EAVREVCSEQ AETGPCIAFF PRWYFDVTEG KCAPFFYGGC GGNRNNFDTE  (SEQ ID No.: 46)

51 EYCMAVCGSA GGSGGSGGSG GSGGDAHKSE VAHRFKDLGE ENFKALVLIA

101 FAQYLQQCPF EDHVKLVNEV TEFAKTCVAD ESAENCDKSL HTLFGDKLCT

151 VATLRETYGE MADCCAKQEP ERNECFLQHK DDNPNLPRLV RPEVDVMCTA

201 FHDNEETFLK KYLYEIARRH PYFYAPELLF FAKRYKAAFT ECCQAADKAA

251 CLLPKLDELR DEGKASSAKQ RLKCASLQKF GERAFKAWAV ARLSQRFPKA

301 EFAEVSKLVT DLTKVHTECC HGDLLECADD RADLAKYICE NQDSISSKLK

351 ECCEKPLLEK SHCIAEVEND EMPADLPSLA ADFVESKDVC KNYAEAKDVF

401 LGMFLYEYAR RHPDYSVVLL LRLAKTYETT LEKCCAAADP HECYAKVFDE

451 FKPLVEEPQN LIKQNCELFE QLGEYKFQNA LLVRYTKKVP QVSTPTLVEV

501 SRNLGKVGSK CCKHPEAKRM PCAEDYLSVV LNQLCVLHEK TPVSDRVTKC

551 CTESLVNRRP CFSALEVDET YVPKEFNAET FTFHADICTL SEKERQIKKQ

601 TALVELVKHK PKATKEQLKA VMDDFAAFVE KCCKADDKET CFAEEGKKLV

651 AASQAALGLG GSGGSGGSGG SGGEACNLPI VRGPCIAFFP RWAFDAVKGK

701 CVLFPYGGCQ GNGNKFYSEK ECREYCGVP
```

EXAMPLE 23

Amino-Acid Sequence of a DPI-14-(GGS)₄GG-HSA Fusion Protein

Table 33 shows the amino-acid sequence of a fusion of DPI14 via a linker comprising (GGS)₄GG to HSA. Construction of a gene to encode the given sequence is simple using the methods and vectors described herein. DPI-14 is a potent inhibitor of HNE and the fusion to HSA produces a molecule with longer serum residence time.

Tables

TABLE 1

Amino-acid sequence of Mature HSA from GenBank entry AAN17825

```
DAHKSEVAHR FKDLGEENFK ALVLIAFAQY    (SEQ ID NO: 18)
LQQCPFEDHV KLVNEVTEFA KTCVADESAE
NCDKSLHTLF GDKLCTVATL RETYGEMADC
CAKQEPERNE CFLQHKDDNP NLPRLVRPEV
DVMCTAFHDN EETFLKKYLY EIARRHPYFY
APELLFFAKR YKAAFTECCQ AADKAACLLP
KLDELRDEGK ASSAKQRLKC ASLQKFGERA
FKAWAVARLS QRFPKAEFAE VSKLVTDLTK
VHTECCHGDL LECADDRADL AKYICENQDS
ISSKLKECCE KPLLEKSHCI AEVENDEMPA
DLPSLAADFV ESKDVCKNYA EAKDVFLGMF
LYEYARRHPD YSVVLLLRLA KTYKTTLEKC
CAAADPHECY AKVFDEFKPL VEEPQNLIKQ
```

TABLE 1-continued

Amino-acid sequence of Mature HSA from GenBank entry AAN17825

```
NCELFEQLGE YKFQNALLVR YTKKVPQVST
PTLVEVSRNL GKVGSKCCKH PEAKRMPCAE
DYLSVVLNQL CVLHEKTPVS DRVTKCCTES
LVNRRPCFSA LEVDETYVPK EFNAETFTFH
ADICTLSEKE RQIKKQTALV ELVKHKPKAT
KEQLKAVMDD FAAFVEKCCK ADDKETCFAE
EGKKLVAASR AALGL
```

TABLE 2

Amino-acid sequences of DX-1000 and DX-88

```
DX-1000
EAMHSFCAFKAETGPCRARFDRWFFNIFTRQCEE  (SEQ ID No.: 47)
FIYGGCEGNQNRFESLEECKKMCTRD

DX-88
EAMHSFCAFKADDGPCRAAHPRWFFNIFTRQCEE  (SEQ ID No.: 48)
FIYGGCEGNQNRFESLEECKKMCTRD
```

TABLE 5

DNA sequence of the N-terminal BglII-BamHI DPI-14 cDNA

```
AGATCTTTGGATAAGAGAGAAGCTGTTAGAGAAG  (SEQ ID No.: 49)
TTTGTTCTGAACAAGCTGAAACTGGTCCATGTAT
```

TABLE 5-continued

DNA sequence of the N-terminal
BglII-BamHI DPI-14 cDNA

TGCTTTCTTCCCAAGATGGTACTTCGATGTTACT

GAAGGTAAGTGCGCGCCATTCTTCTACGGTGGTT

GTGGTGGTAACAGAAACAACTTCGATACTGAAGA

ATACTGTATGGCTGTTTGTGGTTCTGCTGGTGGA

TCC

TABLE 6

DNA sequence of the C-terminal
BamHI-HindIII DPI-14 cDNA

GGATCCGGTGGTGAAGCTGTTAGAGAAGTTTGTT (SEQ ID No.: 50)

CTGAACAAGCTGAAACTGGTCCATGTATTGCTTT

CTTCCCAAGATGGTACTTCGATGTTACTGAAGGT

AAGTGCGCGCCATTCTTCTACGGTGGTTGTGGTG

GTAACAGAAACAACTTCGATACTGAAGAATACTG

TATGGCTGTTTGTGGTTCTGCTTAATAAGCTT

TABLE 7

DNA sequence of the N-terminal
DPI-14-(GGS)$_4$GG-albumin fusion coding region

GAAGCTGTTAGAGAAGTTTGTTCTGAACAAGCTG SEQ ID NO.: 51)

AAACTGGTCCATGTATTGCTTTCTTCCCAAGATG

GTACTTCGATGTTACTGAAGGTAAGTGCGCGCCA

TTCTTCTACGGTGGTTGTGGTGGTAACAGAAACA

ACTTCGATACTGAAGAATACTGTATGGCTGTTTG

TGGTTCTGCTGGTGGATCCGGTGGTTCCGGTGGT

TCTGGTGGTTCCGGTGGTGACGCTCACAAGTCCG

AAGTCGCTCACCGGTTCAAGGACCTAGGTGAGGA

AAACTTCAAGGCTTTGGTCTTGATCGCTTTCGCT

CAATACTTGCAACAATGTCCATTCGAAGATCACG

TCAAGTTGGTCAACGAAGTTACCGAATTCGCTAA

GACTTGTGTTGCTGACGAATCTGCTGAAAACTGT

GACAAGTCCTTGCACACCTTGTTCGGTGATAAGT

TGTGTACTGTTGCTACCTTGAGAGAAACCTACGG

TGAAATGGCTGACTGTTGTGCTAAGCAAGAACCA

GAAAGAAACGAATGTTTCTTGCAACACAAGGACG

ACAACCCAAACTTGCCAAGATTGGTTAGACCAGA

AGTTGACGTCATGTGTACTGCTTTCCACGACAAC

TABLE 7-continued

DNA sequence of the N-terminal
DPI-14-(GGS)$_4$GG-albumin fusion coding region

GAAGAAACCTTCTTGAAGAAGTACTTGTACGAAA

TTGCTAGAAGACACCCATACTTCTACGCTCCAGA

ATTGTTGTTCTTCGCTAAGAGATACAAGGCTGCT

TTCACCGAATGTTGTCAAGCTGCTGATAAGGCTG

CTTGTTTGTTGCCAAAGTTGGATGAATTGAGAGA

CGAAGGTAAGGCTTCTTCCGCTAAGCAAAGATTG

AAGTGTGCTTCCTTGCAAAAGTTCGGTGAAAGAG

CTTTCAAGGCTTGGGCTGTCGCTAGATTGTCTCA

AAGATTCCCAAAGGCTGAATTCGCTGAAGTTTCT

AAGTTGGTTACTGACTTGACTAAGGTTCACACTG

AATGTTGTCACGGTGACTTGTTGGAATGTGCTGA

TGACAGAGCTGACTTGGCTAAGTACATCTGTGAA

AACCAAGACTCTATCTCTTCCAAGTTGAAGGAAT

GTTGTGAAAAGCCATTGTTGGAAAAGTCTCACTG

TATTGCTGAAGTTGAAAACGATGAAATGCCAGCT

GACTTGCCATCTTTGGCTGCTGACTTCGTTGAAT

CTAAGGACGTTTGTAAGAACTACGCTGAAGCTAA

GGACGTCTTCTTGGGTATGTTCTTGTACGAATAC

GCTAGAAGACACCCAGACTACTCCGTTGTCTTGT

TGTTGAGATTGGCTAAGACCTACGAAACTACCTT

GGAAAAGTGTTGTGCTGCTGCTGACCCACACGAA

TGTTACGCTAAGGTTTTCGATGAATTCAAGCCAT

TGGTCGAAGAACCACAAAACTTGATCAAGCAAAA

CTGTGAATTGTTCGAACAATTGGGTGAATACAAG

TTCCAAAACGCTTTGTTGGTTAGATACACTAAGA

AGGTCCCACAAGTCTCCACCCCAACTTTGGTTGA

AGTCTCTAGAAACTTGGGTAAGGTCGGTTCTAAG

TGTTGTAAGCACCCAGAAGCTAAGAGAATGCCAT

GTGCTGAAGATTACTTGTCCGTCGTTTTGAACCA

ATTGTGTGTTTTGCACGAAAAGACCCCAGTCTCT

GATAGAGTCACCAAGTGTTGTACTGAATCTTTGG

TTAACAGAAGACCATGTTTCTCTGCTTTGGAAGT

CGACGAAACTTACGTTCCAAAGGAATTCAACGCT

GAAACTTTCACCTTCCACGCTGATATCTGTACCT

TGTCCGAAAAGGAAAGACAAATTAAGAAGCAAAC

TGCTTTGGTTGAATTGGTCAAGCACAAGCCAAAG

GCTACTAAGGAACAATTGAAGGCTGTCATGGATG

ATTTCGCTGCTTTCGTTGAAAAGTGTTGTAAGGC

TABLE 7-continued

DNA sequence of the N-terminal
DPI-14-(GGS)₄GG-albumin fusion coding region

TGATGATAAGGAAACTTGTTTCGCTGAAGAAGGT

AAGAAGTTGGTCGCTGCTTCCCAAGCTGCTTTGG

GTTTG

TABLE 8

Amino acid sequence of the N-terminal
DPI-14-(GGS)₄GG-albumin fusion protein

EAVREVCSEQAETGPCIAFFPRWYFDVTEGKCAP (SEQ ID No.: 52)

FFYGGCGGNRNNFDTEEYCMAVCGSAGGSGGSGG

SGGSGGDAHKSEVAHRFKDLGEENFKALVLIAFA

QYLQQCPFEDHVKLVNEVTEFAKTCVADESAENC

DKSLHTLFGDKLCTVATLRETYGEMADCCAKQEP

ERNECFLQHKDDNPNLPRLVRPEVDVMCTAFHDN

EETFLKKYLYEIARRHPYFYAPELLFFAKRYKAA

FTECCQAADKAACLLPKLDELRDEGKASSAKQRL

KCASLQKFGERAFKAWAVARLSQRFPKAEFAEVS

KLVTDLTKVHTECCHGDLLECADDRADLAKYICE

NQDSISSKLKECCEKPLLEKSHCIAEVENDEMPA

DLPSLAADFVESKDVCKNYAEAKDVFLGMFLYEY

ARRHPDYSVVLLLRLAKTYETTLEKCCAAADPHE

CYAKVFDEFKPLVEEPQNLIKQNCELFEQLGEYK

FQNALLVRYTKKVPQVSTPTLVEVSRNLGKVGSK

CCKHPEAKRMPCAEDYLSVVLNQLCVLHEKTPVS

DRVTKCCTESLVNRRPCFSALEVDETYVPKEFNA

ETFTFHADICTLSEKERQIKKQTALVELVKHKPK

ATKEQLKAVMDDFAAFVEKCCKADDKETCFAEEG

KKLVAASQAALGL

TABLE 9

DNA sequence of the C-terminal albumin-
(GGS)₄GG-DPI-14 fusion coding region

GATGCACACAAGAGTGAGGTTGCTCATCGGTTTA (SEQ ID No.: 53)

AAGATTTGGGAGAAGAAAATTTCAAAGCCTTGGT

GTTGATTGCCTTTGCTCAGTATCTTCAGCAGTGT

CCATTTGAAGATCATGTAAAATTAGTGAATGAAG

TAACTGAATTTGCAAAAACATGTGTTGCTGATGA

GTCAGCTGAAAATTGTGACAAATCACTTCATACC

CTTTTTGGAGACAAATTATGCACAGTTGCAACTC

TABLE 9-continued

DNA sequence of the C-terminal albumin-
(GGS)₄GG-DPI-14 fusion coding region

TTCGTGAAACCTATGGTGAAATGGCTGACTGCTG

TGCAAAACAAGAACCTGAGAGAAATGAATGCTTC

TTGCAACACAAAGATGACAACCCAAACCTCCCCC

GATTGGTGAGACCAGAGGTTGATGTGATGTGCAC

TGCTTTTCATGACAATGAAGAGACATTTTTGAAA

AAATACTTATATGAAATTGCCAGAAGACATCCTT

ACTTTTATGCCCCGGAACTCCTTTTCTTTGCTAA

AAGGTATAAAGCTGCTTTTACAGAATGTTGCCAA

GCTGCTGATAAAGCTGCCTGCCTGTTGCCAAAGC

TCGATGAACTTCGGGATGAAGGGAAGGCTTCGTC

TGCCAAACAGAGACTCAAGTGTGCCAGTCTCCAA

AAATTTGGAGAAAGAGCTTTCAAAGCATGGGCAG

TAGCTCGCCTGAGCCAGAGATTTCCCAAAGCTGA

GTTTGCAGAAGTTTCCAAGTTAGTGACAGATCTT

ACCAAAGTCCACACGGAATGCTGCCATGGAGATC

TGCTTGAATGCTGATGACAGGGCGGACCTTGC

CAAGTATATCTGTGAAAATCAAGATTCGATCTCC

AGTAAACTGAAGGAATGCTGTGAAAAACCTCTGT

TGGAAAAATCCCACTGCATTGCCGAAGTGGAAAA

TGATGAGATGCCTGCTGACTTGCCTTCATTAGCT

GCTGATTTTGTTGAAAGTAAGGATGTTTGCAAAA

ACTATGCTGAGGCAAAGGATGTCTTCCTGGGCAT

GTTTTTGTATGAATATGCAAGAAGGCATCCTGAT

TACTCTGTCGTGCTGCTGCTGAGACTTGCCAAGA

CATATGAAACCACTCTAGAGAAGTGCTGTGCCGC

TGCAGATCCTCATGAATGCTATGCCAAAGTGTTC

GATGAATTTAAACCTCTTGTGGAAGAGCCTCAGA

ATTTAATCAAACAAAATTGTGAGCTTTTTGAGCA

GCTTGGAGAGTACAAATTCCAGAATGCGCTATTA

GTTCGTTACACCAAGAAAGTACCCCAAGTGTCAA

CTCCAACTCTTGTAGAGGTCTCAAGAAACCTAGG

AAAAGTGGGCAGCAAATGTTGTAAACATCCTGAA

GCAAAAAGAATGCCCTGTGCAGAAGACTATCTAT

CCGTGGTCCTGAACCAGTTATGTGTGTTGCATGA

GAAAACGCCAGTAAGTGACAGAGTCACCAAATGC

TGCACAGAATCCTTGGTGAACAGGCGACCATGCT

TTTCAGCTCTGGAAGTCGATGAAACATACGTTCC

CAAAGAGTTTAATGCTGAAACATTCACCTTCCAT

TABLE 9-continued

DNA sequence of the C-terminal albumin-(GGS)₄GG-DPI-14 fusion coding region

GCAGATATATGCACACTTTCTGAGAAGGAGAGAC

AAATCAAGAAACAAACTGCACTTGTTGAGCTCGT

GAAACACAAGCCCAAGGCAACAAAAGAGCAACTG

AAAGCTGTTATGGATGATTTCGCAGCTTTTGTAG

AGAAGTGCTGCAAGGCTGACGATAAGGAGACCTG

CTTTGCCGAGGAGGGTAAAAAACTTGTTGCTGCA

AGTCAAGCTGCCTTAGGCTTAGGTGGTTCTGGTG

GTTCCGGTGGTTCTGGTGGATCCGGTGGTGAAGC

TGTTAGAGAAGTTTGTTCTGAACAAGCTGAAACT

GGTCCATGTATTGCTTTCTTCCCAAGATGGTACT

TCGATGTTACTGAAGGTAAGTGCGCGCCATTCTT

CTACGGTGGTTGTGGTGGTAACAGAAACAACTTC

GATACTGAAGAATACTGTATGGCTGTTTGTGGTT

CTGCT

TABLE 10

Amino acid sequence of the C-terminal albumin-(GGS)₄GG-DPI-14 fusion protein

DAHKSEVAHRFKDLGEENFKALVLIAFAQYLQQC (SEQ ID No.: 54)

PFEDHVKLVNEVTEFAKTCVADESAENCDKSLHT

LFGDKLCTVATLRETYGEMADCCAKQEPERNECF

LQHKDDNPNLPRLVRPEVDVMCTAFHDNEETFLK

KYLYEIARRHPYFYAPELLFFAKRYKAAFTECCQ

AADKAACLLPKLDELRDEGKASSAKQRLKCASLQ

KFGERAFKAWAVARLSQRFPKAEFAEVSKLVTDL

TKVHTECCHGDLLECADDRADLAKYICENQDSIS

SKLKECCEKPLLEKSHCIAEVENDEMPADLPSLA

ADFVESKDVCKNYAEAKDVFLGMFLYEYARRHPD

YSVVLLLRLAKTYETTLEKCCAAADPHECYAKVF

DEFKPLVEEPQNLIKQNCELFEQLGEYKFQNALL

VRYTKKVPQVSTPTLVEVSRNLGKVGSKCCKHPE

AKRMPCAEDYLSVVLNQLCVLHEKTPVSDRVTKC

CTESLVNRRPCFSALEVDETYVPKEFNAETFTFH

ADICTLSEKERQIKKQTALVELVKHKPKATKEQL

KAVMDDFAAFVEKCCKADDKETCFAEEGKKLVAA

SQAALGLGGSGGSGGSGGSGGEAVREVCSEQAET

GPCIAFFPRWYFDVTEGKCAPFFYGGCGGNRNNF

DTEEYCMAVCGSA

TABLE 11

DNA sequence of the C-terminal BamHI-HindIII DX-1000 cDNA

```
GGA TCC GGT GGT           (SEQ ID No.: 55)
gag gct atg cat tcc
ttc tgc gcc ttc aag
gct gag act ggt cct
tgt aga gct agg ttc
gac cgt tgg ttc ttc
aac atc ttc acg cgt
cag tgc gag gaa ttc
att tac ggt ggt tgt
gaa ggt aac cag aac
cgg ttc gaa tct cta
gag gaa tgt aag aag
atg tgc act cgt gac
TAA TAA GCT T
```

TABLE 12

DNA sequence of the N-terminal BglII-BamHI DX-890 cDNA

AGATCTTTGGATAAGAGAGAAGCCTGTAACTTGC (SEQ ID No.: 56)

CAATTGTTAGAGGTCCATGTATTGCTTTCTTCCC

AAGATGGGCTTTCGATGCTGTTAAGGGTAAGTGT

GTTTTGTTCCCATATGGTGGTTGTCAAGGTAACG

GTAACAAGTTCTACTCTGAAAAGGAATGTAGAGA

ATACTGTGGTGTTCCAGGTGGATCC

TABLE 13

DNA sequence of the C-terminal BamHI-HindIII DX-890 cDNA

GGATCCGGTGGTGAAGCCTGTAACTTGCCAATTG (SEQ ID No.: 57)

TTAGAGGTCCATGTATTGCTTTCTTCCCAAGATG

GGCTTTCGATGCTGTTAAGGGTAAGTGTGTTTTG

TTCCCATATGGTGGTTGTCAAGGTAACGGTAACA

AGTTCTACTCTGAAAAGGAATGTAGAGAATACTG

TGGTGTTCCATAATAAGCTT

TABLE 14

DNA sequence of the N-terminal DX-890-(GGS)₄GG-albumin fusion coding region

GAAGCCTGTAACTTGCCAATTGTTAGAGGTCCAT (SEQ ID No.: 58)
GTATTGCTTTCTTCCCAAGATGGGCTTTCGATGC
TGTTAAGGGTAAGTGTGTTTTGTTCCCATATGGT
GGTTGTCAAGGTAACGGTAACAAGTTCTACTCTG
AAAAGGAATGTAGAGAATACTGTGGTGTTCCAGG
TGGATCCGGTGGTTCCGGTGGTTCTGGTGGTTCC
GGTGGTGACGCTCACAAGTCCGAAGTCGCTCACC
GGTTCAAGGACCTAGGTGAGGAAAACTTCAAGGC
TTTGGTCTTGATCGCTTTCGCTCAATACTTGCAA
CAATGTCCATTCGAAGATCACGTCAAGTTGGTCA
ACGAAGTTACCGAATTCGCTAAGACTTGTGTTGC
TGACGAATCTGCTGAAAACTGTGACAAGTCCTTG
CACACCTTGTTCGGTGATAAGTTGTGTACTGTTG
CTACCTTGAGAGAAACCTACGGTGAAATGGCTGA
CTGTTGTGCTAAGCAAGAACCAGAAAGAAACGAA
TGTTTCTTGCAACACAAGGACGACAACCCAAACT
TGCCAAGATTGGTTAGACCAGAAGTTGACGTCAT
GTGTACTGCTTTCCACGACAACGAAGAAACCTTC
TTGAAGAAGTACTTGTACGAAATTGCTAGAAGAC
ACCCATACTTCTACGCTCCAGAATTGTTGTTCTT
CGCTAAGAGATACAAGGCTGCTTTCACCGAATGT
TGTCAAGCTGCTGATAAGGCTGCTTGTTTGTTGC
CAAAGTTGGATGAATTGAGAGACGAAGGTAAGGC
TTCTTCCGCTAAGCAAAGATTGAAGTGTGCTTCC
TTGCAAAAGTTCGGTGAAAGAGCTTTCAAGGCTT
GGGCTGTCGCTAGATTGTCTCAAAGATTCCCAAA
GGCTGAATTCGCTGAAGTTTCTAAGTTGGTTACT
GACTTGACTAAGGTTCACACTGAATGTTGTCACG
GTGACTTGTTGGAATGTGCTGATGACAGAGCTGA
CTTGGCTAAGTACATCTGTGAAAACCAAGACTCT
ATCTCTTCCAAGTTGAAGGAATGTTGTGAAAAGC
CATTGTTGGAAAAGTCTCACTGTATTGCTGAAGT
TGAAAACGATGAAATGCCAGCTGACTTGCCATCT
TTGGCTGCTGACTTCGTTGAATCTAAGGACGTTT
GTAAGAACTACGCTGAAGCTAAGGACGTCTTCTT
GGGTATGTTCTTGTACGAATACGCTAGAAGACAC
CCAGACTACTCCGTTGTCTTGTTGTTGAGATTGG
CTAAGACCTACGAAACTACCTTGGAAAAGTGTTG

TABLE 14-continued

DNA sequence of the N-terminal DX-890-(GGS)₄GG-albumin fusion coding region

TGCTGCTGCTGACCCACACGAATGTTACGCTAAG
GTTTTCGATGAATTCAAGCCATTGGTCGAAGAAC
CACAAAACTTGATCAAGCAAAACTGTGAATTGTT
CGAACAATTGGGTGAATACAAGTTCCAAAACGCT
TTGTTGGTTAGATACACTAAGAAGGTCCCACAAG
TCTCCACCCCAACTTTGGTTGAAGTCTCTAGAAA
CTTGGGTAAGGTCGGTTCTAAGTGTTGTAAGCAC
CCAGAAGCTAAGAGAATGCCATGTGCTGAAGATT
ACTTGTCCGTCGTTTTGAACCAATTGTGTGTTTT
GCACGAAAAGACCCCAGTCTCTGATAGAGTCACC
AAGTGTTGTACTGAATCTTTGGTTAACAGAAGAC
CATGTTTCTCTGCTTTGGAAGTCGACGAAACTTA
CGTTCCAAAGGAATTCAACGCTGAAACTTTCACC
TTCCACGCTGATATCTGTACCTTGTCCGAAAACG
AAAGACAAATTAAGAAGCAAACTGCTTTGGTTGA
ATTGGTCAAGCACAAGCCAAAGGCTACTAAGGAA
CAATTGAAGGCTGTCATGGATGATTTCGCTGCTT
TCGTTGAAAAGTGTTGTAAGGCTGATGATAAGGA
AACTTGTTTCGCTGAAGAAGGTAAGAAGTTGGTC
GCTGCTTCCCAAGCTGCTTTGGGTTTG

TABLE 15

Amino acid sequence of the N-terminal DX-890-(GGS)₄GG-albumin fusion protein

EACNLPIVRGPCIAFFPRWAFDAVKGKCVLFPYG (SEQ ID No.: 59)
GCQGNGNKFYSEKECREYCGVPGGSGGSGGSGGS
GGDAHKSEVAHRFKDLGEENFKALVLIAFAQYLQ
QCPFEDHVKLVNEVTEFAKTCVADESAENCDKSL
HTLFGDKLCTVATLRETYGEMADCCAKQEPERNE
CFLQHKDDNPNLPRLVRPEVDVMCTAFHDNEETF
LKKYLYEIARRHPYFYAPELLFFAKRYKAAFTEC
CQAADKAACLLPKLDELRDEGKASSAKQRLKCAS
LQKFGERAFKAWAVARLSQRFPKAEFAEVSKLVT
DLTKVHTECCHGDLLECADDRADLAKYICENQDS
ISSKLKECCEKPLLEKSHCIAEVENDEMPADLPS
LAADFVESKDVCKNYAEAKDVFLGMFLYEYARRH
PDYSVVLLLRLAKTYETTLEKCCAAADPHECYAK
VFDEFKPLVEEPQNLIKQNCELFEQLGEYKFQNA

TABLE 15-continued

Amino acid sequence of the N-terminal
DX-890-(GGS)$_4$GG-albumin fusion protein

LLVRYTKKVPQVSTPTLVEVSRNLGKVGSKCCKH

PEAKRMPCAEDYLSVVLNQLCVLHEKTPVSDRVT

KCCTESLVNRRPCFSALEVDETYVPKEFNAETFT

FHADICTLSEKERQIKKQTALVELVKHKPKATKE

QLKAVMDDFAAFVEKCCKADDKETCFAEEGKKLV

AASQAALGL

TABLE 16

DNA sequence of the C-terminal albumin-
(GGS)$_4$GG-DX-890 fusion coding region

GATGCACACA AGAGTGAGGT TGCTCATCGG    (SEQ ID No.: 60)

TTTAAAGATT TGGGAGAAGA AAATTTCAAA

GCCTTGGTGT TGATTGCCTT TGCTCAGTAT

CTTCAGCAGT GTCCATTTGA AGATCATGTA

AAATTAGTGA ATGAAGTAAC TGAATTTGCA

AAAACATGTG TTGCTGATGA GTCAGCTGAA

AATTGTGACA AATCACTTCA TACCCTTTTT

GGAGACAAAT TATGCACAGT TGCAACTCTT

CGTGAAACCT ATGGTGAAAT GGCTGACTGC

TGTGCAAAAC AAGAACCTGA GAGAAATGAA

TGCTTCTTGC AACACAAAGA TGACAACCCA

AACCTCCCCC GATTGGTGAG ACCAGAGGTT

GATGTGATGT GCACTGCTTT TCATGACAAT

GAAGAGACAT TTTTGAAAAA ATACTTATAT

GAAATTGCCA GAAGACATCC TTACTTTTAT

GCCCCGGAAC TCCTTTTCTT TGCTAAAAGG

TATAAAGCTG CTTTTACAGA ATGTTGCCAA

GCTGCTGATA AAGCTGCCTG CCTGTTGCCA

AAGCTCGATG AACTTCGGGA TGAAGGGAAG

GCTTCGTCTG CCAAACAGAG ACTCAAGTGT

GCCAGTCTCC AAAAATTTGG AGAAAGAGCT

TTCAAAGCAT GGGCAGTAGC TCGCCTGAGC

CAGAGATTTC CCAAAGCTGA GTTTGCAGAA

GTTTCCAAGT TAGTGACAGA TCTTACCAAA

GTCCACACGG AATGCTGCCA TGGAGATCTG

CTTGAATGTG CTGATGACAG GGCGGACCTT

GCCAAGTATA TCTGTGAAAA TCAAGATTCG

ATCTCCAGTA AACTGAAGGA ATGCTGTGAA

AAACCTCTGT TGGAAAAATC CCACTGCATT

GCCGAAGTGG AAAATGATGA GATGCCTGCT

GACTTGCCTT CATTAGCTGC TGATTTTGTT

GAAAGTAAGG ATGTTTGCAA AAACTATGCT

GAGGCAAAGG ATGTCTTCCT GGGCATGTTT

TTGTATGAAT ATGCAAGAAG GCATCCTGAT

TACTCTGTCG TGCTGCTGCT GAGACTTGCC

AAGACATATG AAACCACTCT AGAGAAGTGC

TGTGCCGCTG CAGATCCTCA TGAATGCTAT

GCCAAAGTGT TCGATGAATT TAAACCTCTT

GTGGAAGAGC CTCAGAATTT AATCAAACAA

AATTGTGAGC TTTTTGAGCA GCTTGGAGAG

TACAAATTCC AGAATGCGCT ATTAGTTCGT

TACACCAAGA AAGTACCCCA AGTGTCAACT

CCAACTCTTG TAGAGGTCTC AAGAAACCTA

GGAAAAGTGG GCAGCAAATG TTGTAAACAT

CCTGAAGCAA AAGAATGCC CTGTGCAGAA

GACTATCTAT CCGTGGTCCT GAACCAGTTA

TGTGTGTTGC ATGAGAAAAC GCCAGTAAGT

GACAGAGTCA CCAAATGCTG CACAGAATCC

TTGGTGAACA GGCGACCATG CTTTTCAGCT

CTGGAAGTCG ATGAAACATA CGTTCCCAAA

GAGTTTAATG CTGAAACATT CACCTTCCAT

GCAGATATAT GCACACTTTC TGAGAAGGAG

AGACAAATCA GAAACAAAC TGCACTTGTT

GAGCTCGTGA AACACAAGCC AAGGCAACA

AAAGAGCAAC TGAAAGCTGT TATGGATGAT

TTCGCAGCTT TTGTAGAGAA GTGCTGCAAG

GCTGACGATA AGGAGACCTG CTTTGCCGAG

GAGGGTAAAA AACTTGTTGC TGCAAGTCAA

GCTGCCTTAG CTTAGGTGG TTCTGGTGGT

TCCGGTGGTT CTGGTGGATC CGGTGGTGAA

GCCTGTAACT TGCCAATTGT TAGAGGTCCA

TGTATTGCTT TCTTCCCAAG ATGGGCTTTC

GATGCTGTTA AGGGTAAGTG TGTTTTGTTC

CCATATGGTG GTTGTCAAGG TAACGGTAAC

AAGTTCTACT CTGAAAAGGA ATGTAGAGAA

TACTGTGGTG TTCCA

TABLE 17

Amino acid sequence of the C-terminal albumin-(GGS)₄GG-DX-890 fusion protein

DAHKSEVAHR FKDLGEENFK ALVLIAFAQY    (SEQ ID No.: 61)
LQQCPFEDEV KLVNEVTEFA KTCVADESAE
NCDKSLHTLF GDKLCTVATL RETYGEMADC
CAKQEPERNE CFLQHKDDNP NLPRLVRPEV
DVMCTAFHDN EETFLKKYLY EIARRHPYFY
APELLFFAKR YKAAFTECCQ AADKAACLLP
KLDELRDEGK ASSAKQRLKC ASLQKFGERA
FKAWAVARLS QRFPKAEFAE VSKLVTDLTK
VHTECCHGDL LECADDRADL AKYICENQDS
ISSKLKECCE KPLLEKSHCI AEVENDEMPA
DLPSLAADFV ESKDVCKNYA EAKDVFLGMF
LYEYARRHPD YSVVLLLRLA KTYETTLEKC
CAAADPHECY AKVFDEFKPL VEEPQNLIKQ
NCELFEQLGE YKFQNALLVR YTKKVPQVST
PTLVEVSRNL GKVGSKCCKH PEAKRMPCAE
DYLSVVLNQL CVLHEKTPVS DRVTKCCTES
LVNRRPCFSA LEVDETYVPK EFNAETFTFH
ADICTLSEKE RQIKKQTALV ELVKHKPKAT
KEQLKAVMDD FAAFVEKCCK ADDKETCFAE
EGKKLVAASQ AALGLGGSGG SGGSGGSGGE
ACNLPIVRGP CIAFFPRWAF DAVKGKCVLF
PYGGCQGNGN KFYSEKECREY CGVP

TABLE 18

DNA sequence of the N-terminal BglII-BamHI DX-88 cDNA

```
AGA TCT TTG GAT AAG AGA    (SEQ ID No.: 62)
GAA GCT ATG CAC
TCT TTC TGT GCT TTC AAG
GCT GAC GAC GGT CCG TGC
AGA GCT GCT CAC CCA AGA
TGG TTC TTC AAC ATC TTC
ACG CGA CAA TGC GAG GAG
TTC ATC TAC GGT GGT TGT
GAG GGT AAC CAA AAC AGA
TTC GAG TCT CTA GAG GAG
TGT AAG AAG ATG TGT ACT
AGA GAC GGT GGA TCC
```

TABLE 19

DNA sequence of the N-terminal DX-88-(GGS)₄GG-albumin fusion coding region

```
GAA GCT ATG CAC TCT TTC TGT GCT    (SEQ ID No.: 63)
TTC AAG GCT GAC GAC GGT CCG TGC
AGA GCT GCT CAC CCA AGA TGG TTC
TTC AAC ATC TTC ACG CGA CAA TGC
GAG GAG TTC ATC TAC GGT GGT TGT
GAG GGT AAC CAA AAC AGA TTC GAG
TCT CTA GAG GAG TGT AAG AAG ATG
TGT ACT AGA GAC GGT
GGATCCGGTGGTTCCGGTGGTTCTGGTGGTT
CCGGTGGTGACGCTCACAAGTCCGAAGTCGC
TCACCGGTTCAAGGACCTAGGTGAGGAAAAC
TTCAAGGCTTTGGTCTTGATCGCTTTCGCTC
AATACTTGCAACAATGTCCATTCGAAGATCA
CGTCAAGTTGGTCAACGAAGTTACCGAATTC
GCTAAGACTTGTGTTGCTGACGAATCTGCTG
AAAACTGTGACAAGTCCTTGCACACCTTGTT
CGGTGATAAGTTGTGTACTGTTGCTACCTTG
AGAGAAACCTACGGTGAAATGGCTGACTGTT
GTGCTAAGCAAGAACCAGAAAGAAACGAATG
TTTCTTGCAACACAAGGACGACAACCCAAAC
TTGCCAAGATTGGTTAGACCAGAAGTTGACG
TCATGTGTACTGCTTTCCACGACAACGAAGA
AACCTTCTTGAAGAAGTACTTGTACGAAATT
GCTAGAAGACACCCATACTTCTACGCTCCAG
AATTGTTGTTCTTCGCTAAGAGATACAAGGC
TGCTTTCACCGAATGTTGTCAAGCTGCTGAT
AAGGCTGCTTGTTTGTTGCCAAAGTTGGATG
AATTGAGAGACGAAGGTAAGGCTTCTTCCGC
TAAGCAAAGATTGAAGTGTGCTTCCTTGCAA
AAGTTCGGTGAAAGAGCTTTCAAGGCTTGGG
CTGTCGCTAGATTGTCTCAAAGATTCCCAAA
GGCTGAATTCGCTGAAGTTTCTAAGTTGGTT
ACTGACTTGACTAAGGTTCACACTGAATGTT
GTCACGGTGACTTGTTGGAATGTGCTGATGA
CAGAGCTGACTTGGCTAAGTACATCTGTGAA
AACCAAGACTCTATCTCTTCCAAGTTGAAGG
AATGTTGTGAAAAGCCATTGTTGGAAAAGTC
TCACTGTATTGCTGAAGTTGAAAACGATGAA
```

TABLE 19-continued

DNA sequence of the N-terminal DX-88-(GGS)₄GG-albumin fusion coding region

ATGCCAGCTGACTTGCCATCTTTGGCTGCTG
ACTTCGTTGAATCTAAGGACGTTTGTAAGAA
CTACGCTGAAGCTAAGGACGTCTTCTTGGGT
ATGTTCTTGTACGAATACGCTAGAAGACACC
CAGACTACTCCGTTGTCTTGTTGTTGAGATT
GGCTAAGACCTACGAAACTACCTTGGAAAAG
TGTTGTGCTGCTGCTGACCCACACGAATGTT
ACGCTAAGGTTTTCGATGAATTCAAGCCATT
GGTCGAAGAACCACAAAACTTGATCAAGCAA
AACTGTGAATTGTTCGAACAATTGGGTGAAT
ACAAGTTCCAAAACGCTTTGTTGGTTAGATA
CACTAAGAAGGTCCCACAAGTCTCCACCCCA
ACTTTGGTTGAAGTCTCTAGAAACTTGGGTA
AGGTCGGTTCTAAGTGTTGTAAGCACCCAGA
AGCTAAGAGAATGCCATGTGCTGAAGATTAC
TTGTCCGTCGTTTTGAACCAATTGTGTGTTT
TGCACGAAAAGACCCCAGTCTCTGATAGAGT
CACCAAGTGTTGTACTGAATCTTTGGTTAAC
AGAAGACCATGTTTCTCTGCTTTGGAAGTCG
ACGAAACTTACGTTCCAAAGCAATTCAACGC
TGAAACTTTCACCTTCCACGCTGATATCTGT
ACCTTGTCCGAAAAGGAAAGACAAATTAAGA
AGCAAACTGCTTTGGTTGAATTGGTCAAGCA
CAAGCCAAAGGCTACTAAGGAACAATTGAAG
GCTGTCATGGATGATTTCGCTGCTTTCGTTG
AAAAGTGTTGTAAGGCTGATGATAAGGAAAC
TTGTTTCGCTGAAGAAGGTAAGAAGTTGGTC
GCTGCTTCCCAAGCTGCTTTGGGTTTG

TABLE 20

AA sequence of DX-88::HSA

EAMHSFCAFK ADDGPCRAAH PRWFFNIFTR     (SEQ ID No.: 64)
QCEEFIYGGC EGNQRFESL EECKKMCTRD
GGSGGSGGSG GSSGGDAHKSE VAHRFKDLGE
ENFKALVLIA FAQYLQQCPF EDHVKLVNEV
TEFAKTCVAD ESAENCDKSL HTLFGDKLCT
VATLRETYGE MADCCAKQEP ERNECFLQHK

TABLE 20-continued

AA sequence of DX-88::HSA

DDNPNLPRLV RPEVDVMCTA FHDNEETFLK
KYLYEIARRH PYFYAPELLF FAKRYKAAFT
ECCQAADKAA CLLPKLDELR DEGKASSAKQ
RLKCASLQKF GERAFKAWAV ARLSQRFPKA
EFAEVSKLVT DLTKVHTECC HGDLLECADD
RADLAKYICE NQDSISSKLK ECCEKPLLEK
SHCIAEVEND EMPADLPSLA ADFVESKDVC
KNYAEAKDVF LGMFLYEYAR RHPDYSVVLL
LRLAKTYETT LEKCCAAADP HECYAKVFDE
FKPLVEEPQN LIKQNCELFE QLGEYKFQNA
LLVRYTKKVP QVSTPTLVEV SRNLGKVGSK
CCKHPEAKRM PCAEDYLSVV LNQLCVLHEK
TPVSDRVTKC CTESLVNRRP CFSALEVDET
YVPKEFNAET FTFHADICTL SEKERQIKKQ
TALVELVKHK PKATKEH

TABLE 21

DNA sequence of the C-terminal BamHI-HindIII DX-88 cDNA

GGA TCC GGT GGT GAA GCT ATG CAC     (SEQ ID No.: 65)
TCT TTC TGT GCT TTC AAG GCT GAC
GAC GGT CCG TGC AGA GCT GCT CAC
CCA AGA TGG TTC TTC AAC ATC TTC
ACG CGA CAA TGC GAG GAG TTC ATC
TAC GGT GGT TGT GAG GGT AAC CAA
AAC AGA TTC GAG TCT CTA GAG GAG
TGT AAG AAG ATG TGT ACT AGA GAC
TAA TAA GCT T

TABLE 22

HSA::(GGS)4GG::DX-88 gat gca cac aag agt gag gtt gct     (SEQ ID No.: 66)
cat cgg ttt aaa gat ttg gga gaa
gaa aat ttc aaa gcc ttg gtg ttg
att gcc ttt gct cag tat ctt cag
cag tgt cca ttt gaa gat cat gta
aaa tta gtg aat gaa gta act gaa
ttt gca aaa aca tgt gtt gct gat

TABLE 22-continued

HSA::(GGS)4GG::DX-88 gag tca gct gaa aat tgt gac aaa tca ctt cat acc ctt ttt gga gac aaa tta tgc aca gtt gca act ctt cgt gaa acc tat ggt gaa atg gct gac tgc tgt gca aaa caa gaa cct gag aga aat gaa tgc ttc ttg caa cac aaa gat gac aac cca aac ctc ccc cga ttg gtg aga cca gag ttt gat gtg atg tgc act gct ttt cat gac aat gaa gag aca ttt ttg aaa aaa tac tta tat gaa att gcc aga aga cat cct tac ttt tat gcc ccg gaa ctc ctt ttc ttt gct aaa agg tat aaa gct gct ttt aca gaa tgt tgc caa gct gct gat aaa gct gcc tgc ctg ttg cca aag ctc gat gaa ctt cgg gat gaa ggg aag gct tcg tct gcc aaa cag aga ctc aag tgt gcc agt ctc caa aaa ttt gga gaa aga gct ttc aaa gca tgg gca gta gct cgc ctg agc cag aga ttt ccc aaa gct gag ttt gca gaa gtt tcc aag tta gtg aca gat ctt acc aaa gtc cac acg gaa tgc tgc cat gga gat ctg ctt gaa tgt gct gat gac agg gcg gac ctt gcc aag tat atc tgt gaa aat caa gat tcg atc tcc agt aaa ctg aag gaa tgc tgt gaa aaa cct ctg ttg gaa aaa tcc cac tgc att gcc gaa gtg gaa aat gat gag atg cct gct gac ttg cct tca tta gct gct gat ttt gtt gaa agt aag gat gtt tgc aaa aac tat gct gag gca aag gat gtc ttc ctg ggc atg ttt ttg tat gaa tat gca aga agg cat cct gat tac tct gtc gtg ctg ctg ctg aga ctt gcc aag aca tat gaa acc act cta gag aag tgc tgt gcc gct gca gat cct cat gaa tgc tat gcc aaa gtg ttc gat gaa ttt aaa cct ctt gtg gaa gag cct cag aat tta atc aaa caa aat tgt gag ctt ttt gag cag ctt gga gag tac aaa ttc cag aat gcg cta tta gtt cgt tac acc aag aaa gta ccc caa gtg tca act cca act ctt gta gag gtc tca aga aac cta gga aaa gtg ggc agc aaa tgt tgt aaa cat cct gaa gca aaa aga atg ccc tgt gca gaa gac tat cta tcc gtg gtc ctg aac cag tta tgt gtg ttg cat gag aaa acg cca gta agt gac aga gtc acc aaa tgc tgc aca gaa tcc ttg gtg aac agg cga cca tgc ttt tca gct ctg gaa gtc gat gaa aca tac gtt ccc aaa gag ttt aat gct gaa aca ttc acc ttc cat gca gat ata tgc aca ctt tct gag aag gag aga caa atc aag aaa caa act gca ctt gtt gag ctc gtg aaa cac aag ccc aag gca aca aaa gag caa ctg aaa gct gtt atg gat gat ttc gca gct ttt gta gag aag tgc tgc aag gct gac gat aag gag acc tgc ttt gcc gag gag ggt aaa aaa ctt gtt gct gca agt caa gct gcc tta ggc tta ggt ggt tct ggt ggt tcc ggt ggt tct ggt gga tcc ggt ggt

GAA GCT ATG CAC TCT TTC TGT GCT

TTC AAG GCT GAC GAC GGT CCG TGC

AGA GCT GCT CAC CCA AGA TGG TTC

TTC AAC ATC TTC ACG CGA CAA TGC

GAG GAG TTC ATC TAC GGT GGT TGT

GAG GGT AAC CAA AAC AGA TTC GAG

TCT CTA GAG GAG TGT AAG AAG ATG

TGT ACT AGA GAC

TABLE 23

AA sequence of mature protein encoded in Table 22

DAHKSEVAHRFKDLGEENFKALVLIAFAQY    (SEQ. ID No.: 67)

LQQCPFEDHVKLVNEVTEFAKTCVADESAE

NCDKSLHTLFGDKLCTVATLRETYGEMADC

CAKQEPERNECFLQHKDDNPNLPRLVRPEV

DVMCTAFHDNEETFLKKYLYEIARRHPYFY

APELLFFAKRYKAAFTECCQAADKAACLLP

KLDELRDEGKASSAKQRLKCASLQKFGERA

FKAWAVARLSQRFPKAEFAEVSKLVTDLTK

VHTECCHGDLLECADDRADLAKYICENQDS

ISSKLKECCEKPLLEKSHCIAEVENDEMPA

DLPSLAADFVESKDVCKNYAEAKDVFLGMF

TABLE 23-continued

AA sequence of mature protein encoded in Table 22

LYEYARRHPDYSVVLLLRLAKTYETTLEKC

CAAADPHECYAKVFDEFKPLVEEPQNLIKQ

NCELFEQLGEYKFQNALLVRYTKKVPQVST

PTLVEVSRNLGKVGSKCCKHPEAKRMPCAE

DYLSVVLNQLCVLHEKTPVSDRVTKCCTES

LVNRRPCFSALEVDETYVPKEFNAETFTFH

ADICTLSEKERQIKKQTALVELVKHKPKAT

KEQLKAVMDDFAAFVEKCCKADDKETCFAE

EGKKLVAASQAALGLGGSGGSGGSGGSGGE

AMHSFCAFKADDGPCRAAHPRWFFNIFTRQ

CEEFIYGGCEGNQNRFESLEECKKMCTRD

TABLE 25

NotI cassette of pDB2300X1 with 2xGS linkers

```
  1 GCGGCCGCcc gtaatgcggt atcgtgaaag cgaaaaaaaa actaacagta gataagacag
    NotI....

61 atagacagat agagatggac gagaaacagg gggggagaaa aggggaaaag agaaggaaag
121 aaagactcat ctatcgcaga taagacaatc aaccctcatG GCGCCtccaa ccaccatccg
                                                NarI...

181 cactagggac caAGCGCTcg caccgttagc aacgcttgac tcacaaacca actGCCGGCt
                Afel..                                         NgoMIV 241 gaaagagctt gtgcaatggg agtgccaatt caaaggagcc gaatacgtct gctcgccttt
301 taagaggctt tttgaacact gcattgcacc cgacaaatca gccactaact acgaggtcac
361 ggacacatat accaatagtt aaaaattaca tatactctat atagcacagt agtgtgataa
421 ataaaaaatt ttgccaagac ttttttaaaC TGCACccgac agatcaggtc tgtgcctact
                                    BsgI...

481 atgcacttat gcccggggtc ccgggaggag aaaaaacgag ggctgggaaa tgtccgtgga
541 ctttaaacgc tccgggttag cagagtaGCA gggcttTCGg ctttggaaat ttaggtgact
                                   BcgI........

601 tgttgaaaaa gcaaaatttg ggctcagtaa tgCCActgca gTGGcttatc acgccaggac
                                      BstXI........
                                             pStI...

661 tgcgggagtg gcggggcaa acacacccgc gataaagagc gcgatgaata taaaggggg
721 ccaatgttac gtcccgttat attggagttc ttcccataca aaCTTAAGag tccaattagc
                                                      AflI.
```
(SEQ. ID Nos.: 68 (nucleic acid) and 69 (amino acid))

TABLE 25-continued

NotI cassette of pDB2300X1 with 2xGS linkers

```
781 ttcatcgcca ataaaaaaac AAGCTTaacc taattctaac aagcaaag
                        HindIII (1/2)

1   2   3   4   5   6   7   8   9  10  11  12  13  14  15
      M   K   W   V   F   I   V   S   I   L   F   L   F   S   S
 829 atg aag tgg gtt ttc atc gtc tcc att ttg ttc ttg ttc tcc tct 16  17  18  19  20  21  22  23  24  25  26  27  28  29  30
      A   Y   S   R   S   L   D   K   R   G   G   S   G   G   S
 874 gct tac tct AGA TCT ttg gat aag aga ggt GGA TCC ggt ggt tcc
                BglII..                       BamHI..

31  32  33  34  35  36  37  38  39  40  41  42  43  44  45
      G   G   S   G   G   S   G   G   D   A   H   K   S   E   V
 919 ggt ggt tct ggt ggt tcc ggt ggt gac gct cac aag tcc gaa gtc 46  47  48  49  50  51  52  53  54  55  56  57  58  59  60
      A   H   R   F   K   D   L   G   E   E   N   F   K   A   L
 964 gct cAC CGG Ttc aag gaC CTA GGt gag gaa aac ttc aag gct ttg
         AgeI....       AvrII...

61  62  63  64  65  66  67  68  69  70  71  72  73  74  75
      V   L   I   A   F   A   Q   Y   L   Q   Q   C   P   F   E
1009 gtc ttg atc gct ttc gct caa tac ttg caa caa tgt cca ttc gaa 76  77  78  79  80  81  82  83  84  85  86  87  88  89  90
      D   H   V   K   L   V   N   E   V   T   E   F   A   K   T
1054 gat CAC GTC aag ttg gtc aac gaa gtt acc gaa ttc gct aag act
         BmgBI..

91  92  93  94  95  96  97  98  99 100 101 102 103 104 105
      C   V   A   D   E   S   A   E   N   C   D   K   S   L   H
1099 tgt gtt gct gac gaa tct gct gaa aac tgt gac aag tcc ttg cac 106 107 108 109 110 111 112 113 114 115 116 117 118 119 120
      T   L   F   G   D   K   L   C   T   V   A   T   L   R   E
1144 acc ttg ttc ggt gat aag ttg tgt act gtt gct acc ttg aga gaa 121 122 123 124 125 126 127 128 129 130 131 132 133 134 135
      T   Y   G   E   M   A   D   C   C   A   K   Q   E   P   E
1189 acc tac ggt gaa atg gct gac tgt tgt gct aag caa gaa cca gaa 136 137 138 139 140 141 142 143 144 145 146 147 148 149 150
      R   N   E   C   F   L   Q   H   K   D   D   N   P   N   L
1234 aga aac gaa tgt ttc ttg caa cac aag gac gac aac cca aac ttg 151 152 153 154 155 156 157 158 159 160 161 162 163 164 165
      P   R   L   V   R   P   E   V   D   V   M   C   T   A   F
1279 cca aga ttg gtt aga cca gaa gtt gac gtc atg tgt act gct ttc 166 167 168 169 170 171 172 173 174 175 176 177 178 179 180
      H   D   N   E   E   T   F   L   K   K   Y   L   Y   E   I
1324 cac gac aac gaa gaa acc ttc ttg aag aAG TAC Ttg tac gaa att
                                              ScaI....

181 182 183 184 185 186 187 188 189 190 191 192 193 194 195
      A   R   R   H   P   Y   F   Y   A   P   E   L   L   F   F
1369 gct aga aga cac cca tac ttc tac gct cca gaa ttg ttg ttc ttc 196 197 198 199 200 201 202 203 204 205 206 207 208 209 210
      A   K   R   Y   K   A   A   F   T   E   C   C   Q   A   A
1414 gct aag aga tac aag gct gct ttc acc gaa tgt tgt caa gct gct
```

TABLE 25-continued

NotI cassette of pDB2300X1 with 2xGS linkers

```
        211 212 213 214 215 216 217 218 219 220 221 222 223 224 225
         D   K   A   A   C   L   L   P   K   L   D   E   L   R   D
   1459 gat aag gct gct tgt ttg ttg cca aag ttg gat gaa ttg aga gac 226 227 228 229 230 231 232 233 234 235 236 237 238 239 240
         E   G   K   A   S   S   A   K   Q   R   L   K   C   A   S
   1504 gaa ggt aag gct tct tcc gct aag caa aga ttg aag tgt gct tcc 241 242 243 244 245 246 247 248 249 250 251 252 253 254 255
         L   Q   K   F   G   E   R   A   F   K   A   W   A   V   A
   1549 ttg caa aag ttc ggt gaa aga gct ttc aag gct tgg gct gtc gct 256 257 258 259 260 261 262 263 264 265 266 267 268 269 270
         R   L   S   Q   R   F   P   K   A   E   F   A   E   V   S
   1594 aga ttg tct caa aga ttc cca aag gct gaa ttc gct gaa gtt tct 271 272 273 274 275 276 277 278 279 280 281 282 283 284 285
         K   L   V   T   D   L   T   K   V   H   T   E   C   C   H
   1639 aag ttg gtt act gac ttg act aag gtt cac act gaa tgt tgt cac 286 287 288 289 290 291 292 293 294 295 296 297 298 299 300
         G   D   L   L   E   C   A   D   D   R   A   D   L   A   K
   1684 ggt gac ttg ttg gaa tgt gct gat gac aga gct gac ttg gct aag 301 302 303 304 305 306 307 308 309 310 311 312 313 314 315
         Y   I   C   E   N   Q   D   S   I   S   S   K   L   K   E
   1729 tac atc tgt gaa aac caa gac tct atC TCT TCc aag ttg aag gaa
                                              EarI....

316 317 318 319 320 321 322 323 324 325 326 327 328 329 330
         C   C   E   K   P   L   L   E   K   S   H   C   I   A   E
   1774 tgt tgt gaa aag cca ttg ttg gaa aag tct cac tgt att gct gaa 331 332 333 334 335 336 337 338 339 340 341 342 343 344 345
         V   E   N   D   E   M   P   A   D   L   P   D   L   A   A
   1819 gtt gaa aac gat gaa atg cCA GCT Gac ttg cca tct ttg gct gct
                                  PvuII...

346 347 348 349 350 351 352 353 354 355 356 357 358 359 360
         D   F   V   E   S   K   D   V   C   K   N   Y   A   E   A
   1864 gac ttc gtt gaa tct aag gac gtt tgt aag aac tac gct gaa gct 361 362 363 364 365 366 367 368 369 370 371 372 373 374 375
         K   D   V   F   L   G   M   F   L   Y   E   Y   A   R   R
   1909 aag gac gtc ttc ttg ggt atg ttc ttg tac gaa tac gct aga aga 376 377 378 379 380 381 382 383 384 385 386 387 388 389 390
         H   P   D   Y   S   V   V   L   L   R   L   A   K   T
   1954 cac cca gac tac tcc gtt gtc ttg ttg ttg aga ttg gct aag acc 391 392 393 394 395 396 397 398 399 400 401 402 403 404 405
         Y   E   T   T   L   E   K   C   C   A   A   A   D   P   H
   1999 tac gaa act acc ttg gaa aag tgt tgt gct gct gct gac cca cac 406 407 408 409 410 411 412 413 414 415 416 417 418 419 420
         E   C   Y   A   K   V   F   D   E   F   K   P   L   V   E
   2044 gaa tgt tac gct aag gtt ttc gat gaa ttc aag cca ttg gtc gaa 421 422 423 424 425 426 427 428 429 430 431 432 433 434 435
         E   P   Q   N   L   I   K   Q   N   C   E   L   F   E   Q
   2089 gaa cca caa aac tTG ATC Aag caa aac tgt gaa ttg ttc gaa caa
```

TABLE 25-continued

NotI cassette of pDB2300X1 with 2xGS linkers

```
!              BclI....
!
!      436 437 438 439 440 441 442 443 444 445 446 447 448 449 450
!       L   G   E   Y   K   F   Q   N   A   L   L   V   R   Y   T
  2134 ttg ggt gaa tac aag ttc caa aac gct ttg ttg gtt aga tac act !      451 452 453 454 455 456 457 458 459 460 461 462 463 464 465
!       K   K   V   P   Q   V   S   T   P   T   L   V   E   V   S
  2179 aag aag gtc cca caa gtc tCC Acc cca act tTG Gtt gaa gtc TCT
!                              XcmI................

!      466 467 468 469 470 471 472 473 474 475 476 477 478 479 480
!       R   N   L   G   K   V   G   S   K   C   C   K   H   P   E
  2224 AGA aac ttg ggt aag gtc ggt tct aag tgt tgt aag cac cca gaa !      481 482 483 484 485 486 487 488 489 490 491 492 493 494 495
!       A   K   R   M   P   C   A   E   D   Y   L   S   V   V   L
  2269 gct aag aGA ATG Cca tgt gct gaa gat tac ttg tcc gtc gtt ttg
!              BsmI....

!      496 497 498 499 500 501 502 503 504 505 506 507 508 509 510
!       N   Q   L   C   V   L   H   E   K   T   P   V   S   D   R
  2314 aac caa ttg tgt gtt ttg cac gaa aaG ACc cca GTC tct gat aga
!                                          PshAI........
!                                                AlwNI.......

!      511 512 513 514 515 516 517 518 519 520 521 522 523 524 525
!       V   T   K   C   C   T   E   S   L   V   N   R   R   P   C
  2359 gtC ACc aaG TGt tgt act gaa tct ttg GTT AAC aga aga cca tgt
!         DraIII......                    HpaI...

!      526 527 528 529 530 531 532 533 534 535 536 537 538 539 540
!       F   S   A   L   E   V   D   E   T   Y   V   P   K   E   F
  2404 ttc tct gct ttg gaa GTC GAC gaa act tac gtt cca aag GAA TTC
!                              SalI...

!      541 542 543 544 545 546 547 548 549 550 551 552 553 554 555
!       N   A   E   T   F   T   F   H   A   D   I   C   T   L   S
  2449 aac gct gaa act ttc acc ttc cac gct GAT ATC tgt acc ttg tcc
!                                          EcoRV..

!      556 557 558 559 560 561 562 563 564 565 566 567 568 569 570
!       E   K   E   R   Q   I   K   K   Q   T   A   L   V   E   L
  2494 gaa aag gaa aga caa att aag aag caa act gct ttg gtt gaa ttg !      571 572 573 574 575 576 577 578 579 580 581 582 583 584 585
!       V   K   H   K   P   K   A   T   K   E   Q   L   K   A   V
  2539 gtc aag eac aag cca aag gct act aag gaa caa ttg aag gct gtc !      586 587 588 589 590 591 592 593 594 595 596 597 598 599 600
!       M   D   D   F   A   A   F   V   E   K   C   C   K   A   D
  2584 atg gat gat ttc gct gct ttc gtt gaa aag tgt tgt aag gct gat !      601 602 603 604 605 606 607 608 609 610 611 612 613 614 615
!       D   K   E   T   C   F   A   E   E   G   K   K   L   V   A
  2629 gat aag gaa act tgt ttc gct gaa gaa ggt aag aag ttg gtc gct !      616 617 618 619 620 621 622 623 624 625 626 627 628 629 630
!       A   S   Q   A   A   L   G   L   G   G   S   G   G   S   G
  2674 gct tcc caa gct gCC TTA GGc tta ggt ggt tct ggt ggt tcc ggt
!                              Bsu36I...

!      631 632 633 634 635 636 637 638
```

TABLE 25-continued

NotI cassette of pDB2300X1 with 2xGS linkers

```
           G   S   G   G   S   G   G   T
2719     ggt TCC GGA ggt tcc ggt GGT ACC     taa  tAA GCTTa attcttatga
             BspEI..         KpnI...         Stop Stop
                                                  HindIII (2/2)

2764 tttatgattt ttattattaa ataagTTATA Aaaaaaataa gtGTATACaa atttttaaagt
                                PsiI...          BstZ17I 2824 gactcttagg ttttaaaacg aaaattctta ttcttgagta actctttcct gtaggtcagg
2884 ttgctttctc aggtatagca tgaggtcgct cttattgacc acacctctac cgGCATGCcg
                                                                SphI..

2944 agcaaatgcc tgcaaatcgc tccccatttc acccaattgt agatatgcta actccagcaa
3004 tgagttgatg aatctcggtg tgtattttat gtcctcagag acaacacct gttgtaatcg
3064 ttcttccaca cggatCGCGG CCGC
                     NotI......
```

TABLE 26

NotI cassette of pDB2300X2 with DX890(Nterm) and Cterm linker ready for second DX890

```
   1 GCGGCCGCcc gtaatgcggt atcgtgaaag cgaaaaaaaa actaacagta gataagacag      (SEQ. ID Nos.: 70
     NotI....                                                               (nucleic acid) and
                                                                            71 (amino acid))
  61 atagacagat agagatggac gagaaacagg gggggagaaa aggggaaaag agaaggaaag
 121 aaagactcat ctatcgcaga taagacaatc aaccctcatG GCGCCtccaa ccaccatccg
                                                  NarI...

181 cactagggac caAGCGCTcg caccgttagc aacgcttgac tcacaaacca actGCCGGCt
                 AfeI..                                       NgoMIV 241 gaaagagctt gtgcaatggg agtgccaatt caaaggagcc gaatacgtct gctcgccttt
 301 taagaggctt tttgaacact gcattgcacc cgacaaatca gccactaact acgaggtcac
 361 ggacacatat accaatagtt aaaaattaca tatactctat atagcacagt agtgtgataa
 421 ataaaaaatt ttgccaagac tttttttaaaC TGCACccgac agatcaggtc tgtgcctact
                                         BsgI...

481 atgcacttat gcccggggtc ccgggaggag aaaaaacgag ggctgggaaa tgtccgtgga
 541 ctttaaacgc tccgggttag cagagtaGCA gggcttTCGg ctttggaaat ttaggtgact
                                        BcgI.........

601 tgttgaaaaa gcaaaatttg ggctcagtaa tgCCActgca gTGGcttatc acgccaggac
                                         BstXI........
                                               PStI...

661 tgcgggagtg gcggggcaa acacacccgc gataaagagc gcgatgaata taaaaggggg
 721 ccaatgttac gtcccgttat attggagttc ttcccataca aaCTTAAGag tccaattgc
                                                       AflII.

781 ttcatcgcca ataaaaaaac AAGCTTaacc taattctaac aagcaaag
                          HindIII (½)

Signal sequence--------------------------------------
       1   2   3   4   5   6   7   8   9   10  11  12  13  14  15
       M   K   W   V   F   I   V   S   I   L   F   L   F   S   S
 829 atg aag tgg gtt ttc atc gtc tcc att ttg ttc ttg ttc tec tct Signal sequence--------------- DX-890----------------
      16  17  18  19  20  21  22  23  24  25  26  27  28  29  30
       A   Y   S   R   S   L   D   K   R   E   A   C   N   L   P
```

TABLE 26-continued

NotI cassette of pDB2300X2 with
DX890(Nterm) and Cterm linker ready for second DX890

```
 874 gct tac tct AGA TCT ttg gat aag aga gaa gcc tgt aac ttg cca
                 BglII..
             XbaI...(½)

DX890 continued------------------------------------------
      31  32  33  34  35  36  37  38  39  40  41  42  43  44  45
       I   V   R   G   P   C   I   A   F   F   P   R   W   A   F
 919 att gtt aga ggt cca tgt att gct ttc ttc cca aga tgg gct ttc DX890 continued------------------------------------------
      46  47  48  49  50  51  52  53  54  55  56  57  58  59  60
       D   A   V   K   G   K   C   V   L   F   P   Y   G   G   C
 964 gat gct gtt aag ggt aag tgt gtt ttg ttc CCA tat ggT GGt tgt
                                             PflMI.........
                                                 NdeI....

DX890 continued------------------------------------------
      61  62  63  64  65  66  67  68  69  70  71  72  73  74  75
       Q   G   N   G   N   K   F   Y   S   E   K   E   C   R   E
1009 caa ggt aac ggt aac aag ttc tac tct gaa aag gaa tgt aga gaa DX890 continued--- Linker-------------------------------
      76  77  78  79  80  81  82  83  84  85  86  87  88  89  90
       Y   C   G   V   P   G   G   S   G   G   S   G   G   S   G
1054 tac tgt ggt gtt cca ggt GGA TCC ggt ggt tcc ggt ggt tct ggt
                                 BamHI..

Linker-------- rHA-------------- to residue 679
      91  92  93  94  95  96  97  98  99 100 101 102 103 104 105
       G   S   G   G   D   A   H   K   S   E   V   A   H   R   F
1099 ggt tcc ggt ggt gac gct cac aag tcc gaa gtc gct cAC CGG Ttc
                                                         AgeI....

106 107 108 109 110 111 112 113 114 115 116 117 118 119 120
       K   D   L   G   E   E   N   F   K   A   L   V   L   I   A
1144 aag gaC CTA GGt gag gaa aac ttc aag gct ttg gtc ttg atc gct
             AvrII...

121 122 123 124 125 126 127 128 129 130 131 132 133 134 135
       F   A   Q   Y   L   Q   Q   C   P   F   E   D   H   V   K
1189 ttc gct caa tac ttg caa caa tgt cca ttc gaa gat CAC GTC aag
                                                         BmgBI..

136 137 138 139 140 141 142 143 144 145 146 147 148 149 150
       L   V   N   E   V   T   E   F   A   K   T   C   V   A   D
1234 ttg gtc aac gaa gtt acc gaa ttc gct aag act tgt gtt gct gac 151 152 153 154 155 156 157 158 159 160 161 162 163 164 165
       E   S   A   S   N   C   D   K   S   L   H   T   L   F   G
1279 gaa tct gct gaa aac tgt gac aag tcc ttg cac acc ttg ttc ggt 166 167 168 169 170 171 172 173 174 175 176 177 178 179 180
       D   K   L   C   T   V   A   T   L   R   E   T   Y   G   E
1324 gat aag ttg tgt act gtt gct acc ttg aga gaa acc tac ggt gaa 181 182 183 184 185 186 187 188 189 190 191 192 193 194 195
       M   A   D   C   C   A   K   Q   E   P   E   R   N   E   C
1369 atg gct gac tgt tgt gct aag caa gaa cca gaa aga aac gaa tgt 196 197 198 199 200 201 202 203 204 205 206 207 208 209 210
       F   L   Q   H   K   D   D   N   P   N   L   P   R   L   V
1414 ttc ttg caa cac aag gac gac aac cca aac ttg cca aga ttg gtt
```

TABLE 26-continued

NotI cassette of pDB2300X2 with
DX890(Nterm) and Cterm linker ready for second DX890

```
      211 212 213 214 215 216 217 218 219 220 221 222 223 224 225
       R   P   E   V   D   V   M   C   T   A   F   H   D   N   E
1459  aga cca gaa gtt gac gtc atg tgt act gct ttc cac gac aac gaa 226 227 228 229 230 231 232 233 234 235 236 237 238 239 240
       E   T   F   L   K   K   Y   L   Y   E   I   A   R   R   H
1504  gaa acc ttc ttg aag aAG TAC Ttg tac gaa att gct aga aga cac
                              ScaI....

241 242 243 244 245 246 247 248 249 250 251 252 253 254 255
       P   Y   F   Y   A   P   E   L   L   F   F   A   K   R   Y
1549  cca tac ttc tac gct cca gaa ttg ttg ttc ttc gct aag aga tac 256 257 258 259 260 261 262 263 264 265 266 267 268 269 270
       K   A   A   F   T   E   C   C   Q   A   A   D   K   A   A
1594  aag gct gct ttc acc gaa tgt tgt caa gct gct gat aag gct gct 271 272 273 274 275 276 277 278 279 280 281 282 283 284 285
       C   L   L   P   K   L   D   E   L   R   D   E   G   K   A
1639  tgt ttg ttg cca aag ttg gat gaa ttg aga gac gaa ggt aag gct 286 287 288 289 290 291 292 293 294 295 296 297 298 299 300
       S   S   A   K   Q   R   L   K   C   A   S   L   Q   K   F
1684  tct tcc gct aag caa aga ttg aag tgt gct toe ttg caa aag ttc 301 302 303 304 305 306 307 308 309 310 311 312 313 314 315
       G   E   R   A   F   K   A   W   A   V   A   R   L   S   Q
1729  ggt gaa aga gct ttc aag gct tgg gct gtc gct aga ttg tct caa 316 317 318 319 320 321 322 323 324 325 326 327 328 329 330
       R   F   P   K   A   E   F   A   E   V   S   K   L   V   T
1774  aga ttc cca aag gct gaa ttc gct gaa gtt tct aag ttg gtt act 331 332 333 334 335 336 337 338 339 340 341 342 343 344 345
       D   L   T   K   V   H   T   E   C   C   H   G   D   L   L
1819  gac ttg act aag gtt cac act gaa tgt tgt cac ggt gac ttg ttg 346 347 348 349 350 351 352 353 354 355 356 357 358 359 360
       E   C   A   D   D   R   A   D   L   A   K   Y   I   C   E
1864  gaa tgt gct gat gac aga gct gac ttg gct aag tac ate tgt gaa 361 362 363 364 365 366 367 368 369 370 371 372 373 374 375
       N   Q   D   S   I   S   S   K   L   K   E   C   C   E   K
1909  aac caa gac tct atC TCT TCc aag ttg aag gaa tgt tgt gaa aag
                          EarI....

376 377 378 379 380 381 382 383 384 385 386 387 388 389 390
       P   L   L   E   K   S   H   C   I   A   E   V   E   N   D
1954  cca ttg ttg gaa aag tct cac tgt att gct gaa gtt gaa aac gat 391 392 393 394 395 396 397 398 399 400 401 402 403 404 405
       E   M   P   A   D   L   P   S   L   A   A   D   F   V   E
1999  gaa atg cCA GCT Gac ttg cca tct ttg gct gct gac ttc gtt gaa
                   PvuII...

406 407 408 409 410 411 412 413 414 415 416 417 418 419 420
       S   K   D   V   C   K   N   Y   A   E   A   K   D   V   F
2044  tct aag gac gtt tgt aag aac tac gct gaa gct aag gac gtc ttc 421 422 423 424 425 426 427 428 429 430 431 432 433 434 435
       L   G   M   F   L   Y   E   Y   A   R   R   H   P   D   Y
2089  ttg ggt atg ttc ttg tac gaa tac gct aga aga cac cca gac tac
```

TABLE 26-continued

NotI cassette of pDB2300X2 with
DX890(Nterm) and Cterm linker ready for second DX890

```
       436 437 438 439 440 441 442 443 444 445 446 447 448 449 450
        S   V   V   L   L   L   R   L   A   K   T   Y   E   T   T
2134   tcc gtt gtc ttg ttg ttg aga ttg gct aag acc tac gaa act acc 451 452 453 454 455 456 457 458 459 460 461 462 463 464 465
        L   E   K   C   C   A   A   A   D   P   H   E   C   Y   A
2179   ttg gaa aag tgt tgt gct gct gct gac cca eac gaa tgt tac gct 466 467 468 469 470 471 472 473 474 475 476 477 478 479 480
        K   V   F   D   E   F   K   P   L   V   E   E   P   Q   N
2224   aag gtt ttc gat gaa ttc aag cca ttg gtc gaa gaa cca caa aac 481 482 483 484 485 486 487 488 489 490 491 492 493 494 495
        L   I   K   Q   N   C   E   L   F   E   Q   L   G   E   Y
2269   tTG ATC Aag caa aac tgt gaa ttg ttc gaa caa ttg ggt gaa tac
       BclI....

496 497 498 499 500 501 502 503 504 505 506 507 508 509 510
        K   F   Q   N   A   L   L   V   R   Y   T   K   K   V   P
2314   aag ttc caa aac gct ttg ttg gtt aga tac act aag aag gtc cca 511 512 513 514 515 516 517 518 519 520 521 522 523 524 525
        Q   V   S   T   P   T   L   V   E   V   S   R   N   L   G
2359   caa gtc tCC Acc cca act tTC Gtt gaa gtc TCT AGA aac ttg ggt
           XcmI................        XbaI...(2/2)

526 527 528 529 530 531 532 533 534 535 536 537 538 539 540
        K   V   G   S   K   C   C   K   H   P   E   A   K   R   M
2404   aag gtc ggt tct aag tgt tgt aag cac cca gaa gct aag aGA ATG
                                                           BsmI....

541 542 543 544 545 546 547 548 549 550 551 552 553 554 555
        P   C   A   E   D   Y   L   S   V   V   L   N   Q   L   C
2449   Cca tgt gct gaa gat tac ttg tcc gtc gtt ttg aac caa ttg tgt
       BsmI..

556 557 558 559 560 561 562 563 564 565 566 567 568 569 570
        V   L   H   E   K   T   P   V   S   D   R   V   T   K   C
2494   gtt ttg cac gaa aaG ACc cca GTC tct gat aga gtC ACc aaG TGt
                       PshAI........            DraIII
                         AlwNI.......

571 572 573 574 575 576 577 578 579 580 581 582 583 584 585
        C   T   E   S   L   V   N   R   R   P   C   F   S   A   L
2539   tgt act gaa tct ttg GTT AAC aga aga cca tgt ttc tct gct ttg
                           HpaI...

586 587 588 589 590 591 592 593 594 595 596 597 598 599 600
        E   V   D   E   T   Y   V   P   K   E   F   N   A   E   T
2584   gaa GTC GAC gaa act tac gtt cca aag gaa ttc aac gct gaa act
           SalI...

601 602 603 604 605 606 607 608 609 610 611 612 613 614 615
        F   T   F   H   A   D   I   C   T   L   S   E   K   E   R
2629   ttc acc ttc cac gct GAT ATC tgt acc ttg tcc gaa aag gaa aga
                           EcoRV..

616 617 618 619 620 621 622 623 624 625 626 627 628 629 630
        Q   I   K   K   Q   T   A   L   V   E   L   V   K   H   K
2674   caa att aag aag caa act gct ttg gtt gaa ttg gtc aag cac aag 631 632 633 634 635 636 637 638 639 640 641 642 643 644 645
```

TABLE 26-continued

NotI cassette of pDB2300X2 with DX890(Nterm) and Cterm linker ready for second DX890

```
|        P   K   A   T   K   E   Q   L   K   A   V   M   D   D   F
| 2719  cca aag gct act aag gaa caa ttg aag gct gtc atg gat gat ttc
|
|       646 647 648 649 650 651 652 653 654 655 656 657 658 659 660
|        A   A   F   V   E   K   C   C   K   A   D   D   K   E   T
| 2764  gct gct ttc gtt gaa aag tgt tgt aag gct gat gat aag gaa act
|
|       661 662 663 664 665 666 667 668 669 670 671 672 673 674 675
|        C   F   A   E   E   G   K   K   L   V   A   A   S   Q   A
| 2809  tgt ttc gct gaa gaa ggt aag aag ttg gtc gct gct tcc caa gct
|
|       676 677 678 679 680 681 682 683 684 685 686 687 688 689 690
|        A   L   G   L   G   G   S   G   G   S   G   G   S   G   G
| 2854  gCC TTA GGc tta ggt ggt tct ggt ggt tcc ggt ggt TCC GGA ggt
|       Bsu36I...                                    BspEI..
|
|       691 692 693 694
|        S   G   G   T
| 2899  tcc ggt GGT ACC    taa  tAA GCTTa attcttatga
|             KpnI...      Stop Stop
|                               HindIII (2/2)
|
| 2932 tttatgattt ttattattaa ataagTTATA Aaaaaaataa gtGTATACaa attttaaagt
|                            PsiI...             BstZ17I
|
| 2992 gactcttagg ttttaaaacg aaaattctta ttcttgagta actctttcct gtaggtcagg
| 3052 ttgctttctc aggtatagca tgaggtcgct cttattgacc acacctctac cgGCATGCcg
|                                                                SphI..
|
| 3112 agcaaatgcc tgcaaatcgc tccccatttc acccaattgt agatatgcta actccagcaa
| 3172 tgagttgatg aatctcggtg tgtattttat gtcctcagag acaacacct gttgtaatcg
| 3232 ttcttccaca cggatCGCGG CCGC
|                      NotI......
```

TABLE 27

DNA to insert at BspEI/KpnI site for 2nd encoding of DX-890

TCCGGAggta gtggtggctc cggtggtgag (SEQ. ID No.: 72)

gcttgcaatc ttcctatcgt Ccgtggccct tgcatcgcct ttttttcctcg ttgggccttt gacgccgtca Aaggcaaatg cgtccttttt ccttacggcg gttgccaggg caatggcaat Aaattttata gcgagaaaga gtgccgtgag tattgcggcg tcccttaata aGGTACC

TABLE 28

NotI cassette of DDB2300X3 with 2 x DX890

```
|
| DNA sequence has SEQ ID No.: 73
|
| AA Sequence has SEQ ID No.: 74
```

TABLE 28-continued

NotI cassette of DDB2300X3 with 2 x DX890

! Enzymes that cut from 1 to 3 times.

! $ = DAM site, * = DCM site, & = both

| | | | |
|---|---|---|---|
| !NotI GCggccgc | 2 1 | 3434 | |
| !EagI Cggccg | 2 2 | 3435 | |
| !KasI Ggcgcc | 1 | 160 | |
| !AfeI AGCgct | 1 | 193 | |
| !NaeI GCCggc | 1 | 234 | |
| !NgoMIV Gccggc | 1 | 234 | |
| !BsgI ctgcac | 1 | 450 | |
| !BcgI gcannnnnntcg (SEQ ID No.: 80) | 1 | 568 | |
| !BanII GRGCYc | 1 | 620 | |
| !PstI CTGCAg | 1 | 636 | |
| !AflII cttaag | 1 | 763 | |
| !HindIII Aagctt | 2 | 801 | 3101 |
| !BglII Agatct | 1 | 883$ | |
| !PflMI CCANNNNntgg (SEQ ID No.: 81) | 1 | 994 | |
| !NdeI CAtatg | 1 | 995 | |
| !BamHI Ggatcc | 1 | 1072$ | |
| !AgeI Accggt | 1 | 1136 | |
| !AvrII Cctagg | 1 | 1149 | |
| !BmgBI CACgtc | 1 | 1225$ | |
| !ScaI AGTact | 1 | 1520 | |
| !EarI CTCTTCNnnn (SEQ ID No.: 82) | 1 | 1923 | |
| !PvuII CAGctg | 1 | 2006 | |
| !BclI Tgatca | 1 | 2270$ | |
| !XcmI CCANNNNNnnnntgg (SEQ ID No.: 83) | 1 | 2366 | |
| !BsmI GAATGCN | 1 | 2444 | |
| !PshAI GACNNnngtc (SEQ ID No.: 84) | 1 | 2508 | |
| !AlwNI CAGNNNctg | 1 | 2513 | |
| !DraIII CACNNNgtg | 1 | 2529 | |
| !HpaI GTTaac | 1 | 2554 | |
| !SalI Gtcgac | 1 | 2587 | |
| !EcoRV GATatc | 1 | 2644 | |
| !Bsu36I CCtnagg | 1 | 2855 | |
| !BspEI Tccgga | 1 | 2890 | |
| !PflFI GACNnngtc | 1 | 2980 | |
| !Tth111I GACNnngtc | 1 | 2980 | |
| !Acc65I Ggtacc | 1 | 3091 | |
| !KpnI GGTACc | 1 | 3091 | |

TABLE 28-continued

NotI cassette of DDB2300X3 with 2 x DX890

| |PsiI TTAtaa | 1 | 3143 | |
| |BstZ17I GTAtac | 1 | 3160 | |
| |SphI GCATGc | 1 | 3290 | |

```
|----------------------------------------                 (SEQ. ID Nos.: 73
    1 GCGGCCGCcc gtaatgcggt atcgtgaaag cgaaaaaaaa actaacagta gataagacag    (nucleic acid) and
      NotI....                                                             74 (amino acid)).

61 atagacagat agagatggac gagaaacagg gggggagaaa aggggaaaag agaaggaaag
  121 aaagactcat ctatcgcaga taagacaatc aaccctcatG GCGCCtccaa ccaccatccg
|                                                        NarI...

182 cactagggac caAGCGCTcg caccgttagc aacgcttgac tcacaaacca actGCCGGCt
|                 AfeI..                                        NgoMIV 241 gaaagagctt gtgcaatggg agtgccaatt caaaggagcc gaatacgtct gctcgccttt
  301 taagaggctt tttgaacact gcattgcacc cgacaaatca gccactaact acgaggtcac
  361 ggacacatat accaatagtt aaaaattaca tatactctat atagcacagt agtgtgataa
  421 ataaaaaatt ttgccaagac tttttttaaaC TGCACccgac agatcaggtc tgtgcctact
|                                      BsgI...

481 atgcacttat gcccggggtc ccgggaggag aaaaaacgag ggctgggaaa tgtccgtgga
  541 ctttaaacgc tccggggttag cagagtaGCA gggcttTCGg ctttggaaat ttaggtgact
|                                      BcgI.........

601 tgttgaaaaa gcaaaatttg ggctcagtaa tgCCActgca gTGGcttatc acgccaggac
|                                               BstXI........
|                                                   PStI...

661 tgcgggagtg gcggggcaa acacacccgc gataaagagc gcgatgaata taaaaggggg
  721 ccaatgttac gtcccgttat attggagttc ttcccataca aaCTTAAGag tccaattagc
|                                                      AflII.

781 ttcatcgcca ataaaaaaac AAGCTTaacc taattctaac aagcaaag
|     HindIII (¹⁄₂)

|     Signal sequence ----------------------------------------->
|       1   2   3   4   5   6   7   8   9  10  11  12  13  14  15
|       M   K   W   V   F   I   V   S   I   L   F   L   F   S   S
  829 atg aag tgg gtt ttc atc gtc tcc att ttg ttc ttg ttc tcc tct

|     Signal sequence ----------------->  DX890, first instance -->
|      16  17  18  19  20  21  22  23  24  25  26  27  28  29  30
|       A   Y   S   R   S   L   D   K   R   E   A   C   N   L   P
  874 gct tac tct AGA TCT ttg gat aag aga gaa gcc tgt aac ttg cca
|                  BglII..

|      31  32  33  34  35  36  37  38  39  40  41  42  43  44  45
|       I   V   R   G   P   C   I   A   F   F   P   R   W   A   F
  919 att gtt aga ggt cca tgt att gct ttc ttc cca aga tgg gct ttc

|      46  47  48  49  50  51  52  53  54  55  56  57  58  59  60
|       D   A   V   K   G   K   C   V   L   F   P   Y   G   G   C
  964 gat gct gtt aag ggt aag tgt gtt ttg ttc CCA tat ggT GGt tgt
|                                             PflMI.........
|                                                 NdeI....

|      61  62  63  64  65  66  67  68  69  70  71  72  73  74  75
|       Q   G   N   G   N   K   F   Y   S   E   K   E   C   R   E
 1009 caa ggt aac ggt aac aag ttc tac tct gaa aag gaa tgt aga gaa
```

TABLE 28-continued

NotI cassette of DDB2300X3 with 2 x DX890

```
!        ----DX890#1------>  --------------- Linker ---------------
!         76  77  78  79  80  81  82  83  84  85  86  87  88  89  90
!          Y   C   G   V   P   G   G   S   G   G   S   G   G   S   G
    1054  tac tgt ggt gtt cca ggt GGA TCC ggt ggt tcc ggt ggt tct ggt
!                                     BamHI..

!        --- Linker --->  -------------- rHA gene ----until codon 679 -->
!         91  92  93  94  95  96  97  98  99 100 101 102 103 104 105
!          G   S   G   G   D   A   H   K   S   E   V   A   H   R   F
    1099  ggt tcc ggt ggt gac gct cac aag tcc gaa gtc gct cAC CGG Ttc
!                                                             AgeI....

!        106 107 108 109 110 111 112 113 114 115 116 117 118 119 120
!          K   D   L   G   E   E   N   F   K   A   L   V   L   I   A
    1144  aag gaC CTA GGt gag gaa aac ttc aag gct ttg gtc ttg atc gct
!                AvrII...

!        121 122 123 124 125 126 127 128 129 130 131 132 133 134 135
!          F   A   Q   Y   L   Q   Q   C   P   F   E   D   H   V   K
    1189  ttc gct caa tac ttg caa caa tgt cca ttc gaa gat cac gtc aag !        136 137 138 139 140 141 142 143 144 145 146 147 148 149 150
!          L   V   N   E   V   T   E   F   A   K   T   C   V   A   D
    1234  ttg gtc aac gaa gtt acc gaa ttc gct aag act tgt gtt gct gac !        151 152 153 154 155 156 157 158 159 160 161 162 163 164 165
!          E   S   A   E   N   C   D   K   S   L   H   T   L   F   G
    1279  gaa tct gct gaa aac tgt gac aag tcc ttg cac acc ttg ttc ggt !        166 167 168 169 170 171 172 173 174 175 176 177 178 179 180
!          D   K   L   C   T   V   A   T   L   R   E   T   Y   G   E
    1324  gat aag ttg tgt act gtt gct acc ttg aga gaa acc tac ggt gaa !        181 182 183 184 185 186 187 188 189 190 191 192 193 194 195
!          M   A   D   C   C   A   K   Q   E   P   E   R   N   E   C
    1369  atg gct gac tgt tgt gct aag caa gaa cca gaa aga aac gaa tgt !        196 197 198 199 200 201 202 203 204 205 206 207 208 209 210
!          F   L   Q   H   K   D   D   N   P   N   L   P   R   L   V
    1414  ttc ttg caa cac aag gac gac aac cca aac ttg cca aga ttg gtt !        211 212 213 214 215 216 217 218 219 220 221 222 223 224 225
!          R   P   E   V   D   V   M   C   T   A   F   H   D   N   E
    1459  aga cca gaa gtt gac gtc atg tgt act gct ttc cac gac aac gaa !        226 227 228 229 230 231 232 233 234 235 236 237 238 239 240
!          E   T   F   L   K   K   Y   L   Y   E   I   A   R   R   H
    1504  gaa acc ttc ttg aag aag tac ttg tac gaa att gct aga aga cac !        241 242 243 244 245 246 247 248 249 250 251 252 253 254 255
!          P   Y   F   Y   A   P   E   L   L   F   F   A   K   R   Y
    1549  cca tac ttc tac gct cca gaa ttg ttg ttc ttc gct aag aga tac !        256 257 258 259 260 261 262 263 264 265 266 267 268 269 270
!          K   A   A   F   T   E   C   C   Q   A   A   D   K   A   A
    1594  aag gct gct ttc acc gaa tgt tgt caa gct gct gat aag gct gct !        271 272 273 274 275 276 277 278 279 280 281 282 283 284 285
!          C   L   L   P   K   L   D   E   L   R   D   E   G   K   A
    1639  tgt ttg ttg cca aag ttg gat gaa ttg aga gac gaa ggt aag gct !        286 287 288 289 290 291 292 293 294 295 296 297 298 299 300
!          S   S   A   K   Q   R   L   K   C   A   S   L   Q   K   F
```

TABLE 28-continued

NotI cassette of DDB2300X3 with 2 x DX890

1684 tct tcc gct aag caa aga ttg aag tgt gct tcc ttg caa aag ttc

```
      301 302 303 304 305 306 307 308 309 310 311 312 313 314 315
       G   E   R   A   F   K   A   W   A   V   A   R   L   S   Q
1729 ggt gaa aga gct ttc aag gct tgg gct gtc gct aga ttg tct caa 316 317 318 319 320 321 322 323 324 325 326 327 328 329 330
       R   F   P   K   A   E   F   A   E   V   S   K   L   V   T
1774 aga ttc cca aag gct gaa ttc gct gaa gtt tct aag ttg gtt act 331 332 333 334 335 336 337 338 339 340 341 342 343 344 345
       D   L   T   K   V   H   T   E   C   C   H   G   D   L   L
1819 gac ttg act aag gtt cac act gaa tgt tgt cac ggt gac ttg ttg 346 347 348 349 350 351 352 353 354 355 356 357 358 359 360
       E   C   A   D   D   R   A   D   L   A   K   Y   I   C   E
1864 gaa tgt gct gat gac aga gct gac ttg gct aag tac atc tgt gaa 361 362 363 364 365 366 367 368 369 370 371 372 373 374 375
       N   Q   D   S   I   S   S   K   L   K   E   C   C   E   K
1909 aac caa gac tct atc tct tcc aag ttg aag gaa tgt tgt gaa aag 376 377 378 379 380 381 382 383 384 385 386 387 388 389 390
       P   L   L   E   K   S   H   C   I   A   E   V   E   N   D
1954 cca ttg ttg gaa aag tct cac tgt att gct gaa gtt gaa aac gat 391 392 393 394 395 396 397 398 399 400 401 402 403 404 405
       E   M   P   A   D   L   P   S   L   A   A   D   F   V   E
1999 gaa atg cca gct gac ttg cca tct ttg gct gct gac ttc gtt gaa 406 407 408 409 410 411 412 413 414 415 416 417 418 419 420
       S   K   D   V   C   K   N   Y   A   E   A   K   D   V   F
2044 tct aag gac gtt tgt aag aac tac gct gaa gct aag gac gtc ttC 421 422 423 424 425 426 427 428 429 430 431 432 433 434 435
       L   G   M   F   L   Y   E   Y   A   R   R   H   P   D   Y
2089 ttg ggt atg ttc ttg tac gaa tac gct aga aga cac cca gac tac 436 437 438 439 440 441 442 443 444 445 446 447 448 449 450
       S   V   V   L   L   L   R   L   A   K   T   Y   E   T   T
2134 tcc gtt gtc ttg ttg ttg aga ttg gct aag acc tac gaa act acc 451 452 453 454 455 456 457 458 459 460 461 462 463 464 465
       L   E   K   C   C   A   A   A   D   P   H   E   C   Y   A
2179 ttg gaa aag tgt tgt gct gct gct gac cca cac gaa tgt tac gct 466 467 468 469 470 471 472 473 474 475 476 477 478 479 480
       K   V   F   D   E   F   K   P   L   V   E   E   P   Q   N
2224 aag gtt ttc gat gaa ttc aag cca ttg gtc gaa gaa cca caa aac 481 482 483 484 485 486 487 488 489 490 491 492 493 494 495
       L   I   K   Q   N   C   E   L   F   E   Q   L   G   E   Y
2269 ttg atc aag caa aac tgt gaa ttg ttc gaa caa ttg ggt gaa tac 496 497 498 499 500 501 502 503 504 505 506 507 508 509 510
       K   F   Q   N   A   L   L   V   R   Y   T   K   K   V   P
2314 aag ttc caa aac gct ttg ttg gtt aga tac act aag aag gtc cca 511 512 513 514 515 516 517 518 519 520 521 522 523 524 525
       Q   V   S   T   P   T   L   V   E   V   S   R   N   L   G
2359 caa gtc tcc acc cca act ttg gtt gaa gtc tct aga aac ttg ggt
```

TABLE 28-continued

NotI cassette of DDB2300X3 with 2 x DX890

```
      526 527 528 529 530 531 532 533 534 535 536 537 538 539 540
       K   V   G   S   K   C   C   K   H   P   E   A   K   R   M
 2404 aag gtc ggt tct aag tgt tgt aag cac cca gaa gct aag aga atg 541 542 543 544 545 546 547 548 549 550 551 552 553 554 555
       P   C   A   E   D   Y   L   S   V   V   L   N   Q   L   C
 2449 cca tgt gct gaa gat tac ttg tcc gtc gtt ttg aac caa ttg tgt 556 557 558 559 560 561 562 563 564 565 566 567 568 569 570
       V   L   H   E   K   T   P   V   S   D   R   V   T   K   C
 2494 gtt ttg cac gaa aag acc cca gtc tct gat aga gtc acc aag tgt 571 572 573 574 575 576 577 578 579 580 581 582 583 584 585
       C   T   E   S   L   V   N   R   R   P   C   F   S   A   L
 2539 tgt act gaa tct ttg gtt aac aga aga cca tgt ttc tct gct ttg 586 587 588 589 590 591 592 593 594 595 596 597 598 599 600
       E   V   D   E   T   Y   V   P   K   E   F   N   A   E   T
 2584 gaa gtc gac gaa act tac gtt cca aag gaa ttc aac gct gaa act 601 602 603 604 605 606 607 608 609 610 611 612 613 614 615
       F   T   F   H   A   D   I   C   T   L   S   E   K   E   R
 2629 ttc acc ttc cac gct gat atc tgt acc ttg tcc gaa aag gaa aga 616 617 618 619 620 621 622 623 624 625 626 627 628 629 630
       Q   I   K   K   Q   T   A   L   V   E   L   V   K   H   K
 2674 caa att aag aag caa act gct ttg gtt gaa ttg gtc aag cac aag 631 632 633 634 635 636 637 638 639 640 641 642 643 644 645
       P   K   A   T   K   E   Q   L   K   A   V   M   D   D   F
 2719 cca aag gct act aag gaa caa ttg aag gct gtc atg gat gat ttc 646 647 648 649 650 651 652 653 654 655 656 657 658 659 660
       A   A   F   V   E   K   C   C   K   A   D   D   K   E   T
 2764 gct gct ttc gtt gaa aag tgt tgt aag gct gat gat aag gaa act 661 662 663 664 665 666 667 668 669 670 671 672 673 674 675
       C   F   A   S   S   G   K   K   L   V   A   A   S   Q   A
 2809 tgt ttc gct gaa gaa ggt aag aag ttg gtc gct gct tcc caa gct Linker ------------------------------->
      676 677 678 679 680 681 682 683 684 685 686 687 688 689 690
       A   L   G   L   G   G   S   G   G   S   G   G   S   G   G
 2854 gCC TTA GGc tta ggt ggt tct ggt ggt tcc ggt ggt TCC GGA ggt
       Bsu36I...                                     BspEI..

DX-890 (second encoding) ----to end--
      691 692 693 694 695 696 697 698 699 700 701 702 703 704 705
       S   C   C   S   G   C   E   A   C   N   L   P   I   V   R
 2899 agt ggt ggc tcc ggt ggt gag gct tgc aat ctt cct atc gtc cgt 706 707 708 709 710 711 712 713 714 715 716 717 718 719 720
       C   P   C   I   A   F   F   P   R   W   A   F   D   A   V
 2944 ggc cct tgc atc gcc ttt ttt cct cgt tgg gcc ttt gac gcc gtc 721 722 723 724 725 726 727 728 729 730 731 732 733 734 735
       K   G   K   C   V   L   F   P   Y   G   G   C   Q   G   N
 2989 aaa ggc aaa tgc gtc ctt ttt cct tac ggc ggt tgc cag ggc aat 736 737 738 739 740 741 742 743 744 745 746 747 748 749 750
       G   N   K   F   Y   S   E   K   E   C   R   E   Y   C   G
 3034 ggc aat aaa ttt tat agc gag aaa gag tgc cgt gag tat tgc ggc
```

TABLE 28-continued

NotI cassette of DDB2300X3 with 2 x DX890

```
|
|      751 752
|       V   P
 3079 gtc cct taa taa         GGT ACC        taa  tAA GCTTa attcttatga
|                             KpnI...        Stop Stop
|      HindlIl (2/2)
 3118 tttatgattt ttattattaa ataagTTATA Aaaaaaataa gtGTATACaa attttaaagt
                             PsiI...         BstZ17I
|
 3178 gactcttagg ttttaaaacg aaaattctta ttcttgagta actctttcct gtaggtcagg
 3238 ttgctttctc aggtatagca tgaggtcgct cttattgacc acacctctac cgGCATGCcg
|                                                             SphI..
|
 3298 agcaaatgcc tgcaaatcgc tccccatttc acccaattgt agatatgct
 3358 tgagttgatg aatctcggtg tgtattttat gtcctcagag gacaacacc
 3418 ttcttccaca cggatCGCGG CCGC
|                    NotI......
```

TABLE 29

AA sequence of DX890::(GGS)4GG::HA::(GGS)4GG::DX890

EACNLPIVRG PCIAFFPRWA FDAVKGKCVL   (SEQ ID No.: 75)

FPYGGCQGNG NKFYSEKECR EYCGVPGGSG

GSGGSGGSGG DAHKSEVAHR FKDLGEENFK

ALVLIAFAQY LQQCPFEDHV KLVNEVTEFA

KTCVADESAE NCDKSLHTLF GDKLCTVATL

RETYGEMADC CAKQEPERNE CFLQHKDDNP

NLPRLVRPEV DVMCTAFHDN EETFLKKYLY

EIARRHPYFY APELLFFAKR YKAAFTECCQ

AADKAACLLP KLDELRDEGK ASSAKQRLKC

ASLQKFGERA FKAWAVARLS QRFPKAEFAE

VSKLVTDLTK VHTECCHGDL LECADDRADL

AKYICENQDS ISSKLKECCE KPLLEKSHCI

AEVENDEMPA DLPSLAADFV ESKDVCKNYA

EAKDVFLGMF LYEYARRHPD YSVVLLLRLA

KTYETTLEKC CAAADPHECY AKVFDEFKPL

VEEPQNLIKQ NCELFEQLGE YKFQNALLVR

YTKKVPQVST PTLVEVSRNL GKVGSKCCKH

PEAKRMPCAE DYLSVVLNQL CVLHEKTPVS

DRVTKCCTES LVNRRPCFSA LEVDETYVPK

EFNAETFTFH ADICTLSEKE RQIKKQTALV

ELVKHKPKAT KEQLKAVMDD FAAFVEKCCK

ADDKETCFAE EGKKLVAASQ AALGLGGSGG

SGGSGGSGGS GGEACNLPIV RGPCIAFFPR

WAFDAVKGKC VLFPYGGCQG NGNKFYSEKE

CREYCGVP

TABLE 30

DNA sequence of the N-terminal BglII-BamHI DX-1000 cDNA

```
AGA TCT TTG GAT AAG    (SEQ ID No.: 76)
AGA gag gct atg cat tcc
ttc tgc gcc ttc aag gct
gag act ggt cct tgt aga
gct agg ttc gac cgt tgg
ttc ttc aac atc ttc acg
cgt cag tgc gag gaa ttc
att tac ggt ggt tgt gaa
ggt aac cag aac cgg ttc
gaa tct cta gag gaa tgt
aag aag atg tgc act cgt
gac

GGA TCC
```

TABLE 31

AA sequence of DX1000::(GGS)4GG::HA

EAMHSFCAFK AETGPCRARF DRWFFNIFTR (SEQ ID No.: 77)
QCEEFIYGGC EGNQNRFESL EECKKMCTRD
GGSGGSGGSG GSGGDAHKSE VAHRFKDLGE
ENFKALVLIA FAQYLQQCPF EDHVKLVNEV
TEFAKTCVAD ESAENCDKSL HTLFGDKLCT
VATLRETYGE MADCCAKQEP ERNECFLQHK
DDNPNLPRLV RPEVDVMCTA FHDNEETFLK
KYLYEIARRH PYFYAPELLF FAKRYKAAFT
ECCQAADKAA CLLPKLDELR DEGKASSAKQ
RLKCASLQKF GERAFKAWAV ARLSQRFPKA
EFAEVSKLVT DLTKVHTECC HGDLLECADD
RADLAKYICE NQDSISSKLK ECCEKPLLEK
SHCIAEVEND EMPADLPSLA ADFVESKDVC
KNYAEAKDVF LGMFLYEYAR RHPDYSVVLL
LRLAKTYETT LEKCCAAADP HECYAKVFDE
FKPLVEEPQN LIKQNCELFE QLGEYKFQNA
LLVRYTKKVP QVSTPTLVEV SRNLGKVGSK
CCKHPEAKRM PCAEDYLSVV LNQLCVLHEK
TPVSDRVTKC CTESLVNRRP CFSALEVDET
YVPKEFNAET FTFHADICTL SEKERQIKKQ
TALVELVKHK PKATKEH

TABLE 32

DNA sequence of the N-terminal BspEI-KpnI DX-88 cDNA-2<sup>nd</sup> encoding

TCC GGA ggt agt ggt ggc tcc ggt  (SEQ ID No.: 78)
ggt GAg GCc ATG CAt
TCT TTC TGT GCT TTC AAG GCT GAC
GAC GGT CCG TGC AGA GCT GCT CAC
CCA AGA TGG TTC TTC AAC ATC TTC

TABLE 32-continued

DNA sequence of the N-terminal BspEI-KpnI DX-88 cDNA-2<sup>nd</sup> encoding

ACG CGA CAA TGC GAG GAG TTC ATC
TAC GGT GGT TGT GAG GGT AAC CAA
AAC AGA TTC GAG TCT CTA GAG GAG
TGT AAG AAG ATG TGT ACT AGA GAC
GGT taa taa GGT ACC

TABLE 33

AA sequence of DPI14::HSA

EAVREVCSEQ AETGPCIAFF PRWYFDVTEG (SEQ ID No.: 79)
KCAPFFYGGC GGNRNNFDTE EYCMAVCGSA
GGSGGSGGSG GSGGDAHKSE VAHRFKDLGE
ENFKALVLIA FAQYLQQCPF EDHVKLVNEV
TEFAKTCVAD ESAENCDKSL HTLFGDKLCT
VATLRETYGE MADCCAKQEP ERNECFLQHK
DDNPNLPRLV RPEVDVMCTA FHDNEETFLK
KYLYEIARRH PYFYAPELLF FAKRYKAAFT
ECCQAADKAA CLLPKLDELR DEGKASSAKQ
RLKCASLQKF GERAFKAWAV ARLSQRFPKA
EFAEVSKLVT DLTKVHTECC HGDLLECADD
RADLAKYICE NQDSISSKLK ECCEKPLLEK
SHCIAEVEND EMPADLPSLA ADFVESKDVC
KNYAEAKDVF LGMFLYEYAR RHPDYSVVLL
LRLAKTYETT LEKCCAAADP HECYAKVFDE
FKPLVEEPQN LIKQNCELFE QLGEYKFQNA
LLVRYTKKVP QVSTPTLVEV SRNLGKVGSK
CCKHPEAKRM PCAEDYLSVV LNQLCVLHEK
TPVSDRVTKC CTESLVNRRP CFSALEVDET
YVPKEFNAET FTFHADICTL SEKERQIKKQ
TALVELVKHK PKATKEH

---

We claim:

1. A polypeptide comprising (a) the following sequence: EAVREVCSEQAETGPCIAFFPRWYFD-VTEGKCAPFFYGGCGGNRNNFDTE EYCMAVCGSA (SEQ ID NO:39), (b) a sequence that is at least 90% identical to SEQ ID NO:39 and inhibits human neutrophil elastase, (c) a sequence that is encoded by a nucleic acid that hybridizes under highly stringent conditions to a nucleic acid encoding SEQ ID NO:39 and inhibits human neutrophil elastase; or (d) a sequence that is a functional fragment of SEQ ID NO:39, inhibits human neutrophil elastase, and has a length of about 51 to 64 amino acids.

2. A method of inhibiting human neutrophil elastase, comprising contacting the polypeptide of claim 1 to human neutrophil elastase.

3. A method of treating a disorder ameliorated by inhibition of human neutrophil elastase, the method comprising administering the polypeptide of claim 1 to a subject who requires treatment for a disorder ameliorated by inhibition of human neutrophil elastase.

4. The method of claim 3 wherein the disorder is cystic fibrosis or a cystic fibrosis-related disorder.

5. The method of claim 4 wherein the subject has cystic fibrosis.

6. The method of claim 3 wherein the disorder is emphysema.

7. The method of claim 3 wherein the disorder is chronic obstructive pulmonary disease (COPD).

8. The method of claim 3 wherein the disorder is bronchitis.

9. The method of claim 3 wherein the disorder is pulmonary hypertension.

10. The method of claim 3 wherein the disorder is acute respiratory distress syndrome.

11. The method of claim 3 wherein the disorder is interstitial lung disease.

12. The method of claim 3 wherein the disorder is asthma.

13. The method of claim 3 wherein the disorder is broncho-pulmonary dysplasia.

14. The method of claim 3 wherein the disorder is pneumonia.

15. The method of claim 3 wherein the disorder is lung transplant rejection.

16. The method of claim 3 wherein the polypeptide comprises (b) a sequence encoded by a nucleic acid that hybridizes under highly stringent conditions to a nucleic acid encoding SEQ ID NO:39.

17. The method of claim 4 wherein the polypeptide comprises (b) a sequence encoded by a nucleic acid that hybridizes under highly stringent conditions to a nucleic acid encoding SEQ ID NO:39.

18. The method of claim 3 wherein the polypeptide comprises a sequence that is at least 95% identical to SEQ ID NO:39.

19. The method of claim 4 wherein the polypeptide comprises a sequence that is at least 95% identical to SEQ ID NO:39.

20. The method of claim 3 wherein the polypeptide comprises SEQ ID NO:39.

21. The method of claim 4 wherein the polypeptide comprises SEQ ID NO:39.

22. The polypeptide of claim 1 that comprises a sequence that is at least 90% identical to SEQ ID NO:39.

23. The polypeptide of claim 22 that comprises a sequence that is at least 95% identical to SEQ ID NO:39.

24. The polypeptide of claim 23 that comprises a sequence that is at least 98% identical to SEQ ID NO:39.

25. The polypeptide of claim 24 that comprises SEQ ID NO:39.

26. The polypeptide of claim 1 that comprises a sequence encoded by a nucleic acid that hybridizes under highly stringent conditions to a nucleic acid encoding SEQ ID NO:39.

27. A method of treating cystic fibrosis, the method comprising administering a polypeptide that comprises SEQ ID NO:39 and inhibits human neutrophil elastase to a subject who has cystic fibrosis.

* * * * *